(12) United States Patent
Retallack et al.

(10) Patent No.: US 8,906,636 B2
(45) Date of Patent: Dec. 9, 2014

(54) HIGH LEVEL EXPRESSION OF RECOMBINANT TOXIN PROTEINS

(71) Applicant: Pfenex Inc., San Diego, CA (US)

(72) Inventors: Diane M. Retallack, Poway, CA (US); Lawrence Chew, San Diego, CA (US)

(73) Assignee: Pfenex Inc., San Diego, CA (US)

( * ) Notice: Subject to any disclaimer, the term of this patent is extended or adjusted under 35 U.S.C. 154(b) by 0 days.

(21) Appl. No.: 13/952,484

(22) Filed: Jul. 26, 2013

(65) Prior Publication Data

US 2014/0051093 A1    Feb. 20, 2014

Related U.S. Application Data

(60) Division of application No. 13/073,955, and a continuation-in-part of application No. PCT/US2010/030573, filed on Apr. 9, 2010, now Pat. No. 8,530,171.

(60) Provisional application No. 61/325,235, filed on Apr. 16, 2010, provisional application No. 61/319,152, filed on Mar. 30, 2010.

(51) Int. Cl.
| | |
|---|---|
| *C12N 9/10* | (2006.01) |
| *C12P 21/00* | (2006.01) |
| *G01N 33/573* | (2006.01) |
| *C12N 15/78* | (2006.01) |
| *C12P 21/02* | (2006.01) |
| *C07K 14/34* | (2006.01) |

(52) U.S. Cl.
CPC .............. *C12N 9/1051* (2013.01); *C12N 15/78* (2013.01); *C12P 21/00* (2013.01); *C07K 2319/036* (2013.01); *C12P 21/02* (2013.01); *C07K 14/34* (2013.01); *G01N 33/573* (2013.01)
USPC ............... 435/7.4; 435/15; 435/23; 435/69.3; 435/193; 435/471

(58) Field of Classification Search
CPC ...... C12N 15/78; C12N 9/1051; C12P 21/00; G01N 33/573
USPC ........ 435/7.4, 15, 23, 69.3, 193, 471
See application file for complete search history.

(56) References Cited

U.S. PATENT DOCUMENTS

| | | | |
|---|---|---|---|
| 4,551,433 A | 11/1985 | DeBoer | |
| 4,695,455 A | 9/1987 | Barnes et al. | |
| 4,709,017 A | 11/1987 | Collier | |
| 4,755,465 A | 7/1988 | Gray et al. | |
| 4,830,962 A | 5/1989 | Gelfand et al. | |
| 4,861,595 A | 8/1989 | Barnes et al. | |
| 4,892,827 A | 1/1990 | Pastan et al. | |
| 4,925,792 A | 5/1990 | Rappuoli | |
| 5,055,294 A | 10/1991 | Gilroy | |
| 5,085,862 A | 2/1992 | Klein et al. | |
| 5,128,130 A | 7/1992 | Gilroy et al. | |
| 5,169,760 A | 12/1992 | Wilcox | |
| 5,281,532 A | 1/1994 | Rammler et al. | |
| 5,389,540 A | 2/1995 | Makoff et al. | |
| 5,427,788 A | 6/1995 | Rappuoli et al. | |
| 5,443,966 A | 8/1995 | Fairweather et al. | |
| 5,571,694 A | 11/1996 | Makoff et al. | |
| 5,614,382 A | 3/1997 | Metcalf | |
| 5,773,600 A | 6/1998 | Burnette, III | |
| 5,785,971 A | 7/1998 | Rappuoli et al. | |
| 5,792,458 A | 8/1998 | Johnson et al. | |
| 5,834,246 A | 11/1998 | Holmgren et al. | |
| 5,919,463 A | 7/1999 | Thomas, Jr. et al. | |
| 5,935,580 A | 8/1999 | Ladant et al. | |
| 6,010,871 A | 1/2000 | Takahara et al. | |
| 6,043,057 A | 3/2000 | Holmgren et al. | |
| 6,140,082 A | 10/2000 | Loosmore et al. | |
| 6,733,760 B1 | 5/2004 | Wilkins et al. | |
| 6,939,548 B2 | 9/2005 | Wilkins et al. | |
| 7,169,399 B2 | 1/2007 | Roberts | |
| 7,226,597 B2 | 6/2007 | Ballard et al. | |
| 7,232,671 B2 | 6/2007 | Cieplak | |
| 7,273,728 B2 | 9/2007 | Wolfe et al. | |
| 7,427,404 B1 | 9/2008 | Pizza et al. | |
| 7,575,891 B2 | 8/2009 | Wolfe et al. | |
| 7,618,799 B2 | 11/2009 | Coleman et al. | |
| 7,666,436 B1 | 2/2010 | Pizza et al. | |
| 7,985,564 B2 | 7/2011 | Retallack et al. | |
| 8,288,127 B2 | 10/2012 | Schneider et al. | |
| 8,530,171 B2 | 9/2013 | Retallack et al. | |

(Continued)

FOREIGN PATENT DOCUMENTS

| | | |
|---|---|---|
| EP | 0207459 | 1/1978 |
| EP | 0478602 | 1/1996 |
| WO | WO-90-09444 | 8/1990 |
| WO | WO-90-15871 | 12/1990 |
| WO | WO-97-02836 | 1/1997 |
| WO | WO-2005-000346 | 1/2005 |
| WO | WO-2005-052151 | 6/2005 |
| WO | WO-2005-056773 | 6/2005 |
| WO | WO-2005-069913 | 8/2005 |
| WO | WO-2005-089093 | 9/2005 |

(Continued)

OTHER PUBLICATIONS

Yang et al., BMC Microbiology 8, article 192 (2008).*
Ellingsworth, L., *Pseudomonas fluorescens*: Expression System for Producing Recombinant Vaccines and Adjuvants (2006).*
Allured et al., Structure of exotoxin A of *Pseudomonas aeruginosa* at 3.0-Angrstom resolution, PNAS USA 83:1320-1324 (1986).

(Continued)

*Primary Examiner* — Chih-Min Kam
(74) *Attorney, Agent, or Firm* — Wilson Sonsini Goodrich & Rosati

(57) ABSTRACT

The present invention relates to the field of recombinant toxin protein production in bacterial hosts. In particular, the present invention relates to production processes for obtaining high levels of a recombinant CRM197, Diphtheria Toxin, Pertussis Toxin, Tetanus Toxoid Fragment C, Cholera Toxin B, Cholera holotoxin, and *Pseudomonas* Exotoxin A, from a bacterial host.

18 Claims, 59 Drawing Sheets

(56) References Cited

U.S. PATENT DOCUMENTS

Figure 2:
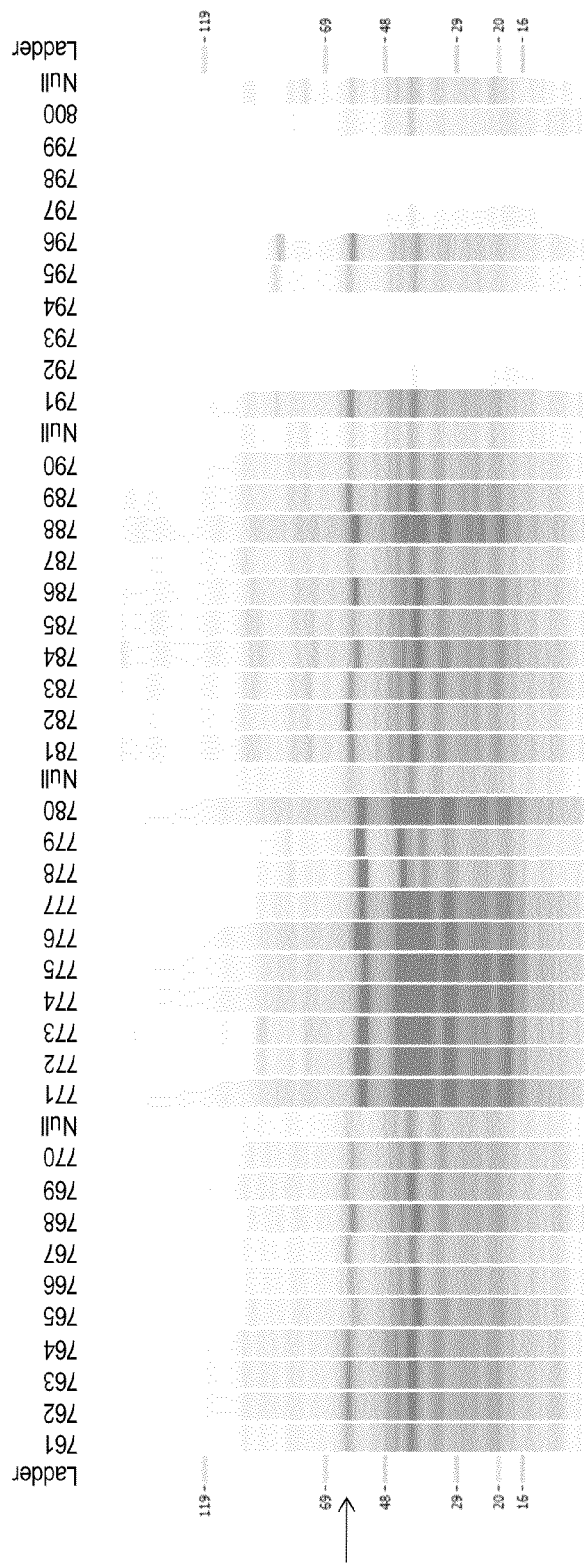

| | | |
|---|---|---|
| 8,603,824 B2 | 12/2013 | Ramseier et al. |
| 2003/0224009 A1 | 12/2003 | Terry et al. |
| 2006/0008877 A1 | 1/2006 | Retallack et al. |
| 2006/0040352 A1 | 2/2006 | Retallack et al. |
| 2006/0110747 A1 | 5/2006 | Ramseier et al. |
| 2006/0234346 A1 | 10/2006 | Retallack et al. |
| 2006/0246036 A1 | 11/2006 | Francis et al. |
| 2007/0292918 A1 | 12/2007 | Stelman et al. |
| 2008/0193974 A1 | 8/2008 | Coleman et al. |
| 2008/0269070 A1 | 10/2008 | Ramseier et al. |
| 2009/0081184 A1 | 3/2009 | Margolin et al. |
| 2009/0325230 A1 | 12/2009 | Schneider et al. |
| 2010/0048864 A1 | 2/2010 | Coleman et al. |
| 2010/0137162 A1 | 6/2010 | Retallack |
| 2011/0287443 A1 | 11/2011 | Retallack et al. |
| 2012/0289688 A1 | 11/2012 | Blais et al. |
| 2014/0051093 A1 | 2/2014 | Retallack et al. |

FOREIGN PATENT DOCUMENTS

| | | |
|---|---|---|
| WO | WO-2006-014899 | 2/2006 |
| WO | WO-2007-146139 | 12/2007 |
| WO | WO-2008-094986 | 8/2008 |
| WO | WO-2008-134461 | 11/2008 |
| WO | WO-2010-008764 | 1/2010 |
| WO | WO-2011-042516 | 4/2011 |

OTHER PUBLICATIONS

Anderson et al., Safety and Immunogenicity of Meningococcal A and C Polysaccharide Conjugate Vaccine in Adults, Infection and Immunity 62(8):3391-3395 (1994).
AU App No. 2010201410 Examination Report dated Jun. 6, 2014.
Barth et al., Binary Bacterial Toxins: Biochemistry, Biology, and Applications of Common *Clostridium* and *Bacillus* Proteins, Microbiol Mol Biol Rev 68(3):373-402 (2004).
Bergey's Manual of Determinative Bacteriology, R.E. Buchanan and N.E. Gibbons eds., pp. 217-289, 8th ed., The Williams & Wilkins Co., Baltimore, MD, 1974.
Bishai et al., High-Level Expression of a Proteolytically Sensitive Diphtheria Toxin Fragment in *Escherichia coli*, J Bacteriology 169(11):5140-5151 (1987).
Burnette et al., Properties of Pertussis Toxin B Oligomer Assembled In Vitro from Recombinant Polypeptides Produced by *Escherichia coli*, Infection and Immunity 60(6):2252-2256 (1992).
Carbonetti et al., Proteolytic cleavage of pertussis toxin S1 subunit is not essential for its activity in mammalian cells, BMC Microbiology 5:7 (2005).
CN201080066026.6 Office Action dated May 12, 2014.
CN201080066026.6 Office Action dated Sep. 23, 2013.
Collier, Diphtheria Toxin: Mode of Action and Structure, Bacteriological Reviews 39(1):54-85 (1975).
Cryz et al., Isolation and characterization of a *Pseudomonas aeruginos* a mutant producing a nontoxic, immunologically crossactive toxin A protein, PNAS 77(12):7199-7203 (1980).
Davis and Mingioli, Mutants of *Escherichia coli* requiring methionine or Vitamin B12, Bact 60:17-28 (1950).
Eisel et al., Tetanus toxin: primary structure, expression in *E. coli*, and homology with botulinum toxins, EMBO J 5(10):2495-2502 (1986).
Ellingsworth, *Pseudomonas fluorescens*: Expression System for Producing Recombinant Vaccines and Adjuvants, (2006).
EP11766437.5 Supplementary European Search Report dated Oct. 9, 2013.
Fairweather and Lyness, The complete nucleotide sequence of tetanus toxin, Nucl Acids Res 14(19):7809-7812 (1986).
Fattom et al., Laboratory and Clinical Evaluation of Conjugate Vaccines Composed of *Staphylococcus aureus* Type 5 and Type 8 Capsular Polysaccharides Bound to *Pseudomonas aeruginosa* Recombinant Exoprotein A, Infection and Immunity 61(3):1023-1032 (1993).
Frishman et al., Starts of Bacterial Genes: Estimating the Reliability of Computer Predictions, Gene 234(20):257-265 (1999).
Giannini et al., The amino acid sequence of two non-toxic mutants of diphtheria toxin: CRM45 and CRM 197, Nucl Acids Res 12(10):4063-4069 (1984).
Greenfield et al., Nucleotide sequence of the structural gene for diphtheria toxin carried by corynebacteriophage β, PNAS USA 80:6853-6857 (1983).
Gurkin and Ellar, Recombinant production of bacterial toxins and their derivatives in the methylotrophic yeast *Pichia pastoris*, Microbial Cell Factories 4:33 (2005).
Haemophilus b Conjugate Vaccine (Diphtheria CRM197 Protein Conjugate (HibTiter) Package Insert, 17 pages dated Jan. 2007.
Harakuni et al., Heteropentameric Cholera Toxin B Subunit Chimeric Molecules Genetically Fused to a Vaccine Antigen Induce Systemic and Mucosal Immune Responses: a Potential New Strategy to Target Recombinant Vaccine Antigens to Mucosal Immune Systems, Infection and Immunity 73(9): 5654-5665 (2005).
Ikehata et al., Primary structure of nitrile hydratase deduced from the nucleotide sequence of a *Rhodococcus* species and its expression in *Escherichia coli*, Eur J Biochem 181(3):563-570 (1989).
Jank and Aktories, Structure and mode of action of clostridial glucosylating toxins: the ABCD model, Trends in Microbiol. 16(5):222-229 (2008).
Kaslow et al., Structure-Activity Analysis of the Activation of Pertussis Toxin, Biochem 26(1):123-127 (1987).
Kink et al, Antibodies to Recombinant *Clostridium dificile* Toxins A and B Are an Effective Treatment and Prevent Relapse of *C. difficile*-Associates Disease in a Hamster Model of Infection, Infection and Immunity, 66(5):2018-2025 (May 1998).
Kulich et al., Expression of Recombinant Exoenzyme S of *Pseudomonas aeruginosa*, Infection and Immunity 63(1): 1-8 (1995).
Lee et al., Characterization of a Cloned Temperature-Sensitive Construct of the Diphtheria Toxin A Domain, Biochem 44(7):2555-2565 (2005) (Abstract).
Lin et al., The Efficacy of a *Salmonella typhi* Vi Conjugate Vaccine in Two-to-Five Year-Old Children, New England J Med 344(17):1263-1269 (2001).
Lukac et al., Toxoid of *Pseudomonas aeruginosa* Exotoxin A Generated by Deletion of an Active-Site Residue, Infection and Immunity 56(12):3095-3098 (1988).
Maunsell et al., Complex regulation of AprA metalloprotease in *Pseudomonas fluorescens* M114: evidence for the involvement of iron, the ECF sigma factor, PbrA and pseudobactin M114 siderophore, Microbiol 152(Pt 1):29-42 (2006).
McCoy et al., PAR1 and PAR2 couple to overlapping and distinct sets of G proteins and linked signaling pathways to differentially regulate cell physiology, Molecular Pharmacology Fast Forward. Published on Mar. 9, 2010 as doi:10.1124/mol.109.062018.
Mekada and Uchida, Binding Properties of Diphtheria Toxin to Cells Are Altered by Mutation in the Fragment A Domain, J Biol Chem 260(22):12148-12153 (1985).
MenACWY-CRM Clinical Trial and Product Overview, Novartis Vaccines Jun. 24, 2009—ACIP Meeting Atlanta.
Menveo product insert Feb. 2010.
Miyaji et al., Induction of Neutralizing Antibodies against Diphtheria Toxin by Priming with Recombinant *Mycobacterium bovis* BCG Expressing CRM197, a Mutant Diphtheria Toxin, Infection and Immunity 69(2):869-874 (2001).
Mueller-Dieckmann et al., Structure of mouse ADP-ribosylhydrolase 3 (mARH3), Acta Cryst F64:156-162 (2008).
Nozoye et al., Production of *Ascaris suum* As14 Protein and Its Fusion Protein with Cholera Toxin B Subunit in Rice Seeds, J. Vet. Med. Sci. 71(7):995-1000 (2009).
NZ602958 Examination Report dated May 17, 2013.
Orr et al., Expression and Immunogenicity of a Mutant Diphtheria Toxin Molecule, CRM197, and Its Fragments in *Salmonella typhi* Vaccine Strain CVD 908-htrA, Infection and Immunity 67(8):4290-4294 (1999).
PCT/US10/30573 International Preliminary Report on Patentabilty mailed Oct. 11, 2012.

(56) References Cited

OTHER PUBLICATIONS

PCT/US10/30573 Search Report and Written Opinion mailed May 27, 2011.
PCT/US2011/030227 International Preliminary Report on Patentabilty mailed Oct. 11, 2012.
PCT/US2011/030227 International Search Report and Written Opinion dated Dec. 22, 2011.
Pneumococcal 7-valent Conjugate Vaccine (Diphtheria CRM197 Protein) Prevnar Package Insert Wyeth Pharmaceuticals Inc. dated Oct. 2008.
Popoff et al., Actin-Specific ADP-Ribosyltransferase Produced by a *Clostridium difficule* Strain, Infection and Immunity 56(9):2299-2306 (1988).
Price et al., Intranasal Administration of Recombinant *Neisseria gonorrhoeae* Transferrin Binding Proteins A and B Conjugated to the Cholera Toxin B Subunit Induces Systemic and Vaginal Antibodies in Mice, Infection and Immunity 73(7):3945-3953 (2005).
Qian et al., Conugating recombinant proteins to *Pseudomonas aeruginosa* ExoProtein A: a strategy for enhancing immunogenicity of malaria vaccine candidates, Vaccine 25(20):3923-3933 (2007).
Retallack, et al., "Transport of heterologous proteins to the periplasmic space of *Pseudomonas fluorescens* using a variety of native signal sequences," Biotechnology Letters, Springer Netherlands, Dordrecht, vol. 29, No. 10, May 31, 2007, pp. 1483-1491.
Riesenberg et al., High cell density cultivation of *Escherichia coli* at controlled specific growth rate, J Biotechnol 20(1):17-27 (1991).
Roberts et al., A Mutant Pertussis Toxin Molecule That Lacks ADP-Ribosyltransferase Activity, PT-9K/129G, Is an Effective Mucosal Adjuvant for Intranasally Delivered Proteins, Infection and Immunity 63(6):2100-2108 (1995).
Rodighiero et al., A Cholera Toxin B-subunit Variant That Binds Ganglioside GM1 but Fails to Induce Toxicity, J Biol Chem 276(40):36939-36945 (2001).
Sakurai et al., *Clostridium perfringens* Iota-Toxin: Structure and Function, Toxins 1:208-228 (2009).
Sanchez-Romero and V. De Lorenzo, Manual of Industrial Microbiology and Biotechnology, A. Demain & J. Davies, eds., pp. 460-474, 1999.
Schirmer et al., The ADP-ribosylating Mosquitocidal Toxin from *Bacillus sphaericus*, J Biol Chem 277(14):11941-11948 (2002).
Schmidt and Schmidt, Inhibition of Pertussis Toxin Binding to Model Receptors by Antipeptide Antibodies Directed at an Antigenic Domain of the S2 Subunit, Infection and Immunity 57(12):3828-3833 (1989).
Schneider et al., Auxotropic markers pyrF and proC can replace sntobiotic markers in protein productions plasmids in hig-cell-density *Pseudomonas fluorescens* fermentation. Biotechnol. Progress 21(2)(2005): 343-8.
Schneider, Enabling Biodefense Countermeasures through Next Generation Vaccines, Presented at/Published in Phacilitate Vaccine Forum, Jan. 28, 2014.
Schweizer, Vectors to express foreign genes and techniques to monitor gene expression in *Pseudomondas*, Curr Op Biotech 12:439-445 (2001).
Sekura et al., Pertussis Toxin. Affinity Purification of a New ADP-Ribosyltransferase, J Biol Chem 258:14647 (1983).
Slater & R. Williams, Molecular Biology and Biotechnology, J. Walker & R. Rapley, eds., pp. 125-154, The Royal Society of Chemistry, Cambridge, UK, 2000.
Stickings et al., Transcutaneous Immunization with Cross-Reacting Material CRM197 of Diphtheria Toxin Boosts Functional Antibody Levels in Mice Primed Parenterally with Adsorbed Diphtheria Toxoid Vaccine, Infection and Immunity 76(4):1766-1773 (2008).
Su et al., Pertussis Toxin Inhibits Induction of Tissue-Specific Autoimmune Disease by Disrupting G Protein-Coupled Signals, J Immunol 167:250-256 (2001).
Sullivan et al., Purification and Characterization of Toxins A and B of *Clostridium difficule*, Infection and Immunity 35(3):1032-1040 (1982).
Sun et al., Intransal Administration of a *Schistosoma mansoni* Glutathione S-Transferase-Cholera Toxoid Conjugate Vaccine Evokes Antiparasitic and Antipathological Immunity in Mice, J Immunol 163:1045-1052 (1999).
Suzek, Baris E., et al., "A Probalistic Method for Identifying Start Codons in Bacterial Genomes." Bioinformatics, 2001, pp. 1123-1130, vol. 17, No. 12, Oxford University Press.
Townsend et al., Tetanus toxin C fragment conjugated nanoparticles for targeted drug delivery to neurons, Biomaterials 28(34):5176-5184 (2007).
Tsuge et al., Structural basis of actin recognition and arginine ADP-ribosylation by *Clostridium perfringens* ι—toxin, PNAS 105(21):7399-7404 (2008).
U.S. Appl. No. 13/073,955 Office Action dated Dec. 7, 2012.
U.S. Appl. No. 13/952,484 Office Action dated Apr. 9, 2014.
Watkins et al., Pertussis Toxin Treatment in Vivo Is Associated with a Decline in G-protein β-Subunits, J Biol Chem 264(7):4186-4194 (1989).
Winram, Development and Preclinical Optimization of a Circumsporozoite Protein (rCSP) Vaccine Candidate Against Malaria Via a Virtual Pharmaceutical Approach, Presented at/Published in BioProcess International 2011, Nov. 3, 2011.
Winram, rCSP Expression Project Utilizing Pfenex Technology rCSP Expression Project Utilizing Pfenex Technology, Presented at/published in Vaccine Production Summit, San Diego, Jun. 14, 2010.
Wozniak et al., Construction and use of a nontoxigenic strain of *Pseudomonas aeruginosa* for the production of recombinant exotoxin A., Applied and Environmental Microbiology, vol. 61, No. 5, May 1, 1995, pp. 1739-1744.
Yang et al., Expression of recombinant *Clostridium difficile* toxin A and B in *Bacillus megaterium*, BMC Microbiol 8:192 (2008).
Zhou et al Secretory expression of recombinant diphtheria toxin mutants in *B. subtilis*, Journal of Tongji Medical University, vol. 19, No. 4, 1999, pp. 253-256.

* cited by examiner

A. CRM197 amino acid sequence

```
  1 Gly Ala Asp Asp Val Val Asp Ser Ser Lys Ser Phe Val Met Glu Asn Phe Ser Ser Tyr
 21 His Gly Thr Lys Pro Gly Tyr Val Asp Ser Ile Gln Lys Gly Ile Gln Lys Pro Lys Ser
 41 Gly Thr Gln Gly Asn Tyr Asp Asp Asp Trp Lys Glu Phe Tyr Ser Thr Asp Asn Lys Tyr
 61 Asp Ala Ala Gly Tyr Ser Val Asp Asn Glu Asn Pro Leu Ser Gly Lys Ala Gly Gly Val
 81 Val Lys Val Thr Tyr Pro Gly Leu Thr Lys Val Leu Ala Leu Lys Val Asp Asn Ala Glu
101 Thr Ile Lys Lys Glu Leu Gly Leu Ser Leu Thr Glu Pro Leu Met Glu Gln Val Gly Thr
121 Glu Glu Phe Ile Lys Arg Phe Gly Asp Gly Ala Ser Arg Val Val Leu Ser Leu Pro Phe
141 Ala Glu Gly Ser Ser Ser Val Glu Tyr Ile Asn Asn Trp Glu Gln Ala Lys Ala Leu Ser
161 Val Glu Leu Glu Ile Asn Phe Glu Thr Arg Gly Lys Arg Gly Gln Asp Ala Met Tyr Glu
181 Tyr Met Ala Gln Ala Cys Ala Gly Asn Arg Val Arg Arg Ser Val Gly Ser Ser Leu Ser
201 Cys Ile Asn Leu Asp Trp Asp Val Ile Arg Asp Lys Thr Lys Thr Lys Ile Glu Ser Leu
221 Lys Glu His Gly Pro Ile Lys Asn Lys Met Ser Glu Ser Pro Asn Lys Thr Val Ser Glu
241 Glu Lys Ala Lys Gln Tyr Leu Glu Glu Phe His Gln Thr Ala Leu Glu His Pro Glu Leu
261 Ser Glu Leu Lys Thr Val Thr Gly Thr Asn Pro Val Phe Ala Gly Ala Asn Tyr Ala Ala
281 Trp Ala Val Asn Val Ala Gln Val Ile Asp Ser Glu Thr Ala Asp Asn Leu Glu Lys Thr
301 Thr Ala Ala Leu Ser Ile Leu Pro Gly Ile Gly Ser Val Met Gly Ile Ala Asp Gly Ala
321 Val His His Asn Thr Glu Glu Ile Val Ala Gln Ser Ile Ala Leu Ser Ser Leu Met Val
341 Ala Gln Ala Ile Pro Leu Val Gly Glu Leu Val Asp Ile Gly Phe Ala Ala Tyr Asn Phe
361 Val Glu Ser Ile Ile Asn Leu Phe Gln Val Val His Asn Ser Tyr Asn Arg Pro Ala Tyr
381 Ser Pro Gly His Lys Thr Gln Pro Phe Leu His Asp Gly Tyr Ala Val Ser Trp Asn Thr
401 Val Glu Asp Ser Ile Ile Arg Thr Gly Phe Gln Gly Glu Ser Gly His Asp Ile Lys Ile
421 Thr Ala Glu Asn Thr Pro Leu Pro Ile Ala Gly Val Leu Leu Pro Thr Ile Pro Gly Lys
441 Leu Asp Val Asn Lys Ser Lys Thr His Ile Ser Val Asn Gly Arg Lys Ile Arg Met Arg
461 Cys Arg Ala Ile Asp Gly Asp Val Thr Phe Cys Arg Pro Lys Ser Pro Val Tyr Val Gly
481 Asn Gly Val His Ala Asn Leu His Val Ala Phe His Arg Ser Ser Ser Glu Lys Ile His
501 Ser Asn Glu Ile Ser Ser Asp Ser Ile Gly Val Leu Gly Tyr Gln Lys Thr Val Asp His
521 Thr Lys Val Asn Ser Lys Leu Ser Leu Phe Phe Glu Ile Lys Ser
```

FIGURE 1A

B. CRM197 DNA sequence with translation

FIGURE 1B

FIGURE 1C

A. Cholera Toxin B Subunit amino acid sequence

```
  1 Thr Pro Gln Asn Ile Thr Asp Leu Cys Ala Glu Tyr His Asn Thr Gln Ile His Thr Leu

21 Asn Asp Lys Ile Phe Ser Tyr Thr Glu Ser Leu Ala Gly Lys Arg Glu Met Ala Ile Ile

41 Thr Phe Lys Asn Gly Ala Thr Phe Gln Val Glu Val Pro Gly Ser Gln His Ile Asp Ser

61 Gln Lys Lys Ala Ile Glu Arg Met Lys Asp Thr Leu Arg Ile Ala Tyr Leu Thr Glu Ala

81 Lys Val Glu Lys Leu Cys Val Trp Asn Asn Lys Thr Pro His Ala Ile Ala Ala Ile Ser

101 Met Ala
```

B. Cholera Toxin B Subunit DNA sequence with translation

```
    Thr Pro Gln Asn Ile Thr Asp Leu Cys Ala Glu Tyr His Asn Thr Gln Ile His Thr Leu
  1 ACG CCG CAA AAT ATC ACC GAC CTG TGC GCA GAA TAT CAC AAT ACC CAA ATC CAT ACT CTG

Asn Asp Lys Ile Phe Ser Tyr Thr Glu Ser Leu Ala Gly Lys Arg Glu Met Ala Ile Ile
 61 AAC GAC AAA ATC TTC AGC TAC ACC GAG AGC CTG GCT GGC AAG CGC GAG ATG GCG ATC ATT

Thr Phe Lys Asn Gly Ala Thr Phe Gln Val Glu Val Pro Gly Ser Gln His Ile Asp Ser
121 ACG TTC AAA AAC GGT GCG ACC TTT CAG GTG GAA GTC CCC GGC AGT CAG CAC ATC GAT TCC

Gln Lys Lys Ala Ile Glu Arg Met Lys Asp Thr Leu Arg Ile Ala Tyr Leu Thr Glu Ala
181 CAG AAA AAG GCC ATT GAA CGG ATG AAG GAC ACC CTC CGT ATC GCC TAC TTG ACC GAA GCC

Lys Val Glu Lys Leu Cys Val Trp Asn Asn Lys Thr Pro His Ala Ile Ala Ala Ile Ser
241 AAG GTG GAG AAG CTG TGC GTT TGG AAC AAC AAA ACC CCG CAC GCC ATC GCG GCC ATC TCG

Met Ala
301 ATG GCC
```

FIGURE 6A

FIGURE 6B

```
                                                            S2
              Leu Leu Ser Ser Thr Asn Ser Arg Leu Cys Ala Val Phe Val Arg Ser Gly Gln Pro Val
     1261     CTG CTC TCC AGC ACC AAC AGC AGG CTA TGC GCG GTC TTC GTC AGA AGC GGG CAA CCG GTC
                                                            S2
              Ile Gly Ala Cys Thr Ser Pro Tyr Asp Tyr Lys Tyr Trp Ser Met Tyr Ser Arg Leu Arg
     1321     ATT GGC GCC TGC ACC AGC CCG TAT GAC AAG TAC TGG AGC ATG TAC AGC CGG CTG CGG
                                                            S2
              Lys Met Leu Tyr Leu Ile Tyr Val Ala Gly Ile Ser Val Arg Val His Val Ser Lys Glu
     1381     AAA ATG CTT TAC CTG ATC TAC GTG GCC GGC ATC TCC GTA CGG GTC CAT GTC AGC AAG GAA
                                                            S2
              Glu Gln Tyr Tyr Asp Tyr Gln Asp Ala Thr Phe Gln Thr Tyr Ala Leu Thr Gly Ile Ser
     1441     GAA CAG TAT TAC GAC TAT CAG GAC GCA ACG TTC GAG ACT TAC GCC CTT ACC GGC ATC TCC
                                                            S2
              Ile Cys Asn Pro Gly Ser Ser Leu Cys
     1501     ATC TGC AAT CCT GGA TCA TCC TTA TGC TGA GAC GCT CCC CCA CTC GAA CCA CCA CCC CGG
                                                                            signal sequence
                                                            Val Arg Ala Leu Ala Trp Leu Ala Ser Gly
     1561     GAC AGG GCG GCC CCC GGC GGT CGC GC GTG CGC CTG GCG TGG CTG TTG CTG GCA TCC GGC
                                                            S4
              Ala Met Thr His Leu Ser Pro Ala Leu Ala Asp Val Pro Tyr Val Leu Val Lys Thr Asn
     1620     GCG ATG ACG CAT CTT TCC CCC GCC CTG GCC GAC GTT CCT TAT GTG CTG GTG AAG ACC AAT
                                                            S4
              Met Val Val Thr Ser Val Ala Met Lys Pro Tyr Glu Val Thr Pro Thr Arg Met Leu Val
     1680     ATG GTG GTC ACC AGC GTA GCC ATG AAG CCG TAT GAA GTC ACC CCG ACG CGC ATG CTG GTC
                                                            S4
              Cys Gly Ile Ala Ala Lys Leu Gly Ala Ala Ser Ser Pro Asp Ala His Val Pro Phe
     1740     TGC GGC ATC GCC GCC AAA CTG GGC GCC GCC AGC AGC CCG GAC GCG CAC GTC CCG TTC
                                                            S4
              Cys Phe Gly Lys Asp Leu Lys Arg Pro Gly Ser Ser Pro Met Gly Val Val Leu Arg Ala
     1800     TGC TTC GGC AAG GAT CTC AAG CGT CCC GGC AGC AGT CCC ATG GGA GTC GTA CTT CGC GCC
                                                            S4
              Val Phe Met Gln Gln Arg Leu Arg Met Phe Leu Gly Cys Pro Gln Leu Thr Phe Glu
     1860     GTC TTC ATG CAA CAA CGG CTG CGC ATG TTT CTG GGT TGC CCC AAG CAA CTC ACT TTC GAA
```

| 1 | Met | Arg | Cys | Thr | Arg | Ala | Ile | Arg | Gln | Thr | Ala | Arg | Thr | Gly | Trp | Leu | Thr | Trp | Leu | Ala |
| 21 | Ile | Leu | Ala | Val | Thr | Ala | Pro | Val | Thr | Ser | Pro | Ala | Trp | Ala | Asp | Asp | Pro | Ala | Thr |
| 41 | Val | Tyr | Lys | Tyr | Asp | Ser | Arg | Pro | Pro | Glu | Asp | Val | Phe | Gln | Asn | Gly | Phe | Thr | Ala | Trp |
| 61 | Gly | Asn | Asp | Asn | Val | Leu | Asp | His | Leu | Thr | Gly | Arg | Ser | Cys | Gln | Val | Gly | Ser | Ser |
| 81 | Asn | Ser | Ala | Phe | Val | Ser | Thr | Ser | Ser | Arg | Arg | Tyr | Thr | Glu | Val | Tyr | Leu | Glu | His |
| 101 | Arg | Met | Gln | Glu | Ala | Val | Glu | Ala | Arg | Ala | Gly | Arg | Gly | Thr | Gly | His | Phe | Ile | Gly |
| 121 | Tyr | Ile | Tyr | Glu | Val | Arg | Ala | Asp | Asn | Phe | Tyr | Gly | Ala | Ala | Ser | Ser | Tyr | Phe | Glu |
| 141 | Tyr | Val | Asp | Thr | Tyr | Gly | Asp | Asn | Ala | Gly | Arg | Ile | Leu | Ala | Gly | Ala | Leu | Ala | Thr | Tyr |
| 161 | Gln | Ser | Ala | Tyr | Leu | Ala | His | Arg | Arg | Ile | Pro | Pro | Glu | Asn | Ile | Arg | Arg | Val | Thr | Arg |
| 181 | Val | Tyr | His | Asn | Gly | Ile | Thr | Gly | Glu | Thr | Thr | Thr | Glu | Tyr | Ser | Asn | Ala | Arg | Tyr |
| 201 | Val | Ser | Gln | Gln | Thr | Arg | Ala | Asn | Pro | Asn | Pro | Tyr | Thr | Ser | Arg | Arg | Ser | Val | Ala | Ser |
| 221 | Ile | Val | Gly | Thr | Leu | Val | Arg | Met | Ala | Pro | Val | Ile | Gly | Ala | Cys | Met | Ala | Arg | Gln | Ala |
| 241 | Glu | Ser | Ser | Glu | Ala | Met | Ala | Trp | Ser | Glu | Arg | Ala | Gly | Glu | Ala | Met | Val | Leu | Val |
| 261 | Tyr | Tyr | Glu | Ser | Ile | Ala | Tyr | Ser | Phe |

FIGURE 7A

```
  1  Met Pro Ile Asp Arg Lys Thr Leu Cys His Leu Leu Ser Val Leu Pro Leu Ala Leu Leu
 21  Gly Ser His Val Ala Arg Ala Ser Thr Pro Gly Ile Val Ile Pro Pro Gln Gln Gly Ile
 41  Thr Gln His Gly Ser Pro Tyr Gly Arg Cys Ala Asn Lys Thr Arg Ala Leu Thr Val Ala
 61  Glu Leu Arg Gly Ser Gly Asp Leu Gln Glu Tyr Leu Arg His Val Thr Arg Gly Trp Ser
 81  Ile Phe Ala Leu Tyr Asp Gly Thr Gly Phe Leu Lys Tyr Gly Glu Tyr Gly Val Ile Lys Asp
101  Gly Thr Pro Gly Ala Phe Ala Leu Lys Thr Ile Met Thr Phe Ile Met Thr Arg Asn
121  Thr Gly Gln Pro Ala Thr Asp His Tyr Tyr Ser Asn Val Thr Ala Thr Ala Arg Leu Leu Ser
141  Ser Thr Asn Ser Arg Leu Cys Ala Val Phe Val Arg Ser Gly Gln Pro Val Ile Gly Ala
161  Cys Thr Ser Pro Tyr Asp Gly Lys Tyr Trp Ser Met Tyr Ser Arg Leu Arg Lys Met Leu
181  Tyr Leu Ile Tyr Val Ala Gly Ile Ser Val Arg Val His Val Ser Lys Glu Gln Gln Tyr
201  Tyr Asp Tyr Glu Asp Ala Thr Phe Glu Thr Tyr Ala Leu Thr Tyr Gly Ile Ser Cys Asn
221  Pro Gly Ser Ser Leu Cys
```

FIGURE 7B

```
  1 Met Leu Ile Asn Asn Lys Lys Leu Leu His His Ile Leu Pro Ile Leu Val Leu Ala Leu
 21 Leu Gly Met Arg Thr Ala Gln Ala Val Ala Pro Gly Ile Val Ile Pro Pro Lys Ala Leu
 41 Phe Thr Gln Gln Gly Gly Ala Tyr Gly Arg Cys Pro Asn Gly Thr Arg Ala Leu Thr Val
 61 Ala Glu Leu Arg Gly Asn Ala Glu Leu Gln Thr Tyr Leu Arg Gln Ile Thr Pro Gly Trp
 81 Ser Ile Tyr Gly Leu Tyr Asp Gly Thr Tyr Leu Gly Gln Ala Tyr Gly Gly Ile Ile Lys
101 Asp Ala Pro Pro Gly Ala Gly Phe Ile Tyr Arg Glu Thr Phe Cys Ile Thr Thr Ile Tyr
121 Lys Thr Gly Gln Pro Ala Ala Asp His Tyr Tyr Ser Lys Val Thr Ala Thr Arg Leu Leu
141 Ala Ser Thr Asn Ser Arg Leu Cys Ala Val Phe Val Arg Asp Gly Gln Ser Val Ile Gly
161 Ala Cys Ala Ser Pro Tyr Glu Gly Arg Tyr Arg Asp Met Tyr Asp Ala Leu Arg Arg Leu
181 Leu Tyr Met Ile Tyr Met Ser Gly Leu Ala Val Arg Val His Val Ser Lys Glu Glu Gln
201 Tyr Tyr Asp Tyr Glu Asp Ala Thr Phe Gln Thr Tyr Ala Leu Thr Gly Ile Ser Leu Cys
221 Asn Pro Ala Ala Ser Ile Cys
```

FIGURE 7C

```
  1 Val Arg Ala Leu Ala Trp Leu Leu Ala Ser Gly Ala Met Thr His Leu Ser Pro Ala Leu
 21 Ala Asp Val Pro Tyr Val Leu Val Lys Thr Asn Met Val Val Thr Ser Val Ala Met Lys
 41 Pro Tyr Glu Val Thr Pro Thr Arg Met Leu Val Cys Gly Ile Ala Ala Lys Leu Gly Ala
 61 Ala Ser Ser Pro Asp Ala His Val Pro Phe Cys Phe Gly Lys Asp Leu Lys Arg Pro
 81 Gly Ser Ser Pro Met Glu Val Met Leu Arg Ala Val Phe Met Gln Gln Arg Pro Leu Arg
101 Met Phe Leu Gly Pro Lys Gln Leu Thr Phe Glu Gly Lys Pro Ala Leu Glu Leu Ile Arg
121 Met Val Glu Cys Ser Gly Lys Gln Asp Cys Pro
```

FIGURE 7D

```
  1 Met His Thr Ile Ala Ser Ile Leu Leu Ser Val Leu Gly Ile Tyr Ser Pro Ala Asp Val
 21 Ala Gly Leu Pro Thr His Leu Tyr Lys Asn Phe Thr Val Gln Glu Leu Ala Leu Lys Leu
 41 Lys Gly Lys Asn Gln Glu Cys Leu Thr Ala Phe Met Ser Gly Arg Ser Leu Val Arg Arg
 61 Ala Cys Leu Ser Asp Ala Gly His Glu His Asp Thr Trp Phe Asp Thr Met Leu Gly Phe
 81 Ala Ile Ser Ala Tyr Ala Leu Lys Ser Arg Ile Ala Leu Thr Val Glu Asp Ser Pro Tyr
101 Pro Gly Thr Pro Gly Asp Leu Leu Glu Leu Gln Ile Cys Pro Leu Asn Gly Tyr Cys Glu
```

FIGURE 7E

A. Tetanus Toxin C Fragment Amino Acid Sequence

```
  1 Lys Asn Leu Asp Cys Trp Val Asp Asn Glu Glu Asp Ile Asp Val Ile Leu Lys Lys Ser
 21 Thr Ile Leu Asn Leu Asp Ile Asn Asn Asp Ile Ser Asp Ile Ser Gly Phe Asn Ser
 41 Ser Val Ile Thr Tyr Pro Asp Ala Gln Leu Val Pro Gly Ile Asn Gly Lys Ala Ile His
 61 Leu Val Asn Asn Glu Ser Ser Glu Val Ile Val His Lys Ala Met Asp Ile Glu Tyr Asn
 81 Asp Met Phe Asn Asn Phe Thr Val Ser Phe Trp Leu Arg Val Pro Lys Val Ser Ala Ser
101 His Leu Glu Gln Tyr Gly Thr Asn Glu Tyr Ser Ile Ile Ser Ser Met Lys Lys His Ser
121 Leu Ser Ile Gly Ser Gly Trp Ser Val Ser Leu Lys Gly Asn Asn Leu Ile Trp Thr Leu
141 Lys Asp Ser Ala Gly Glu Val Arg Gln Ile Thr Phe Arg Asp Leu Pro Asp Lys Phe Asn
161 Ala Tyr Leu Ala Asn Lys Trp Val Phe Ile Thr Ile Thr Asn Asp Arg Leu Ser Ser Ala
181 Asn Leu Tyr Ile Asn Gly Val Leu Met Gly Ser Ala Glu Ile Thr Gly Leu Gly Ala Ile
201 Arg Glu Asp Asn Asn Ile Thr Leu Lys Leu Asp Arg Cys Asn Asn Asn Asn Gln Tyr Val
221 Ser Ile Asp Lys Phe Arg Ile Phe Cys Lys Ala Leu Asn Pro Lys Glu Ile Glu Lys Leu
241 Tyr Thr Ser Tyr Leu Ser Ile Thr Phe Leu Arg Asp Phe Trp Gly Asn Pro Leu Arg Tyr
261 Asp Thr Glu Tyr Tyr Leu Ile Pro Val Ala Ser Ser Ser Lys Asp Val Gln Leu Lys Asn
281 Ile Thr Asp Tyr Met Tyr Leu Thr Asn Ala Pro Ser Tyr Thr Asn Gly Lys Leu Asn Ile
301 Tyr Tyr Arg Arg Leu Tyr Asn Gly Leu Lys Phe Ile Ile Lys Arg Tyr Thr Pro Asn Asn
321 Glu Ile Asp Ser Phe Val Lys Ser Gly Asp Phe Ile Lys Leu Tyr Val Ser Tyr Asn Asn
341 Asn Glu His Ile Val Gly Tyr Pro Lys Asp Gly Asn Ala Phe Asn Asn Leu Asp Arg Ile
361 Leu Arg Val Gly Tyr Asn Ala Pro Gly Ile Pro Leu Tyr Lys Lys Met Glu Ala Val Lys
381 Leu Arg Asp Leu Lys Thr Tyr Ser Val Gln Leu Lys Leu Tyr Asp Asp Lys Asn Ala Ser
401 Leu Gly Leu Val Gly Thr His Asn Gly Gln Ile Gly Asn Asp Pro Asn Arg Asp Ile Leu
421 Ile Ala Ser Asn Trp Tyr Phe Asn His Leu Lys Asp Lys Ile Leu Gly Cys Asp Trp Tyr
441 Phe Val Pro Thr Asp Glu Gly Trp Thr Asn Asp
```

FIGURE 9A

B. Tetanus Toxin C DNA Sequence with Translation

FIGURE 9B

```
 961   Glu Ile Asp Ser Phe Val Lys Ser Gly Asp Phe Ile Lys Leu Tyr Val Ser Tyr Asn Asn
       GAA ATC GAC AGT TTT GTC AAG AGC GGC GAC TTC ATC AAG TTG TAC GTG AGC TAC AAT AAC

1021   Asn Glu His Ile Val Gly Tyr Pro Lys Asp Gly Asn Ala Phe Asn Leu Asp Arg Ile
       AAC GAG CAC ATC GTT GGT TAC CCT AAG GAT GGC AAC GCT TTC AAC CTC GAT CGT ATC

1081   Leu Thr Val Gly Tyr Asn Ala Pro Gly Ile Pro Leu Tyr Lys Met Glu Ala Val Lys
       CTG ACC GTT GGC TAC AAC GCA CCA GGC ATT CCG CTG TAT AAG ATG GAA GCG GTC AAA

1141   Leu Arg Asp Leu Lys Thr Tyr Ser Val Gln Leu Lys Leu Tyr Asp Lys Asn Ala Ser
       CTG CGT GAC CTG AAA ACC TAC TCC GTG CAA CTG AAG CTG TAC GAC AAG AAT GCC TCG

1201   Leu Gly Leu Val Leu Thr Thr His Asn Gly Gly Ile Gln Ile Asp Asn Arg Asp Ile Leu
       TTG GGT CTG GTC GCC ACG CAT AAT GGT CAG ATT GGC AAC CGG GAC ATC CTG

1261   Ile Ala Ser Asn Trp Tyr Phe Asn His Leu Lys Ile Leu Gly Cys Asp Trp Tyr
       ATC GCC AGC AAC TGG TAT TTC AAC CAC CTC AAG ATC CTG GGC TGC GAT TGG TAC

1321   Phe Val Pro Tyr Asp Glu Gly Trp Thr Asn Asp
       TTC GTC CCT ACC GAT GAG GGC TGG ACT AAT GAC
```

FIGURE 9C

A. C. difficile VPI TcdB Amino Acid Sequence

```
  1  Met Ser Leu Val Asn Arg Lys Gln Leu Glu Lys Met Ala Asn Val Arg Phe Arg Thr Gln
 21  Glu Asp Glu Tyr Val Ala Ile Leu Asp Ala Leu Glu Glu Tyr His Asn Met Ser Glu Asn
 41  Thr Val Val Glu Lys Tyr Leu Lys Leu Lys Asp Ile Asn Ser Leu Thr Asp Ile Tyr Ile
 61  Asp Thr Tyr Lys Lys Ser Gly Arg Asn Lys Ala Leu Lys Lys Phe Lys Glu Tyr Leu Val
 81  Thr Glu Val Leu Glu Leu Lys Asn Asn Asn Leu Thr Pro Val Glu Lys Asn Leu His Phe
101  Val Trp Ile Gly Gly Gln Ile Asn Asp Thr Ala Ile Asn Tyr Ile Asn Gln Trp Lys Asp
121  Val Asn Ser Asp Tyr Asn Val Asn Val Phe Tyr Asp Ser Asn Ala Phe Leu Ile Asn Thr
141  Leu Lys Lys Thr Val Val Glu Ser Ala Ile Asn Asp Thr Leu Glu Ser Phe Arg Glu Asn
161  Leu Asn Asp Pro Arg Phe Asp Tyr Asn Lys Phe Phe Arg Lys Arg Met Glu Ile Ile Tyr
181  Asp Lys Gln Lys Asn Phe Ile Asn Tyr Tyr Lys Thr Tyr Leu Ser Ala Gln Arg Glu Glu Asn Pro Glu Leu
```

I need to keep to 20 per line.

```
181  Asp Lys Gln Lys Asn Phe Ile Asn Tyr Tyr Lys Ala Gln Arg Glu Glu Asn Pro Glu Leu
201  Ile Ile Asp Asp Ile Val Lys Thr Tyr Leu Ser Asn Glu Tyr Ser Lys Glu Ile Asp Glu
221  Leu Asn Thr Tyr Ile Glu Glu Ser Leu Asn Lys Ile Thr Gln Asn Ser Gly Asn Asp Val
241  Arg Asn Phe Glu Glu Phe Lys Asn Gly Glu Ser Phe Asn Leu Tyr Glu Gln Glu Leu Val
261  Glu Arg Trp Asn Leu Ala Ala Ala Ser Asp Ile Leu Arg Ile Ser Ala Leu Lys Glu Ile
281  Gly Gly Met Tyr Leu Asp Val Asp Met Leu Pro Gly Ile Gln Pro Asp Leu Phe Glu Ser
301  Ile Glu Lys Pro Ser Ser Val Thr Val Asp Phe Trp Glu Met Thr Lys Leu Glu Ala Ile
321  Met Lys Tyr Lys Glu Tyr Ile Pro Glu Tyr Thr Ser Glu His Phe Asp Met Leu Asp Glu
341  Glu Val Gln Ser Ser Phe Glu Ser Val Leu Ala Ser Lys Ser Asp Lys Ser Glu Ile Phe
361  Ser Ser Leu Gly Asp Met Glu Ala Ser Pro Leu Glu Val Lys Ile Ala Phe Asn Ser Lys
381  Gly Ile Ile Asn Gln Gly Leu Ile Ser Val Lys Asp Ser Tyr Cys Ser Asn Leu Ile Val
```

FIGURE 11A

| | | | | | | | | | | | | | | | | | | | |
|---|---|---|---|---|---|---|---|---|---|---|---|---|---|---|---|---|---|---|---|
| 401 | Lys | Gln | Ile | Glu | Asn | Arg | Tyr | Lys | Ile | Leu | Asn | Asn | Ser | Leu | Asn | Pro | Ala | Ile | Ser | Glu |
| 421 | Asp | Asn | Asp | Phe | Asn | Thr | Thr | Asn | Phe | Ile | Asp | Ser | Ile | Met | Ala | Glu | Ala | Asn |
| 441 | Ala | Asp | Asn | Gly | Arg | Phe | Met | Met | Glu | Leu | Gly | Lys | Tyr | Leu | Arg | Val | Gly | Phe | Phe | Pro |
| 461 | Asp | Val | Lys | Thr | Thr | Ile | Asn | Leu | Ser | Gly | Pro | Glu | Ala | Tyr | Ala | Ala | Tyr | Gln | Asp |
| 481 | Leu | Leu | Met | Phe | Lys | Glu | Gly | Ser | Met | Asn | Ile | His | Leu | Ile | Glu | Ala | Asp | Leu | Arg | Asn |
| 501 | Phe | Glu | Ile | Ser | Lys | Thr | Asn | Ile | Ser | Gln | Ser | Thr | Glu | Gln | Glu | Met | Ala | Ser | Leu | Trp |
| 521 | Ser | Phe | Asp | Asp | Ala | Arg | Ala | Lys | Ala | Gln | Phe | Glu | Glu | Tyr | Lys | Arg | Asn | Tyr | Phe | Glu |
| 541 | Gly | Ser | Leu | Gly | Glu | Asp | Asp | Asn | Leu | Asp | Phe | Ser | Gln | Asn | Ile | Val | Val | Asp | Lys | Glu |
| 561 | Tyr | Leu | Leu | Glu | Lys | Ile | Ser | Ser | Leu | Ala | Arg | Ser | Ser | Glu | Arg | Gly | Tyr | Ile | His | Tyr |
| 581 | Ile | Val | Gln | Leu | Gln | Gly | Asp | Lys | Ile | Ser | Tyr | Glu | Ala | Ala | Cys | Asn | Leu | Phe | Ala | Lys |
| 601 | Thr | Pro | Tyr | Asp | Ser | Val | Leu | Phe | Gln | Lys | Asn | Ile | Glu | Asp | Ser | Glu | Ile | Ala | Tyr | Tyr |
| 621 | Tyr | Asn | Pro | Gly | Asp | Gly | Glu | Ile | Gln | Glu | Ile | Asp | Lys | Tyr | Lys | Ile | Pro | Ser | Ile | Ile |
| 641 | Ser | Asp | Arg | Pro | Lys | Ile | Lys | Leu | Thr | Phe | Ile | Gly | His | Gly | Lys | Asp | Glu | Phe | Asn | Thr |
| 661 | Asp | Ile | Phe | Ala | Gly | Phe | Asp | Ile | Ser | Leu | Asp | Ser | Leu | Ser | Thr | Glu | Ile | Glu | Ala | Ala | Ile | Asp |
| 681 | Leu | Ala | Lys | Glu | Asp | Ile | Ser | Pro | Lys | Ser | Ile | Glu | Thr | Pro | Gly | Lys | Ser | Ile | Asn | Leu | Gly | Cys | Asn | Met |
| 701 | Phe | Ser | Tyr | Ile | Asn | Val | Glu | Gln | Thr | Tyr | Pro | Lys | Leu | Leu | Leu | Leu | Lys | Val | Lys |
| 721 | Asp | Lys | Ile | Ser | Glu | Leu | Met | Pro | Ser | Ile | Ser | Gln | Asn | Asp | Ser | Ile | Ile | Val | Ser | Ala | Asn |
| 741 | Gln | Tyr | Glu | Val | Arg | Ile | Asn | Ser | Ile | Gly | Arg | Arg | Glu | Leu | Leu | Asp | His | Ser | Gly | Glu |
| 761 | Trp | Ile | Asn | Lys | Glu | Glu | Ser | Ile | Ile | Lys | Asp | Ile | Ser | Ser | Lys | Glu | Tyr | Ile | Ser | Phe |
| 781 | Asn | Pro | Lys | Glu | Asn | Lys | Ile | Thr | Val | Lys | Ser | Lys | Asn | Leu | Pro | Glu | Leu | Ser | Thr | Leu |
| 801 | Leu | Gln | Glu | Ile | Arg | Asn | Asn | Ser | Asn | Ser | Ser | Asp | Ile | Glu | Leu | Glu | Glu | Lys | Val | Met |

FIGURE 11B

```
 821  Leu Thr Glu Cys Glu Ile Asn Val Ile Ser Asn Ile Asp Thr Gln Ile Val Glu Glu Arg
 841  Ile Glu Ala Lys Asn Leu Thr Ser Asp Ser Ile Asn Tyr Ile Lys Asp Glu Phe Lys
 861  Leu Ile Glu Ser Ile Asp Ala Leu Cys Asp Leu Lys Gln Asn Gln Asn Gln Leu Glu Asp
 881  Ser His Phe Ile Ser Phe Glu Asp Ile Ser Glu Thr Asp Glu Gly Phe Ser Ile Arg Phe
 901  Ile Asn Lys Glu Thr Gly Glu Ser Ile Phe Val Glu Thr Lys Thr Ile Phe Ser Glu
 921  Tyr Ala Asn His Ile Thr Glu Gly Ile Ser Lys Ile Lys Gly Ile Phe Asp Thr Val
 941  Asn Gly Lys Leu Val Lys Lys Val Asn Leu Asp Thr His Glu Val Asn Thr Leu Asn
 961  Ala Ala Phe Phe Ile Gln Ser Leu Ile Glu Tyr Asn Ser Ser Lys Glu Ser Leu Ser Asn
 981  Leu Ser Val Ala Met Lys Val Val Gln Val Tyr Ala Gln Leu Phe Ser Thr Gly Leu Asn Thr
1001  Ile Thr Asp Ala Ala Lys Val Val Glu Leu Val Ser Thr Ala Leu Asp Glu Thr Ile Asp
1021  Leu Leu Pro Thr Leu Ser Glu Gly Leu Pro Ile Ile Ala Thr Ile Ile Asp Gly Val Ser
1041  Leu Gly Ala Ala Ile Lys Glu Leu Ser Glu Thr Ser Asp Pro Leu Leu Arg Gln Glu Ile
1061  Glu Ala Ile Gly Ile Met Ala Val Asn Leu Thr Thr Ala Thr Thr Ala Ile Ile Thr
1081  Ser Ser Leu Gly Ile Ala Ser Gly Phe Ser Ile Leu Val Pro Leu Ala Gly Ile Ser
1101  Ala Gly Ile Pro Ser Leu Val Asn Asn Glu Leu Val Leu Arg Asp Lys Ala Thr Lys Val
1121  Val Asp Tyr Phe Lys His Val Ser Leu Val Glu Thr Gly Val Phe Thr Leu Leu Asp
1141  Asp Lys Ile Met Met Pro Gln Asp Asp Leu Val Ile Ser Glu Ile Asp Phe Asn Asn Asn
1161  Ser Ile Val Leu Gly Lys Cys Glu Ile Trp Arg Met Glu Gly Gly Ser Gly His Thr Val
1181  Thr Asp Ile Asp His Phe Ser Ala Pro Ser Ile Thr Tyr Arg Glu Pro His Leu
1201  Ser Ile Tyr Asp Val Leu Glu Val Gln Lys Glu Leu Asp Leu Ser Lys Asp Leu Met
1221  Val Leu Pro Asn Ala Pro Asn Arg Val Phe Ala Trp Glu Thr Gly Trp Thr Pro Gly Leu
```

FIGURE 11C

| | | | | | | | | | | | | |
|---|---|---|---|---|---|---|---|---|---|---|---|---|
| 1241 | Arg | Ser | Leu | Glu | Asn | Asp | Gly | Thr | Lys | Leu | Leu | Asp | Arg | Ile | Arg | Asp | Asn | Tyr | Glu | Gly |
| 1261 | Glu | Phe | Tyr | Arg | Trp | Arg | Tyr | Phe | Ala | Phe | Ile | Ala | Asp | Ala | Leu | Ile | Thr | Leu | Lys | Pro |
| 1281 | Arg | Tyr | Glu | Asp | Thr | Asn | Ile | Arg | Ile | Asn | Leu | Asp | Ser | Asn | Thr | Arg | Ser | Phe | Ile | Val |
| 1301 | Pro | Ile | Thr | Thr | Glu | Tyr | Ile | Arg | Glu | Lys | Ser | Leu | Ser | Tyr | Ser | Phe | Gly | Ser | Gly |
| 1321 | Gly | Thr | Tyr | Ala | Leu | Ser | Leu | Ser | Gln | Tyr | Asn | Met | Gly | Ile | Asn | Ile | Glu | Leu | Ser | Glu |
| 1341 | Ser | Asp | Val | Trp | Ile | Ile | Asp | Val | Asp | Asn | Val | Val | Arg | Asp | Val | Thr | Ile | Glu | Ser | Asp |
| 1361 | Lys | Ile | Lys | Lys | Gly | Asp | Leu | Ile | Gly | Ile | Leu | Ser | Thr | Leu | Ser | Ile | Glu | Glu | Asn |
| 1381 | Lys | Ile | Ile | Leu | Asn | Ser | His | Glu | Ile | Asn | Phe | Ser | Gly | Glu | Val | Asn | Gly | Ser | Asn | Gly |
| 1401 | Phe | Val | Ser | Leu | Thr | Phe | Ser | Ile | Leu | Glu | Gly | Ile | Asn | Ala | Ile | Ile | Glu | Val | Asp | Leu |
| 1421 | Leu | Ser | Lys | Tyr | Lys | Ser | Gly | Leu | Ile | Ser | Gly | Glu | Leu | Lys | Ile | Leu | Met | Leu | Asn | Ser |
| 1441 | Asn | His | Ile | Gln | Gln | Lys | Ile | Leu | Asp | Tyr | Ile | Gly | Phe | Asn | Ser | Glu | Leu | Gln | Lys | Asn | Ile |
| 1461 | Pro | Tyr | Ser | Phe | Val | Asp | Ser | Glu | Gly | Lys | Glu | Asn | Gly | Phe | Ile | Asn | Gly | Ser | Thr | Lys |
| 1481 | Glu | Gly | Leu | Phe | Val | Ser | Glu | Leu | Pro | Asp | Val | Val | Leu | Ile | Ser | Lys | Val | Tyr | Met | Asp |
| 1501 | Asp | Ser | Lys | Pro | Ile | Asn | Leu | Thr | Gly | Tyr | Tyr | Ser | Asn | Asn | Leu | Lys | Asp | Val | Lys | Val | Ile | Thr |
| 1521 | Lys | Asp | Asn | Val | Asn | Ile | Leu | Thr | Gly | Lys | Tyr | Tyr | Ile | Lys | Asn | Ser | Val | His | Leu | Asp | Ser | Leu |
| 1541 | Ser | Leu | Thr | Leu | Gln | Asp | Glu | Lys | Leu | Lys | Phe | Met | Asn | Arg | Lys | Gly | Asn | Thr | Asn | Thr | Ser | Asp | Ser |
| 1561 | Gly | Val | Ala | Glu | Ile | Leu | Lys | Ser | Met | Asn | Ala | Asn | Ile | Lys | Ser | Ile | Phe | Val | Asn | Phe | Leu | Gln | Ser |
| 1581 | Leu | Met | Ser | Phe | Leu | Glu | Phe | Ile | Phe | Ala | Asn | Ile | Lys | Ser | Ile | Ser | Gly | Thr | Thr | Ser | Ile | Gly | Gln |
| 1601 | Asn | Ile | Lys | Phe | Ile | Leu | Cys | Asp | Ala | Asn | Asp | Asn | Ile | Gln | Pro | Tyr | Phe | Ile | Lys | Phe | Asn | Thr |
| 1621 | Phe | Glu | Ile | Thr | Asn | Tyr | Val | Gly | Asn | Arg | Gln | Asn | Met | Ile | Val | Glu | Pro | Asn |
| 1641 | Leu | Glu | Thr | Asn | Tyr | Leu | Tyr | Val | Gly | Asn | Arg | Gln | Asn | Met | Ile | Val | Glu | Pro | Asn |

FIGURE 11D

| | | | | | | | | | | |
|---|---|---|---|---|---|---|---|---|---|---|
|1661|Tyr|Asp|Leu|Asp|Ser|Gly|Asp|Ile|Ser|Ser|Thr|Val|Ile|Asn|Phe|Ser|Gln|Lys|Tyr|
|1681|Leu|Tyr|Gly|Ile|Asp|Ser|Cys|Val|Asn|Lys|Val|Ile|Ser|Pro|Asn|Ile|Tyr|Thr|Asp|
|1701|Glu|Ile|Asn|Ile|Thr|Pro|Val|Tyr|Glu|Thr|Asn|Asn|Thr|Tyr|Pro|Glu|Val|Ile|Val|Leu|
|1721|Asp|Ala|Asn|Tyr|Ile|Asn|Glu|Lys|Ile|Leu|Asn|Val|Asn|Ile|Asn|Asp|Leu|Ser|Ile|Arg|Tyr|
|1741|Val|Trp|Ser|Asn|Asp|Gly|Asn|Asp|Phe|Ile|Leu|Met|Ser|Thr|Ser|Glu|Glu|Asn|Lys|Val|
|1761|Ser|Gln|Val|Lys|Ile|Arg|Phe|Val|Asn|Val|Phe|Lys|Asp|Lys|Thr|Leu|Ala|Asn|Lys|Leu|
|1781|Ser|Phe|Asn|Phe|Ser|Asp|Lys|Gln|Asp|Val|Pro|Val|Ser|Glu|Ile|Ile|Leu|Ser|Phe|Thr|
|1801|Pro|Ser|Tyr|Tyr|Glu|Asp|Gly|Leu|Ile|Gly|Tyr|Asp|Leu|Gly|Leu|Val|Ser|Leu|Tyr|Asn|
|1821|Glu|Lys|Phe|Tyr|Ile|Asn|Asn|Phe|Gly|Met|Met|Val|Ser|Gly|Leu|Ile|Tyr|Ile|Asn|Asp|
|1841|Ser|Leu|Tyr|Tyr|Phe|Lys|Pro|Pro|Val|Asn|Asn|Leu|Ile|Thr|Gly|Phe|Val|Thr|Val|Gly|
|1861|Asp|Asp|Lys|Tyr|Tyr|Phe|Asn|Pro|Ile|Asn|Gly|Gly|Ala|Ala|Ser|Ile|Gly|Glu|Thr|Ile|
|1881|Ile|Asp|Asp|Lys|Asn|Tyr|Tyr|Phe|Asn|Gln|Ser|Gly|Val|Leu|Gln|Thr|Gly|Val|Phe|Ser|
|1901|Thr|Glu|Asp|Gly|Phe|Lys|Tyr|Phe|Ala|Pro|Ala|Asn|Thr|Leu|Asp|Glu|Asn|Leu|Glu|Gly|
|1921|Glu|Ala|Ile|Asp|Phe|Thr|Gly|Lys|Leu|Ile|Ile|Asp|Glu|Asn|Ile|Tyr|Tyr|Phe|Asp|Asp|
|1941|Asn|Tyr|Arg|Gly|Ala|Val|Glu|Trp|Lys|Glu|Leu|Asp|Gly|Glu|Met|His|Tyr|Phe|Ser|Pro|
|1961|Glu|Thr|Gly|Lys|Ala|Phe|Lys|Gly|Leu|Asn|Gln|Ile|Gly|Asp|Tyr|Lys|Tyr|Tyr|Phe|Asn|
|1981|Ser|Asp|Gly|Val|Met|Gln|Lys|Gly|Phe|Val|Ser|Ile|Asn|Asp|Asn|Lys|His|Tyr|Phe|Asp|
|2001|Asp|Ser|Gly|Val|Met|Lys|Val|Gly|Tyr|Thr|Glu|Ile|Asp|Gly|Lys|His|Phe|Tyr|Phe|Ala|
|2021|Glu|Asn|Gly|Glu|Met|Gln|Ile|Gly|Val|Phe|Asn|Thr|Glu|Asp|Gly|Phe|Lys|Tyr|Phe|Ala|
|2041|His|His|Asn|Glu|Asp|Leu|Gly|Asn|Glu|Gly|Glu|Gly|Ile|Ser|Tyr|Ser|Gly|Ile|Leu|
|2061|Asn|Phe|Asn|Asn|Lys|Ile|Tyr|Tyr|Phe|Asp|Asp|Ser|Phe|Thr|Ala|Val|Val|Gly|Trp|Lys|

FIGURE 11E

```
2081  Asp Leu Glu Asp Gly Ser Lys Tyr Tyr Phe Asp Glu Asp Thr Ala Glu Ala Tyr Ile Gly
2101  Leu Ser Leu Ile Asn Asp Gly Gln Tyr Tyr Phe Asn Asp Asp Gly Ile Met Gln Val Gly
2121  Phe Val Thr Ile Asn Asp Lys Val Phe Tyr Phe Ser Asp Ser Gly Ile Ile Glu Ser Gly
2141  Val Gln Asn Ile Asp Asp Asn Tyr Phe Tyr Ile Asp Asp Asn Gly Ile Val Gln Ile Gly
2161  Val Phe Asp Thr Ser Asp Gly Tyr Lys Tyr Phe Ala Pro Ala Asn Thr Val Asn Asp Asn
2181  Ile Tyr Gly Gln Ala Val Glu Tyr Ser Gly Leu Val Arg Val Gly Leu Asp Val Tyr Tyr
2201  Phe Gly Glu Thr Tyr Thr Ile Glu Thr Gly Trp Ile Tyr Asp Met Glu Asn Glu Ser Asp
2221  Lys Tyr Tyr Phe Asn Pro Glu Thr Lys Lys Ala Cys Lys Gly Ile Asn Leu Ile Asp Asp
2241  Ile Lys Tyr Tyr Phe Asp Glu Lys Gly Ile Met Arg Thr Gly Leu Ile Ser Phe Glu Asn
2261  Asn Asn Tyr Tyr Phe Asn Glu Asn Gly Met Gln Phe Gly Tyr Ile Asn Ile Glu Asp
2281  Lys Met Phe Tyr Phe Gly Glu Asp Gly Val Met Gln Ile Gly Val Phe Asn Thr Pro Asp
2301  Gly Phe Lys Tyr Phe Ala His Gln Asn Thr Leu Asp Asn Phe Gly Asn Gly Glu Ser Ile
2321  Asn Tyr Thr Gly Trp Leu Asp Leu Asp Glu Lys Arg Tyr Tyr Phe Thr Asp Glu Tyr Ile
2341  Ala Ala Thr Gly Ser Val Ile Ile Asp Gly Glu Glu Tyr Tyr Phe Asp Pro Asp Thr Ala
2361  Gln Leu Val Ile Ser Glu
```

FIGURE 11F

B. Clostridium difficile VPI TcdB DNA sequence with translation

Pseudomonas Exotoxin A Amino Acid Sequence

```
  1  Ala Glu Glu Ala Phe Asp Leu Trp Asn Glu Cys Ala Lys Ala Cys Val Leu Asp Leu Lys
 21  Asp Gly Val Arg Ser Ser Arg Met Ser Val Asp Pro Ala Ile Ala Asp Thr Asn Gly Gln
 41  Gly Val Leu His Tyr Ser Met Val Leu Glu Gly Gly Asn Asp Ala Leu Lys Leu Ala Ile
 61  Asp Asn Ala Leu Ser Ile Thr Ser Asp Gly Leu Thr Ile Arg Leu Glu Gly Gly Val Glu
 81  Pro Asn Lys Pro Val Arg Tyr Ser Tyr Thr Arg Gln Ala Arg Gly Ser Trp Ser Leu Asn
101  Trp Leu Val Pro Ile Gly His Glu Lys Pro Ser Asn Ile Lys Val Phe Ile His Glu Leu
121  Asn Ala Gly Asn Gln Leu Ser His Met Ser Pro Ile Tyr Thr Ile Glu Met Gly Asp Glu
141  Leu Leu Ala Lys Leu Ala Arg Asp Ala Thr Phe Phe Val Arg Ala His Glu Ser Asn Glu
161  Met Gln Pro Thr Leu Ala Ile Ser His Ala Gly Val Ser Val Val Met Ala Gln Ala Gln
181  Pro Arg Arg Glu Lys Arg Trp Ser Glu Trp Ala Ser Gly Lys Val Leu Cys Leu Leu Asp
201  Pro Leu Asp Gly Val Tyr Asn Tyr Leu Ala Gln Gln Arg Cys Asn Leu Asp Asp Thr Trp
221  Glu Gly Lys Ile Tyr Arg Val Leu Ala Gly Asn Pro Ala Lys His Asp Leu Asp Ile Lys
241  Pro Thr Val Ile Ser His Arg Leu His Phe Pro Glu Gly Gly Ser Leu Ala Ala Leu Thr
261  Ala His Gln Ala Cys His Leu Pro Leu Glu Thr Phe Thr Arg His Arg Gln Pro Arg Gly
281  Trp Glu Gln Leu Glu Gln Cys Gly Tyr Pro Val Gln Arg Leu Val Ala Leu Tyr Leu Ala
301  Ala Arg Leu Ser Trp Asn Gln Val Asp Gln Val Ile Arg Asn Ala Leu Ala Ser Pro Gly
321  Ser Gly Gly Asp Leu Gly Glu Ala Ile Arg Glu Gln Pro Glu Gln Ala Arg Leu Ala Leu
341  Thr Leu Ala Ala Ala Glu Ser Glu Arg Phe Val Arg Gln Gly Thr Gly Asn Asp Glu Ala
361  Gly Ala Ala Ser Ala Asp Val Val Ser Leu Thr Cys Pro Val Ala Ala Gly Glu Cys Ala
```

FIGURE 13A

```
381   Gly Pro Ala Asp Ser Gly Asp Ala Leu Leu Glu Arg Asn Tyr Pro Thr Gly Ala Glu Phe
401   Leu Gly Asp Gly Gly Asp Ile Ser Phe Ser Thr Arg Gly Thr Gln Asn Trp Thr Val Glu
                          Tyr - CRM66
421   Arg Leu Leu Gln Ala His Arg Gln Leu Glu Glu Arg Gly Tyr Val Phe Val Gly Tyr His
441   Gly Thr Phe Leu Glu Ala Ala Gln Ser Ile Val Phe Gly Gly Val Arg Ala Arg Ser Gln
461   Asp Leu Asp Ala Ile Trp Arg Gly Phe Tyr Ile Ala Gly Asp Pro Ala Leu Ala Tyr Gly
481   Tyr Ala Gln Asp Gln Glu Pro Asp Ala Arg Gly Arg Ile Arg Asn Gly Ala Leu Leu Arg
501   Val Tyr Val Pro Arg Ser Ser Leu Pro Gly Phe Tyr Arg Thr Gly Leu Thr Leu Ala Ala
521   Pro Glu Ala Ala Gly Glu Val Glu Arg Leu Ile Gly His Pro Leu Pro Leu Arg Leu Asp
                                                  Δ - rEPA
541   Ala Ile Thr Gly Pro Glu Glu Glu Gly Gly Arg Leu Glu Thr Ile Leu Gly Trp Pro Leu
561   Ala Glu Arg Thr Val Val Ile Pro Ser Ala Ile Pro Thr Asp Pro Arg Asn Val Gly Gly
581   Asp Leu Asp Pro Ser Ser Ile Pro Asp Lys Glu Gln Ala Ile Ser Ala Leu Pro Asp Tyr
601   Ala Ser Gln Pro Gly Lys Pro Pro Arg Glu Asp Leu Lys
```

```
                                    signal sequence
                                         S1
     Met Arg Cys Thr Arg Ala Ile Arg Gln Thr Gly Ala Arg Thr Gly Trp Leu Thr Ala
  1  ATG CGT TGC ACT CGG GCA ATT CGC CAA ACC GCA AGA ACA GGC TGG CTG ACG CTG GCG
                              signal sequence
                                    S1
     Ile Leu Ala Val Thr Ala Pro Val Thr Ser Pro Ala Trp Ala Asp Asp Pro Ala Thr
 61  ATT CTT GCC GTC ACG GCG CCC GTG ACT TCG CCG GCA TGG GCC GAT CCT GCC ACC
                                    S1
     Val Tyr Arg Ser Arg Tyr Asp Pro Pro Gln Pro Asp Val Phe Gln Asn Gly Thr Ala Trp
121  GTA TAC CGC TAT GAC CCG CCG CAG CCG GAG GAC GTT TTC CAG AAC GGA GCG TGG
                                    S1
     Gly Asn Asp Asn Val Leu Asp His Leu Thr Gly Arg Ser Cys Gln Val Gly Ser Ser
181  GGA AAC GAC AAT GTG CTC GAC CAT CTG ACC GGA CGT TCC TGC CAG GTC GGC AGC AGC
                                    S1
     Asn Ser Ala Phe Val Ser Thr Ser Ser Arg Arg Tyr Thr Gln Val Tyr Leu Gln His
241  AAC AGC GCT TTC GTC TCC ACC AGC AGC CGG CGC TAT ACC GAG GTC TAT CTC GAA CAT
                                    S1
     Arg Met Gln Glu Ala Val Glu Ala Gly Ala Gly Arg Ala Gly Thr Gly His Phe Ile Gly
301  CGC ATG CAG GAA GCG GTC GAG GCC GAA GGC GCC GGC ACC GGC CAC TTC ATC GGC
                                    S1
     Tyr Ile Tyr Glu Val Arg Ala Asp Asn Phe Tyr Ala Ala Ser Tyr Ser Tyr Phe Glu
361  TAC ATC TAC GAA GTC CGC GCC GAC AAC TTC TAC GCC GCC AGC TCC TAC TTC GAA
                                    S1
     Tyr Val Asp Thr Tyr Gly Asp Asn Ala Gly Arg Ile Leu Ala Gly Ala Leu Ala Thr Tyr
421  TAC GTC GAC ACT TAT GGC GAC AAT GCC GGC CGT ATC CTC GCC GGC GCG CTG GCC ACC TAC
                                    S1
     Gln Ser Glu Tyr Leu Ala His His Arg Arg Pro Gln Pro Gln Asn Ile Arg Arg Val Thr Arg
481  CAG AGC GAA TAT CTC GCA CAC CCC CCG ATT CCG CCC GAA AAC ATC CGC ACG GTA CGC
                                    S1
     Val Tyr His Asn Gly Ile Thr Thr Thr Glu Thr Gly Tyr Ser Asn Ala Arg Tyr
541  GTC TAT CAC AAC GGC ATC ACC ACG ACG GAG ACG GGC TAT TCC AAC GCT CGC TAC
```

FIGURE 17A

```
                                                                    S1
         Val Ser Gln Gln Thr Arg Ala Asn Pro Tyr Thr Ser Arg Arg Ser Val Ala Ser
  601    GTC AGC CAG CAG ACT CGG GCC AAT CCC TAC ACA TCG CGA AGG TCC GTA GCG TCG
                                                                    S1

Ile Val Gly Thr Leu Val Arg Met Ala Pro Val Ile Gly Met Ala Cys Met Ala Arg Gln Ala
  661    ATC GTC GGC ACA TTG GTG CGC ATG GCG CCG GTG ATA GGC GCT TGC ATG GCG CGG CAG GCC

Gln Ser Ser Gln Ala Met Ala Ala Trp Ser Gln Arg Ala Gly Gln Ala Met Val Leu Val
  721    GAA AGC TCC GAG GCC ATG GCC GCA TGG TCC GAA CGC GCC GGC GAG GCA ATG GTT CTC GTG
                S1

Tyr Tyr Gln Ser Ile Ala Tyr Ser Phe
  781    TAC TAC CAA ACC ATC GCC TAT TCG TTC TAG ACC TCC CCC ACC CCC CAA CTC CGG TAA
                                                  signal sequence
                                                                         S2

Met Pro Ile Asp Arg Lys Cys His Leu Cys Thr Leu Ser Val Leu Pro Leu
  841    TTG AAC AGC ATG CCG ATC GAC CGC AAG TGC CAT CTC TGC ACG CTC GTT CTG CCG TTG
                                              signal sequence
                                                                                S2

Ala Leu Leu Gly Ser His Val Ala Arg Ala Ser Thr Gly Ile Val Ile Pro Pro Gln
  901    GCC CTC GGA ACT CAC GTG GCG CGG GCC TCC ACG GGC ATC ATT CCG CCG CAG
                                                            S2

Glu Gln Ile Thr Gln His Gly Ser Pro Tyr Gly Arg Cys Ala Asn Lys Thr Arg Ala Leu
  961    GAA CAG ATT ACC CAG CAT GGC AGC CCC TAT GGA CGC TGC GCG AAC AAG ACC CGT GCC CTG
                                                                                S2

Thr Val Ala Glu Leu Arg Gly Ser Gly Asp Leu Gln Gln Tyr Leu Arg His Val Thr Arg
 1021    ACC GTG GCG GAA TTG CGC GGC AGC GGC GAT CTG CAG CAG TAC CTG CGT CAT GTG ACG CGC
                                                                                S2

Gly Trp Ser Ile Phe Ala Leu Tyr Asp Gly Thr Tyr Leu Gly Cly Gln Tyr Gly Val
 1081    GGC TGG TCA ATA TTT GCG CTC TAC GAT GGC ACC TAT CTC GGC GGC CAA TAC GGC GTC CTG
                                                                                S2

Ile Lys Asp Gly Thr Pro Gly Gly Ala Phe Asp Leu Lys Thr Thr Phe Cys Ile Met Thr
 1141    ATC AAG GAC GGA ACA CCC GGC GCA TTC GAC CTG AAA ACG ACG TTC TGC ATC ATG ACC
                                                                                S2

Thr Arg Asn Thr Gly Gln Pro Ala His Tyr Tyr Asp His Tyr Ser Asn Val Thr Ala Thr Arg
 1201    ACG CGC AAT ACG GGT CAA CCC GCA ACG GAT CAC TAC AGC GTC ACC GCC ACT CGC
```

```
       signal sequence
       //
                  Val Ala Pro Gly Ile Val Ile Pro Pro Lys Ala Leu Phe Thr Gln Gln Gly Gly Ala Tyr
                  CC GTT GCG CCA GGC ATC GTC ATC CCG CCG AAG GCA CTG TTC ACC CAA CAG GGC GGC T
2521                                          S3

Gly Arg Cys Pro Asn Gly Thr Arg Ala Leu Thr Val Ala Glu Leu Arg Gly Asn Ala Gly
        AT GGA CGC TGC CCG AAC GGA ACC CGC GCC TTG ACC GTG GCC GAA CTG CGG AAC GCC G
2581                                          S3

Leu Gln Thr Tyr Leu Arg Gln Ile Thr Pro Gly Trp Ser Ile Tyr Gly Leu Tyr Asp Gly
        AA TTG CAG ACG TAT TTG CGC CAG ATA ACG CCC GGC TGG TCC ATA TAC GGT CTC TAT GAC G
2641                                          S3

Thr Tyr Leu Gly Gln Ala Tyr Gly Gly Ile Ile Lys Asp Ala Pro Gly Ala Gly Phe
        GT ACG TAC CTG GGC CAG GCG TAC GGC GGC ATC ATC AAG GAC GCG CCG GCA GGC GGG T
2701                                          S3

Ile Tyr Arg Glu Thr Phe Cys Ile Thr Thr Ile Tyr Lys Thr Gly Gln Pro Ala Ala Asp
        TC ATT TAT CGC GAA ACT TTC TGC ATC ACC ACG ATC TAC AAG ACC GGG CAA CCG GCT GCG G
2761                                          S3

His Tyr Tyr Ser Lys Val Thr Ala Thr Arg Leu Leu Arg Ala Ser Thr Asn Ser Arg Leu Cys
        AT CAC TAC TAC AGC AAG GTC ACG GCC ACG CGC CTG CTC CGC GCC AGC ACC AAC AGC AGG CTG T
2821                                          S3

Ala Val Phe Val Arg Asp Gly Gly r Ser Val Ile Gly Ala Cys Ala Ser Pro Tyr Glu Gly
        CC GCC GTA TTC GTC AGG GAC GGC CAA TCC CTC ATC CCA TCC GGC AGC CCG TAT GAA G
2881                                          S3

Arg Tyr Arg Asp Met Tyr Asp Ala a Leu Arg Arg Leu Leu Tyr Met Tyr Met Ser Gly
        CC AGC TAC AGA GAC ATG TAC GAC GCC CTC CGC CTC CTG TAC ATG TAC ATG TCC C
2941                                          S3

Leu Ala Val Arg Val His Val Ser Lys Ile Gln Gln Tyr Tyr Asp Tyr Glu Asp Ala Thr
        CC CTT GCC GTA CGC GTC CAC GTC AGC AAG CAC CAA CAG TAT TAC GAC TAC GAG GCC ACC A
3001                                          S3

Phe Gln Thr Tyr Ala Leu Thr Gly Ile Ser Leu Cys Asn Pro Ala Ala Ser Ile Cys
        CA TTC CAG ACC TAT GCC CTC ACC GGC ATT TCC CTC TGC AAC CCG GCA GCG TCG ATA TGC
3061
```

FIGURE 17E

A. Diptheria Toxin amino acid sequence

```
  1 Gly Ala Asp Asp Val Val Asp Ser Ser Lys Ser Phe Val Met Glu Asn Phe Ser Ser Tyr
 21 His Gly Thr Lys Pro Gly Tyr Val Asp Ser Ile Gln Lys Gly Ile Gln Lys Pro Lys Ser
 41 Gly Thr Gln Gly Asn Tyr Asp Asp Asp Trp Lys Gly Phe Tyr Ser Thr Asp Asn Lys Tyr
 61 Asp Ala Ala Gly Tyr Ser Val Asp Asn Glu Asn Pro Leu Ser Gly Lys Ala Gly Gly Val
 81 Val Lys Val Thr Tyr Pro Gly Leu Thr Lys Val Leu Ala Leu Lys Val Asp Asn Ala Glu
101 Thr Ile Lys Lys Glu Leu Gly Leu Ser Leu Thr Glu Pro Leu Met Glu Gln Val Gly Thr
121 Glu Glu Phe Ile Lys Arg Phe Gly Asp Gly Ala Ser Arg Val Val Leu Ser Leu Pro Phe
141 Ala Glu Gly Ser Ser Ser Val Glu Tyr Ile Asn Asn Trp Glu Gln Ala Lys Ala Leu Ser
161 Val Glu Leu Glu Ile Asn Phe Glu Thr Arg Gly Lys Arg Gly Gln Asp Ala Met Tyr Glu
181 Tyr Met Ala Gln Ala Cys Ala Gly Asn Arg Val Arg Arg Ser Val Gly Ser Ser Leu Ser
201 Cys Ile Asn Leu Asp Trp Asp Val Ile Arg Asp Lys Thr Lys Thr Lys Ile Glu Ser Leu
221 Lys Glu His Gly Pro Ile Lys Asn Lys Met Ser Glu Ser Pro Asn Lys Thr Val Ser Glu
241 Glu Lys Ala Lys Gln Tyr Leu Glu Glu Phe His Gln Thr Ala Leu Glu His Pro Glu Leu
261 Ser Glu Leu Lys Thr Val Thr Gly Thr Asn Pro Val Phe Ala Gly Ala Asn Tyr Ala Ala
281 Trp Ala Val Asn Val Ala Gln Val Ile Asp Ser Glu Thr Ala Asp Asn Leu Glu Lys Thr
301 Thr Ala Ala Leu Ser Ile Leu Pro Gly Ile Gly Ser Val Met Gly Ile Ala Asp Gly Ala
321 Val His His Asn Thr Glu Glu Ile Val Ala Gln Ser Ile Ala Leu Ser Ser Leu Met Val
341 Ala Gln Ala Ile Pro Leu Val Gly Glu Leu Val Asp Ile Gly Phe Ala Ala Tyr Asn Phe
361 Val Glu Ser Ile Ile Asn Leu Phe Gln Val Val His Asn Ser Tyr Asn Arg Pro Ala Tyr
381 Ser Pro Gly His Lys Thr Gln Pro Phe Leu His Asp Gly Tyr Ala Val Ser Trp Asn Thr
401 Val Glu Asp Ser Ile Ile Arg Thr Gly Phe Gln Gly Glu Ser Gly His Asp Ile Lys Ile
421 Thr Ala Glu Asn Thr Pro Leu Pro Ile Ala Gly Val Leu Leu Pro Thr Ile Pro Gly Lys
441 Leu Asp Val Asn Lys Ser Lys Thr His Ile Ser Val Asn Gly Arg Lys Ile Arg Met Arg
461 Cys Arg Ala Ile Asp Gly Asp Val Thr Phe Cys Arg Pro Lys Ser Pro Val Tyr Val Gly
481 Asn Gly Val His Ala Asn Leu His Val Ala Phe His Arg Ser Ser Ser Glu Lys Ile His
501 Ser Asn Glu Ile Ser Ser Asp Ser Ile Gly Val Leu Gly Tyr Gln Lys Thr Val Asp His
521 Thr Lys Val Asn Ser Lys Leu Ser Leu Phe Phe Glu Ile Lys Ser
```

FIGURE 18A

B. Diphtheria Toxin DNA sequence with translation

FIGURE 18B

A. Cholera Toxin A Subunit (AE003852; Protein ID AAF94614.1) with secretion leader underlined

```
  1  Met Val Lys Ile Ile Phe Val Phe Phe Ile Phe Leu Ser Ser Phe Ser Tyr Ala Asn Asp
 21  Asp Lys Leu Tyr Arg Ala Asp Ser Arg Pro Pro Asp Glu Ile Lys Gln Ser Gly Gly Leu
 41  Met Pro Arg Gly Gln Ser Glu Tyr Phe Asp Arg Gly Thr Gln Met Asn Ile Asn Leu Tyr
 61  Asp His Ala Arg Gly Thr Gln Thr Gly Phe Val Arg His Asp Asp Gly Tyr Val Ser Thr
 81  Ser Ile Ser Leu Arg Ser Ala His Leu Val Gly Gln Thr Ile Leu Ser Gly His Ser Thr
101  Tyr Tyr Ile Tyr Val Ile Ala Thr Ala Pro Asn Met Phe Asn Val Asn Asp Val Leu Gly
121  Ala Tyr Ser Pro His Pro Asp Glu Gln Glu Val Ser Ala Leu Gly Gly Ile Pro Tyr Ser
141  Gln Ile Tyr Gly Trp Tyr Arg Val His Phe Gly Val Leu Asp Glu Gln Leu His Arg Asn
161  Arg Gly Tyr Arg Asp Arg Tyr Tyr Ser Asn Leu Asp Ile Ala Pro Ala Ala Asp Gly Tyr
181  Gly Leu Ala Gly Phe Pro Pro Glu His Arg Ala Trp Arg Glu Glu Pro Trp Ile His His
201  Ala Pro Pro Gly Cys Gly Asn Ala Pro Arg Ser Ser Met Ser Asn Thr Cys Asp Glu Lys
221  Thr Gln Ser Leu Gly Val Lys Phe Leu Asp Glu Tyr Gln Ser Lys Val Lys Arg Gln Ile
241  Phe Ser Gly Tyr Gln Ser Asp Ile Asp Thr His Asn Arg Ile Lys Asp Glu Leu
```

FIGURE 19A

B. Cholera Toxin B Amino Acid Sequence with secretion leader underlined (AE003852; Protein ID AAF94613.1)

```
  1  Met Ile Lys Leu Lys Phe Gly Val Phe Thr Val Leu Leu Ser Ser Ala Tyr Ala His
 21  Gly Thr Pro Gln Asn Ile Thr Asp Leu Cys Ala Glu Tyr His Asn Thr Gln Ile Tyr Thr
 41  Leu Asn Asp Lys Ile Phe Ser Tyr Thr Glu Ser Leu Ala Gly Lys Arg Glu Met Ala Ile
 61  Ile Thr Phe Lys Asn Gly Ala Ile Phe Gln Val Glu Val Pro Gly Ser Gln His Ile Asp
 81  Ser Gln Lys Lys Ala Ile Glu Arg Met Lys Asp Thr Leu Arg Ile Ala Tyr Leu Thr Glu
101  Ala Lys Val Glu Lys Leu Cys Val Trp Asn Asn Lys Thr Pro His Ala Ile Ala Ala Ile
121  Ser Met Ala Asn
```

FIGURE 19B

C. Cholera Toxin DNA Sequences (A and B subunit coding regions Genbank AE003852)

```
                               Secretion Leader
      ~~~~~~~~~~~~~~~~~~~~~~~~~~~~~~~~~~~~~~~~~~~~~~~~~~~~~~~~~~~~~~~~~~~~~~~~
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Met Val Lys Ile Ile Phe Val Phe Phe Ile Phe Leu Ser Ser Phe Ser Tyr Ala Asn Asp
   1  ATG GTA AAG ATA ATA TTT GTG TTT TTT ATT TTC TTA TCA TCA TTT TCA TAT GCA AAT GAT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Asp Lys Leu Tyr Arg Ala Asp Ser Arg Pro Pro Asp Glu Ile Lys Gln Ser Gly Gly Leu
  61  GAT AAG TTA TAT CGG GCA GAT TCT AGA CCT CCT GAT GAA ATA AAG CAG TCA GGT GGT CTT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Met Pro Arg Gly Gln Ser Glu Tyr Phe Asp Arg Gly Thr Gln Met Asn Ile Asn Leu Tyr
 121  ATG CCA AGA GGA CAG AGT GAG TAC TTT GAC CGA GGT ACT CAA ATG AAT ATC AAC CTT TAT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Asp His Ala Arg Gly Thr Gln Thr Gly Phe Val Arg His Asp Asp Gly Tyr Val Ser Thr
 181  GAT CAT GCA AGA GGA ACT CAG ACG GGA TTT GTT AGG CAC GAT GAT GGA TAT GTT TCC ACC
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Ser Ile Ser Leu Arg Ser Ala His Leu Val Gly Gln Thr Ile Leu Ser Gly His Ser Thr
 241  TCA ATT AGT TTG AGA AGT GCC CAC TTA GTG GGT CAA ACT ATA TTG TCT GGT CAT TCT ACT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Tyr Tyr Ile Tyr Val Ile Ala Thr Ala Pro Asn Met Phe Asn Val Asn Asp Val Leu Gly
 301  TAT TAT ATA TAT GTT ATA GCC ACT GCA CCC AAC ATG TTT AAC GTT AAT GAT GTA TTA GGG
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Ala Tyr Ser Pro His Pro Asp Glu Gln Glu Val Ser Ala Leu Gly Gly Ile Pro Tyr Ser
 361  GCA TAC AGT CCT CAT CCA GAT GAA CAA GAA GTT TCT GCT TTA GGT GGG ATT CCA TAC TCC
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Gln Ile Tyr Gly Trp Tyr Arg Val His Phe Gly Val Leu Asp Glu Gln Leu His Arg Asn
 421  CAA ATA TAT GGA TGG TAT CGA GTT CAT TTT GGG GTG CTT GAT GAA CAA TTA CAT CGT AAT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Arg Gly Tyr Arg Asp Arg Tyr Tyr Ser Asn Leu Asp Ile Ala Pro Ala Ala Asp Gly Tyr
 481  AGG GGC TAC AGA GAT AGA TAT TAC AGT AAC TTA GAT ATT GCT CCA GCA GCA GAT GGT TAT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Gly Leu Ala Gly Phe Pro Pro Glu His Arg Ala Trp Arg Glu Glu Pro Trp Ile His His
 541  GGA TTG GCA GGT TTC CCT CCG GAG CAT AGA GCT TGG AGG GAA GAG CCG TGG ATT CAT CAT
                                  CTA
      ~~~~~~~~~~~~~~~~~~~~~~~~~~~~~~~~~~~~~~~~~~~~~~~~~~~~~~~~~~~~~~~~~~~~~~~~~~~~~~
      Ala Pro Pro Gly Cys Gly Asn Ala Pro Arg Ser Ser Met Ser Asn Thr Cys Asp Glu Lys
 601  GCA CCG CCG GGT TGT GGG AAT GCT CCA AGA TCA TCG ATG AGT AAT ACT TGC GAT GAA AAA
```

FIGURE 19C

FIGURE 19D

SEQUENCE LISTING

```
<160> NUMBER OF SEQ ID NOS: 46

<210> SEQ ID NO 1
<211> LENGTH: 535
<212> TYPE: PRT
<213> ORGANISM: Corynebacterium diphtheriae

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110
```

-continued

```
Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510
```

| Gly | Tyr | Gln | Lys | Thr | Val | Asp | His | Thr | Lys | Val | Asn | Ser | Lys | Leu | Ser |
|---|---|---|---|---|---|---|---|---|---|---|---|---|---|---|---|
| | | 515 | | | | 520 | | | | | 525 | | | | |

| Leu | Phe | Phe | Glu | Ile | Lys | Ser |
|---|---|---|---|---|---|---|
| | 530 | | | | | 535 |

<210> SEQ ID NO 2
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1605)

<400> SEQUENCE: 2

```
ggg gcg gac gat gtg gtg gat tcc tcc aag tcg ttt gtc atg gaa aat       48
Gly Ala Asp Asp Val Val Asp Ser Ser Lys Ser Phe Val Met Glu Asn
1               5                   10                  15 ttc tcg tcg tac cat ggc act aag cca ggc tac gtg gat agc att caa       96
Phe Ser Ser Tyr His Gly Thr Lys Pro Gly Tyr Val Asp Ser Ile Gln
            20                  25                  30 aag ggc atc cag aag ccc aag agc ggt act cag ggg aac tat gac gac      144
Lys Gly Ile Gln Lys Pro Lys Ser Gly Thr Gln Gly Asn Tyr Asp Asp
        35                  40                  45 gac tgg aag gaa ttt tac agc acc gac aat aag tac gat gct gcg ggc      192
Asp Trp Lys Glu Phe Tyr Ser Thr Asp Asn Lys Tyr Asp Ala Ala Gly
    50                  55                  60 tat agc gtg gac aac gaa aac cca ttg tcg ggc aag gcc ggt ggc gtg      240
Tyr Ser Val Asp Asn Glu Asn Pro Leu Ser Gly Lys Ala Gly Gly Val
65                  70                  75                  80 gtg aag gtg acc tat cct ggt ctg acg aaa gtt ctg gcg ttg aaa gtg      288
Val Lys Val Thr Tyr Pro Gly Leu Thr Lys Val Leu Ala Leu Lys Val
                85                  90                  95 gac aac gcc gag act atc aag aaa gaa ttg ggc ttg agt ttg acc gag      336
Asp Asn Ala Glu Thr Ile Lys Lys Glu Leu Gly Leu Ser Leu Thr Glu
            100                 105                 110 ccg ctg atg gaa cag gtg ggt acc gaa gaa ttc att aaa cgt ttt ggg      384
Pro Leu Met Glu Gln Val Gly Thr Glu Glu Phe Ile Lys Arg Phe Gly
        115                 120                 125 gac ggc gcg tcg cgc gtg gtc ctg tcg ttg ccg ttc gcc gaa ggg tcg      432
Asp Gly Ala Ser Arg Val Val Leu Ser Leu Pro Phe Ala Glu Gly Ser
    130                 135                 140 tcg tcg gtg gaa tat atc aac aac tgg gaa cag gcc aag gcg ctg tcg      480
Ser Ser Val Glu Tyr Ile Asn Asn Trp Glu Gln Ala Lys Ala Leu Ser
145                 150                 155                 160 gtg gaa ctg gaa att aac ttc gaa acg cgg ggc aaa cgg ggc cag gac      528
Val Glu Leu Glu Ile Asn Phe Glu Thr Arg Gly Lys Arg Gly Gln Asp
                165                 170                 175 gcc atg tac gaa tac atg gcg cag gcg tgc gcc ggg aac cgg gtg cgg      576
Ala Met Tyr Glu Tyr Met Ala Gln Ala Cys Ala Gly Asn Arg Val Arg
            180                 185                 190 cgc agc gtg ggc agt tcc ttg agt tgc atc aat ctg gac tgg gac gtc      624
Arg Ser Val Gly Ser Ser Leu Ser Cys Ile Asn Leu Asp Trp Asp Val
        195                 200                 205 atc cgc gat aag acg aag acg aaa atc gag tcg ctc aaa gag cac ggc      672
Ile Arg Asp Lys Thr Lys Thr Lys Ile Glu Ser Leu Lys Glu His Gly
    210                 215                 220 ccg atc aaa aac aaa atg agc gag tcg ccg aat aaa acg gtg tcc gag      720
Pro Ile Lys Asn Lys Met Ser Glu Ser Pro Asn Lys Thr Val Ser Glu
225                 230                 235                 240
```

-continued

| | | |
|---|---|---|
| gag aag gcg aag caa tac ctg gag gaa ttc cac cag acg gct ctg gag<br>Glu Lys Ala Lys Gln Tyr Leu Glu Glu Phe His Gln Thr Ala Leu Glu<br>245 250 255 | 768 | |
| cac ccg gag ctg agc gaa ctc aaa acc gtt acc ggt acg aac ccg gtg<br>His Pro Glu Leu Ser Glu Leu Lys Thr Val Thr Gly Thr Asn Pro Val<br>260 265 270 | 816 | |
| ttt gcc ggg gca aac tat gca gct tgg gcc gtc aac gtg gcc caa gtg<br>Phe Ala Gly Ala Asn Tyr Ala Ala Trp Ala Val Asn Val Ala Gln Val<br>275 280 285 | 864 | |
| atc gac tcc gaa acg gcc gac aac ctg gaa aag act acc gcc gcg ttg<br>Ile Asp Ser Glu Thr Ala Asp Asn Leu Glu Lys Thr Thr Ala Ala Leu<br>290 295 300 | 912 | |
| tcg atc ctc ccg ggc atc ggg agc gtc atg ggt att gcc gat ggt gcg<br>Ser Ile Leu Pro Gly Ile Gly Ser Val Met Gly Ile Ala Asp Gly Ala<br>305 310 315 320 | 960 | |
| gtg cat cac aac acc gaa gag atc gtc gcg cag tcg atc gca ttg tcc<br>Val His His Asn Thr Glu Glu Ile Val Ala Gln Ser Ile Ala Leu Ser<br>325 330 335 | 1008 | |
| tcc ctg atg gtc gcc caa gct atc ccg ctg gtc ggc gag ctg gtc gat<br>Ser Leu Met Val Ala Gln Ala Ile Pro Leu Val Gly Glu Leu Val Asp<br>340 345 350 | 1056 | |
| atc ggc ttt gcc gct tat aac ttt gtt gaa tcg atc att aac ctg ttc<br>Ile Gly Phe Ala Ala Tyr Asn Phe Val Glu Ser Ile Ile Asn Leu Phe<br>355 360 365 | 1104 | |
| cag gtg gtg cat aac agc tac aac cgg cca gcg tac tcg ccc ggt cac<br>Gln Val Val His Asn Ser Tyr Asn Arg Pro Ala Tyr Ser Pro Gly His<br>370 375 380 | 1152 | |
| aag acc cag ccc ttt ctc cac gac ggc tat gcc gtg tcg tgg aac acc<br>Lys Thr Gln Pro Phe Leu His Asp Gly Tyr Ala Val Ser Trp Asn Thr<br>385 390 395 400 | 1200 | |
| gtg gag gac agc atc atc cgc acc ggt ttc cag ggc gag agc ggc cat<br>Val Glu Asp Ser Ile Ile Arg Thr Gly Phe Gln Gly Glu Ser Gly His<br>405 410 415 | 1248 | |
| gac atc aaa att acc gcg gaa aac acg ccc ttg ccg atc gct ggc gtg<br>Asp Ile Lys Ile Thr Ala Glu Asn Thr Pro Leu Pro Ile Ala Gly Val<br>420 425 430 | 1296 | |
| ttg ctc ccg acg atc ccg ggt aag ctc gac gtc aac aag tcc aag acc<br>Leu Leu Pro Thr Ile Pro Gly Lys Leu Asp Val Asn Lys Ser Lys Thr<br>435 440 445 | 1344 | |
| cat atc agc gtc aat ggc cgc aag atc cgc atg cgc tgt cgg gcc att<br>His Ile Ser Val Asn Gly Arg Lys Ile Arg Met Arg Cys Arg Ala Ile<br>450 455 460 | 1392 | |
| gat ggc gac gtc acg ttt tgc cgg ccg aag agt ccc gtc tat gtc ggg<br>Asp Gly Asp Val Thr Phe Cys Arg Pro Lys Ser Pro Val Tyr Val Gly<br>465 470 475 480 | 1440 | |
| aac ggt gtc cat gcc aac ctg cac gtc gca ttc cac cgg agc agc tcg<br>Asn Gly Val His Ala Asn Leu His Val Ala Phe His Arg Ser Ser Ser<br>485 490 495 | 1488 | |
| gaa aag atc cac agc aat gag atc agc agc gac agc atc ggc gtg ctg<br>Glu Lys Ile His Ser Asn Glu Ile Ser Ser Asp Ser Ile Gly Val Leu<br>500 505 510 | 1536 | |
| ggg tat caa aag acg gtc gat cac acc aag gtg aac agt aaa ctg agc<br>Gly Tyr Gln Lys Thr Val Asp His Thr Lys Val Asn Ser Lys Leu Ser<br>515 520 525 | 1584 | |
| ttg ttc ttt gaa atc aag tcg<br>Leu Phe Phe Glu Ile Lys Ser<br>530 535 | 1605 | |

-continued

```
<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Arg Asn Leu Ile Leu Ser Ala Ala Leu Val Thr Ala Ser Leu Phe
1               5                   10                  15

Gly Met Thr Ala Gln Ala
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Phe Ala Lys Leu Val Ala Val Ser Leu Leu Thr Leu Ala Ser Gly
1               5                   10                  15

Gln Leu Leu Ala
            20

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asn Arg Ser Ser Ala Leu Leu Leu Ala Phe Val Phe Leu Ser Gly
1               5                   10                  15

Cys Gln Ala Met Ala
            20

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Met Leu Phe Arg Thr Leu Leu Ala Ser Leu Thr Phe Ala Val Ile Ala
1               5                   10                  15

Gly Leu Pro Ser Thr Ala His Ala
            20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ser Cys Thr Arg Ala Phe Lys Pro Leu Leu Leu Ile Gly Leu Ala
1               5                   10                  15

Thr Leu Met Cys Ser His Ala Phe Ala
            20                  25

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Arg Leu Ala Ala Leu Pro Leu Leu Leu Ala Pro Leu Phe Ile Ala
1               5                   10                  15

Pro Met Ala Val Ala
            20

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Lys Leu Lys Arg Leu Met Ala Ala Met Thr Phe Val Ala Ala Gly
1               5                   10                  15

Val Ala Thr Val Asn Ala Val Ala
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Arg Leu Thr Gln Ile Ile Ala Ala Ala Ala Ile Ala Leu Val Ser
1               5                   10                  15

Thr Phe Ala Leu Ala
            20

<210> SEQ ID NO 12
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Arg Asn Leu Leu Arg Gly Met Leu Val Val Ile Cys Cys Met Ala
1               5                   10                  15

Gly Ile Ala Ala Ala
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Gln Asn Tyr Lys Lys Phe Leu Leu Ala Ala Ala Val Ser Met Ala
1               5                   10                  15

Phe Ser Ala Thr Ala Met Ala
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Pro Pro Arg Ser Ile Ala Ala Cys Leu Gly Leu Leu Gly Leu Leu
1               5                   10                  15

Met Ala Thr Gln Ala Ala Ala
            20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Lys Lys Ser Thr Leu Ala Val Ala Val Thr Leu Gly Ala Ile Ala
1               5                   10                  15
```

Gln Gln Ala Gly Ala
            20

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Lys Phe Lys Gln Leu Met Ala Met Ala Leu Leu Leu Ala Leu Ser
1               5                   10                  15

Ala Val Ala Gln Ala
            20

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala

<210> SEQ ID NO 20
<211> LENGTH: 25
<212> TYPE: PRT
<213> ORGANISM: Corynebacterium diphtheriae
<220> FEATURE:
<221> NAME/KEY: MOD_RES
<222> LOCATION: (9)..(9)
<223> OTHER INFORMATION: Any amino acid

<400> SEQUENCE: 20

Met Ser Arg Lys Leu Phe Ala Ser Xaa Leu Ile Gly Ala Leu Leu Gly
1 5 10 15

Ile Gly Ala Pro Pro Ser Ala His Ala
20 25

<210> SEQ ID NO 21
<211> LENGTH: 4
<212> TYPE: PRT
<213> ORGANISM: Corynebacterium diphtheriae

<400> SEQUENCE: 21

Gly Ala Asp Asp
1

<210> SEQ ID NO 22
<211> LENGTH: 102
<212> TYPE: PRT
<213> ORGANISM: Vibrio cholerae

<400> SEQUENCE: 22

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala
            100

<210> SEQ ID NO 23
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(306)

<400> SEQUENCE: 23 acg ccg caa aat atc acc gac ctg tgc gca gaa tat cac aat acc caa      48
Thr Pro Gln Asn Ile Thr Asp Leu Cys Ala Glu Tyr His Asn Thr Gln
1               5                   10                  15 atc cat act ctg aac gac aaa atc ttc agc tac acc gag agc ctg gct      96
Ile His Thr Leu Asn Asp Lys Ile Phe Ser Tyr Thr Glu Ser Leu Ala
            20                  25                  30 ggc aag cgc gag atg gcg atc att acg ttc aaa aac ggt gcg acc ttt      144
Gly Lys Arg Glu Met Ala Ile Ile Thr Phe Lys Asn Gly Ala Thr Phe
        35                  40                  45 cag gtg gaa gtc ccc ggc agt cag cac atc gat tcc cag aaa aag gcc      192
Gln Val Glu Val Pro Gly Ser Gln His Ile Asp Ser Gln Lys Lys Ala
    50                  55                  60 att gaa cgg atg aag gac acc ctc cgt atc gcc tac ttg acc gaa gcc      240
Ile Glu Arg Met Lys Asp Thr Leu Arg Ile Ala Tyr Leu Thr Glu Ala
65                  70                  75                  80 aag gtg gag aag ctg tgc gtt tgg aac aac aaa acc ccg cac gcc atc      288
Lys Val Glu Lys Leu Cys Val Trp Asn Asn Lys Thr Pro His Ala Ile
                85                  90                  95 gcg gcc atc tcg atg gcc                                              306
Ala Ala Ile Ser Met Ala
            100

<210> SEQ ID NO 24

```
<211> LENGTH: 3119
<212> TYPE: DNA
<213> ORGANISM: Bordetella pertussis
<220> FEATURE:
<221> NAME/KEY: CDS
<222> LOCATION: (1)..(807)
<220> FEATURE:
<221> NAME/KEY: CDS
<222> LOCATION: (850)..(1527)
<220> FEATURE:
<221> NAME/KEY: CDS
<222> LOCATION: (1587)..(1979)
<220> FEATURE:
<221> NAME/KEY: CDS
<222> LOCATION: (1994)..(2353)
<220> FEATURE:
<221> NAME/KEY: CDS
<222> LOCATION: (2439)..(3119)

<400> SEQUENCE: 24
```

| | | | | | | | | | | | | | | | | |
|---|---|---|---|---|---|---|---|---|---|---|---|---|---|---|---|---|
| atg | cgt | tgc | act | cgg | gca | att | cgc | caa | acc | gca | aga | aca | ggc | tgg | ctg | 48 |
| Met | Arg | Cys | Thr | Arg | Ala | Ile | Arg | Gln | Thr | Ala | Arg | Thr | Gly | Trp | Leu | |
| 1 | | | | 5 | | | | | 10 | | | | | 15 | | |
| acg | tgg | ctg | gcg | att | ctt | gcc | gtc | acg | gcg | ccc | gtg | act | tcg | ccg | gca | 96 |
| Thr | Trp | Leu | Ala | Ile | Leu | Ala | Val | Thr | Ala | Pro | Val | Thr | Ser | Pro | Ala | |
| | | | 20 | | | | | 25 | | | | | 30 | | | |
| tgg | gcc | gac | gat | cct | ccc | gcc | acc | gta | tac | aaa | tat | gac | tcc | cgc | ccg | 144 |
| Trp | Ala | Asp | Asp | Pro | Pro | Ala | Thr | Val | Tyr | Lys | Tyr | Asp | Ser | Arg | Pro | |
| | 35 | | | | | 40 | | | | | 45 | | | | | |
| ccg | gag | gac | gtt | ttc | cag | aac | gga | ttc | acg | gcg | tgg | gga | aac | aac | gac | 192 |
| Pro | Glu | Asp | Val | Phe | Gln | Asn | Gly | Phe | Thr | Ala | Trp | Gly | Asn | Asn | Asp | |
| 50 | | | | | 55 | | | | | 60 | | | | | | |
| aat | gtg | ctc | gac | cat | ctg | acc | gga | cgt | tcc | tgc | cag | gtc | ggc | agc | agc | 240 |
| Asn | Val | Leu | Asp | His | Leu | Thr | Gly | Arg | Ser | Cys | Gln | Val | Gly | Ser | Ser | |
| 65 | | | | | 70 | | | | | 75 | | | | | 80 | |
| aac | agc | gct | ttc | gtc | tcc | acc | agc | agc | cgg | cgc | tat | acc | gag | gtc | | 288 |
| Asn | Ser | Ala | Phe | Val | Ser | Thr | Ser | Ser | Arg | Arg | Tyr | Thr | Glu | Val | | |
| | | | | 85 | | | | | 90 | | | | | 95 | | |
| tat | ctc | gaa | cat | cgc | atg | cag | gaa | gcg | gtc | gag | gcc | gaa | cgc | gcc | ggc | 336 |
| Tyr | Leu | Glu | His | Arg | Met | Gln | Glu | Ala | Val | Glu | Ala | Glu | Arg | Ala | Gly | |
| | | | 100 | | | | | 105 | | | | | 110 | | | |
| agg | ggc | acc | ggc | cac | ttc | atc | ggc | tac | atc | tac | gaa | gtc | cgc | gcc | gac | 384 |
| Arg | Gly | Thr | Gly | His | Phe | Ile | Gly | Tyr | Ile | Tyr | Glu | Val | Arg | Ala | Asp | |
| | 115 | | | | | 120 | | | | | 125 | | | | | |
| aac | aat | ttc | tac | ggc | gcc | gcc | agc | tcg | tac | ttc | gaa | tac | gtc | gac | act | 432 |
| Asn | Asn | Phe | Tyr | Gly | Ala | Ala | Ser | Ser | Tyr | Phe | Glu | Tyr | Val | Asp | Thr | |
| 130 | | | | | 135 | | | | | 140 | | | | | | |
| tat | ggc | gac | aat | gcc | ggc | cgt | atc | ctc | gcc | ggc | gcg | ctg | gcc | acc | tac | 480 |
| Tyr | Gly | Asp | Asn | Ala | Gly | Arg | Ile | Leu | Ala | Gly | Ala | Leu | Ala | Thr | Tyr | |
| 145 | | | | | 150 | | | | | 155 | | | | | 160 | |
| cag | agc | gca | tat | ctg | gca | cac | cgg | cgc | att | ccg | ccc | gaa | aac | atc | cgc | 528 |
| Gln | Ser | Ala | Tyr | Leu | Ala | His | Arg | Arg | Ile | Pro | Pro | Glu | Asn | Ile | Arg | |
| | | | | 165 | | | | | 170 | | | | | 175 | | |
| agg | gta | acg | cgg | gtc | tat | cac | aac | ggc | atc | acc | ggc | gag | acc | acg | acc | 576 |
| Arg | Val | Thr | Arg | Val | Tyr | His | Asn | Gly | Ile | Thr | Gly | Glu | Thr | Thr | Thr | |
| | | | 180 | | | | | 185 | | | | | 190 | | | |
| acg | gag | tat | tcc | aac | gct | cgc | tac | gtc | agc | cag | cag | act | cgc | gcc | aat | 624 |
| Thr | Glu | Tyr | Ser | Asn | Ala | Arg | Tyr | Val | Ser | Gln | Gln | Thr | Arg | Ala | Asn | |
| | 195 | | | | | 200 | | | | | 205 | | | | | |
| ccc | aac | ccc | tac | aca | tcg | cga | agg | tcc | gta | gcg | tcg | atc | gtc | ggc | aca | 672 |
| Pro | Asn | Pro | Tyr | Thr | Ser | Arg | Arg | Ser | Val | Ala | Ser | Ile | Val | Gly | Thr | |
| 210 | | | | | 215 | | | | | 220 | | | | | | |
| ttg | gtg | cgc | atg | gcg | ccg | gtg | ata | ggc | gct | tgc | atg | gcg | cgg | cag | gcc | 720 |
| Leu | Val | Arg | Met | Ala | Pro | Val | Ile | Gly | Ala | Cys | Met | Ala | Arg | Gln | Ala | |

```
                225                 230                 235                 240
gaa agc tcc gag gcc atg gca gcc tgg tcc gaa cgc gcc ggc gag gcg      768
Glu Ser Ser Glu Ala Met Ala Ala Trp Ser Glu Arg Ala Gly Glu Ala
                    245                 250                 255 atg gtt ctc gtg tac tac gaa agc atc gcg tat tcg ttc tagacctggc      817
Met Val Leu Val Tyr Tyr Glu Ser Ile Ala Tyr Ser Phe
                    260                 265 ccagccccgc caactccgg taattgaaca gc atg ccg atc gac cgc aag acg      870
                                   Met Pro Ile Asp Arg Lys Thr
                                       270                 275 ctc tgc cat ctc ctg tcc gtt ctg ccg ttg gcc ctc ctc gga tct cac     918
Leu Cys His Leu Leu Ser Val Leu Pro Leu Ala Leu Leu Gly Ser His
                280                 285                 290 gtg gcg cgg gcc tcc acg cca ggc atc gtc att ccg ccg cag gaa cag     966
Val Ala Arg Ala Ser Thr Pro Gly Ile Val Ile Pro Pro Gln Glu Gln
            295                 300                 305 att acc cag cat ggc agc ccc tat gga cgc tgc gcg aac aag acc cgt     1014
Ile Thr Gln His Gly Ser Pro Tyr Gly Arg Cys Ala Asn Lys Thr Arg
        310                 315                 320 gcc ctg acc gtg gcg gaa ttg cgc ggc agc ggc gat ctg cag gag tac     1062
Ala Leu Thr Val Ala Glu Leu Arg Gly Ser Gly Asp Leu Gln Glu Tyr
325                 330                 335                 340 ctg cgt cat gtg acg cgc ggc tgg tca ata ttt gcg ctc tac gat ggc     1110
Leu Arg His Val Thr Arg Gly Trp Ser Ile Phe Ala Leu Tyr Asp Gly
                345                 350                 355 acc tat ctc ggc ggc gaa tat ggc ggc gtg atc aag gac gga aca ccc     1158
Thr Tyr Leu Gly Gly Glu Tyr Gly Gly Val Ile Lys Asp Gly Thr Pro
                    360                 365                 370 ggc ggc gca ttc gac ctg aaa acg acg ttc tgc atc atg acc acg cgc     1206
Gly Gly Ala Phe Asp Leu Lys Thr Thr Phe Cys Ile Met Thr Thr Arg
                375                 380                 385 aat acg ggt caa ccc gca acg gat cac tac tac agc aac gtc acc gcc     1254
Asn Thr Gly Gln Pro Ala Thr Asp His Tyr Tyr Ser Asn Val Thr Ala
            390                 395                 400 act cgc ctg ctc tcc agc acc aac agc agg cta tgc gcg gtc ttc gtc     1302
Thr Arg Leu Leu Ser Ser Thr Asn Ser Arg Leu Cys Ala Val Phe Val
405                 410                 415                 420 aga agc ggg caa ccg gtc att ggc gcc tgc acc agc ccg tat gac ggc     1350
Arg Ser Gly Gln Pro Val Ile Gly Ala Cys Thr Ser Pro Tyr Asp Gly
                425                 430                 435 aag tac tgg agc atg tac agc cgg ctg cgg aaa atg ctt tac ctg atc     1398
Lys Tyr Trp Ser Met Tyr Ser Arg Leu Arg Lys Met Leu Tyr Leu Ile
                    440                 445                 450 tac gtg gcc ggc atc tcc gta cgc gtc cat gtc agc aag gaa gaa cag     1446
Tyr Val Ala Gly Ile Ser Val Arg Val His Val Ser Lys Glu Glu Gln
                455                 460                 465 tat tac gac tat gag gac gca acg ttc gag act tac gcc ctt acc ggc     1494
Tyr Tyr Asp Tyr Glu Asp Ala Thr Phe Glu Thr Tyr Ala Leu Thr Gly
            470                 475                 480 atc tcc atc tgc aat cct gga tca tcc tta tgc tgagacgctt ccccactcga   1547
Ile Ser Ile Cys Asn Pro Gly Ser Ser Leu Cys
485                 490                 495 accaccgccc cgggacaggg cggcgccggg cggtcgcgc gtg cgc gcc ctg gcg      1601
                                           Val Arg Ala Leu Ala
                                                           500 tgg ttg ctg gca tcc ggc gcg atg acg cat ctt tcc ccc gcc ctg gcc     1649
Trp Leu Leu Ala Ser Gly Ala Met Thr His Leu Ser Pro Ala Leu Ala
                505                 510                 515 gac gtt cct tat gtg ctg gtg aag acc aat atg gtg gtc acc agc gta     1697
```

```
                                                               -continued

Asp Val Pro Tyr Val Leu Val Lys Thr Asn Met Val Thr Ser Val
            520                 525                 530 gcc atg aag ccg tat gaa gtc acc ccg acg cgc atg ctg gtc tgc ggc      1745
Ala Met Lys Pro Tyr Glu Val Thr Pro Thr Arg Met Leu Val Cys Gly
            535                 540                 545 atc gcc gcc aaa ctg ggc gcc gcg gcc agc agc ccg gac gcg cac gtg      1793
Ile Ala Ala Lys Leu Gly Ala Ala Ala Ser Ser Pro Asp Ala His Val
550             555                 560 ccg ttc tgc ttc ggc aag gat ctc aag cgt ccc ggc agc agt ccc atg      1841
Pro Phe Cys Phe Gly Lys Asp Leu Lys Arg Pro Gly Ser Ser Pro Met
565                 570                 575                 580 gaa gtc atg ttg cgc gcc gtc ttc atg caa caa cgg ccg ctg cgc atg      1889
Glu Val Met Leu Arg Ala Val Phe Met Gln Gln Arg Pro Leu Arg Met
                585                 590                 595 ttt ctg ggt ccc aag caa ctc act ttc gaa ggc aag ccc gcg ctc gaa      1937
Phe Leu Gly Pro Lys Gln Leu Thr Phe Glu Gly Lys Pro Ala Leu Glu
            600                 605                 610 ctg atc cgg atg gtc gaa tgc agc ggc aag cag gat tgc ccc              1979
Leu Ile Arg Met Val Glu Cys Ser Gly Lys Gln Asp Cys Pro
            615                 620                 625 tgaaggcgaa cccc atg cat acc atc gca tcc atc ctg ttg tcc gtg ctc      2029
                Met His Thr Ile Ala Ser Ile Leu Leu Ser Val Leu
                                630                 635 ggc ata tac agc ccg gct gac gtc gcc ggc ttg ccg acc cat ctg tac      2077
Gly Ile Tyr Ser Pro Ala Asp Val Ala Gly Leu Pro Thr His Leu Tyr
            640                 645                 650 aag aac ttc act gtc cag gag ctg gcc ttg aaa ctg aag ggc aag aat      2125
Lys Asn Phe Thr Val Gln Glu Leu Ala Leu Lys Leu Lys Gly Lys Asn
655                 660                 665                 670 cag gag ttc tgc ctg acc gcc ttc atg tcg ggc aga agc ctg gtc cgg      2173
Gln Glu Phe Cys Leu Thr Ala Phe Met Ser Gly Arg Ser Leu Val Arg
                675                 680                 685 gcg tgc ctg tcc gac gcg gga cac gag cac gac acg tgg ttc gac acc      2221
Ala Cys Leu Ser Asp Ala Gly His Glu His Asp Thr Trp Phe Asp Thr
            690                 695                 700 atg ctt ggc ttt gcc ata tcc gcg tat gcg ctc aag agc cgg atc gcg      2269
Met Leu Gly Phe Ala Ile Ser Ala Tyr Ala Leu Lys Ser Arg Ile Ala
            705                 710                 715 ctg acg gtg gaa gac tcg ccg tat ccg ggc act ccc ggc gat ctg ctc      2317
Leu Thr Val Glu Asp Ser Pro Tyr Pro Gly Thr Pro Gly Asp Leu Leu
            720                 725                 730 gaa ctg cag atc tgc ccg ctc aac gga tat tgc gaa tgaacccttc           2363
Glu Leu Gln Ile Cys Pro Leu Asn Gly Tyr Cys Glu
735                 740                 745 cggaggtttc gacgtttccg cgcaatccgc ttgagacgat cttccgccct ggttccattc    2423
cgggaacacc gcaac atg ctg atc aac aac aag aag ctg ctt cat cac att     2474
                Met Leu Ile Asn Asn Lys Lys Leu Leu His His Ile
                                750                 755 ctg ccc atc ctg gtg ctc gcc ctg ctg ggc atg cgc acg gcc cag gcc      2522
Leu Pro Ile Leu Val Leu Ala Leu Leu Gly Met Arg Thr Ala Gln Ala
            760                 765                 770 gtt gcg cca ggc atc gtc atc ccg ccg aag gca ctg ttc acc caa cag      2570
Val Ala Pro Gly Ile Val Ile Pro Pro Lys Ala Leu Phe Thr Gln Gln
775                 780                 785                 790 ggc ggc gcc tat gga cgc tgc ccg aac gga acc cgc gcc ttg acc gtg      2618
Gly Gly Ala Tyr Gly Arg Cys Pro Asn Gly Thr Arg Ala Leu Thr Val
                795                 800                 805 gcc gaa ctg cgc ggc aac gcc gaa ttg cag acg tat ttg cgc cag ata      2666
Ala Glu Leu Arg Gly Asn Ala Glu Leu Gln Thr Tyr Leu Arg Gln Ile
```

-continued

```
                        810                     815                     820
acg ccc ggc tgg tcc ata tac ggt ctc tat gac ggt acg tac ctg ggc        2714
Thr Pro Gly Trp Ser Ile Tyr Gly Leu Tyr Asp Gly Thr Tyr Leu Gly
            825                     830                     835 cag gcg tac ggc ggc atc atc aag gac gcg ccg cca ggc gcg ggg ttc        2762
Gln Ala Tyr Gly Gly Ile Ile Lys Asp Ala Pro Pro Gly Ala Gly Phe
840                     845                     850 att tat cgc gaa act ttc tgc atc acg acc ata tac aag acc ggg caa        2810
Ile Tyr Arg Glu Thr Phe Cys Ile Thr Thr Ile Tyr Lys Thr Gly Gln
855                     860                     865                     870 ccg gct gcg gat cac tac tac agc aag gtc acg gcc acg cgc ctg ctc        2858
Pro Ala Ala Asp His Tyr Tyr Ser Lys Val Thr Ala Thr Arg Leu Leu
                875                     880                     885 gcc agc acc aac agc agg ctg tgc gcg gta ttc gtc agg gac ggg caa        2906
Ala Ser Thr Asn Ser Arg Leu Cys Ala Val Phe Val Arg Asp Gly Gln
            890                     895                     900 tcg gtc atc gga gcc tgc gcc agc ccg tat gaa ggc agg tac aga gac        2954
Ser Val Ile Gly Ala Cys Ala Ser Pro Tyr Glu Gly Arg Tyr Arg Asp
        905                     910                     915 atg tac gac gcg ctg cgg cgc ctg ctg tac atg atc tat atg tcc ggc        3002
Met Tyr Asp Ala Leu Arg Arg Leu Leu Tyr Met Ile Tyr Met Ser Gly
920                     925                     930 ctt gcc gta cgc gtc cac gtc agc aag gag gaa cag tat tac gac tac        3050
Leu Ala Val Arg Val His Val Ser Lys Glu Glu Gln Tyr Tyr Asp Tyr
935                     940                     945                     950 gag gac gcc aca ttc cag acc tat gcc ctc acc ggc att tcc ctc tgc        3098
Glu Asp Ala Thr Phe Gln Thr Tyr Ala Leu Thr Gly Ile Ser Leu Cys
                955                     960                     965 aac ccg gca gcg tcg ata tgc                                            3119
Asn Pro Ala Ala Ser Ile Cys
            970

<210> SEQ ID NO 25
<211> LENGTH: 269
<212> TYPE: PRT
<213> ORGANISM: Bordetella pertussis

<400> SEQUENCE: 25

Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Lys Tyr Asp Ser Arg Pro
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Arg Arg Tyr Thr Glu Val
                85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Val Arg Ala Asp
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160
```

```
Gln Ser Ala Tyr Leu Ala His Arg Arg Ile Pro Pro Glu Asn Ile Arg
                165                 170                 175

Arg Val Thr Arg Val Tyr His Asn Gly Ile Thr Gly Glu Thr Thr Thr
            180                 185                 190

Thr Glu Tyr Ser Asn Ala Arg Tyr Val Ser Gln Gln Thr Arg Ala Asn
        195                 200                 205

Pro Asn Pro Tyr Thr Ser Arg Arg Ser Val Ala Ser Ile Val Gly Thr
    210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
                245                 250                 255

Met Val Leu Val Tyr Tyr Glu Ser Ile Ala Tyr Ser Phe
            260                 265

<210> SEQ ID NO 26
<211> LENGTH: 226
<212> TYPE: PRT
<213> ORGANISM: Bordetella pertussis

<400> SEQUENCE: 26

Met Pro Ile Asp Arg Lys Thr Leu Cys His Leu Leu Ser Val Leu Pro
1               5                   10                  15

Leu Ala Leu Leu Gly Ser His Val Ala Arg Ala Ser Thr Pro Gly Ile
            20                  25                  30

Val Ile Pro Pro Gln Glu Gln Ile Thr Gln His Gly Ser Pro Tyr Gly
        35                  40                  45

Arg Cys Ala Asn Lys Thr Arg Ala Leu Thr Val Ala Glu Leu Arg Gly
    50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asp Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
    130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
            180                 185                 190

His Val Ser Lys Glu Glu Gln Tyr Tyr Asp Tyr Glu Asp Ala Thr Phe
        195                 200                 205

Glu Thr Tyr Ala Leu Thr Gly Ile Ser Ile Cys Asn Pro Gly Ser Ser
    210                 215                 220

Leu Cys
225

<210> SEQ ID NO 27
<211> LENGTH: 227
<212> TYPE: PRT
```

<213> ORGANISM: Bordetella pertussis

<400> SEQUENCE: 27

Met Leu Ile Asn Asn Lys Lys Leu Leu His Ile Leu Pro Ile Leu
1               5                   10                  15

Val Leu Ala Leu Leu Gly Met Arg Thr Ala Gln Ala Val Ala Pro Gly
            20                  25                  30

Ile Val Ile Pro Pro Lys Ala Leu Phe Thr Gln Gln Gly Gly Ala Tyr
        35                  40                  45

Gly Arg Cys Pro Asn Gly Thr Arg Ala Leu Thr Val Ala Glu Leu Arg
    50                  55                  60

Gly Asn Ala Glu Leu Gln Thr Tyr Leu Arg Gln Ile Thr Pro Gly Trp
65                  70                  75                  80

Ser Ile Tyr Gly Leu Tyr Asp Gly Thr Tyr Leu Gly Gln Ala Tyr Gly
                85                  90                  95

Gly Ile Ile Lys Asp Ala Pro Pro Gly Ala Gly Phe Ile Tyr Arg Glu
            100                 105                 110

Thr Phe Cys Ile Thr Thr Ile Tyr Lys Thr Gly Gln Pro Ala Ala Asp
        115                 120                 125

His Tyr Tyr Ser Lys Val Thr Ala Thr Arg Leu Leu Ala Ser Thr Asn
    130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Ala
                165                 170                 175

Leu Arg Arg Leu Leu Tyr Met Ile Tyr Met Ser Gly Leu Ala Val Arg
            180                 185                 190

Val His Val Ser Lys Glu Glu Gln Tyr Tyr Asp Tyr Glu Asp Ala Thr
        195                 200                 205

Phe Gln Thr Tyr Ala Leu Thr Gly Ile Ser Leu Cys Asn Pro Ala Ala
    210                 215                 220

Ser Ile Cys
225

<210> SEQ ID NO 28
<211> LENGTH: 131
<212> TYPE: PRT
<213> ORGANISM: Bordetella pertussis

<400> SEQUENCE: 28

Val Arg Ala Leu Ala Trp Leu Leu Ala Ser Gly Ala Met Thr His Leu
1               5                   10                  15

Ser Pro Ala Leu Ala Asp Val Pro Tyr Val Leu Val Lys Thr Asn Met
            20                  25                  30

Val Val Thr Ser Val Ala Met Lys Pro Tyr Glu Val Thr Pro Thr Arg
        35                  40                  45

Met Leu Val Cys Gly Ile Ala Ala Lys Leu Gly Ala Ala Ala Ser Ser
    50                  55                  60

Pro Asp Ala His Val Pro Phe Cys Phe Gly Lys Asp Leu Lys Arg Pro
65                  70                  75                  80

Gly Ser Ser Pro Met Glu Val Met Leu Arg Ala Val Phe Met Gln Gln
                85                  90                  95

Arg Pro Leu Arg Met Phe Leu Gly Pro Lys Gln Leu Thr Phe Glu Gly
            100                 105                 110

Lys Pro Ala Leu Glu Leu Ile Arg Met Val Glu Cys Ser Gly Lys Gln

-continued

```
                     115                 120                 125

Asp Cys Pro
    130

<210> SEQ ID NO 29
<211> LENGTH: 120
<212> TYPE: PRT
<213> ORGANISM: Bordetella pertussis

<400> SEQUENCE: 29

Met His Thr Ile Ala Ser Ile Leu Leu Ser Val Leu Gly Ile Tyr Ser
1               5                   10                  15

Pro Ala Asp Val Ala Gly Leu Pro Thr His Leu Tyr Lys Asn Phe Thr
            20                  25                  30

Val Gln Glu Leu Ala Leu Lys Leu Lys Gly Lys Asn Gln Glu Phe Cys
        35                  40                  45

Leu Thr Ala Phe Met Ser Gly Arg Ser Leu Val Arg Ala Cys Leu Ser
    50                  55                  60

Asp Ala Gly His Glu His Asp Thr Trp Phe Asp Thr Met Leu Gly Phe
65                  70                  75                  80

Ala Ile Ser Ala Tyr Ala Leu Lys Ser Arg Ile Ala Leu Thr Val Glu
                85                  90                  95

Asp Ser Pro Tyr Pro Gly Thr Pro Gly Asp Leu Leu Glu Leu Gln Ile
            100                 105                 110

Cys Pro Leu Asn Gly Tyr Cys Glu
        115                 120

<210> SEQ ID NO 30
<211> LENGTH: 451
<212> TYPE: PRT
<213> ORGANISM: Clostridium tetani

<400> SEQUENCE: 30

Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

Ser Asp Ile Ser Gly Phe Asn Ser Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
        115                 120                 125

Val Ser Leu Lys Gly Asn Asn Leu Ile Trp Thr Leu Lys Asp Ser Ala
    130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
```

```
                    180                 185                 190
        Glu Ile Thr Gly Leu Gly Ala Ile Arg Glu Asp Asn Asn Ile Thr Leu
                    195                 200                 205
        Lys Leu Asp Arg Cys Asn Asn Asn Gln Tyr Val Ser Ile Asp Lys
            210                 215                 220
        Phe Arg Ile Phe Cys Lys Ala Leu Asn Pro Lys Glu Ile Glu Lys Leu
        225                 230                 235                 240
        Tyr Thr Ser Tyr Leu Ser Ile Thr Phe Leu Arg Asp Phe Trp Gly Asn
                        245                 250                 255
        Pro Leu Arg Tyr Asp Thr Glu Tyr Tyr Leu Ile Pro Val Ala Ser Ser
                    260                 265                 270
        Ser Lys Asp Val Gln Leu Lys Asn Ile Thr Asp Tyr Met Tyr Leu Thr
                275                 280                 285
        Asn Ala Pro Ser Tyr Thr Asn Gly Lys Leu Asn Ile Tyr Tyr Arg Arg
            290                 295                 300
        Leu Tyr Asn Gly Leu Lys Phe Ile Ile Lys Arg Tyr Thr Pro Asn Asn
        305                 310                 315                 320
        Glu Ile Asp Ser Phe Val Lys Ser Gly Asp Phe Ile Lys Leu Tyr Val
                        325                 330                 335
        Ser Tyr Asn Asn Asn Glu His Ile Val Gly Tyr Pro Lys Asp Gly Asn
                    340                 345                 350
        Ala Phe Asn Asn Leu Asp Arg Ile Leu Arg Val Gly Tyr Asn Ala Pro
                355                 360                 365
        Gly Ile Pro Leu Tyr Lys Lys Met Glu Ala Val Lys Leu Arg Asp Leu
            370                 375                 380
        Lys Thr Tyr Ser Val Gln Leu Lys Leu Tyr Asp Asp Lys Asn Ala Ser
        385                 390                 395                 400
        Leu Gly Leu Val Gly Thr His Asn Gly Gln Ile Gly Asn Asp Pro Asn
                        405                 410                 415
        Arg Asp Ile Leu Ile Ala Ser Asn Trp Tyr Phe Asn His Leu Lys Asp
                    420                 425                 430
        Lys Ile Leu Gly Cys Asp Trp Tyr Phe Val Pro Thr Asp Glu Gly Trp
                435                 440                 445
        Thr Asn Asp
            450

<210> SEQ ID NO 31
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1353)

<400> SEQUENCE: 31 aaa aac ctg gac tgt tgg gtt gac aac gaa gaa gat atc gat gtc atc      48
Lys Asn Leu Asp Cys Trp Val Asp Asn Glu Glu Asp Ile Asp Val Ile
1               5                   10                  15 ctg aag aaa tcc acc att ttg aac ctc gac atc aac aat gac atc att      96
Leu Lys Lys Ser Thr Ile Leu Asn Leu Asp Ile Asn Asn Asp Ile Ile
            20                  25                  30 tcc gac att agc ggt ttc aac tcg tcc gtg att acg tac cca gat gct     144
Ser Asp Ile Ser Gly Phe Asn Ser Ser Val Ile Thr Tyr Pro Asp Ala
        35                  40                  45
```

```
                                                   -continued cag ctg gtg ccc ggg att aac ggc aag gct atc cac ctc gtc aac aac      192
Gln Leu Val Pro Gly Ile Asn Gly Lys Ala Ile His Leu Val Asn Asn
    50                  55                  60 gag tcg tcg gaa gtc atc gtc cat aaa gcg atg gac atc gag tat aac      240
Glu Ser Ser Glu Val Ile Val His Lys Ala Met Asp Ile Glu Tyr Asn
65                  70                  75                  80 gac atg ttt aat aat ttc acc gtg tcc ttt tgg ctg cgc gtg ccc aag      288
Asp Met Phe Asn Asn Phe Thr Val Ser Phe Trp Leu Arg Val Pro Lys
                85                  90                  95 gtg tcc gcc tcc cac ctg gaa cag tac ggg acc aac gag tac agc atc      336
Val Ser Ala Ser His Leu Glu Gln Tyr Gly Thr Asn Glu Tyr Ser Ile
            100                 105                 110 atc agc tcg atg aag aag cac tcg ttg agc atc ggc agc ggc tgg tcg      384
Ile Ser Ser Met Lys Lys His Ser Leu Ser Ile Gly Ser Gly Trp Ser
        115                 120                 125 gtt agt ctc aaa ggg aac aac ctg att tgg acc ctg aaa gat agc gcc      432
Val Ser Leu Lys Gly Asn Asn Leu Ile Trp Thr Leu Lys Asp Ser Ala
130                 135                 140 ggc gag gtg cgt cag atc act ttc cgg gac ctg ccg gat aag ttc aac      480
Gly Glu Val Arg Gln Ile Thr Phe Arg Asp Leu Pro Asp Lys Phe Asn
145                 150                 155                 160 gcc tac ctg gca aac aaa tgg gtg ttc att acc atc acg aac gac cgc      528
Ala Tyr Leu Ala Asn Lys Trp Val Phe Ile Thr Ile Thr Asn Asp Arg
                165                 170                 175 ctg agt agc gcg aat ctc tac atc aat ggc gtg ctg atg ggc agc gcg      576
Leu Ser Ser Ala Asn Leu Tyr Ile Asn Gly Val Leu Met Gly Ser Ala
            180                 185                 190 gaa atc acg ggc ttg ggt gcc atc cgc gaa gat aac aat atc acc ttg      624
Glu Ile Thr Gly Leu Gly Ala Ile Arg Glu Asp Asn Asn Ile Thr Leu
        195                 200                 205 aag ctg gac cgc tgc aac aac aac aac caa tac gtg tcc att gat aag      672
Lys Leu Asp Arg Cys Asn Asn Asn Asn Gln Tyr Val Ser Ile Asp Lys
210                 215                 220 ttc cgc atc ttt tgc aag gcc ctg aac ccg aaa gag atc gaa aag ctc      720
Phe Arg Ile Phe Cys Lys Ala Leu Asn Pro Lys Glu Ile Glu Lys Leu
225                 230                 235                 240 tac acc agc tac ttg agt atc acc ttc ctg cgc gac ttt tgg ggt aat      768
Tyr Thr Ser Tyr Leu Ser Ile Thr Phe Leu Arg Asp Phe Trp Gly Asn
                245                 250                 255 ccg ttg cgt tat gac acc gag tat tat ctg atc ccc gtg gcc agc agc      816
Pro Leu Arg Tyr Asp Thr Glu Tyr Tyr Leu Ile Pro Val Ala Ser Ser
            260                 265                 270 agc aag gac gtc cag ctg aag aac atc acc gac tac atg tac ttg act      864
Ser Lys Asp Val Gln Leu Lys Asn Ile Thr Asp Tyr Met Tyr Leu Thr
        275                 280                 285 aac gcg ccc tcg tat acc aat ggc aaa ctg aac att tac tac cgc cgg      912
Asn Ala Pro Ser Tyr Thr Asn Gly Lys Leu Asn Ile Tyr Tyr Arg Arg
290                 295                 300 ctc tac aac ggg ctc aag ttc atc atc aaa cgc tat acg ccg aat aat      960
Leu Tyr Asn Gly Leu Lys Phe Ile Ile Lys Arg Tyr Thr Pro Asn Asn
305                 310                 315                 320 gaa atc gac agt ttt gtc aag agc ggc gac ttc atc aag ttg tac gtg     1008
Glu Ile Asp Ser Phe Val Lys Ser Gly Asp Phe Ile Lys Leu Tyr Val
                325                 330                 335 agc tac aat aac aac gag cac atc gtt ggt tac cct aag gat ggc aac     1056
Ser Tyr Asn Asn Asn Glu His Ile Val Gly Tyr Pro Lys Asp Gly Asn
            340                 345                 350 gct ttc aac aac ctc gat cgt atc ctg cgg gtt ggc tac aac gca cca     1104
Ala Phe Asn Asn Leu Asp Arg Ile Leu Arg Val Gly Tyr Asn Ala Pro
        355                 360                 365
```

```
ggc att ccg ctg tat aag aag atg gaa gcg gtc aaa ctg cgt gac ctg        1152
Gly Ile Pro Leu Tyr Lys Lys Met Glu Ala Val Lys Leu Arg Asp Leu
    370                 375                 380 aaa acc tac tcc gtg caa ctg aag ctg tac gac gac aag aat gcc tcg        1200
Lys Thr Tyr Ser Val Gln Leu Lys Leu Tyr Asp Asp Lys Asn Ala Ser
385                 390                 395                 400 ttg ggt ctg gtc ggc acg cat aat ggt cag att ggc aac gac ccg aac        1248
Leu Gly Leu Val Gly Thr His Asn Gly Gln Ile Gly Asn Asp Pro Asn
                405                 410                 415 cgg gac atc ctg atc gcc agc aac tgg tat ttc aat cac ctg aag gat        1296
Arg Asp Ile Leu Ile Ala Ser Asn Trp Tyr Phe Asn His Leu Lys Asp
            420                 425                 430 aag atc ttg ggc tgc gat tgg tat ttc gtc cct acc gat gag ggc tgg        1344
Lys Ile Leu Gly Cys Asp Trp Tyr Phe Val Pro Thr Asp Glu Gly Trp
        435                 440                 445 act aat gac                                                            1353
Thr Asn Asp
    450
```

<210> SEQ ID NO 32
<211> LENGTH: 2366
<212> TYPE: PRT
<213> ORGANISM: Clostridium difficile

<400> SEQUENCE: 32

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
```

-continued

```
                245                 250                 255
Gln Glu Leu Val Glu Arg Trp Asn Leu Ala Ala Ala Ser Asp Ile Leu
                260                 265                 270
Arg Ile Ser Ala Leu Lys Glu Ile Gly Gly Met Tyr Leu Asp Val Asp
            275                 280                 285
Met Leu Pro Gly Ile Gln Pro Asp Leu Phe Glu Ser Ile Glu Lys Pro
        290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
                340                 345                 350
Lys Ser Asp Lys Ser Glu Ile Phe Ser Ser Leu Gly Asp Met Glu Ala
            355                 360                 365
Ser Pro Leu Glu Val Lys Ile Ala Phe Asn Ser Lys Gly Ile Ile Asn
        370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
                420                 425                 430
Asp Ser Ile Met Ala Glu Ala Asn Ala Asp Asn Gly Arg Phe Met Met
            435                 440                 445
Glu Leu Gly Lys Tyr Leu Arg Val Gly Phe Phe Pro Asp Val Lys Thr
        450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
                500                 505                 510
Glu Gln Glu Met Ala Ser Leu Trp Ser Phe Asp Asp Ala Arg Ala Lys
            515                 520                 525
Ala Gln Phe Glu Glu Tyr Lys Arg Asn Tyr Phe Glu Gly Ser Leu Gly
        530                 535                 540
Glu Asp Asp Asn Leu Asp Phe Ser Gln Asn Ile Val Val Asp Lys Glu
545                 550                 555                 560
Tyr Leu Leu Glu Lys Ile Ser Ser Leu Ala Arg Ser Ser Glu Arg Gly
                565                 570                 575
Tyr Ile His Tyr Ile Val Gln Leu Gln Gly Asp Lys Ile Ser Tyr Glu
                580                 585                 590
Ala Ala Cys Asn Leu Phe Ala Lys Thr Pro Tyr Asp Ser Val Leu Phe
            595                 600                 605
Gln Lys Asn Ile Glu Asp Ser Glu Ile Ala Tyr Tyr Tyr Asn Pro Gly
        610                 615                 620
Asp Gly Glu Ile Gln Glu Ile Asp Lys Tyr Lys Ile Pro Ser Ile Ile
625                 630                 635                 640
Ser Asp Arg Pro Lys Ile Lys Leu Thr Phe Ile Gly His Gly Lys Asp
                645                 650                 655
Glu Phe Asn Thr Asp Ile Phe Ala Gly Phe Asp Val Asp Ser Leu Ser
                660                 665                 670
```

```
Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
            690                 695                 700

Ile Asn Val Glu Thr Tyr Pro Gly Lys Leu Leu Lys Val Lys
705             710                 715                 720

Asp Lys Ile Ser Glu Leu Met Pro Ser Ile Ser Gln Asp Ser Ile Ile
                    725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
            770                 775                 780

Asn Lys Ile Thr Val Lys Ser Lys Asn Leu Pro Glu Leu Ser Thr Leu
785             790                 795                 800

Leu Gln Glu Ile Arg Asn Asn Ser Asn Ser Ser Asp Ile Glu Leu Glu
                    805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
            850                 855                 860

Ile Ser Asp Ala Leu Cys Asp Leu Lys Gln Gln Asn Glu Leu Glu Asp
865             870                 875                 880

Ser His Phe Ile Ser Phe Glu Asp Ile Ser Glu Thr Asp Glu Gly Phe
                    885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
            930                 935                 940

Val Lys Lys Val Asn Leu Asp Thr Thr His Glu Val Asn Thr Leu Asn
945             950                 955                 960

Ala Ala Phe Phe Ile Gln Ser Leu Ile Glu Tyr Asn Ser Ser Lys Glu
                    965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro
            1010                1015                1020

Thr Leu Ser Glu Gly Leu Pro Ile Ile Ala Thr Ile Ile Asp Gly
            1025                1030                1035

Val Ser Leu Gly Ala Ala Ile Lys Glu Leu Ser Glu Thr Ser Asp
            1040                1045                1050

Pro Leu Leu Arg Gln Glu Ile Glu Ala Lys Ile Gly Ile Met Ala
            1055                1060                1065

Val Asn Leu Thr Thr Ala Thr Thr Ala Ile Ile Thr Ser Ser Leu
            1070                1075                1080
```

```
Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Ile Ile Thr Thr Glu Tyr Ile
    1295                1300                1305

Arg Glu Lys Leu Ser Tyr Ser Phe Tyr Gly Ser Gly Gly Thr Tyr
    1310                1315                1320

Ala Leu Ser Leu Ser Gln Tyr Asn Met Gly Ile Asn Ile Glu Leu
    1325                1330                1335

Ser Glu Ser Asp Val Trp Ile Ile Asp Val Asp Asn Val Val Arg
    1340                1345                1350

Asp Val Thr Ile Glu Ser Asp Lys Ile Lys Lys Gly Asp Leu Ile
    1355                1360                1365

Glu Gly Ile Leu Ser Thr Leu Ser Ile Glu Glu Asn Lys Ile Ile
    1370                1375                1380

Leu Asn Ser His Glu Ile Asn Phe Ser Gly Glu Val Asn Gly Ser
    1385                1390                1395

Asn Gly Phe Val Ser Leu Thr Phe Ser Ile Leu Glu Gly Ile Asn
    1400                1405                1410

Ala Ile Ile Glu Val Asp Leu Leu Ser Lys Ser Tyr Lys Leu Leu
    1415                1420                1425

Ile Ser Gly Glu Leu Lys Ile Leu Met Leu Asn Ser Asn His Ile
    1430                1435                1440

Gln Gln Lys Ile Asp Tyr Ile Gly Phe Asn Ser Glu Leu Gln Lys
    1445                1450                1455

Asn Ile Pro Tyr Ser Phe Val Asp Ser Glu Gly Lys Glu Asn Gly
    1460                1465                1470

Phe Ile Asn Gly Ser Thr Lys Glu Gly Leu Phe Val Ser Glu Leu
```

-continued

```
            1475                1480                1485

Pro Asp Val Val Leu Ile Ser Lys Val Tyr Met Asp Asp Ser Lys
    1490                1495                1500

Pro Ser Phe Gly Tyr Tyr Ser Asn Asn Leu Lys Asp Val Lys Val
    1505                1510                1515

Ile Thr Lys Asp Asn Val Asn Ile Leu Thr Gly Tyr Tyr Leu Lys
    1520                1525                1530

Asp Asp Ile Lys Ile Ser Leu Ser Leu Thr Leu Gln Asp Glu Lys
    1535                1540                1545

Thr Ile Lys Leu Asn Ser Val His Leu Asp Glu Ser Gly Val Ala
    1550                1555                1560

Glu Ile Leu Lys Phe Met Asn Arg Lys Gly Asn Thr Asn Thr Ser
    1565                1570                1575

Asp Ser Leu Met Ser Phe Leu Glu Ser Met Asn Ile Lys Ser Ile
    1580                1585                1590

Phe Val Asn Phe Leu Gln Ser Asn Ile Lys Phe Ile Leu Asp Ala
    1595                1600                1605

Asn Phe Ile Ile Ser Gly Thr Thr Ser Ile Gly Gln Phe Glu Phe
    1610                1615                1620

Ile Cys Asp Glu Asn Asp Asn Ile Gln Pro Tyr Phe Ile Lys Phe
    1625                1630                1635

Asn Thr Leu Glu Thr Asn Tyr Thr Leu Tyr Val Gly Asn Arg Gln
    1640                1645                1650

Asn Met Ile Val Glu Pro Asn Tyr Asp Leu Asp Asp Ser Gly Asp
    1655                1660                1665

Ile Ser Ser Thr Val Ile Asn Phe Ser Gln Lys Tyr Leu Tyr Gly
    1670                1675                1680

Ile Asp Ser Cys Val Asn Lys Val Val Ile Ser Pro Asn Ile Tyr
    1685                1690                1695

Thr Asp Glu Ile Asn Ile Thr Pro Val Tyr Glu Thr Asn Asn Thr
    1700                1705                1710

Tyr Pro Glu Val Ile Val Leu Asp Ala Asn Tyr Ile Asn Glu Lys
    1715                1720                1725

Ile Asn Val Asn Ile Asn Asp Leu Ser Ile Arg Tyr Val Trp Ser
    1730                1735                1740

Asn Asp Gly Asn Asp Phe Ile Leu Met Ser Thr Ser Glu Glu Asn
    1745                1750                1755

Lys Val Ser Gln Val Lys Ile Arg Phe Val Asn Val Phe Lys Asp
    1760                1765                1770

Lys Thr Leu Ala Asn Lys Leu Ser Phe Asn Phe Ser Asp Lys Gln
    1775                1780                1785

Asp Val Pro Val Ser Glu Ile Ile Leu Ser Phe Thr Pro Ser Tyr
    1790                1795                1800

Tyr Glu Asp Gly Leu Ile Gly Tyr Asp Leu Gly Leu Val Ser Leu
    1805                1810                1815

Tyr Asn Glu Lys Phe Tyr Ile Asn Asn Phe Gly Met Met Val Ser
    1820                1825                1830

Gly Leu Ile Tyr Ile Asn Asp Ser Leu Tyr Tyr Phe Lys Pro Pro
    1835                1840                1845

Val Asn Asn Leu Ile Thr Gly Phe Val Thr Val Gly Asp Asp Lys
    1850                1855                1860

Tyr Tyr Phe Asn Pro Ile Asn Gly Gly Ala Ala Ser Ile Gly Glu
    1865                1870                1875
```

```
Thr Ile Ile Asp Asp Lys Asn Tyr Tyr Phe Asn Gln Ser Gly Val
    1880            1885                1890

Leu Gln Thr Gly Val Phe Ser Thr Glu Asp Gly Phe Lys Tyr Phe
    1895            1900                1905

Ala Pro Ala Asn Thr Leu Asp Glu Asn Leu Glu Gly Glu Ala Ile
    1910            1915                1920

Asp Phe Thr Gly Lys Leu Ile Ile Asp Glu Asn Ile Tyr Tyr Phe
    1925            1930                1935

Asp Asp Asn Tyr Arg Gly Ala Val Glu Trp Lys Glu Leu Asp Gly
    1940            1945                1950

Glu Met His Tyr Phe Ser Pro Glu Thr Gly Lys Ala Phe Lys Gly
    1955            1960                1965

Leu Asn Gln Ile Gly Asp Tyr Lys Tyr Tyr Phe Asn Ser Asp Gly
    1970            1975                1980

Val Met Gln Lys Gly Phe Val Ser Ile Asn Asp Asn Lys His Tyr
    1985            1990                1995

Phe Asp Asp Ser Gly Val Met Lys Val Gly Tyr Thr Glu Ile Asp
    2000            2005                2010

Gly Lys His Phe Tyr Phe Ala Glu Asn Gly Glu Met Gln Ile Gly
    2015            2020                2025

Val Phe Asn Thr Glu Asp Gly Phe Lys Tyr Phe Ala His His Asn
    2030            2035                2040

Glu Asp Leu Gly Asn Glu Glu Gly Glu Ile Ser Tyr Ser Gly
    2045            2050                2055

Ile Leu Asn Phe Asn Asn Lys Ile Tyr Tyr Phe Asp Asp Ser Phe
    2060            2065                2070

Thr Ala Val Val Gly Trp Lys Asp Leu Glu Asp Gly Ser Lys Tyr
    2075            2080                2085

Tyr Phe Asp Glu Asp Thr Ala Glu Ala Tyr Ile Gly Leu Ser Leu
    2090            2095                2100

Ile Asn Asp Gly Gln Tyr Tyr Phe Asn Asp Asp Gly Ile Met Gln
    2105            2110                2115

Val Gly Phe Val Thr Ile Asn Asp Lys Val Phe Tyr Phe Ser Asp
    2120            2125                2130

Ser Gly Ile Ile Glu Ser Gly Val Gln Asn Ile Asp Asp Asn Tyr
    2135            2140                2145

Phe Tyr Ile Asp Asp Asn Gly Ile Val Gln Ile Gly Val Phe Asp
    2150            2155                2160

Thr Ser Asp Gly Tyr Lys Tyr Phe Ala Pro Ala Asn Thr Val Asn
    2165            2170                2175

Asp Asn Ile Tyr Gly Gln Ala Val Glu Tyr Ser Gly Leu Val Arg
    2180            2185                2190

Val Gly Glu Asp Val Tyr Tyr Phe Gly Glu Thr Tyr Thr Ile Glu
    2195            2200                2205

Thr Gly Trp Ile Tyr Asp Met Glu Asn Glu Ser Asp Lys Tyr Tyr
    2210            2215                2220

Phe Asn Pro Glu Thr Lys Lys Ala Cys Lys Gly Ile Asn Leu Ile
    2225            2230                2235

Asp Asp Ile Lys Tyr Tyr Phe Asp Glu Lys Gly Ile Met Arg Thr
    2240            2245                2250

Gly Leu Ile Ser Phe Glu Asn Asn Asn Tyr Tyr Phe Asn Glu Asn
    2255            2260                2265
```

```
Gly Glu Met Gln Phe Gly Tyr Ile Asn Ile Glu Asp Lys Met Phe
    2270            2275                2280

Tyr Phe Gly Glu Asp Gly Val Met Gln Ile Gly Val Phe Asn Thr
        2285            2290                2295

Pro Asp Gly Phe Lys Tyr Phe Ala His Gln Asn Thr Leu Asp Glu
    2300            2305                2310

Asn Phe Glu Gly Glu Ser Ile Asn Tyr Thr Gly Trp Leu Asp Leu
    2315            2320                2325

Asp Glu Lys Arg Tyr Tyr Phe Thr Asp Glu Tyr Ile Ala Ala Thr
    2330            2335                2340

Gly Ser Val Ile Ile Asp Gly Glu Glu Tyr Tyr Phe Asp Pro Asp
    2345            2350                2355

Thr Ala Gln Leu Val Ile Ser Glu
    2360            2365

<210> SEQ ID NO 33
<211> LENGTH: 7098
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(7098)

<400> SEQUENCE: 33 atg tcc ctc gtc aat cgc aag cag ctg gag aag atg gcc aac gtt cgt      48
Met Ser Leu Val Asn Arg Lys Gln Leu Glu Lys Met Ala Asn Val Arg
1               5                   10                  15 ttc cgc acc caa gag gac gaa tac gtc gcc atc ctc gac gcc ctg gaa      96
Phe Arg Thr Gln Glu Asp Glu Tyr Val Ala Ile Leu Asp Ala Leu Glu
                20                  25                  30 gaa tac cat aac atg agc gaa aac acc gtt gtc gag aag tac ctc aag     144
Glu Tyr His Asn Met Ser Glu Asn Thr Val Val Glu Lys Tyr Leu Lys
            35                  40                  45 ctg aag gac atc aac agc ctg acg gac atc tat atc gac acg tac aag     192
Leu Lys Asp Ile Asn Ser Leu Thr Asp Ile Tyr Ile Asp Thr Tyr Lys
        50                  55                  60 aag tcc ggt cgc aac aag gca ctc aag aag ttc aaa gag tac ctg gtc     240
Lys Ser Gly Arg Asn Lys Ala Leu Lys Lys Phe Lys Glu Tyr Leu Val
65                  70                  75                  80 acc gaa gtg ttg gaa ctc aag aac aac aac ctc acg ccg gtg gaa aag     288
Thr Glu Val Leu Glu Leu Lys Asn Asn Asn Leu Thr Pro Val Glu Lys
                85                  90                  95 aac ctg cat ttc gtg tgg att ggc ggc cag atc aac gac acc gcc atc     336
Asn Leu His Phe Val Trp Ile Gly Gly Gln Ile Asn Asp Thr Ala Ile
                100                 105                 110 aac tac att aac cag tgg aaa gac gtc aac tcg gac tac aat gtg aat     384
Asn Tyr Ile Asn Gln Trp Lys Asp Val Asn Ser Asp Tyr Asn Val Asn
            115                 120                 125 gtg ttc tat gac tcg aac gcc ttt ttg atc aac acg ctg aag aaa acc     432
Val Phe Tyr Asp Ser Asn Ala Phe Leu Ile Asn Thr Leu Lys Lys Thr
        130                 135                 140 gtc gtg gaa tcg gcc atc aat gac acc ctg gaa agc ttc cgt gaa aac     480
Val Val Glu Ser Ala Ile Asn Asp Thr Leu Glu Ser Phe Arg Glu Asn
145                 150                 155                 160 ctc aac gat cct cgg ttt gac tac aac aag ttt ttc cgc aag cgc atg     528
Leu Asn Asp Pro Arg Phe Asp Tyr Asn Lys Phe Phe Arg Lys Arg Met
                165                 170                 175
```

```
gag atc atc tat gac aag cag aaa aac ttt atc aac tac tac aaa gcg      576
Glu Ile Ile Tyr Asp Lys Gln Lys Asn Phe Ile Asn Tyr Tyr Lys Ala
            180                 185                 190 cag cgc gaa gag aac ccg gag ctg atc atc gac gat atc gtg aaa acc      624
Gln Arg Glu Glu Asn Pro Glu Leu Ile Ile Asp Asp Ile Val Lys Thr
        195                 200                 205 tat ctg tcc aac gag tat agt aaa gaa atc gat gag ctg aac acg tat      672
Tyr Leu Ser Asn Glu Tyr Ser Lys Glu Ile Asp Glu Leu Asn Thr Tyr
        210                 215                 220 atc gaa gag agt ctg aac aag atc act cag aac agc ggt aac gac gtc      720
Ile Glu Glu Ser Leu Asn Lys Ile Thr Gln Asn Ser Gly Asn Asp Val
225                 230                 235                 240 cgg aac ttt gaa gag ttc aaa aac ggc gag tcg ttc aac ctc tac gaa      768
Arg Asn Phe Glu Glu Phe Lys Asn Gly Glu Ser Phe Asn Leu Tyr Glu
                245                 250                 255 cag gag ctg gtc gag cgc tgg aac ctg gca gcg gcg tcg gac atc ctg      816
Gln Glu Leu Val Glu Arg Trp Asn Leu Ala Ala Ala Ser Asp Ile Leu
            260                 265                 270 cgt atc agc gct ctg aaa gag atc ggc ggc atg tac ctg gac gtg gat      864
Arg Ile Ser Ala Leu Lys Glu Ile Gly Gly Met Tyr Leu Asp Val Asp
        275                 280                 285 atg ctc cct ggc atc cag cct gat ctg ttt gaa tcg att gaa aag cca      912
Met Leu Pro Gly Ile Gln Pro Asp Leu Phe Glu Ser Ile Glu Lys Pro
        290                 295                 300 tcg agc gtg acc gtc gac ttt tgg gag atg acc aag ctg gag gcg atc      960
Ser Ser Val Thr Val Asp Phe Trp Glu Met Thr Lys Leu Glu Ala Ile
305                 310                 315                 320 atg aag tac aaa gaa tac atc ccg gag tat acg agt gaa cac ttt gat     1008
Met Lys Tyr Lys Glu Tyr Ile Pro Glu Tyr Thr Ser Glu His Phe Asp
                325                 330                 335 atg ctg gac gaa gaa gtg caa tcc tcg ttt gaa agc gtc ctg gcg agc     1056
Met Leu Asp Glu Glu Val Gln Ser Ser Phe Glu Ser Val Leu Ala Ser
            340                 345                 350 aag agt gat aag agc gaa atc ttc tcg tcc ttg ggc gat atg gag gcg     1104
Lys Ser Asp Lys Ser Glu Ile Phe Ser Ser Leu Gly Asp Met Glu Ala
        355                 360                 365 tcc cca ctg gag gtc aaa atc gcc ttc aac agc aag ggc att atc aat     1152
Ser Pro Leu Glu Val Lys Ile Ala Phe Asn Ser Lys Gly Ile Ile Asn
        370                 375                 380 cag ggc ctg att tcg gtc aag gat agc tac tgc agc aac ctg atc gtc     1200
Gln Gly Leu Ile Ser Val Lys Asp Ser Tyr Cys Ser Asn Leu Ile Val
385                 390                 395                 400 aag cag atc gag aac cgt tac aag atc ctg aac aac agt ctg aac ccc     1248
Lys Gln Ile Glu Asn Arg Tyr Lys Ile Leu Asn Asn Ser Leu Asn Pro
                405                 410                 415 gcc atc agc gaa gat aat gac ttc aat acc acg acg aac acg ttt atc     1296
Ala Ile Ser Glu Asp Asn Asp Phe Asn Thr Thr Thr Asn Thr Phe Ile
            420                 425                 430 gac tcc atc atg gcc gaa gcc aac gcg gac aac ggc cgc ttt atg atg     1344
Asp Ser Ile Met Ala Glu Ala Asn Ala Asp Asn Gly Arg Phe Met Met
        435                 440                 445 gag ttg ggg aag tac ctg cgc gtg ggc ttc ttc ccg gac gtg aaa acc     1392
Glu Leu Gly Lys Tyr Leu Arg Val Gly Phe Phe Pro Asp Val Lys Thr
450                 455                 460 acg atc aat ctc tcc ggc cca gaa gcg tat gca gcc gca tac caa gat     1440
Thr Ile Asn Leu Ser Gly Pro Glu Ala Tyr Ala Ala Ala Tyr Gln Asp
465                 470                 475                 480 ctg ctc atg ttc aaa gag ggc tcg atg aac atc cat ctg att gag gcg     1488
Leu Leu Met Phe Lys Glu Gly Ser Met Asn Ile His Leu Ile Glu Ala
                485                 490                 495
```

```
gac ttg cgc aac ttc gaa atc tcg aaa acg aac atc agc caa tcg acg      1536
Asp Leu Arg Asn Phe Glu Ile Ser Lys Thr Asn Ile Ser Gln Ser Thr
            500                 505                 510 gag cag gaa atg gcg agc ctg tgg tcc ttc gac gat gct cgc gcc aag      1584
Glu Gln Glu Met Ala Ser Leu Trp Ser Phe Asp Asp Ala Arg Ala Lys
        515                 520                 525 gcc caa ttt gaa gag tac aaa cgg aac tac ttc gaa ggc tcg ctg ggt      1632
Ala Gln Phe Glu Glu Tyr Lys Arg Asn Tyr Phe Glu Gly Ser Leu Gly
    530                 535                 540 gag gat gac aac ttg gac ttc tcg caa aac atc gtc gtg gac aaa gaa      1680
Glu Asp Asp Asn Leu Asp Phe Ser Gln Asn Ile Val Val Asp Lys Glu
545                 550                 555                 560 tac ctg ttg gaa aag atc agc tcc ctg gcc cgg agc tcg gaa cgg ggc      1728
Tyr Leu Leu Glu Lys Ile Ser Ser Leu Ala Arg Ser Ser Glu Arg Gly
                565                 570                 575 tac atc cac tac att gtt cag ctg caa ggg gat aag atc tcg tat gaa      1776
Tyr Ile His Tyr Ile Val Gln Leu Gln Gly Asp Lys Ile Ser Tyr Glu
            580                 585                 590 gcg gcg tgc aat ctc ttc gcc aag acg ccg tac gac tcc gtg ctg ttc      1824
Ala Ala Cys Asn Leu Phe Ala Lys Thr Pro Tyr Asp Ser Val Leu Phe
        595                 600                 605 cag aag aac atc gag gac agt gaa atc gcc tac tat tac aac ccc ggt      1872
Gln Lys Asn Ile Glu Asp Ser Glu Ile Ala Tyr Tyr Tyr Asn Pro Gly
    610                 615                 620 gac ggc gaa atc caa gaa att gat aag tac aag atc ccg tcc att atc      1920
Asp Gly Glu Ile Gln Glu Ile Asp Lys Tyr Lys Ile Pro Ser Ile Ile
625                 630                 635                 640 tcc gat cgt ccg aag atc aaa ctc acc ttc att ggc cac ggg aag gac      1968
Ser Asp Arg Pro Lys Ile Lys Leu Thr Phe Ile Gly His Gly Lys Asp
                645                 650                 655 gag ttc aac acc gat atc ttc gca ggt ttt gac gtg gat agt ctc tcg      2016
Glu Phe Asn Thr Asp Ile Phe Ala Gly Phe Asp Val Asp Ser Leu Ser
            660                 665                 670 acc gag atc gag gcc gcg atc gac ctg gcg aaa gag gac att tcg cca      2064
Thr Glu Ile Glu Ala Ala Ile Asp Leu Ala Lys Glu Asp Ile Ser Pro
        675                 680                 685 aag tcg atc gaa atc aac ctg ctg ggc tgc aat atg ttt tcg tat agt      2112
Lys Ser Ile Glu Ile Asn Leu Leu Gly Cys Asn Met Phe Ser Tyr Ser
    690                 695                 700 atc aac gtt gaa gaa acc tat ccg ggc aaa ctc ctg ctg aag gtc aag      2160
Ile Asn Val Glu Glu Thr Tyr Pro Gly Lys Leu Leu Leu Lys Val Lys
705                 710                 715                 720 gac aag att agc gaa ctg atg ccg agc atc tcg cag gat agc atc atc      2208
Asp Lys Ile Ser Glu Leu Met Pro Ser Ile Ser Gln Asp Ser Ile Ile
                725                 730                 735 gtg agt gct aac cag tat gag gtg cgt atc aac agc gag ggt cgc cgc      2256
Val Ser Ala Asn Gln Tyr Glu Val Arg Ile Asn Ser Glu Gly Arg Arg
            740                 745                 750 gag ctg ctc gat cac tcg ggc gag tgg atc aac aaa gaa gag agc atc      2304
Glu Leu Leu Asp His Ser Gly Glu Trp Ile Asn Lys Glu Glu Ser Ile
        755                 760                 765 atc aaa gat atc agc agt aaa gaa tac att agt ttc aac ccg aaa gag      2352
Ile Lys Asp Ile Ser Ser Lys Glu Tyr Ile Ser Phe Asn Pro Lys Glu
    770                 775                 780 aac aag atc acg gtg aaa tcg aag aat ttg ccg gag ttg agt acc ctg      2400
Asn Lys Ile Thr Val Lys Ser Lys Asn Leu Pro Glu Leu Ser Thr Leu
785                 790                 795                 800 ctg cag gag atc cgt aac aat tcc aac tcc agt gat atc gaa ctc gaa      2448
Leu Gln Glu Ile Arg Asn Asn Ser Asn Ser Ser Asp Ile Glu Leu Glu
```

|  |  |  |  |  |  |  |  |  |  |  |  |  |  |  |  |
|---|---|---|---|---|---|---|---|---|---|---|---|---|---|---|---|
|  |  |  |  | 805 |  |  |  | 810 |  |  |  | 815 |  |  |  |
| gaa | aag | gtc | atg | ctg | acc | gag | tgc | gag | atc | aat | gtc | atc | agc | aac | atc |
| Glu | Lys | Val | Met | Leu | Thr | Glu | Cys | Glu | Ile | Asn | Val | Ile | Ser | Asn | Ile |
|  |  |  | 820 |  |  |  | 825 |  |  |  | 830 |  |  |  |  |

2496 gac act cag atc gtg gaa gaa cgc att gaa gag gcc aag aac ctg acc    2544
Asp Thr Gln Ile Val Glu Glu Arg Ile Glu Glu Ala Lys Asn Leu Thr
            835                 840                 845 tcg gac tcg atc aac tat atc aaa gac gag ttc aag ctg att gaa tcc    2592
Ser Asp Ser Ile Asn Tyr Ile Lys Asp Glu Phe Lys Leu Ile Glu Ser
    850                 855                 860 atc tcg gat gcc ctg tgc gac ctg aag cag cag aac gag ttg gag gat    2640
Ile Ser Asp Ala Leu Cys Asp Leu Lys Gln Gln Asn Glu Leu Glu Asp
865                 870                 875                 880 agc cac ttc atc agt ttc gag gat atc tcg gag act gac gag ggc ttc    2688
Ser His Phe Ile Ser Phe Glu Asp Ile Ser Glu Thr Asp Glu Gly Phe
                885                 890                 895 agc atc cgt ttc atc aac aaa gaa acc ggt gaa tcc att ttc gtt gaa    2736
Ser Ile Arg Phe Ile Asn Lys Glu Thr Gly Glu Ser Ile Phe Val Glu
            900                 905                 910 acg gag aaa acc att ttc agc gaa tac gcc aat cac atc acc gaa gag    2784
Thr Glu Lys Thr Ile Phe Ser Glu Tyr Ala Asn His Ile Thr Glu Glu
        915                 920                 925 atc agc aag atc aag ggt act atc ttt gac acg gtg aat ggc aaa ctg    2832
Ile Ser Lys Ile Lys Gly Thr Ile Phe Asp Thr Val Asn Gly Lys Leu
    930                 935                 940 gtg aag aaa gtc aac ctg gac acc acc cac gag gtc aac acc ctg aac    2880
Val Lys Lys Val Asn Leu Asp Thr Thr His Glu Val Asn Thr Leu Asn
945                 950                 955                 960 gcc gcg ttc ttc atc caa agc ctg atc gaa tac aac agc tcc aaa gaa    2928
Ala Ala Phe Phe Ile Gln Ser Leu Ile Glu Tyr Asn Ser Ser Lys Glu
                965                 970                 975 tcc ttg agc aac ttg agc gtg gcc atg aaa gtg cag gtg tat gcc cag    2976
Ser Leu Ser Asn Leu Ser Val Ala Met Lys Val Gln Val Tyr Ala Gln
            980                 985                 990 ttg ttc tcg acc ggc ctg aac acc att acg gac gcg gca aag gtg gtt    3024
Leu Phe Ser Thr Gly Leu Asn Thr Ile Thr Asp Ala Ala Lys Val Val
        995                 1000                1005 gaa ctg gtc agc acc gcc ttg gac gaa acc atc gac ctg ctg ccg        3069
Glu Leu Val Ser Thr Ala Leu Asp Glu Thr Ile Asp Leu Leu Pro
    1010                1015                1020 acc ctg agc gag ggc ctg ccc atc atc gcc acg atc att gac ggg        3114
Thr Leu Ser Glu Gly Leu Pro Ile Ile Ala Thr Ile Ile Asp Gly
1025                1030                1035 gtc agc ctg ggc gca gcc atc aaa gag ttg agc gag act tcc gac        3159
Val Ser Leu Gly Ala Ala Ile Lys Glu Leu Ser Glu Thr Ser Asp
    1040                1045                1050 ccg ctg ctg cgc cag gaa atc gaa gct aag atc ggg atc atg gcc        3204
Pro Leu Leu Arg Gln Glu Ile Glu Ala Lys Ile Gly Ile Met Ala
    1055                1060                1065 gtg aat ctg acc acc gcg acc acc gcg atc att acc tcc agc ctc        3249
Val Asn Leu Thr Thr Ala Thr Thr Ala Ile Ile Thr Ser Ser Leu
    1070                1075                1080 ggc att gcg tcc ggc ttc tcc atc ctg ctg gtc ccc ttg gcg ggc        3294
Gly Ile Ala Ser Gly Phe Ser Ile Leu Leu Val Pro Leu Ala Gly
    1085                1090                1095 atc agc gcc ggt atc cct agc ttg gtg aac aac gag ttg gtc ctg        3339
Ile Ser Ala Gly Ile Pro Ser Leu Val Asn Asn Glu Leu Val Leu
    1100                1105                1110 cgt gat aaa gcg acc aag gtt gtg gat tac ttc aag cat gtc tcc        3384

|  |  |  |  |  |  |  |  |  |  |  |
|---|---|---|---|---|---|---|---|---|---|---|
| Arg | Asp | Lys | Ala | Thr | Lys | Val | Asp | Tyr | Phe | Lys | His | Val | Ser |
| 1115 |  |  |  | 1120 |  |  |  | 1125 |  |  |

```
ctg gtc gaa acg gaa ggg gtg ttc acc ctg ctg gac gat aag att      3429
Leu Val Glu Thr Glu Gly Val Phe Thr Leu Leu Asp Asp Lys Ile
1130                1135                1140 atg atg ccc caa gac gat ttg gtc atc agc gaa att gac ttt aac      3474
Met Met Pro Gln Asp Asp Leu Val Ile Ser Glu Ile Asp Phe Asn
1145                1150                1155 aac aat tcg atc gtc ctc ggg aag tgt gaa atc tgg cgg atg gag      3519
Asn Asn Ser Ile Val Leu Gly Lys Cys Glu Ile Trp Arg Met Glu
1160                1165                1170 ggc ggt tcg ggc cac acc gtg acc gat gat atc gac cat ttc ttt      3564
Gly Gly Ser Gly His Thr Val Thr Asp Asp Ile Asp His Phe Phe
1175                1180                1185 agt gcg ccc tcc atc acg tac cgc gag ccg cac ctg agc atc tac      3609
Ser Ala Pro Ser Ile Thr Tyr Arg Glu Pro His Leu Ser Ile Tyr
1190                1195                1200 gac gtg ctc gag gtg cag aaa gaa gaa ctg gat ctg tcc aaa gat      3654
Asp Val Leu Glu Val Gln Lys Glu Glu Leu Asp Leu Ser Lys Asp
1205                1210                1215 ctg atg gtt ctg ccg aac gct ccc aat cgg gtg ttc gct tgg gaa      3699
Leu Met Val Leu Pro Asn Ala Pro Asn Arg Val Phe Ala Trp Glu
1220                1225                1230 acg ggc tgg acg cca ggc ctc cgc tcg ctg gag aac gac ggg act      3744
Thr Gly Trp Thr Pro Gly Leu Arg Ser Leu Glu Asn Asp Gly Thr
1235                1240                1245 aag ttg ctg gat cgc att cgc gac aat tac gaa ggc gaa ttc tac      3789
Lys Leu Leu Asp Arg Ile Arg Asp Asn Tyr Glu Gly Glu Phe Tyr
1250                1255                1260 tgg cgc tac ttt gcg ttt atc gcc gac gct ctg att acc acc ctg      3834
Trp Arg Tyr Phe Ala Phe Ile Ala Asp Ala Leu Ile Thr Thr Leu
1265                1270                1275 aag ccg cgg tac gag gac act aac atc cgc atc aat ctg gat agc      3879
Lys Pro Arg Tyr Glu Asp Thr Asn Ile Arg Ile Asn Leu Asp Ser
1280                1285                1290 aac act cgc agc ttc att gtc ccg atc atc acc act gaa tac att      3924
Asn Thr Arg Ser Phe Ile Val Pro Ile Ile Thr Thr Glu Tyr Ile
1295                1300                1305 cgc gaa aag ctg agc tac agc ttt tac ggt agc ggt ggt acc tat      3969
Arg Glu Lys Leu Ser Tyr Ser Phe Tyr Gly Ser Gly Gly Thr Tyr
1310                1315                1320 gcc ctg agc ctg tcc cag tac aac atg ggc atc aac att gaa ttg      4014
Ala Leu Ser Leu Ser Gln Tyr Asn Met Gly Ile Asn Ile Glu Leu
1325                1330                1335 tcg gag agc gat gtg tgg atc att gac gtg gat aat gtc gtc cgc      4059
Ser Glu Ser Asp Val Trp Ile Ile Asp Val Asp Asn Val Val Arg
1340                1345                1350 gat gtg acc att gag agc gac aaa atc aag aaa ggg gat ttg atc      4104
Asp Val Thr Ile Glu Ser Asp Lys Ile Lys Lys Gly Asp Leu Ile
1355                1360                1365 gaa ggc atc ctg tcg acc ttg agc atc gaa gag aat aag atc atc      4149
Glu Gly Ile Leu Ser Thr Leu Ser Ile Glu Glu Asn Lys Ile Ile
1370                1375                1380 ctg aat agc cac gaa atc aac ttc tcc ggc gaa gtg aac ggc agc      4194
Leu Asn Ser His Glu Ile Asn Phe Ser Gly Glu Val Asn Gly Ser
1385                1390                1395 aac ggc ttc gtc agc ctg acc ttt tcc atc ctg gaa ggt atc aac      4239
Asn Gly Phe Val Ser Leu Thr Phe Ser Ile Leu Glu Gly Ile Asn
1400                1405                1410
```

```
gcc atc att gag gtc gat ctg ctc agc aaa agc tac aag ctg ctc    4284
Ala Ile Ile Glu Val Asp Leu Leu Ser Lys Ser Tyr Lys Leu Leu
    1415            1420                1425 atc tcg ggc gag ctg aaa atc ctc atg ttg aat tcg aat cac atc    4329
Ile Ser Gly Glu Leu Lys Ile Leu Met Leu Asn Ser Asn His Ile
            1430                1435                1440 caa cag aaa atc gac tat atc ggc ttc aac agc gag ctg caa aag    4374
Gln Gln Lys Ile Asp Tyr Ile Gly Phe Asn Ser Glu Leu Gln Lys
        1445                1450                1455 aac atc ccc tac tcg ttt gtg gac agc gaa ggc aaa gag aac ggc    4419
Asn Ile Pro Tyr Ser Phe Val Asp Ser Glu Gly Lys Glu Asn Gly
    1460                1465                1470 ttc atc aac ggc tcc acc aaa gag ggg ctg ttc gtg agc gag ctg    4464
Phe Ile Asn Gly Ser Thr Lys Glu Gly Leu Phe Val Ser Glu Leu
        1475                1480                1485 ccg gac gtg gtg ctc atc agc aaa gtg tat atg gac gac agc aag    4509
Pro Asp Val Val Leu Ile Ser Lys Val Tyr Met Asp Asp Ser Lys
    1490                1495                1500 cct agt ttt ggc tac tac tcc aat aac ctg aaa gat gtt aaa gtg    4554
Pro Ser Phe Gly Tyr Tyr Ser Asn Asn Leu Lys Asp Val Lys Val
    1505                1510                1515 att acc aag gat aac gtg aac atc ctc acc ggt tac tac ctg aag    4599
Ile Thr Lys Asp Asn Val Asn Ile Leu Thr Gly Tyr Tyr Leu Lys
    1520                1525                1530 gac gac att aag atc agc ctg tcc ctg acc ctg caa gat gaa aag    4644
Asp Asp Ile Lys Ile Ser Leu Ser Leu Thr Leu Gln Asp Glu Lys
    1535                1540                1545 acc atc aaa ttg aat agc gtc cat ctc gac gag agt ggt gtc gcc    4689
Thr Ile Lys Leu Asn Ser Val His Leu Asp Glu Ser Gly Val Ala
    1550                1555                1560 gag atc ttg aag ttc atg aat cgc aag ggt aat acc aac acg agc    4734
Glu Ile Leu Lys Phe Met Asn Arg Lys Gly Asn Thr Asn Thr Ser
    1565                1570                1575 gac tcg ttg atg tcc ttc ctg gaa agc atg aac atc aag agc att    4779
Asp Ser Leu Met Ser Phe Leu Glu Ser Met Asn Ile Lys Ser Ile
    1580                1585                1590 ttc gtg aac ttc ctg caa agc aat atc aag ttc att ttg gac gcg    4824
Phe Val Asn Phe Leu Gln Ser Asn Ile Lys Phe Ile Leu Asp Ala
    1595                1600                1605 aac ttt atc atc tcc ggg acc acg tcc atc ggc cag ttt gag ttc    4869
Asn Phe Ile Ile Ser Gly Thr Thr Ser Ile Gly Gln Phe Glu Phe
    1610                1615                1620 atc tgt gac gag aac gac aac att cag ccg tat ttc atc aag ttc    4914
Ile Cys Asp Glu Asn Asp Asn Ile Gln Pro Tyr Phe Ile Lys Phe
    1625                1630                1635 aat acc ttg gaa act aac tac acc ctg tac gtt ggc aac cgg caa    4959
Asn Thr Leu Glu Thr Asn Tyr Thr Leu Tyr Val Gly Asn Arg Gln
    1640                1645                1650 aac atg att gtc gaa ccc aac tat gac ttg gat gac agt ggt gat    5004
Asn Met Ile Val Glu Pro Asn Tyr Asp Leu Asp Asp Ser Gly Asp
    1655                1660                1665 atc agt agc acc gtg att aac ttt tcc cag aag tac ctg tat ggc    5049
Ile Ser Ser Thr Val Ile Asn Phe Ser Gln Lys Tyr Leu Tyr Gly
    1670                1675                1680 atc gac tcc tgc gtg aac aaa gtg gtg atc tcg ccg aat atc tac    5094
Ile Asp Ser Cys Val Asn Lys Val Val Ile Ser Pro Asn Ile Tyr
    1685                1690                1695 acg gac gaa atc aat atc act ccc gtc tat gaa acc aac aac acc    5139
Thr Asp Glu Ile Asn Ile Thr Pro Val Tyr Glu Thr Asn Asn Thr
    1700                1705                1710
```

| | | | | | | | | | | |
|---|---|---|---|---|---|---|---|---|---|---|
| tac | ccc | gag | gtg | att | gtc | ttg | gat | gcg | aac tac att aac gaa aag | 5184 |
| Tyr | Pro | Glu | Val | Ile | Val | Leu | Asp | Ala | Asn Tyr Ile Asn Glu Lys | |
| | 1715 | | | | 1720 | | | | 1725 | |
| att | aac | gtg | aac | att | aac | gac | ctg | agc | atc cgg tat gtg tgg agt | 5229 |
| Ile | Asn | Val | Asn | Ile | Asn | Asp | Leu | Ser | Ile Arg Tyr Val Trp Ser | |
| | 1730 | | | | 1735 | | | | 1740 | |
| aat | gac | ggg | aac | gac | ttc | att | ctg | atg | agc acc tcc gaa gaa aac | 5274 |
| Asn | Asp | Gly | Asn | Asp | Phe | Ile | Leu | Met | Ser Thr Ser Glu Glu Asn | |
| | 1745 | | | | 1750 | | | | 1755 | |
| aaa | gtc | tcg | caa | gtc | aag | atc | cgc | ttc | gtt aac gtt ttc aaa gac | 5319 |
| Lys | Val | Ser | Gln | Val | Lys | Ile | Arg | Phe | Val Asn Val Phe Lys Asp | |
| | 1760 | | | | 1765 | | | | 1770 | |
| aag | acc | ttg | gcc | aac | aaa | ctc | agc | ttc | aat ttc tcg gac aaa cag | 5364 |
| Lys | Thr | Leu | Ala | Asn | Lys | Leu | Ser | Phe | Asn Phe Ser Asp Lys Gln | |
| | 1775 | | | | 1780 | | | | 1785 | |
| gac | gtg | cct | gtg | tcg | gag | atc | att | ctc | agt ttc acc ccg agc tac | 5409 |
| Asp | Val | Pro | Val | Ser | Glu | Ile | Ile | Leu | Ser Phe Thr Pro Ser Tyr | |
| | 1790 | | | | 1795 | | | | 1800 | |
| tac | gag | gac | ggc | ctg | atc | ggt | tac | gac | ctg ggc ctg gtt agc ctc | 5454 |
| Tyr | Glu | Asp | Gly | Leu | Ile | Gly | Tyr | Asp | Leu Gly Leu Val Ser Leu | |
| | 1805 | | | | 1810 | | | | 1815 | |
| tac | aac | gaa | aag | ttc | tat | atc | aac | aat | ttc ggg atg atg gtt tcg | 5499 |
| Tyr | Asn | Glu | Lys | Phe | Tyr | Ile | Asn | Asn | Phe Gly Met Met Val Ser | |
| | 1820 | | | | 1825 | | | | 1830 | |
| ggt | ctg | atc | tat | atc | aat | gac | agc | ttg | tac tac ttc aaa cct ccg | 5544 |
| Gly | Leu | Ile | Tyr | Ile | Asn | Asp | Ser | Leu | Tyr Tyr Phe Lys Pro Pro | |
| | 1835 | | | | 1840 | | | | 1845 | |
| gtg | aac | aat | ttg | atc | acc | ggc | ttc | gtg | acc gtg ggc gat gac aag | 5589 |
| Val | Asn | Asn | Leu | Ile | Thr | Gly | Phe | Val | Thr Val Gly Asp Asp Lys | |
| | 1850 | | | | 1855 | | | | 1860 | |
| tac | tat | ttc | aac | ccg | att | aac | ggt | ggc | gct gcg tcg att ggc gaa | 5634 |
| Tyr | Tyr | Phe | Asn | Pro | Ile | Asn | Gly | Gly | Ala Ala Ser Ile Gly Glu | |
| | 1865 | | | | 1870 | | | | 1875 | |
| acc | atc | atc | gac | gac | aag | aac | tac | tat | ttc aac cag agc ggt gtg | 5679 |
| Thr | Ile | Ile | Asp | Asp | Lys | Asn | Tyr | Tyr | Phe Asn Gln Ser Gly Val | |
| | 1880 | | | | 1885 | | | | 1890 | |
| ctg | caa | acc | ggg | gtc | ttt | agc | acg | gag | gat ggg ttt aag tat ttc | 5724 |
| Leu | Gln | Thr | Gly | Val | Phe | Ser | Thr | Glu | Asp Gly Phe Lys Tyr Phe | |
| | 1895 | | | | 1900 | | | | 1905 | |
| gcg | cct | gcc | aat | acc | ctg | gac | gag | aat | ttg gag ggc gaa gcc att | 5769 |
| Ala | Pro | Ala | Asn | Thr | Leu | Asp | Glu | Asn | Leu Glu Gly Glu Ala Ile | |
| | 1910 | | | | 1915 | | | | 1920 | |
| gac | ttc | acc | ggc | aaa | ctg | att | atc | gac | gaa aac atc tac tat ttc | 5814 |
| Asp | Phe | Thr | Gly | Lys | Leu | Ile | Ile | Asp | Glu Asn Ile Tyr Tyr Phe | |
| | 1925 | | | | 1930 | | | | 1935 | |
| gat | gac | aac | tac | cgc | ggt | gcg | gtc | gaa | tgg aaa gag ttg gac ggg | 5859 |
| Asp | Asp | Asn | Tyr | Arg | Gly | Ala | Val | Glu | Trp Lys Glu Leu Asp Gly | |
| | 1940 | | | | 1945 | | | | 1950 | |
| gag | atg | cac | tat | ttc | tcg | cca | gag | act | ggt aag gcc ttc aag ggc | 5904 |
| Glu | Met | His | Tyr | Phe | Ser | Pro | Glu | Thr | Gly Lys Ala Phe Lys Gly | |
| | 1955 | | | | 1960 | | | | 1965 | |
| ctg | aac | cag | atc | ggc | gac | tac | aag | tac | tat ttc aat agc gac ggc | 5949 |
| Leu | Asn | Gln | Ile | Gly | Asp | Tyr | Lys | Tyr | Tyr Phe Asn Ser Asp Gly | |
| | 1970 | | | | 1975 | | | | 1980 | |
| gtg | atg | cag | aag | ggg | ttc | gtc | agc | atc | aac gac aac aag cat tac | 5994 |
| Val | Met | Gln | Lys | Gly | Phe | Val | Ser | Ile | Asn Asp Asn Lys His Tyr | |
| | 1985 | | | | 1990 | | | | 1995 | |
| ttc | gac | gat | agc | ggc | gtt | atg | aag | gtg | ggc tat act gag atc gac | 6039 |
| Phe | Asp | Asp | Ser | Gly | Val | Met | Lys | Val | Gly Tyr Thr Glu Ile Asp | |

```
                    2000                 2005                  2010
ggc aag cac ttc tat ttc gcc gag aac ggc gag atg caa atc ggc    6084
Gly Lys His Phe Tyr Phe Ala Glu Asn Gly Glu Met Gln Ile Gly
    2015                 2020                 2025 gtg ttc aac acc gag gac ggc ttc aaa tac ttc gct cat cac aac    6129
Val Phe Asn Thr Glu Asp Gly Phe Lys Tyr Phe Ala His His Asn
    2030                 2035                 2040 gaa gat ctc ggt aat gaa gaa ggt gaa gag att tcc tat tcg ggc    6174
Glu Asp Leu Gly Asn Glu Glu Gly Glu Glu Ile Ser Tyr Ser Gly
    2045                 2050                 2055 atc ctg aac ttc aac aat aag atc tac tac ttt gat gac tcg ttc    6219
Ile Leu Asn Phe Asn Asn Lys Ile Tyr Tyr Phe Asp Asp Ser Phe
    2060                 2065                 2070 acc gcc gtg gtg ggt tgg aag gac ttg gag gac ggg agc aag tat    6264
Thr Ala Val Val Gly Trp Lys Asp Leu Glu Asp Gly Ser Lys Tyr
    2075                 2080                 2085 tac ttc gac gaa gat acc gcc gag gca tac atc ggc ttg tcg ctc    6309
Tyr Phe Asp Glu Asp Thr Ala Glu Ala Tyr Ile Gly Leu Ser Leu
    2090                 2095                 2100 atc aac gac ggt cag tac tac ttc aac gac gat ggc atc atg cag    6354
Ile Asn Asp Gly Gln Tyr Tyr Phe Asn Asp Asp Gly Ile Met Gln
    2105                 2110                 2115 gtg ggc ttc gtg act atc aac gac aag gtg ttc tac ttc agt gac    6399
Val Gly Phe Val Thr Ile Asn Asp Lys Val Phe Tyr Phe Ser Asp
    2120                 2125                 2130 agt ggc atc att gag tcg ggc gtg cag aat atc gac gat aac tat    6444
Ser Gly Ile Ile Glu Ser Gly Val Gln Asn Ile Asp Asp Asn Tyr
    2135                 2140                 2145 ttc tat atc gat gac aat ggc att gtg cag atc ggc gtg ttt gat    6489
Phe Tyr Ile Asp Asp Asn Gly Ile Val Gln Ile Gly Val Phe Asp
    2150                 2155                 2160 acc tcc gat ggg tat aag tat ttc gca cca gca aat acc gtc aat    6534
Thr Ser Asp Gly Tyr Lys Tyr Phe Ala Pro Ala Asn Thr Val Asn
    2165                 2170                 2175 gac aac atc tac ggc cag gcc gtg gag tac agc ggg ctg gtt cgt    6579
Asp Asn Ile Tyr Gly Gln Ala Val Glu Tyr Ser Gly Leu Val Arg
    2180                 2185                 2190 gtg ggc gag gac gtt tac tat ttc ggt gag act tat act atc gaa    6624
Val Gly Glu Asp Val Tyr Tyr Phe Gly Glu Thr Tyr Thr Ile Glu
    2195                 2200                 2205 acc ggc tgg atc tat gat atg gaa aac gaa tcg gat aag tac tac    6669
Thr Gly Trp Ile Tyr Asp Met Glu Asn Glu Ser Asp Lys Tyr Tyr
    2210                 2215                 2220 ttt aac cca gaa acg aag aaa gcc tgc aag ggc atc aac ctc att    6714
Phe Asn Pro Glu Thr Lys Lys Ala Cys Lys Gly Ile Asn Leu Ile
    2225                 2230                 2235 gat gac atc aag tat tac ttt gac gaa aag ggt atc atg cgc acc    6759
Asp Asp Ile Lys Tyr Tyr Phe Asp Glu Lys Gly Ile Met Arg Thr
    2240                 2245                 2250 ggc ctg atc tcg ttt gag aac aac aac tac tat ttc aac gag aat    6804
Gly Leu Ile Ser Phe Glu Asn Asn Asn Tyr Tyr Phe Asn Glu Asn
    2255                 2260                 2265 ggc gaa atg cag ttt ggg tac atc aat atc gag gat aag atg ttc    6849
Gly Glu Met Gln Phe Gly Tyr Ile Asn Ile Glu Asp Lys Met Phe
    2270                 2275                 2280 tac ttt ggg gag gac ggc gtc atg cag att ggt gtg ttt aac acc    6894
Tyr Phe Gly Glu Asp Gly Val Met Gln Ile Gly Val Phe Asn Thr
    2285                 2290                 2295 ccg gat ggc ttc aag tac ttc gcc cat cag aac act ctg gac gaa    6939
```

```
Pro Asp Gly Phe Lys Tyr Phe Ala His Gln Asn Thr Leu Asp Glu
    2300                2305                2310 aac ttc gag ggc gaa agc atc aat tac act ggc tgg ctg gac ctg        6984
Asn Phe Glu Gly Glu Ser Ile Asn Tyr Thr Gly Trp Leu Asp Leu
    2315                2320                2325 gat gag aaa cgc tac tac ttc acc gac gag tac att gcc gcc acg        7029
Asp Glu Lys Arg Tyr Tyr Phe Thr Asp Glu Tyr Ile Ala Ala Thr
    2330                2335                2340 ggc tcc gtg att atc gac ggc gaa gaa tac tat ttc gat ccc gac        7074
Gly Ser Val Ile Ile Asp Gly Glu Glu Tyr Tyr Phe Asp Pro Asp
    2345                2350                2355 acc gcc cag ttg gtc att agc gaa                                    7098
Thr Ala Gln Leu Val Ile Ser Glu
    2360                2365

<210> SEQ ID NO 34
<211> LENGTH: 613
<212> TYPE: PRT
<213> ORGANISM: Pseudomonas aeruginosa
<220> FEATURE:
<221> NAME/KEY: MOD_RES
<222> LOCATION: (426)..(426)
<223> OTHER INFORMATION: His or Tyr
<220> FEATURE:
<221> NAME/KEY: MOD_RES
<222> LOCATION: (553)..(553)
<223> OTHER INFORMATION: May or may not be present

<400> SEQUENCE: 34

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu
        50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240
```

```
Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Ser Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Ile Ser Phe Ser Thr Arg Gly Thr Gln Asn
                405                 410                 415

Trp Thr Val Glu Arg Leu Leu Gln Ala Xaa Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 35
<211> LENGTH: 3119
<212> TYPE: DNA
<213> ORGANISM: Bordetella pertussis
<220> FEATURE:
```

```
<221> NAME/KEY: CDS
<222> LOCATION: (1)..(807)
<220> FEATURE:
<221> NAME/KEY: CDS
<222> LOCATION: (850)..(1527)
<220> FEATURE:
<221> NAME/KEY: CDS
<222> LOCATION: (1587)..(1979)
<220> FEATURE:
<221> NAME/KEY: CDS
<222> LOCATION: (1994)..(2353)
<220> FEATURE:
<221> NAME/KEY: CDS
<222> LOCATION: (2439)..(3119)

<400> SEQUENCE: 35
```

| | | | | | | | | | | | | | | | | |
|---|---|---|---|---|---|---|---|---|---|---|---|---|---|---|---|---|
| atg | cgt | tgc | act | cgg | gca | att | cgc | caa | acc | gca | aga | aca | ggc | tgg | ctg | 48 |
| Met | Arg | Cys | Thr | Arg | Ala | Ile | Arg | Gln | Thr | Ala | Arg | Thr | Gly | Trp | Leu | |
| 1 | | | | 5 | | | | | 10 | | | | | 15 | | |
| acg | tgg | ctg | gcg | att | ctt | gcc | gtc | acg | gcg | ccc | gtg | act | tcg | ccg | gca | 96 |
| Thr | Trp | Leu | Ala | Ile | Leu | Ala | Val | Thr | Ala | Pro | Val | Thr | Ser | Pro | Ala | |
| | | | 20 | | | | | 25 | | | | | 30 | | | |
| tgg | gcc | gac | gat | cct | ccc | gcc | acc | gta | tac | cgc | tat | gac | tcc | cgc | ccg | 144 |
| Trp | Ala | Asp | Asp | Pro | Pro | Ala | Thr | Val | Tyr | Arg | Tyr | Asp | Ser | Arg | Pro | |
| | | 35 | | | | | 40 | | | | | 45 | | | | |
| ccg | gag | gac | gtt | ttc | cag | aac | gga | ttc | acg | gcg | tgg | gga | aac | aac | gac | 192 |
| Pro | Glu | Asp | Val | Phe | Gln | Asn | Gly | Phe | Thr | Ala | Trp | Gly | Asn | Asn | Asp | |
| | 50 | | | | | 55 | | | | | 60 | | | | | |
| aat | gtg | ctc | gac | cat | ctg | acc | gga | cgt | tcc | tgc | cag | gtc | ggc | agc | agc | 240 |
| Asn | Val | Leu | Asp | His | Leu | Thr | Gly | Arg | Ser | Cys | Gln | Val | Gly | Ser | Ser | |
| 65 | | | | | 70 | | | | | 75 | | | | | 80 | |
| aac | agc | gct | ttc | gtc | tcc | acc | agc | agc | cgg | cgc | tat | acc | gag | gtc | | 288 |
| Asn | Ser | Ala | Phe | Val | Ser | Thr | Ser | Ser | Arg | Arg | Tyr | Thr | Glu | Val | | |
| | | | | 85 | | | | | 90 | | | | | 95 | | |
| tat | ctc | gaa | cat | cgc | atg | cag | gaa | gcg | gtc | gag | gcc | gaa | cgc | gcc | ggc | 336 |
| Tyr | Leu | Glu | His | Arg | Met | Gln | Glu | Ala | Val | Glu | Ala | Glu | Arg | Ala | Gly | |
| | | | 100 | | | | | 105 | | | | | 110 | | | |
| agg | ggc | acc | ggc | cac | ttc | atc | ggc | tac | atc | tac | gaa | gtc | cgc | gcc | gac | 384 |
| Arg | Gly | Thr | Gly | His | Phe | Ile | Gly | Tyr | Ile | Tyr | Glu | Val | Arg | Ala | Asp | |
| | | 115 | | | | | 120 | | | | | 125 | | | | |
| aac | aat | ttc | tac | ggc | gcc | gcc | agc | tcg | tac | ttc | gaa | tac | gtc | gac | act | 432 |
| Asn | Asn | Phe | Tyr | Gly | Ala | Ala | Ser | Ser | Tyr | Phe | Glu | Tyr | Val | Asp | Thr | |
| | 130 | | | | | 135 | | | | | 140 | | | | | |
| tat | ggc | gac | aat | gcc | ggc | cgt | atc | ctc | gcc | ggc | gcg | ctg | gcc | acc | tac | 480 |
| Tyr | Gly | Asp | Asn | Ala | Gly | Arg | Ile | Leu | Ala | Gly | Ala | Leu | Ala | Thr | Tyr | |
| 145 | | | | | 150 | | | | | 155 | | | | | 160 | |
| cag | agc | gaa | tat | ctg | gca | cac | cgg | cgc | att | ccg | ccc | gaa | aac | atc | cgc | 528 |
| Gln | Ser | Glu | Tyr | Leu | Ala | His | Arg | Arg | Ile | Pro | Pro | Glu | Asn | Ile | Arg | |
| | | | | 165 | | | | | 170 | | | | | 175 | | |
| agg | gta | acg | cgg | gtc | tat | cac | aac | ggc | atc | acc | ggc | gag | acc | acg | acc | 576 |
| Arg | Val | Thr | Arg | Val | Tyr | His | Asn | Gly | Ile | Thr | Gly | Glu | Thr | Thr | Thr | |
| | | | 180 | | | | | 185 | | | | | 190 | | | |
| acg | gag | tat | tcc | aac | gct | cgc | tac | gtc | agc | cag | cag | act | cgc | gcc | aat | 624 |
| Thr | Glu | Tyr | Ser | Asn | Ala | Arg | Tyr | Val | Ser | Gln | Gln | Thr | Arg | Ala | Asn | |
| | | 195 | | | | | 200 | | | | | 205 | | | | |
| ccc | aac | ccc | tac | aca | tcg | cga | agg | tcc | gta | gcg | tcg | atc | gtc | ggc | aca | 672 |
| Pro | Asn | Pro | Tyr | Thr | Ser | Arg | Arg | Ser | Val | Ala | Ser | Ile | Val | Gly | Thr | |
| | 210 | | | | | 215 | | | | | 220 | | | | | |
| ttg | gtg | cgc | atg | gcg | ccg | gtg | ata | ggc | gct | tgc | atg | gcg | cgg | cag | gcc | 720 |
| Leu | Val | Arg | Met | Ala | Pro | Val | Ile | Gly | Ala | Cys | Met | Ala | Arg | Gln | Ala | |
| 225 | | | | | 230 | | | | | 235 | | | | | 240 | |
| gaa | agc | tcc | gag | gcc | atg | gca | gcc | tgg | tcc | gaa | cgc | gcc | ggc | gag | gcg | 768 |
| Glu | Ser | Ser | Glu | Ala | Met | Ala | Ala | Trp | Ser | Glu | Arg | Ala | Gly | Glu | Ala | |

```
                      245                 250                 255
atg gtt ctc gtg tac tac gaa agc atc gcg tat tcg ttc tagacctggc       817
Met Val Leu Val Tyr Tyr Glu Ser Ile Ala Tyr Ser Phe
        260                 265 ccagccccgc ccaactccgg taattgaaca gc atg ccg atc gac cgc aag acg     870
                                  Met Pro Ile Asp Arg Lys Thr
                                      270                 275 ctc tgc cat ctc ctg tcc gtt ctg ccg ttg gcc ctc ctc gga tct cac     918
Leu Cys His Leu Leu Ser Val Leu Pro Leu Ala Leu Leu Gly Ser His
            280                 285                 290 gtg gcg cgg gcc tcc acg cca ggc atc gtc att ccg ccg cag gaa cag     966
Val Ala Arg Ala Ser Thr Pro Gly Ile Val Ile Pro Pro Gln Glu Gln
                295                 300                 305 att acc cag cat ggc agc ccc tat gga cgc tgc gcg aac aag acc cgt    1014
Ile Thr Gln His Gly Ser Pro Tyr Gly Arg Cys Ala Asn Lys Thr Arg
        310                 315                 320 gcc ctg acc gtg gcg gaa ttg cgc ggc agc ggc gat ctg cag gag tac    1062
Ala Leu Thr Val Ala Glu Leu Arg Gly Ser Gly Asp Leu Gln Glu Tyr
325                 330                 335                 340 ctg cgt cat gtg acg cgc ggc tgg tca ata ttt gcg ctc tac gat ggc    1110
Leu Arg His Val Thr Arg Gly Trp Ser Ile Phe Ala Leu Tyr Asp Gly
            345                 350                 355 acc tat ctc ggc ggc gaa tat ggc ggc gtg atc aag gac gga aca ccc    1158
Thr Tyr Leu Gly Gly Glu Tyr Gly Gly Val Ile Lys Asp Gly Thr Pro
        360                 365                 370 ggc ggc gca ttc gac ctg aaa acg acg ttc tgc atc atg acc acg cgc    1206
Gly Gly Ala Phe Asp Leu Lys Thr Thr Phe Cys Ile Met Thr Thr Arg
                375                 380                 385 aat acg ggt caa ccc gca acg gat cac tac tac agc aac gtc acc gcc    1254
Asn Thr Gly Gln Pro Ala Thr Asp His Tyr Tyr Ser Asn Val Thr Ala
        390                 395                 400 act cgc ctg ctc tcc agc acc aac agc agg cta tgc gcg gtc ttc gtc    1302
Thr Arg Leu Leu Ser Ser Thr Asn Ser Arg Leu Cys Ala Val Phe Val
405                 410                 415                 420 aga agc ggg caa ccg gtc att ggc gcc tgc acc agc ccg tat gac ggc    1350
Arg Ser Gly Gln Pro Val Ile Gly Ala Cys Thr Ser Pro Tyr Asp Gly
            425                 430                 435 aag tac tgg agc atg tac agc cgg ctg cgg aaa atg ctt tac ctg atc    1398
Lys Tyr Trp Ser Met Tyr Ser Arg Leu Arg Lys Met Leu Tyr Leu Ile
        440                 445                 450 tac gtg gcc ggc atc tcc gta cgc gtc cat gtc agc aag gaa gaa cag    1446
Tyr Val Ala Gly Ile Ser Val Arg Val His Val Ser Lys Glu Glu Gln
                455                 460                 465 tat tac gac tat gag gac gca acg ttc gag act tac gcc ctt acc ggc    1494
Tyr Tyr Asp Tyr Glu Asp Ala Thr Phe Glu Thr Tyr Ala Leu Thr Gly
        470                 475                 480 atc tcc atc tgc aat cct gga tca tcc tta tgc tgagacgctt ccccactcga  1547
Ile Ser Ile Cys Asn Pro Gly Ser Ser Leu Cys
485                 490                 495 accaccgccc cgggacaggg cggcgccggg cggtcgcgc gtg cgc gcc ctg gcg     1601
                                           Val Arg Ala Leu Ala
                                                           500 tgg ttg ctg gca tcc ggc gcg atg acg cat ctt tcc ccc gcc ctg gcc    1649
Trp Leu Leu Ala Ser Gly Ala Met Thr His Leu Ser Pro Ala Leu Ala
            505                 510                 515 gac gtt cct tat gtg ctg gtg aag acc aat atg gtg gtc acc agc gta    1697
Asp Val Pro Tyr Val Leu Val Lys Thr Asn Met Val Val Thr Ser Val
        520                 525                 530 gcc atg aag ccg tat gaa gtc acc ccg acg cgc atg ctg gtc tgc ggc    1745
```

|  |  |
|---|---|
| Ala Met Lys Pro Tyr Glu Val Thr Pro Thr Arg Met Leu Val Cys Gly<br>            535                  540                  545 |  |
| atc gcc gcc aaa ctg ggc gcc gcg gcc agc agc ccg gac gcg cac gtg<br>Ile Ala Ala Lys Leu Gly Ala Ala Ser Ser Pro Asp Ala His Val<br>550                    555                  560 | 1793 |
| ccg ttc tgc ttc ggc aag gat ctc aag cgt ccc ggc agc agt ccc atg<br>Pro Phe Cys Phe Gly Lys Asp Leu Lys Arg Pro Gly Ser Ser Pro Met<br>565                    570                  575                  580 | 1841 |
| gaa gtc atg ttg cgc gcc gtc ttc atg caa caa cgg ccg ctg cgc atg<br>Glu Val Met Leu Arg Ala Val Phe Met Gln Gln Arg Pro Leu Arg Met<br>                    585                  590                  595 | 1889 |
| ttt ctg ggt ccc aag caa ctc act ttc gaa ggc aag ccc gcg ctc gaa<br>Phe Leu Gly Pro Lys Gln Leu Thr Phe Glu Gly Lys Pro Ala Leu Glu<br>            600                  605                  610 | 1937 |
| ctg atc cgg atg gtc gaa tgc agc ggc aag cag gat tgc ccc<br>Leu Ile Arg Met Val Glu Cys Ser Gly Lys Gln Asp Cys Pro<br>615                    620                  625 | 1979 |
| tgaaggcgaa cccc atg cat acc atc gca tcc atc ctg ttg tcc gtg ctc<br>                    Met His Thr Ile Ala Ser Ile Leu Leu Ser Val Leu<br>                                    630                  635 | 2029 |
| ggc ata tac agc ccg gct gac gtc gcc ggc ttg ccg acc cat ctg tac<br>Gly Ile Tyr Ser Pro Ala Asp Val Ala Gly Leu Pro Thr His Leu Tyr<br>      640                    645                  650 | 2077 |
| aag aac ttc act gtc cag gag ctg gcc ttg aaa ctg aag ggc aag aat<br>Lys Asn Phe Thr Val Gln Glu Leu Ala Leu Lys Leu Lys Gly Lys Asn<br>655                    660                  665                  670 | 2125 |
| cag gag ttc tgc ctg acc gcc ttc atg tcg ggc aga agc ctg gtc cgg<br>Gln Glu Phe Cys Leu Thr Ala Phe Met Ser Gly Arg Ser Leu Val Arg<br>            675                  680                  685 | 2173 |
| gcg tgc ctg tcc gac gcg gga cac gag cac gac acg tgg ttc gac acc<br>Ala Cys Leu Ser Asp Ala Gly His Glu His Asp Thr Trp Phe Asp Thr<br>                  690                  695                  700 | 2221 |
| atg ctt ggc ttt gcc ata tcc gcg tat gcg ctc aag agc cgg atc gcg<br>Met Leu Gly Phe Ala Ile Ser Ala Tyr Ala Leu Lys Ser Arg Ile Ala<br>                705                  710                  715 | 2269 |
| ctg acg gtg gaa gac tcg ccg tat ccg ggc act ccc ggc gat ctg ctc<br>Leu Thr Val Glu Asp Ser Pro Tyr Pro Gly Thr Pro Gly Asp Leu Leu<br>720                    725                  730 | 2317 |
| gaa ctg cag atc tgc ccg ctc aac gga tat tgc gaa tgaacccttc<br>Glu Leu Gln Ile Cys Pro Leu Asn Gly Tyr Cys Glu<br>735                    740                  745 | 2363 |
| cggaggtttc gacgtttccg cgcaatccgc ttgagacgat cttccgccct ggttccattc | 2423 |
| cgggaacacc gcaac atg ctg atc aac aac aag aag ctg ctt cat cac att<br>                 Met Leu Ile Asn Asn Lys Lys Leu Leu His His Ile<br>                                    750                  755 | 2474 |
| ctg ccc atc ctg gtg ctc gcc ctg ctg ggc atg cgc acg gcc cag gcc<br>Leu Pro Ile Leu Val Leu Ala Leu Leu Gly Met Arg Thr Ala Gln Ala<br>            760                  765                  770 | 2522 |
| gtt gcg cca ggc atc gtc atc ccg ccg aag gca ctg ttc acc caa cag<br>Val Ala Pro Gly Ile Val Ile Pro Pro Lys Ala Leu Phe Thr Gln Gln<br>775                    780                  785                  790 | 2570 |
| ggc ggc gcc tat gga cgc tgc ccg aac gga acc cgc gcc ttg acc gtg<br>Gly Gly Ala Tyr Gly Arg Cys Pro Asn Gly Thr Arg Ala Leu Thr Val<br>                795                  800                  805 | 2618 |
| gcc gaa ctg cgc ggc aac gcc gaa ttg cag acg tat ttg cgc cag ata<br>Ala Glu Leu Arg Gly Asn Ala Glu Leu Gln Thr Tyr Leu Arg Gln Ile<br>            810                  815                  820 | 2666 |
| acg ccc ggc tgg tcc ata tac ggt ctc tat gac ggt acg tac ctg ggc<br>Thr Pro Gly Trp Ser Ile Tyr Gly Leu Tyr Asp Gly Thr Tyr Leu Gly | 2714 |

```
                       825                 830                 835
cag gcg tac ggc ggc atc atc aag gac gcg ccg cca ggc gcg ggg ttc        2762
Gln Ala Tyr Gly Gly Ile Ile Lys Asp Ala Pro Pro Gly Ala Gly Phe
    840                 845                 850 att tat cgc gaa act ttc tgc atc acg acc ata tac aag acc ggg caa        2810
Ile Tyr Arg Glu Thr Phe Cys Ile Thr Thr Ile Tyr Lys Thr Gly Gln
855                 860                 865                 870 ccg gct gcg gat cac tac tac agc aag gtc acg gcc acg cgc ctg ctc        2858
Pro Ala Ala Asp His Tyr Tyr Ser Lys Val Thr Ala Thr Arg Leu Leu
                875                 880                 885 gcc agc acc aac agc agg ctg tgc gcg gta ttc gtc agg gac ggg caa        2906
Ala Ser Thr Asn Ser Arg Leu Cys Ala Val Phe Val Arg Asp Gly Gln
            890                 895                 900 tcg gtc atc gga gcc tgc gcc agc ccg tat gaa ggc agg tac aga gac        2954
Ser Val Ile Gly Ala Cys Ala Ser Pro Tyr Glu Gly Arg Tyr Arg Asp
        905                 910                 915 atg tac gac gcg ctg cgg cgc ctg ctc tac atg atc tat atg tcc ggc        3002
Met Tyr Asp Ala Leu Arg Arg Leu Leu Tyr Met Ile Tyr Met Ser Gly
    920                 925                 930 ctt gcc gta cgc gtc cac gtc agc aag gag gaa cag tat tac gac tac        3050
Leu Ala Val Arg Val His Val Ser Lys Glu Glu Gln Tyr Tyr Asp Tyr
935                 940                 945                 950 gag gac gcc aca ttc cag acc tat gcc ctc acc ggc att tcc ctc tgc        3098
Glu Asp Ala Thr Phe Gln Thr Tyr Ala Leu Thr Gly Ile Ser Leu Cys
                955                 960                 965 aac ccg gca gcg tcg ata tgc                                            3119
Asn Pro Ala Ala Ser Ile Cys
            970

<210> SEQ ID NO 36
<211> LENGTH: 535
<212> TYPE: PRT
<213> ORGANISM: Corynebacterium diphtheriae

<400> SEQUENCE: 36

Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

L

```
Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 37
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

<222> LOCATION: (1)..(960)

<400> SEQUENCE: 37

| | | | | | | | | | | | | | | | | |
|---|---|---|---|---|---|---|---|---|---|---|---|---|---|---|---|---|
| ggg | gcg | gac | gat | gtg | gtg | gat | tcc | tcc | aag | tcg | ttt | gtc | atg | gaa | aat | 48 |
| Gly | Ala | Asp | Asp | Val | Val | Asp | Ser | Ser | Lys | Ser | Phe | Val | Met | Glu | Asn | |
| 1 | | | | 5 | | | | | 10 | | | | | 15 | | |
| ttc | tcg | tcg | tac | cat | ggc | act | aag | cca | ggc | tac | gtg | gat | agc | att | caa | 96 |
| Phe | Ser | Ser | Tyr | His | Gly | Thr | Lys | Pro | Gly | Tyr | Val | Asp | Ser | Ile | Gln | |
| | | | 20 | | | | | 25 | | | | | 30 | | | |
| aag | ggc | atc | cag | aag | ccc | aag | agc | ggt | act | cag | ggg | aac | tat | gac | gac | 144 |
| Lys | Gly | Ile | Gln | Lys | Pro | Lys | Ser | Gly | Thr | Gln | Gly | Asn | Tyr | Asp | Asp | |
| | | 35 | | | | | 40 | | | | | 45 | | | | |
| gac | tgg | aag | gga | ttt | tac | agc | acc | gac | aat | aag | tac | gat | gct | gcg | ggc | 192 |
| Asp | Trp | Lys | Gly | Phe | Tyr | Ser | Thr | Asp | Asn | Lys | Tyr | Asp | Ala | Ala | Gly | |
| | 50 | | | | | 55 | | | | | 60 | | | | | |
| tat | agc | gtg | gac | aac | gaa | aac | cca | ttg | tcg | ggc | aag | gcc | ggt | ggc | gtg | 240 |
| Tyr | Ser | Val | Asp | Asn | Glu | Asn | Pro | Leu | Ser | Gly | Lys | Ala | Gly | Gly | Val | |
| 65 | | | | 70 | | | | | 75 | | | | | 80 | | |
| gtg | aag | gtg | acc | tat | cct | ggt | ctg | acg | aaa | gtt | ctg | gcg | ttg | aaa | gtg | 288 |
| Val | Lys | Val | Thr | Tyr | Pro | Gly | Leu | Thr | Lys | Val | Leu | Ala | Leu | Lys | Val | |
| | | | 85 | | | | | 90 | | | | | 95 | | | |
| gac | aac | gcc | gag | act | atc | aag | aaa | gaa | ttg | ggc | ttg | agt | ttg | acc | gag | 336 |
| Asp | Asn | Ala | Glu | Thr | Ile | Lys | Lys | Glu | Leu | Gly | Leu | Ser | Leu | Thr | Glu | |
| | | | 100 | | | | | 105 | | | | | 110 | | | |
| ccg | ctg | atg | gaa | cag | gtg | ggt | acc | gaa | gaa | ttc | att | aaa | cgt | ttt | ggg | 384 |
| Pro | Leu | Met | Glu | Gln | Val | Gly | Thr | Glu | Glu | Phe | Ile | Lys | Arg | Phe | Gly | |
| | | 115 | | | | | 120 | | | | | 125 | | | | |
| gac | ggc | gcg | tcg | cgc | gtg | gtc | ctg | tcg | ttg | ccg | ttc | gcc | gaa | ggg | tcg | 432 |
| Asp | Gly | Ala | Ser | Arg | Val | Val | Leu | Ser | Leu | Pro | Phe | Ala | Glu | Gly | Ser | |
| | 130 | | | | | 135 | | | | | 140 | | | | | |
| tcg | tcg | gtg | gaa | tat | atc | aac | aac | tgg | gaa | cag | gcc | aag | gcg | ctg | tcg | 480 |
| Ser | Ser | Val | Glu | Tyr | Ile | Asn | Asn | Trp | Glu | Gln | Ala | Lys | Ala | Leu | Ser | |
| 145 | | | | 150 | | | | | 155 | | | | | 160 | | |
| gtg | gaa | ctg | gaa | att | aac | ttc | gaa | acg | cgg | ggc | aaa | cgg | ggc | cag | gac | 528 |
| Val | Glu | Leu | Glu | Ile | Asn | Phe | Glu | Thr | Arg | Gly | Lys | Arg | Gly | Gln | Asp | |
| | | | 165 | | | | | 170 | | | | | 175 | | | |
| gcc | atg | tac | gaa | tac | atg | gcg | cag | gcg | tgc | gcc | ggg | aac | cgg | gtg | cgg | 576 |
| Ala | Met | Tyr | Glu | Tyr | Met | Ala | Gln | Ala | Cys | Ala | Gly | Asn | Arg | Val | Arg | |
| | | 180 | | | | | 185 | | | | | 190 | | | | |
| cgc | agc | gtg | ggc | agt | tcc | ttg | agt | tgc | atc | aat | ctg | gac | tgg | gac | gtc | 624 |
| Arg | Ser | Val | Gly | Ser | Ser | Leu | Ser | Cys | Ile | Asn | Leu | Asp | Trp | Asp | Val | |
| | 195 | | | | | 200 | | | | | 205 | | | | | |
| atc | cgc | gat | aag | acg | aag | acg | aaa | atc | gag | tcg | ctc | aaa | gag | cac | ggc | 672 |
| Ile | Arg | Asp | Lys | Thr | Lys | Thr | Lys | Ile | Glu | Ser | Leu | Lys | Glu | His | Gly | |
| 210 | | | | | 215 | | | | | 220 | | | | | | |
| ccg | atc | aaa | aac | aaa | atg | agc | gag | tcg | ccg | aat | aaa | acg | gtg | tcc | gag | 720 |
| Pro | Ile | Lys | Asn | Lys | Met | Ser | Glu | Ser | Pro | Asn | Lys | Thr | Val | Ser | Glu | |
| 225 | | | | 230 | | | | | 235 | | | | | 240 | | |
| gag | aag | gcg | aag | caa | tac | ctg | gag | gaa | ttc | cac | cag | acg | gct | ctg | gag | 768 |
| Glu | Lys | Ala | Lys | Gln | Tyr | Leu | Glu | Glu | Phe | His | Gln | Thr | Ala | Leu | Glu | |
| | | | 245 | | | | | 250 | | | | | 255 | | | |
| cac | ccg | gag | ctg | agc | gaa | ctc | aaa | acc | gtt | acc | ggt | acg | aac | ccg | gtg | 816 |
| His | Pro | Glu | Leu | Ser | Glu | Leu | Lys | Thr | Val | Thr | Gly | Thr | Asn | Pro | Val | |
| | | 260 | | | | | 265 | | | | | 270 | | | | |
| ttt | gcc | ggg | gca | aac | tat | gca | gct | tgg | gcc | gtc | aac | gtg | gcc | caa | gtg | 864 |
| Phe | Ala | Gly | Ala | Asn | Tyr | Ala | Ala | Trp | Ala | Val | Asn | Val | Ala | Gln | Val | |
| | 275 | | | | | 280 | | | | | 285 | | | | | |
| atc | gac | tcc | gaa | acg | gcc | gac | aac | ctg | gaa | aag | act | acc | gcc | gcg | ttg | 912 |
| Ile | Asp | Ser | Glu | Thr | Ala | Asp | Asn | Leu | Glu | Lys | Thr | Thr | Ala | Ala | Leu | |
| 290 | | | | | 295 | | | | | 300 | | | | | | |

```
tcg atc ctc ccg ggc atc ggg agc gtc atg ggt att gcc gat ggt gcg    960
Ser Ile Leu Pro Gly Ile Gly Ser Val Met Gly Ile Ala Asp Gly Ala
305                 310                 315                 320
```

<210> SEQ ID NO 38
<211> LENGTH: 258
<212> TYPE: PRT
<213> ORGANISM: Vibrio cholerae

<400> SEQUENCE: 38

```
Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
                20                  25                  30

Glu Ile Lys Gln Ser Gly Gly Leu Met Pro Arg Gly Gln Ser Glu Tyr
            35                  40                  45

Phe Asp Arg Gly Thr Gln Met Asn Ile Asn Leu Tyr Asp His Ala Arg
        50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu
```

<210> SEQ ID NO 39
<211> LENGTH: 124
<212> TYPE: PRT
<213> ORGANISM: Vibrio cholerae

<400> SEQUENCE: 39

```
Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
                20                  25                  30

Tyr His Asn Thr Gln Ile Tyr Thr Leu Asn Asp Lys Ile Phe Ser Tyr
            35                  40                  45
```

```
Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 40
<211> LENGTH: 1148
<212> TYPE: DNA
<213> ORGANISM: Vibrio cholerae

<400> SEQUENCE: 40
atggtaaaga taatatttgt gttttttatt ttcttatcat cattttcata tgcaaatgat     60
gataagttat atcgggcaga ttctagacct cctgatgaaa taaagcagtc aggtggtctt    120
atgccaagag gacagagtga gtactttgac cgaggtactc aaatgaatat caacctttat    180
gatcatgcaa gaggaactca gacgggattt gttaggcacg atgatggata tgtttccacc    240
tcaattagtt tgagaagtgc ccacttagtg ggtcaaacta tattgtctgg tcattctact    300
tattatatat atgttatagc cactgcaccc aacatgttta acgttaatga tgtattaggg    360
gcatacagtc ctcatccaga tgaacaagaa gtttctgctt taggtgggat tccatactcc    420
caaatatatg gatggtatcg agttcatttt ggggtgcttg atgaacaatt acatcgtaat    480
aggggctaca gagatagata ttacagtaac ttagatattg ctccagcagc agatggttat    540
ggattggcag gtttccctcc ggagcataga gcttggaggg aagagccgtg gattcatcat    600
gcaccgccgg gttgtgggaa tgctccaaga tcatcgatga gtaatacttg cgatgaaaaa    660
acccaaagtc taggtgtaaa attccttgac gaataccaat ctaaagttaa aagacaaata    720
ttttcaggct atcaatctga tattgataca cataatagaa ttaaggatga attatgatta    780
aattaaaatt tggtgttttt tttacagttt tactatcttc agcatatgca catggaacac    840
ctcaaaatat tactgatttg tgtgcagaat accacaacac acaaatatat acgctaaatg    900
ataagatatt ttcgtataca gaatctctag ctggaaaaag agagatggct atcattactt    960
ttaagaatgg tgcaattttt caagtagaag taccaggtag tcaacatata gattcacaaa   1020
aaaaagcgat tgaaaggatg aaggataccc tgaggattgc atatcttact gaagctaaag   1080
tcgaaaagtt atgtgtatgg aataataaaa cgcctcatgc gattgccgca attagtatgg   1140
caaattaa                                                            1148

<210> SEQ ID NO 41
<211> LENGTH: 269
<212> TYPE: PRT
<213> ORGANISM: Bordetella pertussis

<400> SEQUENCE: 41

Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Arg Tyr Asp Ser Arg Pro
```

```
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Ser Arg Arg Tyr Thr Glu Val
                85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Val Arg Ala Asp
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175

Arg Val Thr Arg Val Tyr His Asn Gly Ile Thr Gly Glu Thr Thr Thr
            180                 185                 190

Thr Glu Tyr Ser Asn Ala Arg Tyr Val Ser Gln Gln Thr Arg Ala Asn
        195                 200                 205

Pro Asn Pro Tyr Thr Ser Arg Arg Ser Val Ala Ser Ile Val Gly Thr
    210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
                245                 250                 255

Met Val Leu Val Tyr Tyr Glu Ser Ile Ala Tyr Ser Phe
            260                 265

<210> SEQ ID NO 42
<211> LENGTH: 226
<212> TYPE: PRT
<213> ORGANISM: Bordetella pertussis

<400> SEQUENCE: 42

Met Pro Ile Asp Arg Lys Thr Leu Cys His Leu Leu Ser Val Leu Pro
1               5                   10                  15

Leu Ala Leu Leu Gly Ser His Val Ala Arg Ala Ser Thr Pro Gly Ile
            20                  25                  30

Val Ile Pro Pro Gln Glu Gln Ile Thr Gln His Gly Ser Pro Tyr Gly
        35                  40                  45

Arg Cys Ala Asn Lys Thr Arg Ala Leu Thr Val Ala Glu Leu Arg Gly
    50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asp Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
    130                 135                 140
```

```
Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
            180                 185                 190

His Val Ser Lys Glu Glu Gln Tyr Tyr Asp Tyr Glu Asp Ala Thr Phe
        195                 200                 205

Glu Thr Tyr Ala Leu Thr Gly Ile Ser Ile Cys Asn Pro Gly Ser Ser
    210                 215                 220

Leu Cys
225

<210> SEQ ID NO 43
<211> LENGTH: 131
<212> TYPE: PRT
<213> ORGANISM: Bordetella pertussis
<400> SEQUENCE: 43

Val Arg Ala Leu Ala Trp Leu Leu Ala Ser Gly Ala Met Thr His Leu
1               5                   10                  15

Ser Pro Ala Leu Ala Asp Val Pro Tyr Val Leu Val Lys Thr Asn Met
            20                  25                  30

Val Val Thr Ser Val Ala Met Lys Pro Tyr Glu Val Thr Pro Thr Arg
        35                  40                  45

Met Leu Val Cys Gly Ile Ala Ala Lys Leu Gly Ala Ala Ala Ser Ser
    50                  55                  60

Pro Asp Ala His Val Pro Phe Cys Phe Gly Lys Asp Leu Lys Arg Pro
65                  70                  75                  80

Gly Ser Ser Pro Met Glu Val Met Leu Arg Ala Val Phe Met Gln Gln
                85                  90                  95

Arg Pro Leu Arg Met Phe Leu Gly Pro Lys Gln Leu Thr Phe Glu Gly
            100                 105                 110

Lys Pro Ala Leu Glu Leu Ile Arg Met Val Glu Cys Ser Gly Lys Gln
        115                 120                 125

Asp Cys Pro
    130

<210> SEQ ID NO 44
<211> LENGTH: 120
<212> TYPE: PRT
<213> ORGANISM: Bordetella pertussis
<400> SEQUENCE: 44

Met His Thr Ile Ala Ser Ile Leu Leu Ser Val Leu Gly Ile Tyr Ser
1               5                   10                  15

Pro Ala Asp Val Ala Gly Leu Pro Thr His Leu Tyr Lys Asn Phe Thr
            20                  25                  30

Val Gln Glu Leu Ala Leu Lys Leu Lys Gly Lys Asn Gln Glu Phe Cys
        35                  40                  45

Leu Thr Ala Phe Met Ser Gly Arg Ser Leu Val Arg Ala Cys Leu Ser
    50                  55                  60

Asp Ala Gly His Glu His Asp Thr Trp Phe Asp Thr Met Leu Gly Phe
65                  70                  75                  80

```
Ala Ile Ser Ala Tyr Ala Leu Lys Ser Arg Ile Ala Leu Thr Val Glu
                85                  90                  95

Asp Ser Pro Tyr Pro Gly Thr Pro Gly Asp Leu Leu Glu Leu Gln Ile
            100                 105                 110

Cys Pro Leu Asn Gly Tyr Cys Glu
        115                 120

<210> SEQ ID NO 45
<211> LENGTH: 227
<212> TYPE: PRT
<213> ORGANISM: Bordetella pertussis

<400> SEQUENCE: 45

Met Leu Ile Asn Asn Lys Lys Leu Leu His His Ile Leu Pro Ile Leu
1               5                   10                  15

Val Leu Ala Leu Leu Gly Met Arg Thr Ala Gln Ala Val Ala Pro Gly
            20                  25                  30

Ile Val Ile Pro Pro Lys Ala Leu Phe Thr Gln Gln Gly Gly Ala Tyr
        35                  40                  45

Gly Arg Cys Pro Asn Gly Thr Arg Ala Leu Thr Val Ala Glu Leu Arg
    50                  55                  60

Gly Asn Ala Glu Leu Gln Thr Tyr Leu Arg Gln Ile Thr Pro Gly Trp
65                  70                  75                  80

Ser Ile Tyr Gly Leu Tyr Asp Gly Thr Tyr Leu Gly Gln Ala Tyr Gly
                85                  90                  95

Gly Ile Ile Lys Asp Ala Pro Pro Gly Ala Gly Phe Ile Tyr Arg Glu
            100                 105                 110

Thr Phe Cys Ile Thr Thr Ile Tyr Lys Thr Gly Gln Pro Ala Ala Asp
        115                 120                 125

His Tyr Tyr Ser Lys Val Thr Ala Thr Arg Leu Leu Ala Ser Thr Asn
    130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Ala
                165                 170                 175

Leu Arg Arg Leu Leu Tyr Met Ile Tyr Met Ser Gly Leu Ala Val Arg
            180                 185                 190

Val His Val Ser Lys Glu Glu Gln Tyr Tyr Asp Tyr Glu Asp Ala Thr
        195                 200                 205

Phe Gln Thr Tyr Ala Leu Thr Gly Ile Ser Leu Cys Asn Pro Ala Ala
    210                 215                 220

Ser Ile Cys
225

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5
```

HIGH LEVEL EXPRESSION OF RECOMBINANT TOXIN PROTEINS

CLAIM OF PRIORITY

This application is a divisional of U.S. patent application Ser. No. 13/073,955, filed on Mar. 28, 2011 and issued as U.S. Pat. No. 8,530,171 on Sep. 10, 2013, which claims priority under 35 U.S.C. §119(e) to U.S. Provisional Application Ser. No. 61/325,235 filed on Apr. 16, 2010, PCT/US10/30573 filed on Apr. 9, 2010, and U.S. Provisional Application Ser. No. 61/319,152 filed on Mar. 30, 2010, and is a continuation-in-part of PCT/US10/30573, filed on Apr. 9, 2010, which claims priority to U.S. Provisional Application Ser. No. 61/319,152 filed on Mar. 30, 2010. The contents of these applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 16, 2011, is named 38194201.txt and is 156,975 bytes in size.

BACKGROUND OF THE INVENTION

Microbial toxin proteins are used in medicine, as immunogens for vaccination against the toxin-producing microbe and as carrier proteins and adjuvants for other vaccines, and in scientific research as tools for studying molecular pathways.

Diphtheria toxin (DT) is a proteinaceous toxin that is synthesized and secreted by toxigenic strains of *Corynebacterium diphtheriae*. Toxigenic strains contain a bacteriophage lysogen carrying the toxin gene. DT is synthesized as a 535-amino-acid polypeptide, which undergoes proteolysis to form the mature toxin. The mature toxin comprises two subunits, A and B, joined by a disulfide bridge. The B subunit, formed from the C-terminal portion of intact DT, enables binding and entry of DT through the cell membrane and into the cytoplasm. Upon cell entry, the enzymatic A subunit, formed from the N terminal portion of intact DT, catalyzes ADP ribosylation of Elongation Factor 2 (EF-2). As a result, EF-2 is inactivated, protein synthesis stops, and the cell dies. Diphtheria toxin is highly cytotoxic; a single molecule can be lethal to a cell, and a dose of 10 ng/kg can kill animals and humans.

The CRM197 protein is a nontoxic, immunologically cross-reacting form of DT. It has been studied for its potential use as a DT booster or vaccine antigen. CRM197 is produced by *C. diphtheriae* that has been infected by the nontoxigenic phage β197tox-created by nitrosoguanidine mutagenesis of the toxigenic corynephage β. The CRM197 protein has the same molecular weight as DT but differs by a single base change (guanine to adenine) in the A subunit. This single base change results in an amino acid substitution (glutamic acid for glycine) and eliminates the toxic properties of DT.

Conjugated polysaccharide vaccines that use CRM197 as a carrier protein have been approved for human use. Vaccines include: Menveo® (Novartis Vaccines and Diagnostics), a vaccine indicated for preventing invasive meningococcal disease caused by *Neisseria meningitidis* subgroups A, C, Y, and W-135; Menjugate (Novartis Vaccines), a meningococcal group C conjugate vaccine; and Prevnar® (Wyeth Pharmaceuticals, Inc.), a childhood pneumonia vaccine that targets seven serotypes of *Streptococcus pneumoniae*, and HibTITER® (Wyeth), a *Haemophilus influenzae* type b vaccine. In addition, CRM197 has potential use as a boosting antigen for *C. diphtheria* vaccination and is being investigated as a carrier protein for use in other vaccines.

A method for high-level expression of CRM197 for approved therapeutics and investigational use has not been reported. CRM197 has been expressed in, e.g., *C. diphtheriae, B. subtilis*, and *E. coli*, at levels that range in the tens of mg/L. A single dose of the Prevnar conjugate vaccine contains about 20 μg of CRM197. Therefore, a method for economically producing CRM197 at levels of about 1 g/L or more would greatly facilitate vaccine research and manufacture.

Cholera Toxin (CTX), produced by *Vibrio cholera*, a bacterial pathogen that causes an infection characterized by diarrhea and vomiting, is also an ADP-ribosylating toxin. CTX is an oligomeric complex made up of six protein subunits: a single copy of the Cholera toxin A subunit (CTA), and five copies of the Cholera Toxin B subunit (CTB). The five B subunits, each weighing 12 kDa, form a five-membered ring. The A subunit has an A1 portion, CTA1, a globular enzyme that ADP-ribosylates G proteins, and an A2 chain, CTA2, that forms an extended alpha helix which sits snugly in the central pore of the B subunit ring. This ring binds to GM1 ganglioside receptors on the host cell surface, resulting in internalization of the entire complex. Once internalized, the CTA1 chain is released by reduction of a disulfide bridge. CTA1 is then activated and catalyzes ADP ribosylation of adenylate cyclase. The resulting increase in adenylate cyclase activity increases cyclic AMP synthesis, which causes massive fluid and electrolyte efflux and results in diarrhea.

The B subunit of CTX, though relatively harmless, retains its ability to bind to the GM1 ganglioside receptor. CTB therefore finds use in facilitating mucosal uptake of chemically or genetically conjugated foreign antigens. It has been demonstrated to induce both mucosal and systemic immunity, and is a candidate for use in edible vaccine production. Because of its binding preference, CTB also finds use as a neuronal tracer.

Pertussis toxin (PTX) is an exotoxin and virulence factor produced by *Bordetella pertussis*, a bacterial pathogen of the human respiratory tract that causes the disease whooping cough. The pertussis holotoxin is a multi-subunit complex with an AB 5 structure. The enzymatically active A subunit (S1) is an ADP-ribosyltransferase that modifies the alpha subunit of several heterotrimeric G proteins in mammalian cells, and the B oligomer (S2, S3, two copies of S4, and S5) binds glycoconjugate receptors on cells. The five subunits of the toxin are expressed from the Pertussis Toxoid operon.

Nontoxic variants of Pertussis toxin have been explored for use in protective vaccines and as a vaccine adjuvant. There is also a need for Pertussis toxin protein to use in research, e.g., for studies of G protein signaling pathways.

Tetanus Toxin, produced by *Clostridium tetani*, is a neurotoxin having a molecular weight of 150 kDa. It is made up of two parts: a 100 kDa heavy or B-chain and a 50 kDa light or A-chain. The chains are connected by a disulfide bond. The B-chain binds to disialogangliosides (GD2 and GD1b) on the neuronal membrane. The A-chain, a zinc endopeptidase, attacks the vesicle-associated membrane protein (VAMP).

The action of the A-chain stops the affected neurons from releasing the inhibitory neurotransmitters GABA (gamma-aminobutyric acid) and glycine by degrading the protein synaptobrevin. The consequence of this is dangerous overactivity in the muscles from the smallest stimulus—the failure of inhibition of motor reflexes by sensory stimulation. This causes generalized contractions of the agonist and antagonist musculature, termed a tetanic spasm.

Tetanus Toxin Fragment C (Tet C or TTC) is a 50 kD polypeptide generated by protease cleavage (e.g., with papain) of Tetanus toxin, or through recombinant expression of the fragment. It corresponds to the 451 amino acids at the C-terminus (amino acid positions 865-1315).

Fragment C has been shown to be non-toxic. Because it binds to neurons with high specificity and affinity, TTC finds use as a targeting molecule for neuronal drug delivery or for research purposes. TTC protein is also potentially useful as a vaccine carrier protein and for use in a vaccine to protect against *C. tetani* infection.

*Clostridium difficile* Toxin B (TcdB) is a virulence factor produced by *Clostridium difficile*, which causes hospital acquired diarrhea and pseudomembranous colitis. TcdB, and a second large clostridial toxin, TcdA, are involved in the development of pseudomembranous colitis.

TcdB is a glucosylating toxin of about 270 kD, and can be divided into enzymatic, translocation and receptor binding domains. The first 546 amino acids of TcdB contain the enzymatic region, which is followed by a putative translocation and receptor-binding domain. TcdB has potential use as a protective vaccine for *C. difficile* infection, as well as in diagnostic tests and their development.

Exotoxin A (ETA or PE) of *Pseudomonas aeruginosa* is a Type II ADPRT. Like its family members Diphtheria toxin and Cholera Toxin, it inhibits protein synthesis by the ADP-ribosylation of cellular elongation factor 2. *P. aeruginosa* Exotoxin A exists as a monomer, consisting of a single polypeptide chain of 613 amino acids (66 Kd).

ETA is potentially useful as a vaccine conjugate. Nontoxic mutants of ETA have been studied as vaccine conjugates for vaccinations that protect against *Staphylococcus aureus*, malaria, and *Salmonella Typhi*.

Producing these toxins in amounts sufficient to meet expanding needs has presented significant challenges. When made in conventional protein overexpression systems, the toxin proteins are recovered in active form only at very low concentration due to degradation, improper folding, or both, depending on the specific characteristics, e.g., size and secondary structure, of the toxin. Therefore, methods for producing large amounts of these toxins, in soluble and/or active form, and at low cost is needed.

SUMMARY OF THE INVENTION

The present invention relates to a method for producing a recombinant toxin protein in a Pseudomonad host cell, said method comprising: ligating into an expression vector a nucleotide sequence encoding a toxin protein; transforming the *Pseudomonas* host cell with the expression vector; and culturing the transformed *Pseudomonas* host cell in a culture media suitable for the expression of the recombinant toxin protein; wherein the recombinant toxin protein is CRM197, Diphtheria Toxin, Cholera holotoxin, Cholera Toxin B, Pertussis toxin, Tetanus Toxin Fragment C, *C. difficile* Toxin B, or *P. aeruginosa* Exotoxin A.

In embodiments, the recombinant toxin protein is Cholera Toxin B, Cholera holotoxin, Pertussis toxin, Tetanus Toxin Fragment C, *C. difficile* Toxin B, or *P. aeruginosa* Exotoxin A.

In other embodiments, the recombinant toxin protein is Cholera Toxin B, Cholera holotoxin, Pertussis toxin, Tetanus Toxin Fragment C, or *C. difficile* Toxin B.

In other embodiments, the recombinant toxin protein is CRM197, Diphtheria Toxin, Cholera holotoxin, Cholera Toxin B, Pertussis toxin, Tetanus Toxin Fragment C, or *C. difficile* Toxin B.

In certain embodiments, the recombinant protein is produced at a yield of soluble and/or active toxin protein of about 0.2 grams per liter to about 12 grams per liter. In specific embodiments, the yield of soluble and/or active toxin protein is about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

In embodiments, the nucleotide sequence encoding the toxin protein is fused to a secretion signal coding sequence that when expressed directs transfer of the toxin protein to the periplasm. In embodiments, the host cell is defective in the expression of at least one protease or the host cell overexpresses at least one folding modulator, or a combination thereof.

In embodiments, the recombinant toxin protein is CRM197 and the host cell is defective in the expression of HslU, HslV, Prc1, DegP1, DegP2, and AprA. In related embodiments, the recombinant toxin protein is fused to a secretion leader that is Azu, IbpS31A, CupA2, PbpA20V, or Pbp. In embodiments, the recombinant toxin protein is CRM197 and the host cell is defective in the expression of HslU and HslV, or Prc1, or DegP1, or DegP2, or AprA. In specific embodiments, the recombinant toxin protein is CRM197 and the host cell is defective in the expression of Serralysin, HslU, HslV, Prc1, DegP1, DegP2, or AprA, or the host cell overexpresses DsbA, DsbB, DsbC, and DsbD. In embodiments, the host cell overexpresses DsbA, DsbB, DsbC, and DsbD, and the recombinant toxin protein is fused to the secretion leader Azu. In embodiments, the host cell is defective in the expression of Serralysin, and the recombinant toxin protein is fused to the secretion leader Pbp or Azu. In embodiments, the host cell is defective in the expression of HslU and HslV, and the recombinant toxin protein is fused to the secretion leader Pbp or Azu. In embodiments, the recombinant toxin protein is CRM197, the host cell is wild-type and wherein the recombinant toxin protein is fused to the secretion leader Pbp or Azu. In embodiments, the recombinant toxin protein is CRM197 and the recombinant toxin protein is fused to the secretion leader Azu, Pbp, IbpS31A, CupA2, or PbpA20V.

In other embodiments, the recombinant toxin protein is Cholera Toxin B and the host cell is defective in the expression of Lon, La, and AprA, or the host cell is defective in the expression of HslU, HslV, Prc1, DegP1, DegP2, and AprA. In related embodiments, the host cell is defective in the expression of Lon, La, and AprA and wherein the recombinant toxin protein is fused to the secretion leader Pbp A20V.

In other embodiments, the recombinant toxin protein is Pertussis toxin S1 E129A R9K and the host cell is defective in the expression of: Lon, La, and AprA; GrpE, DnaK, and DnaJ; HtpX; RXF01590; or ppiB (RXF05345). In related embodiments, the recombinant toxin protein is fused to its native secretion leader.

In other embodiments, the recombinant toxin protein is Tetanus Toxin C and the host cell is defective in the expression of HslU, HslV, Prc1, DegP1, DegP2, and AprA. In related embodiments, the recombinant toxin protein is fused to the secretion leader DsbC, Pbp A20V, or CupA2.

In other embodiments, the recombinant toxin protein is Tetanus Toxin C and the host cell is defective in the expression of Lon, La, and AprA. In related embodiments, the recombinant toxin protein is fused to the secretion leader DsbA.

In other embodiments, the recombinant toxin protein is Tetanus Toxin C and the host cell is defective in the expression of GrpE, DnaK, and DnaJ. In related embodiments, the recombinant toxin protein is fused to the secretion leader NikA.

In other embodiments, the recombinant toxin protein is *C. difficile* Toxin B and the host cell is defective in the expression of: HtpX; DegP1; HslU, HslV, Prc1 and Prc2; or Lon and DegP2, or the host cell is both defective in the expression of Lon, Prc1, DegP2, AprA and overexpresses DegP2 S219A.

In embodiments, the activity of the recombinant toxin protein is measured in an activity assay, wherein about 40% to about 100% of the soluble toxin protein produced is determined to be active. In related embodiments, the activity assay is an immunological assay, a receptor-binding assay, or an enzyme assay.

In embodiments of the invention, the expression vector comprises a lac derivative promoter operatively linked to the protein coding sequence, and wherein the culturing comprises induction of the promoter using IPTG at a concentration of about 0.02 to about 1.0 mM, the cell density at induction is an optical density of about 40 to about 200 absorbance units (AU), the pH of the culture is from about 6 to about 7.5, and the growth temperature is about 20 to about 35° C.

In embodiments, the host cell is a *Pseudomonas* cell. In related embodiments, the host cell is *Pseudomonas fluorescens*.

In embodiments of the invention, the nucleotide sequence has been optimized for expression in the Pseudomonad host cell. In related embodiments, the nucleotide sequence has been optimized for expression in the *Pseudomonas* host cell. In other related embodiments, the nucleotide sequence has been optimized for expression in the *Pseudomonas fluorescens* host cell.

In embodiments, the Pertussis toxin is wild-type or S1 E129A R9K. In embodiments, the *P. aeruginosa* Exotoxin A is wild-type, CRM66, or rEPA.

In embodiments of the invention, the expression vector further comprises a tag sequence adjacent to the coding sequence for the secretion signal. In embodiments, the expression vector further comprises a tag sequence adjacent to the coding sequence for the toxin protein.

The present invention also provides a recombinant toxin protein produced according to the methods described herein. In embodiments, the recombinant toxin protein is CRM197, Diphtheria Toxin, Cholera holotoxin, Cholera Toxin B, Pertussis Toxin, Tetanus Toxin fragment C, *C. difficile* Toxin B, or *P. aeruginosa* Exotoxin A. In embodiments, the Exotoxin A is wild-type, CRM66, or rEPA. In certain embodiments, the recombinant toxin protein is produced in a strain of *P. fluorescens* identified herein as producing a high yield of the toxin or producing high quality toxin. In certain embodiments, the recombinant toxin protein is produced in a strain of *P. fluorescens* described herein as producing the highest yield of the toxin protein. In other embodiments, the recombinant toxin protein is produced in a strain described herein as one used for fermentation production of the toxin.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

Figure 1B:
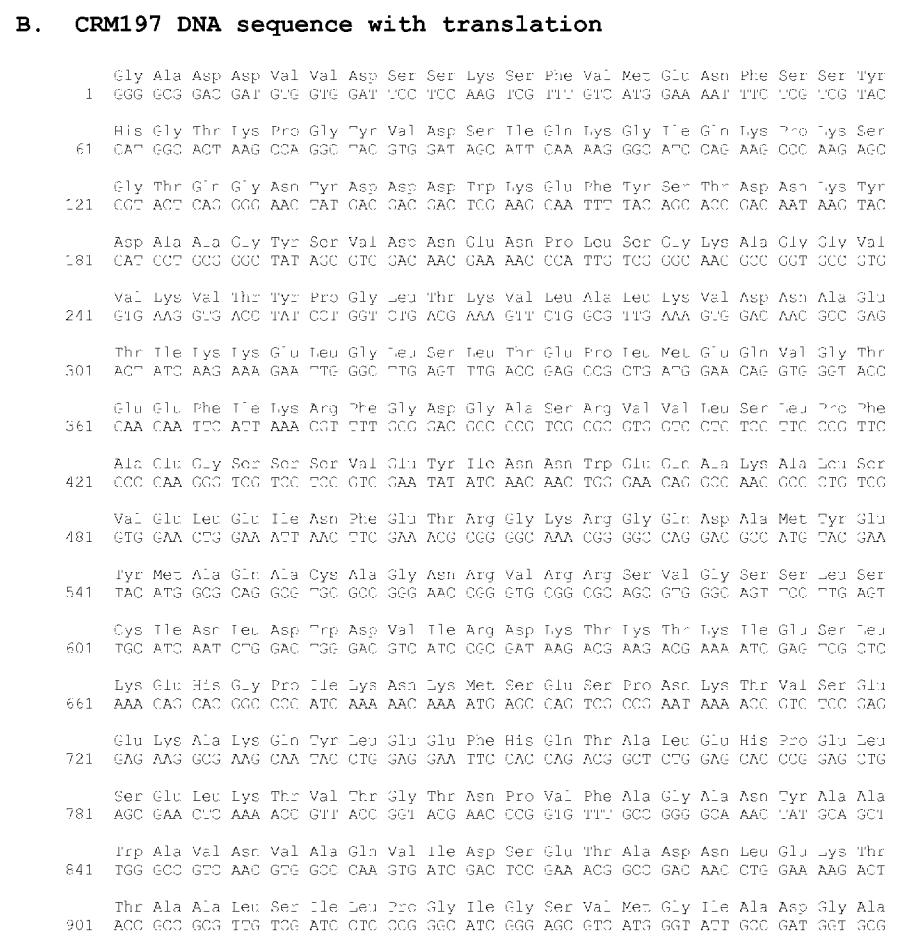

FIG. 1A to 1C. CRM197 Amino Acid and DNA Sequences. 1A. Amino acid sequence (SEQ ID NO: 1). 1B. First segment of an optimized DNA sequence (SEQ ID NO:2) encoding the CRM197 protein, with translation shown. 1C. Second segment of an optimized DNA sequence (SEQ ID NO:2) encoding the CRM197 protein, with translation shown. This optimized sequence is a non-limiting example of an optimized sequence useful in the methods of the present invention.

FIG. 2. High Throughput Expression Analysis of CRM197. CRM197 protein expressed using the DNA sequence shown in FIG. 1B was analyzed using capillary gel electrophoresis (SDS-CGE). Soluble fractions of 40 CRM197-expression strains tested are shown in a gel-like image generated from the SDS-CGE data. Strain names as described in Table 10 are listed above each lane. *P. fluorescens*-expressed CRM197 migrated as a single band at ~58 kDa on SDS-CGE (arrow at left). Molecular weight markers in first and last lanes are 16, 20, 29, 48, 69 and 119 kDa.

FIG. 3. Cholera Toxin B Amino Acid and DNA Sequences. A. Amino acid sequence (SEQ ID NO: 22). B. An optimized DNA sequence (SEQ ID NO: 23) encoding the CTB protein, with translation. This optimized sequence is a non-limiting example of an optimized sequence useful in the methods of the present invention.

Figure 4:
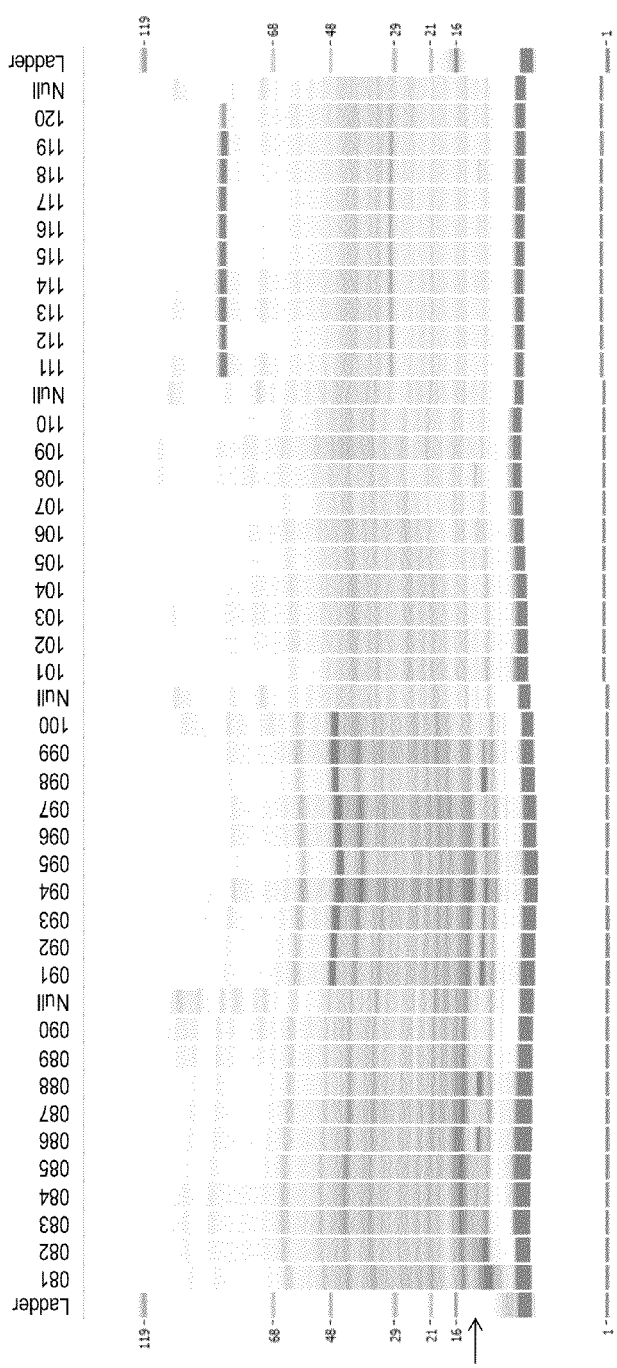

FIG. 4. High Throughput Expression Analysis of Cholera Toxin B. Cholera Toxin B protein expressed using the DNA sequence shown in FIG. 3B was analyzed using capillary gel electrophoresis (SDS-CGE). Soluble fractions from 40 cholera toxin-expression strains tested are shown in a gel-like image generated from the SDS-CGE data. Strain names as described in Table 11 are listed above each lane. Induced CTB migrated as a single band at ~11.5 kDa on SDS-CGE (arrow at left). Molecular weight markers in first and last lanes are 16, 20, 29, 48, 69 and 119 kDa.

Figure 5:
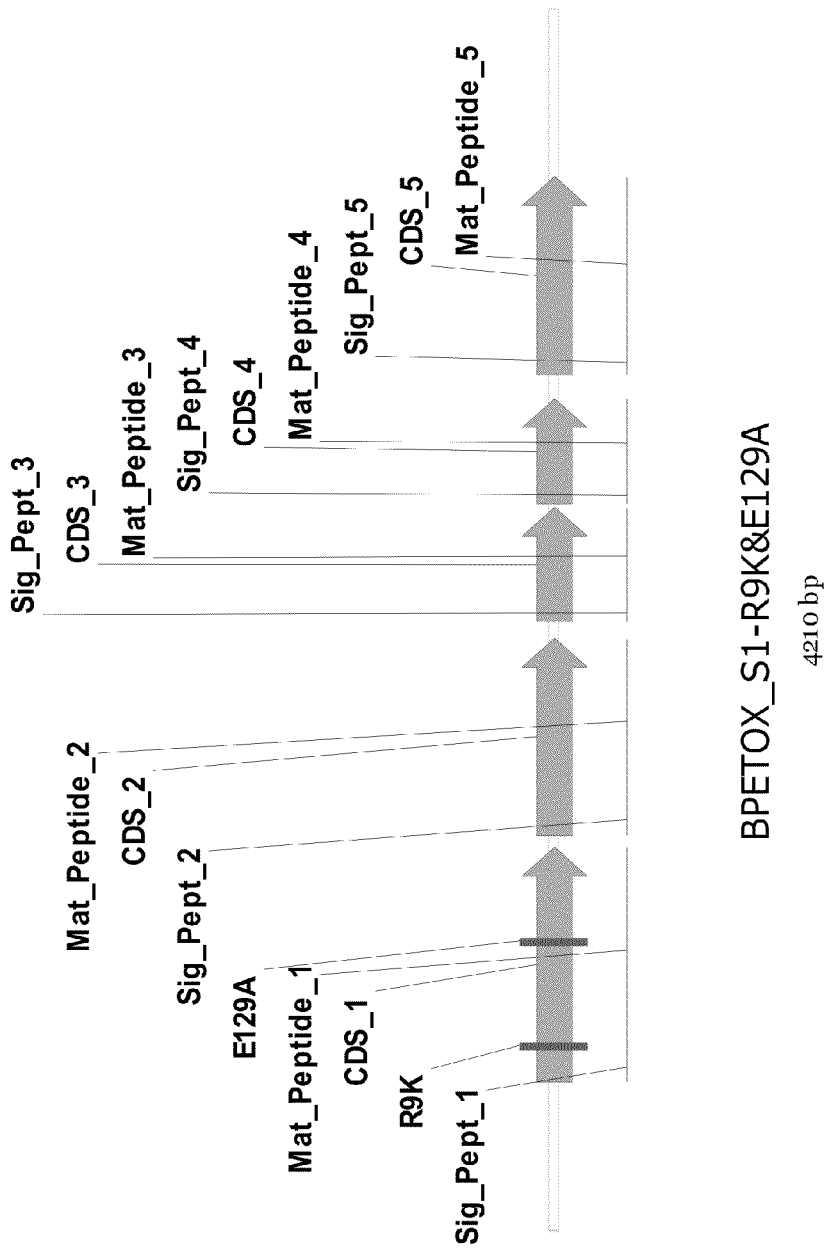

FIG. 5. Pertussis Toxoid Operon. BPETOX_S1-R9K & E129A, having 4210 basepairs, is shown.

Figure 6A:
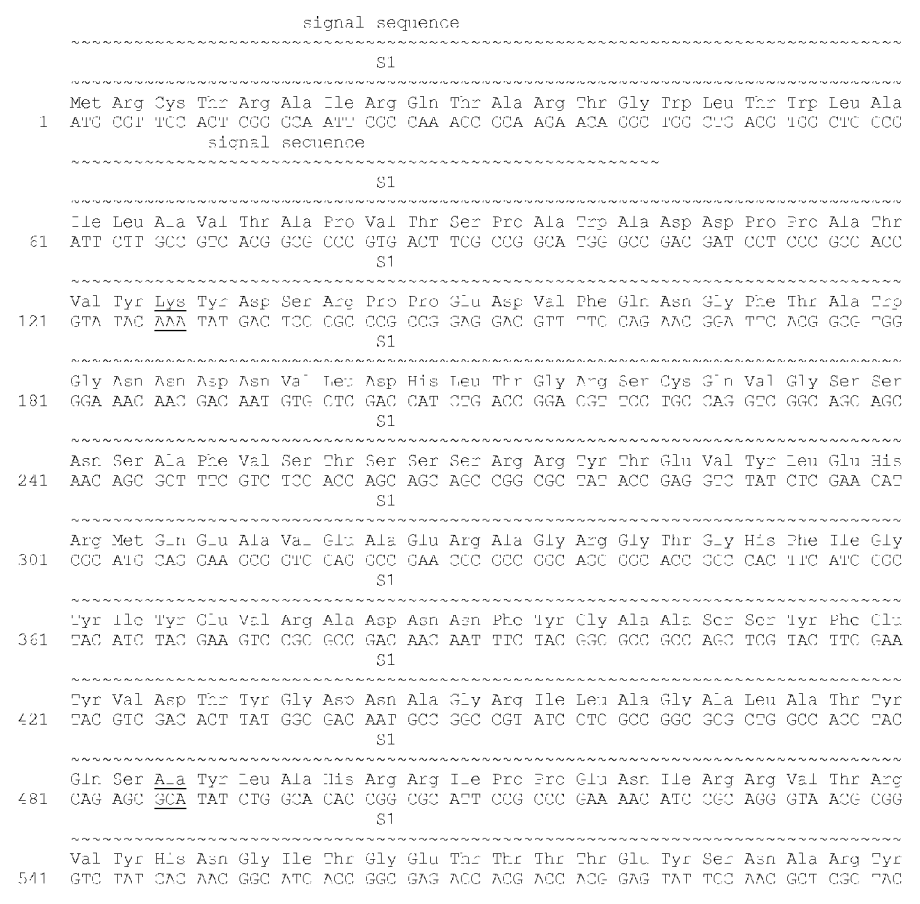
Figure 6B:
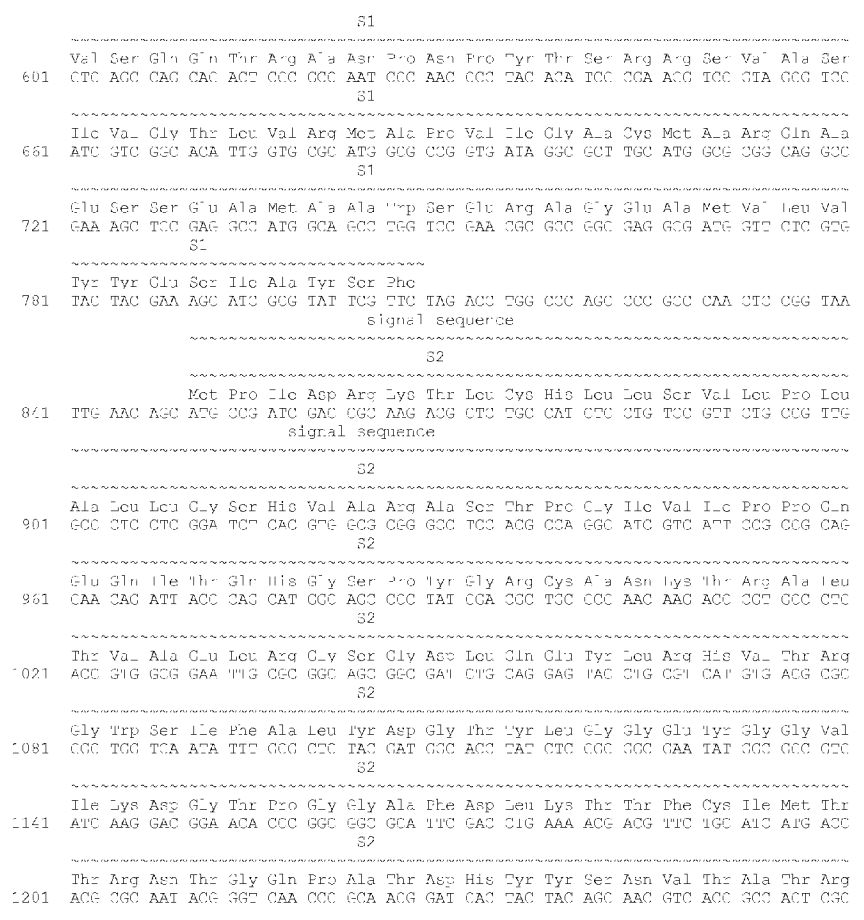
Figure 6D:
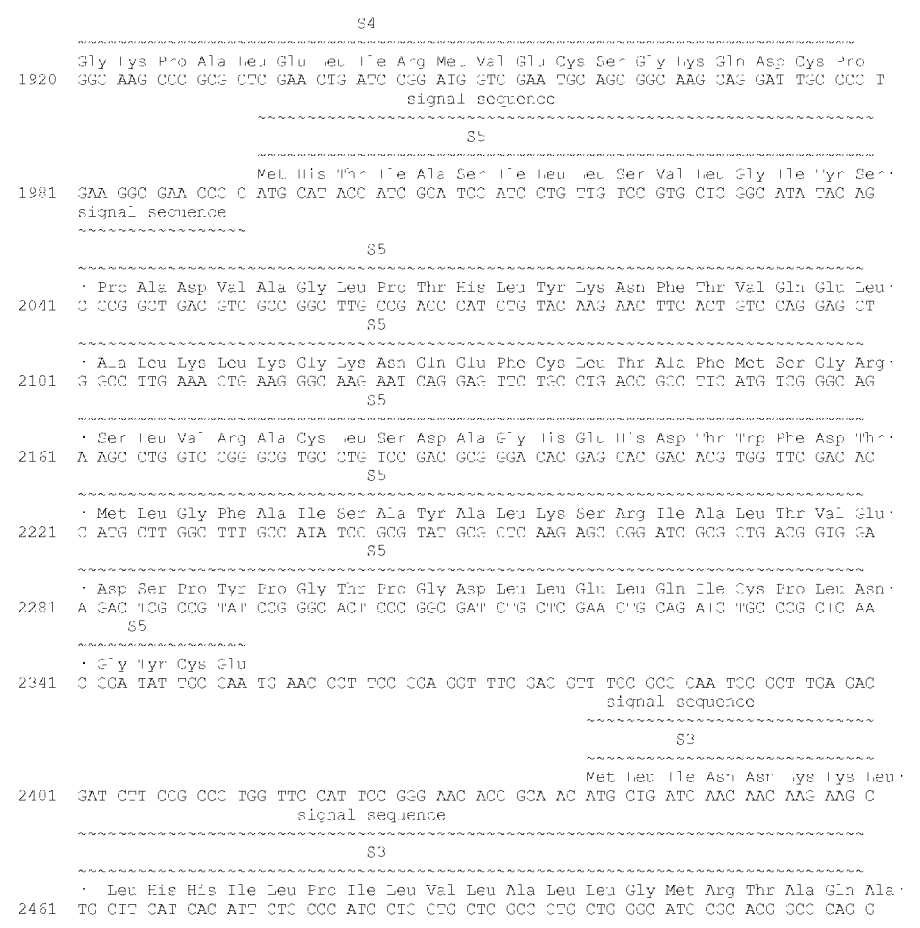
Figure 6E:
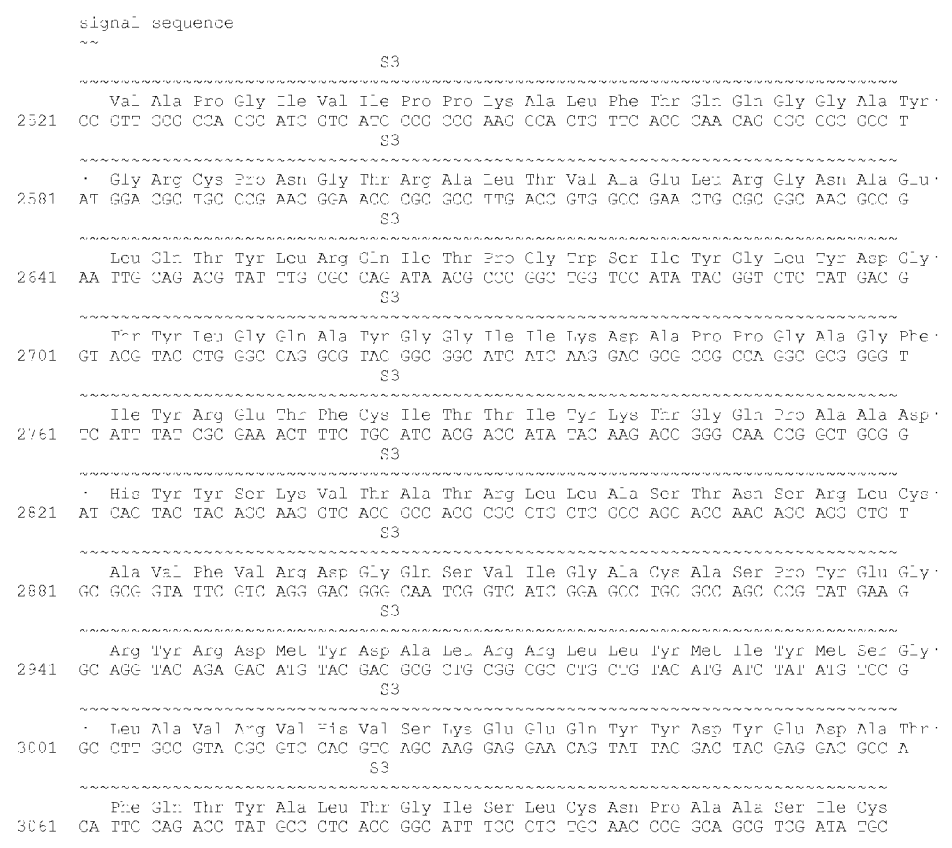

FIG. 6A to 6E. DNA Sequence of the Pertussis Toxoid. 6A. First segment of the Pertussis toxin S1 R9K E129A DNA sequence with translation is shown (SEQ ID NO:24). The sequence is derived from Genebank entry M13223. Subunits S1-S5 and signal sequences are indicated above the sequences. The R9K and E129A mutations in S1 are underlined. Encoded proteins are disclosed as SEQ ID NOS 25, 26, 28, 29, and 27, respectively, in order of appearance. 6B. Second segment of the Pertussis toxin S1 R9K E129A DNA sequence with translation is shown (SEQ ID NO:24). 6C. Third segment of the Pertussis toxin S1 R9K E129A DNA sequence with translation is shown (SEQ ID NO:24). 6D. Fourth segment of the Pertussis toxin S1 R9K E129A DNA sequence with translation is shown (SEQ ID NO:24). 6E. Fifth segment of the Pertussis toxin S1 R9K E129A DNA sequence with translation is shown (SEQ ID NO:24).

FIG. 7A to 7E. Amino Acid Sequences of Pertussis Toxoid Subunits. Secretion signals are underlined. 7A. S1 subunit (R9K E129A) (SEQ ID NO:25). 7B. S2 subunit (SEQ ID NO:26). 7C. S3 subunit (SEQ ID NO:27). 7D. S4 subunit (SEQ ID NO:28). 7E. S5 subunit (SEQ ID NO:29).

Figure 8:
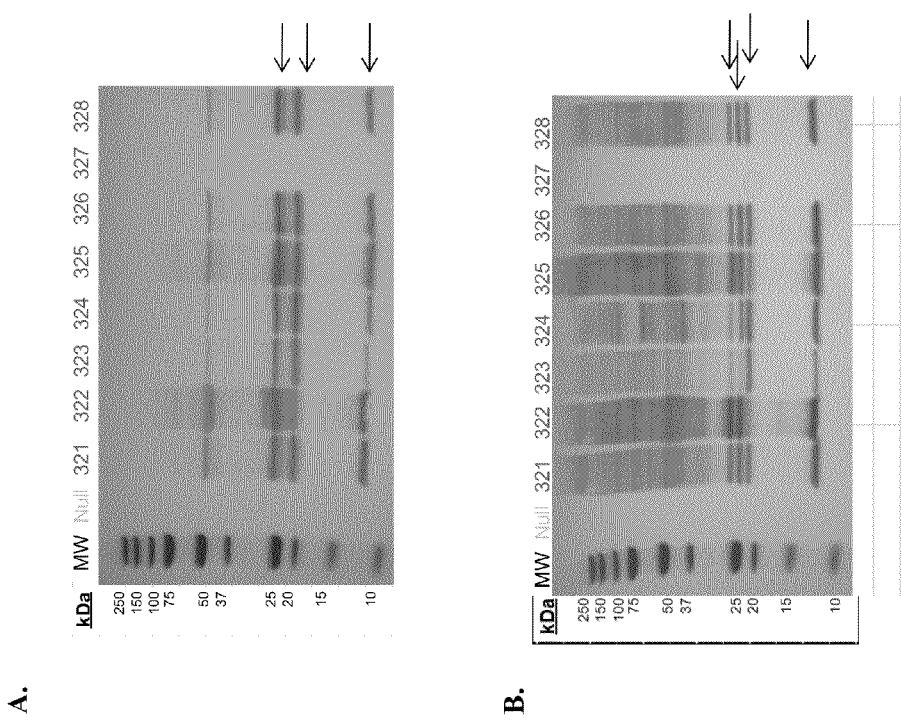

FIG. 8. Western blot analysis of Pertussis Toxoid expression samples. Strain names are listed above each lane. Induced Ptx migrated as multiple bands range from 11 to 26 kDa (S1: 26.1 Kda, S2: 20.9 Kda, S3: 21.8 KDa, S4 (2×): 12 KDa, S5: 11 KDa) A. Reduced samples. B. Non-reduced samples. Both panels: Lane 1—molecular weight markers (10, 15, 20, 25, 37, 50, 75, 100, 150, 250 kDa); Lane 2—Null; Lane 3—strain 321; Lane 4—strain 322; Lane 5—strain 323; Lane 6—strain 324; Lane 7—strain 325; Lane 8—strain 326; Lane 9—strain 327; Lane 10—strain 328.

FIG. 9A to 9C. Tetanus Toxin C Amino Acid and DNA Sequences. 9A. Amino acid sequence (SEQ ID NO:30). 9B. First segment of an optimized DNA sequence encoding the Tetanus Toxin C protein, with translation (SEQ ID NO:31). 9C. Second segment of an optimized DNA sequence encoding the Tetanus Toxin C protein, with translation (SEQ ID NO:31). This optimized sequence is a non-limiting example of an optimized sequence useful in the methods of the present invention.

Figure 10:
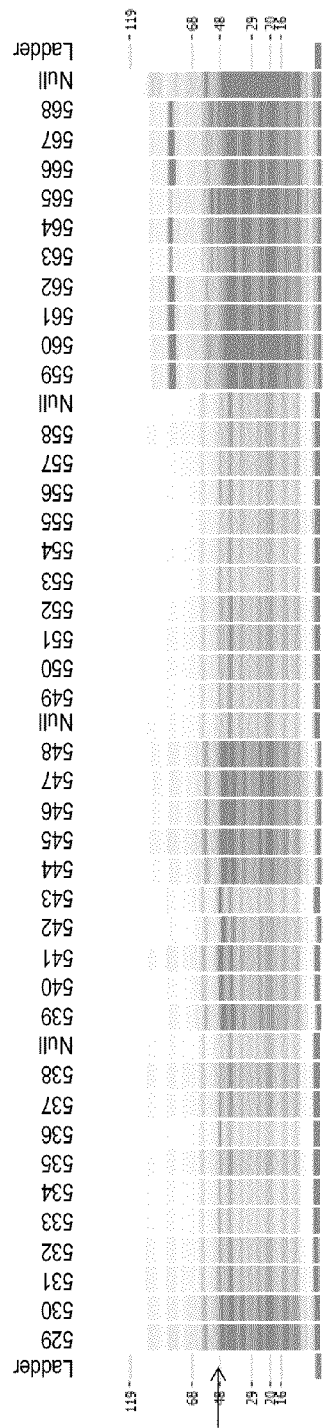

FIG. 10. Tetanus Toxin C Fragment Expression. Tetanus Toxin C Fragment expressed in *P. fluorescens* was analyzed using capillary gel electrophoresis (SDS-CGE). Soluble fractions from 40 tetanus toxin-expression strains tested are shown in a gel-like image generated from the SDS-CGE data. Strain names as described in Table 15 are listed above each lane. Induced Tetanus Toxin C Fragment migrated as a single band at ~51.6 kDa on SDS-CGE (arrow at left). Molecular weight markers in first and last lanes are 16, 20, 29, 48, 69 and 119 kDa.

Figure 11H:
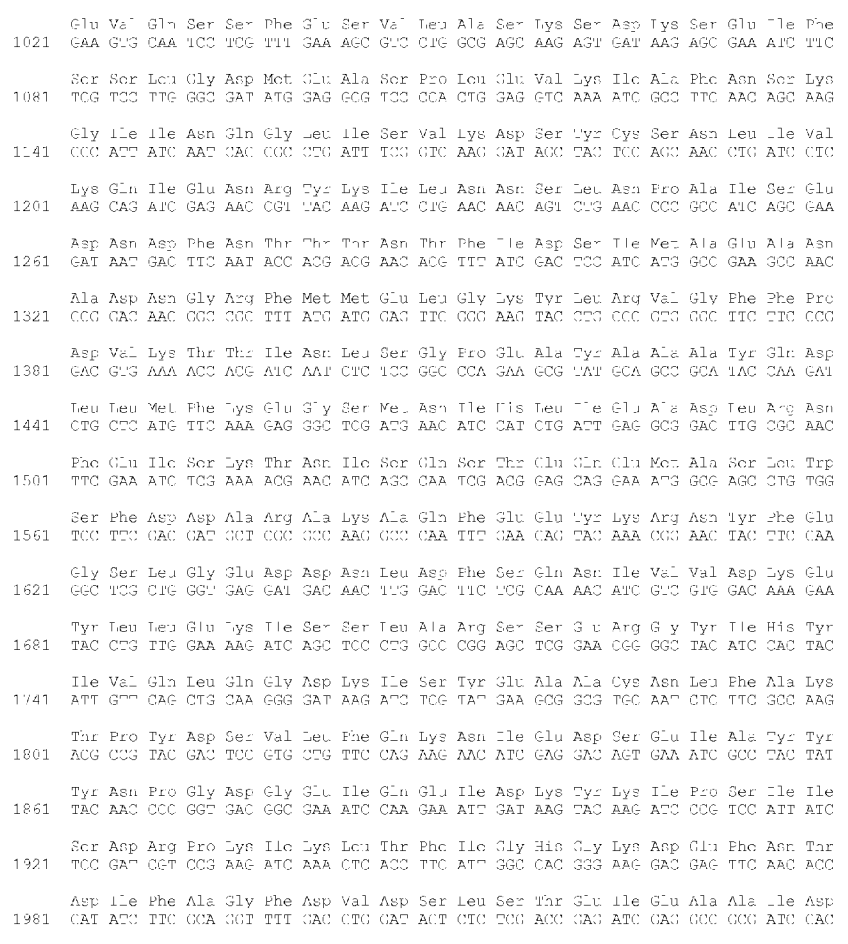
Figure 11I:
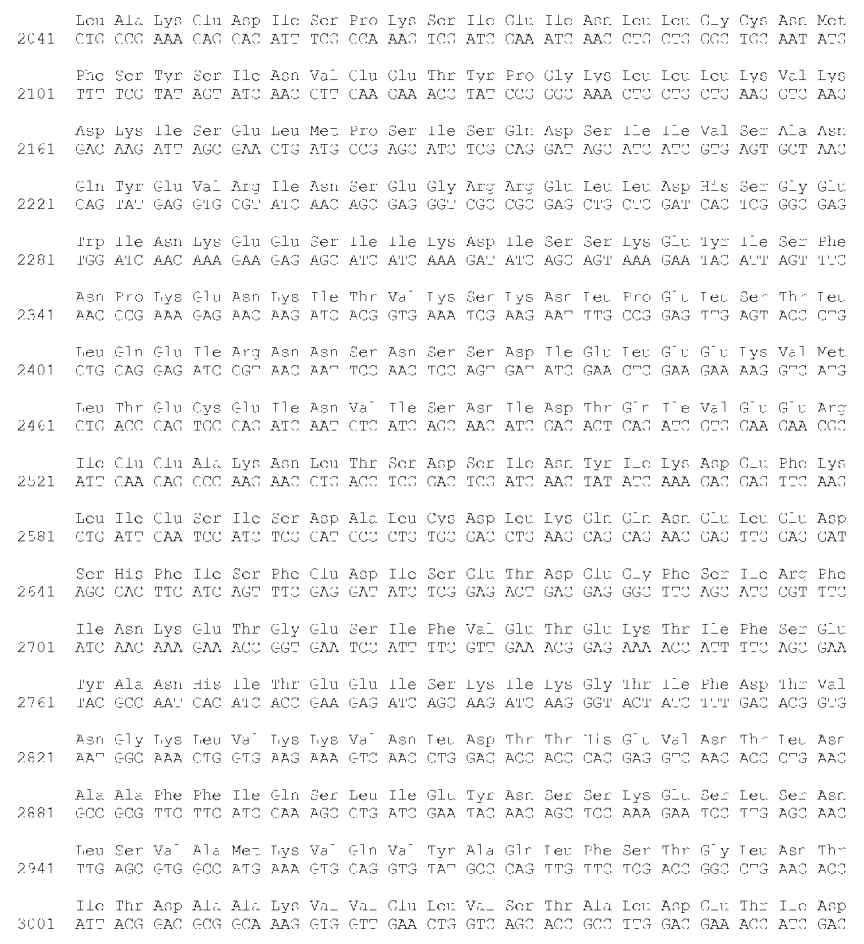
Figure 11J:
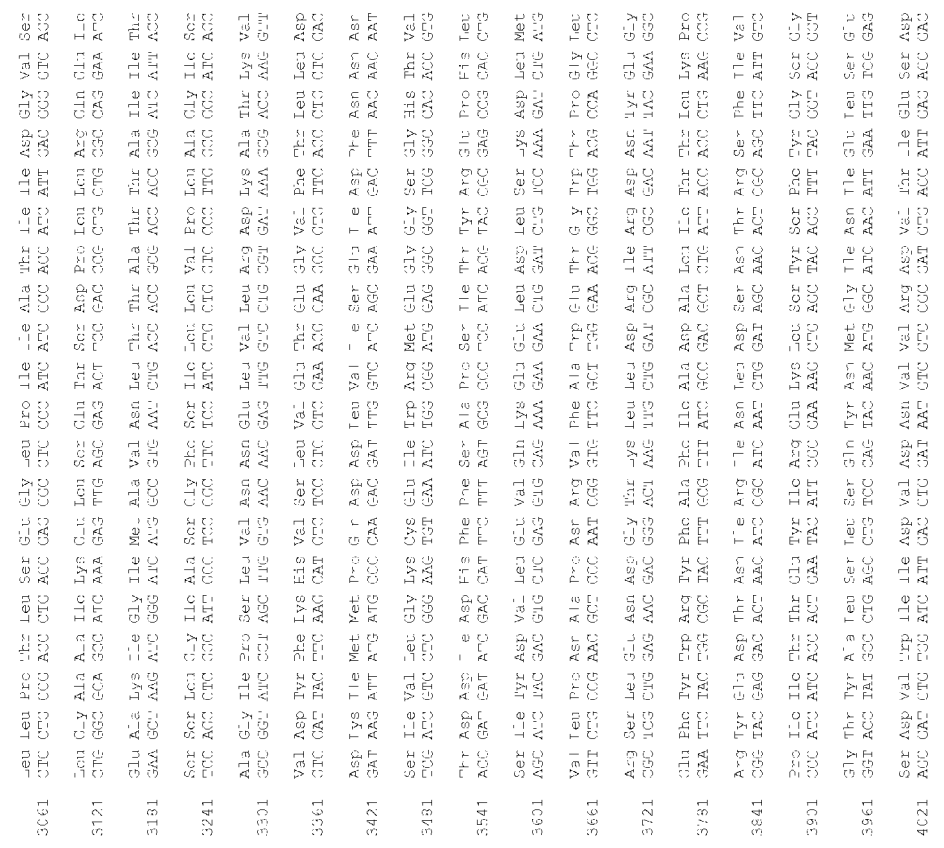
Figure 11K:
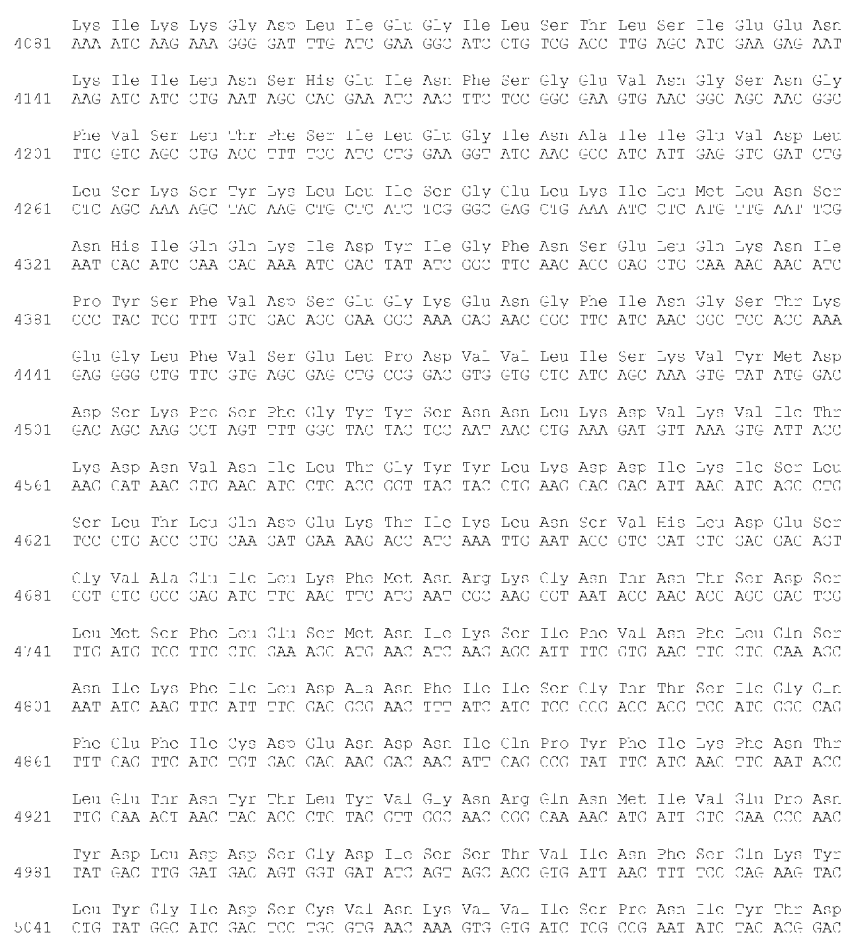
Figure 11M:
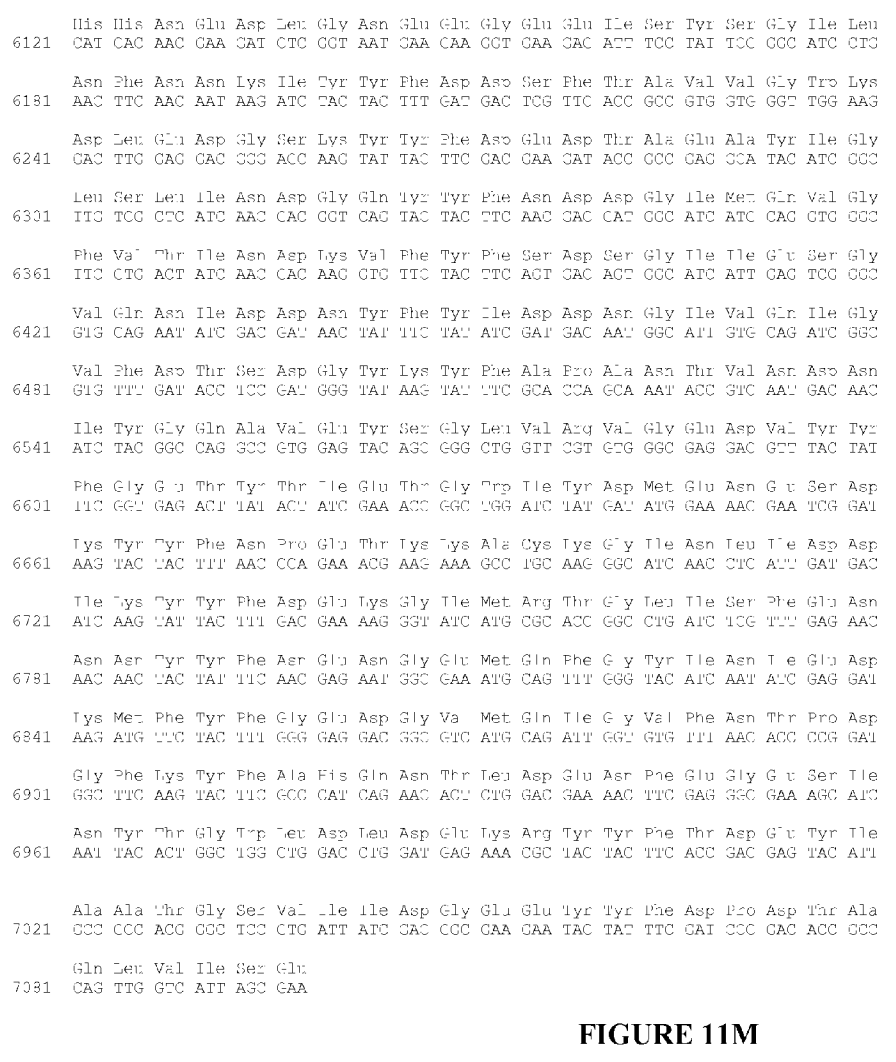

FIG. 11A to 11M. TcdB Amino Acid and DNA Sequences. 11A. First segment of amino acid sequence (SEQ ID NO:32). 11B. Second segment of amino acid sequence (SEQ ID NO:32). 11C. Third segment of amino acid sequence (SEQ ID NO:32). 11D. Fourth segment of amino acid sequence (SEQ ID NO:32). 11E. Fifth segment of amino acid sequence (SEQ ID NO:32). 11F. Sixth segment of amino acid sequence (SEQ ID NO:32). 11G. First segment of an optimized DNA sequence encoding the TcdB protein, with translation (SEQ ID NO:33). 11H. Second segment of an optimized DNA sequence encoding the TcdB protein, with translation (SEQ ID NO:33). 11I. Third segment of an optimized DNA sequence encoding the TcdB protein, with translation (SEQ ID NO:33). 11J. Fourth segment of an optimized DNA sequence encoding the TcdB protein, with translation (SEQ ID NO:33). 11K. Fifth segment of an optimized DNA sequence encoding the TcdB protein, with translation (SEQ ID NO:33). 11L. Sixth segment of an optimized DNA sequence encoding the TcdB protein, with translation (SEQ ID NO:33). 11M. Seventh segment of an optimized DNA sequence encoding the TcdB protein, with translation (SEQ ID NO:33). This optimized sequence is a non-limiting example of an optimized sequence useful in the methods of the present invention.

Figure 12:
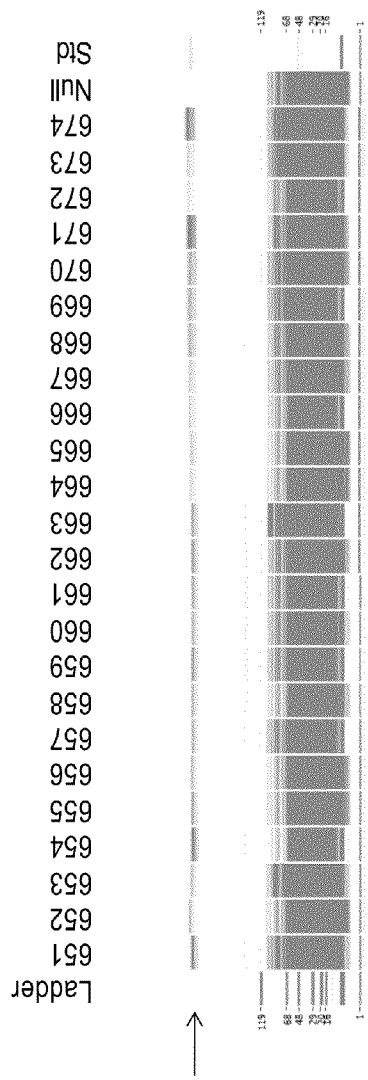

FIG. 12. TcdB Expression. TcdB expressed in *P. fluorescens* was analyzed using capillary gel electrophoresis (SDS-CGE). Soluble fractions from 24 TcdB-expression strains tested are shown in a gel-like image generated from the SDS-CGE data. Strain names as described in Table 18 as well as null extract and reference standard (List Biologicals) are listed above each lane. Induced TcdB migrated as a single band at ~300 kDa on SDS-CGE (arrow at left). Molecular weight markers in first and last lanes are 16, 20, 29, 48, 69 and 119 kDa.

FIG. 13A to 13B. Exotoxin A Amino Acid Sequence. 13A. First segment of the amino acid sequence of *P. aeruginosa* Exotoxin A is shown (SEQ ID NO:34). 13B. Second segment of the amino acid sequence of *P. aeruginosa* Exotoxin A is shown (SEQ ID NO:34). Three Exotoxin A proteins are indicated by the drawing: wild-type, CRM66, and rEPA. In variant CRM66, His 426 (bold, underlined text) is replaced by a Tyr as indicated above the sequence. In rEPA, Glu 553 (bold, underlined text) is deleted as indicated above the sequence.

Figure 14:
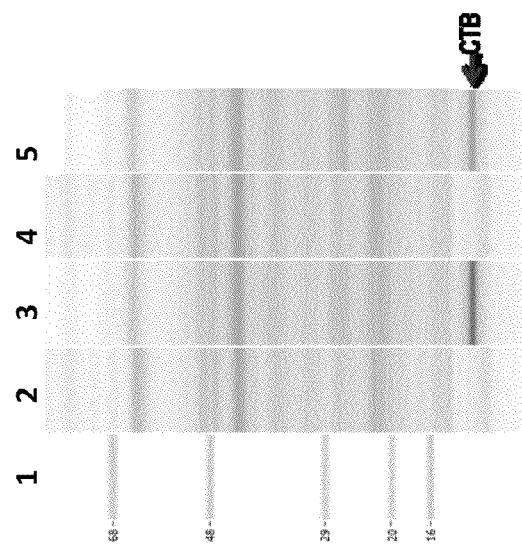

FIG. 14. Soluble Cholera Toxin B Production in *P. fluorescens* Fermentation Cultures. SDS-CGE Analysis. Lane 1-16, 20, 29, 48, 69 and 119 kDa molecular weight markers. Lanes 2 and 4-pre-induction samples and lanes 3 and 5 post-induction samples, respectively, of PS538-088 U5 and U6 fermentations expressing Cholera Toxin B, indicated by arrow at right.

FIG. 15. Soluble Tetanus Toxin Fragment C Production in *P. fluorescens* Fermentation Cultures. A. SDS-CGE Analysis. Lane 1-16, 20, 29, 48, 69 and 119 kDa molecular markers. Lanes 2, 3 and 4 are post-induction samples of PS538-529 U1 PS538-546 U5 and PS538-547 U7 fermentations, respectively, expressing Tetanus Toxin Fragment C, indicated by arrow at right. B. Western Blot Analysis. Fermentation samples from strains PS538-538 (U1 and U2), PS538-548 (U3 and U4), PS538-558 (U5 and U6) and PS538-568 (U7 and U8) were evaluated by Western blot. Fermentation unit and hours post induction (I0, I8, I24) are indicated above each lane. Molecular weight (MW) standards are shown on the left of the blot and Tetanus Toxin C reference standard (Std; List Biological, Cat#193) is shown on the right. Blots were probed with Polyclonal Anti-Tetanus Toxin C Fragment, derived in Rabbit (Abcam, Cat#: ab34890) followed by Anti-Rabbit IgG Peroxidase, derived in Goat (Pierce, Cat#: 31460). Immunopure Metal Enhanced DAB (Pierce 34065) was used for detection.

Figure 16:
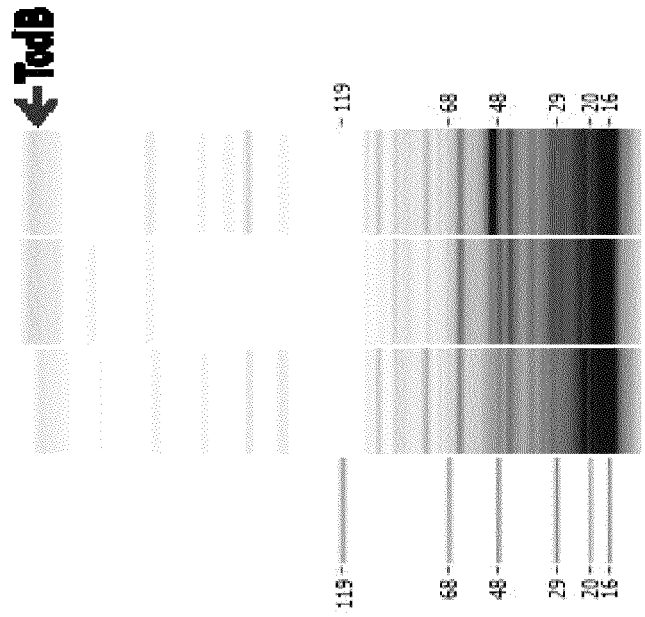

FIG. 16. Soluble *C. difficile* B Toxin Protein Production in *P. fluorescens* Fermentation Cultures. Lane 1-16, 20, 29, 48, 69 and 119 kDa molecular weight markers. The marker sizes are also indicated in their respective positions at the right, based on migration in Lane 1. Lanes 2, 3 and 4 are post-induction samples of PS538-671 U5 and U6, and PS538-674 U7 fermentations, respectively, expressing *C. difficile* B Toxin Protein, indicated by arrow at right.

Figure 17C:
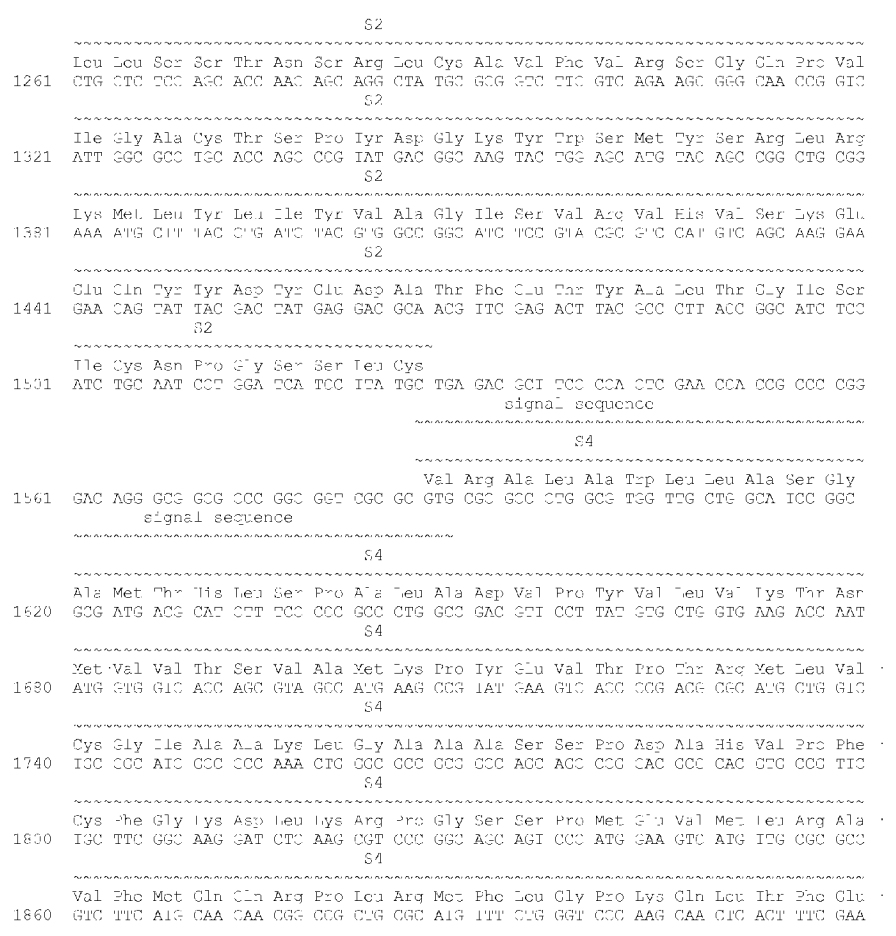
Figure 17D:
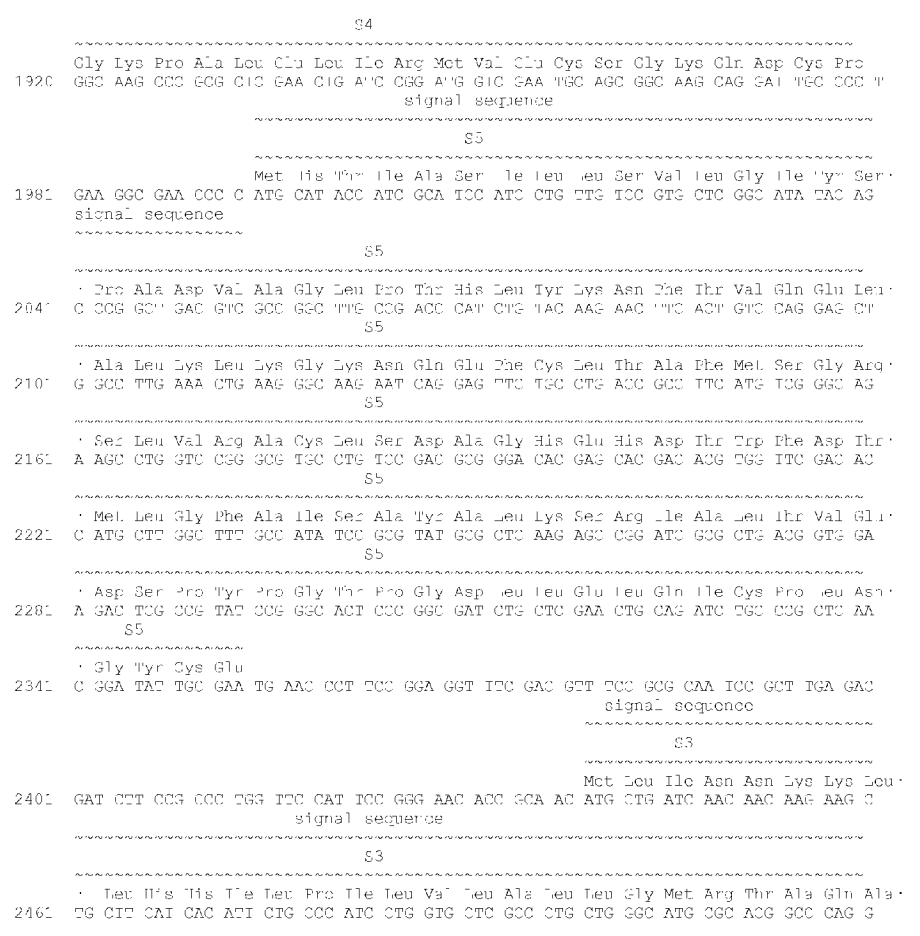

FIG. 17A to 17 E. DNA Sequence of Wild-Type Pertussis Toxoid. 17A. First segment of the wild-type Pertussis toxin DNA sequence with translation is shown (SEQ ID NO:35). 17B. Second segment of the wild-type Pertussis toxin DNA sequence with translation is shown (SEQ ID NO:35). 17C. Third segment of the wild-type Pertussis toxin DNA sequence with translation is shown (SEQ ID NO:35). 17D. Fourth segment of the wild-type Pertussis toxin DNA sequence with translation is shown (SEQ ID NO:35). 17E. Fifth segment of the wild-type Pertussis toxin DNA sequence with translation is shown (SEQ ID NO:35). The sequence is from Genebank entry M13223. Subunits S1-S5 and signal sequences are indicated above the sequences. The encoded proteins are disclosed as SEQ ID NOS 41-45, respectively, in order of appearance.

FIG. 18A to 18B. Amino Acid and DNA Sequence of Wild-Type Diphtheria toxin. 18A. Amino acid sequence (SEQ ID NO: 36). 18B. An optimized DNA sequence (SEQ ID NO:37) encoding the DT protein, with translation shown. This optimized sequence is a non-limiting example of an optimized sequence useful in the methods of the present invention. The encoded protein is disclosed as residues 1-320 of SEQ ID NO: 36.

Figure 19D:
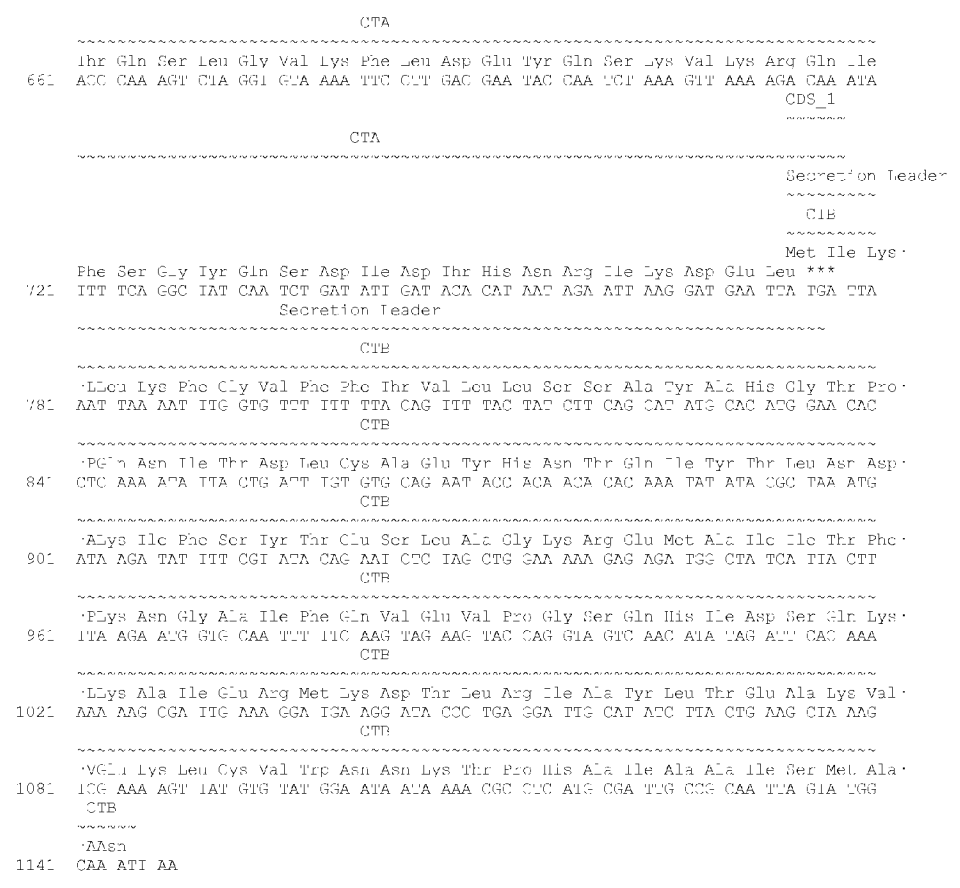

FIG. 19A to D. Amino Acid and DNA Sequence of Cholera Holotoxin. 19A. CTA amino acid sequence (SEQ ID NO: 38), with secretion leader (underlined) (AE003852; Protein ID AAF94614.1). 19B. CTB amino acid sequence (SEQ ID NO: 39), with secretion leader (underlined) (GenBank AE003852; Protein ID AAF94613.1). 19C. First segment of CTX DNA sequence (SEQ ID NO:40) indicating the A and B subunits, with translation shown (Genbank AE003852). 19D. Second segment of CTX DNA sequence (SEQ ID NO:40) indicating the A and B subunits, with translation shown (Genbank AE003 852). The encoded proteins are disclosed as SEQ ID NOS 38 and 39, respectively, in order of appearance.

Figure 20:
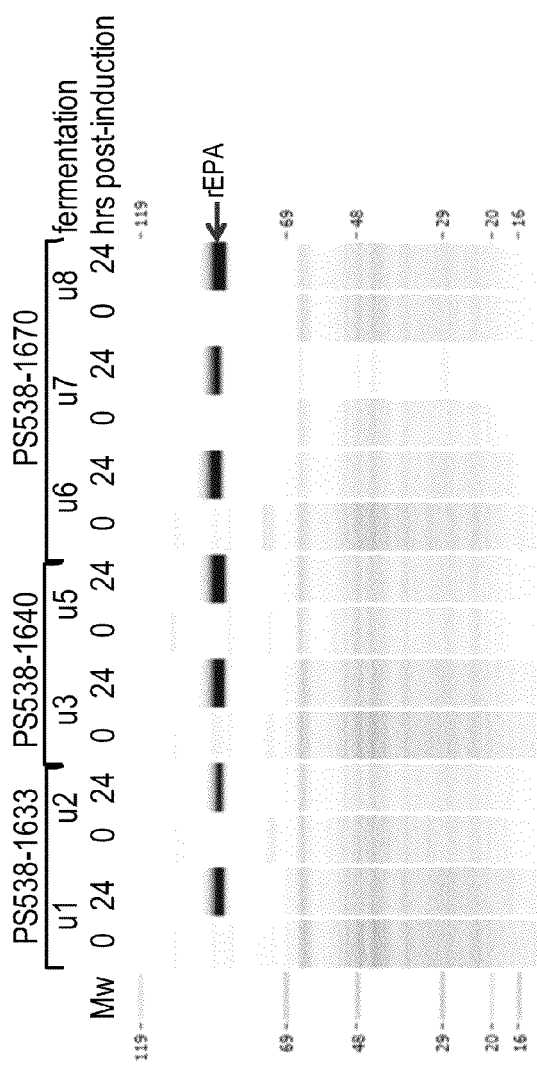

FIG. 20. SDS-CGE Gel-like Image of Soluble rEPA Production in *P. fluorescens* Fermentation Cultures. Soluble rEPA expressed in fermentation cultures of *P. fluorescens* was analyzed using capillary gel electrophoresis (SDS-CGE). Soluble fractions from fermentations of expression strains PS538-1633 (u1 and u2), PS538-1640 (u3 and u5) and PS538-1670 (u6, u7 and u8) at 0 and 24 hours post-induction tested are shown in a gel-like image generated from the SDS-CGE data. Mw=molecular weight standards (16, 20, 29, 48, and 69 kilodaltons).

Figure 21:
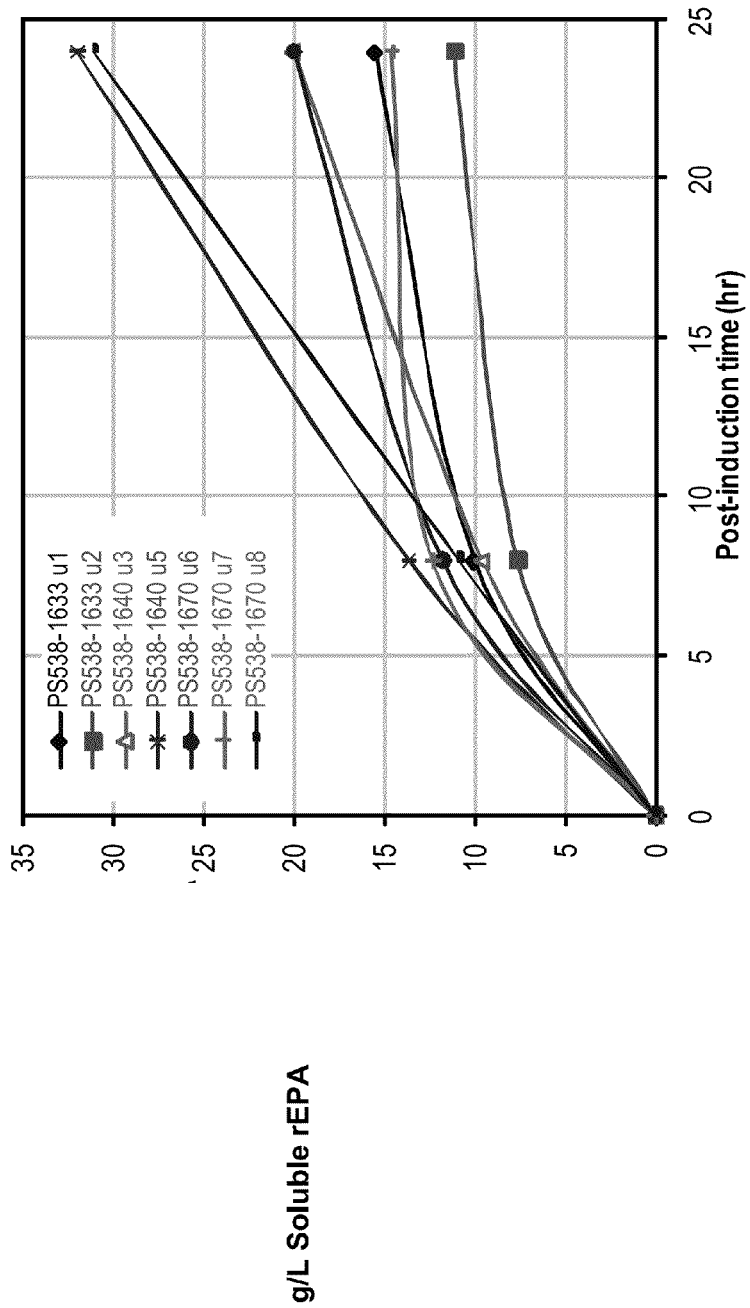

FIG. 21. Soluble rEPA Production Trends in *P. fluorescens* Fermentation Cultures. Soluble rEPA expression levels, as determined by SDS-CGE analysis of strains (PS538-1633, PS538-1640 and PS538-1670) in their respective fermentations (u1, u2, u3, u6, u7 and u8), are plotted against post-induction times.

Figure 22:
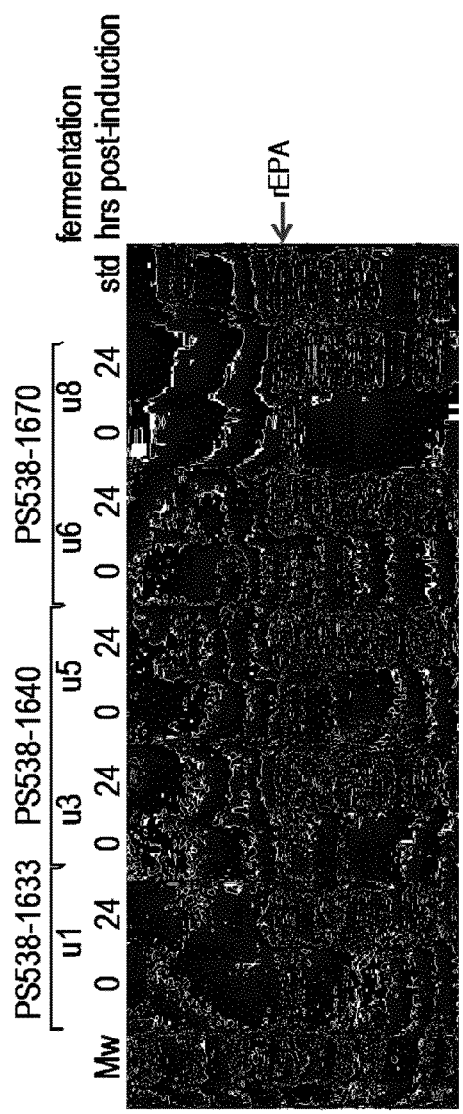

FIG. 22. Western Blot of Soluble rEPA Production in *P. fluorescens* Fermentation Cultures. Soluble rEPA expressed in fermentation cultures of *P. fluorescens* were analyzed using Western blot analysis. Soluble fractions from fermentations of expression strains PS538-1633 (u1), PS538-1640 (u3 and u5) and PS538-1670 (u6 and u8) at 0 and 24 hours post-induction are shown in a Western blot analysis using an antibody specific for *P. aeruginosa* Exotoxin A. Mw=molecular weight standards. std=rEPA standard.

Figure 23:
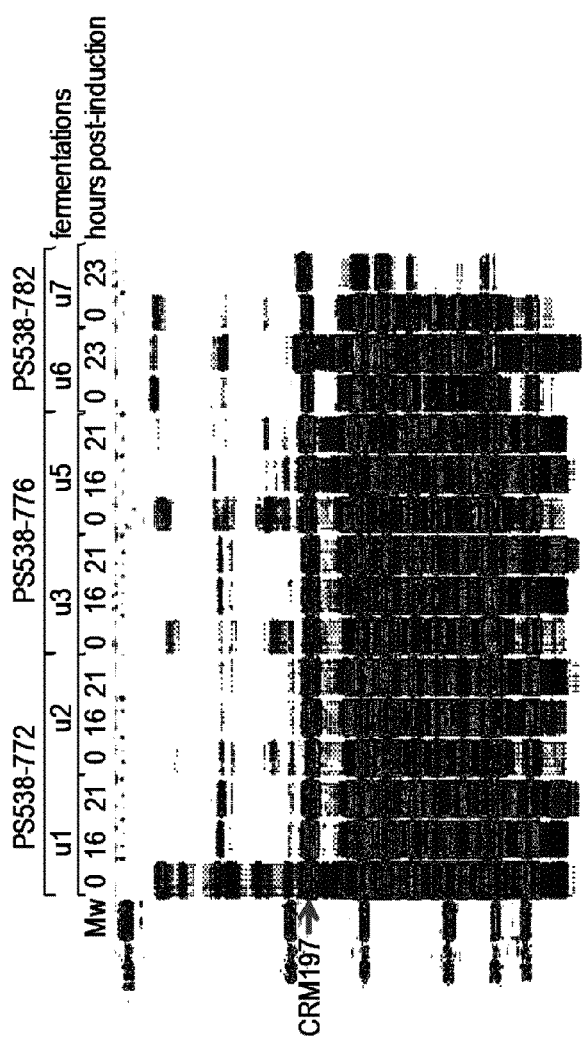

FIG. 23. SDS-CGE Gel-like Image of Soluble CRM197 Production in *P. fluorescens* Fermentation Cultures. CRM197 expressed in fermentation cultures of *P. fluorescens* was analyzed using capillary gel electrophoresis (SDS-CGE). Soluble fractions from various fermentations of expression strains PS538-772 (u1 and u2), PS538-776 (u3 and u5) and PS538-782 (u6 and u7) at various times post-induction (0, 16, 21 and 23 hours) tested are shown in a gel-like image generated from the SDS-CGE data. Mw=molecular weight standards (16, 20, 29, 48, 68, and 119 kilodaltons).

Figure 24:
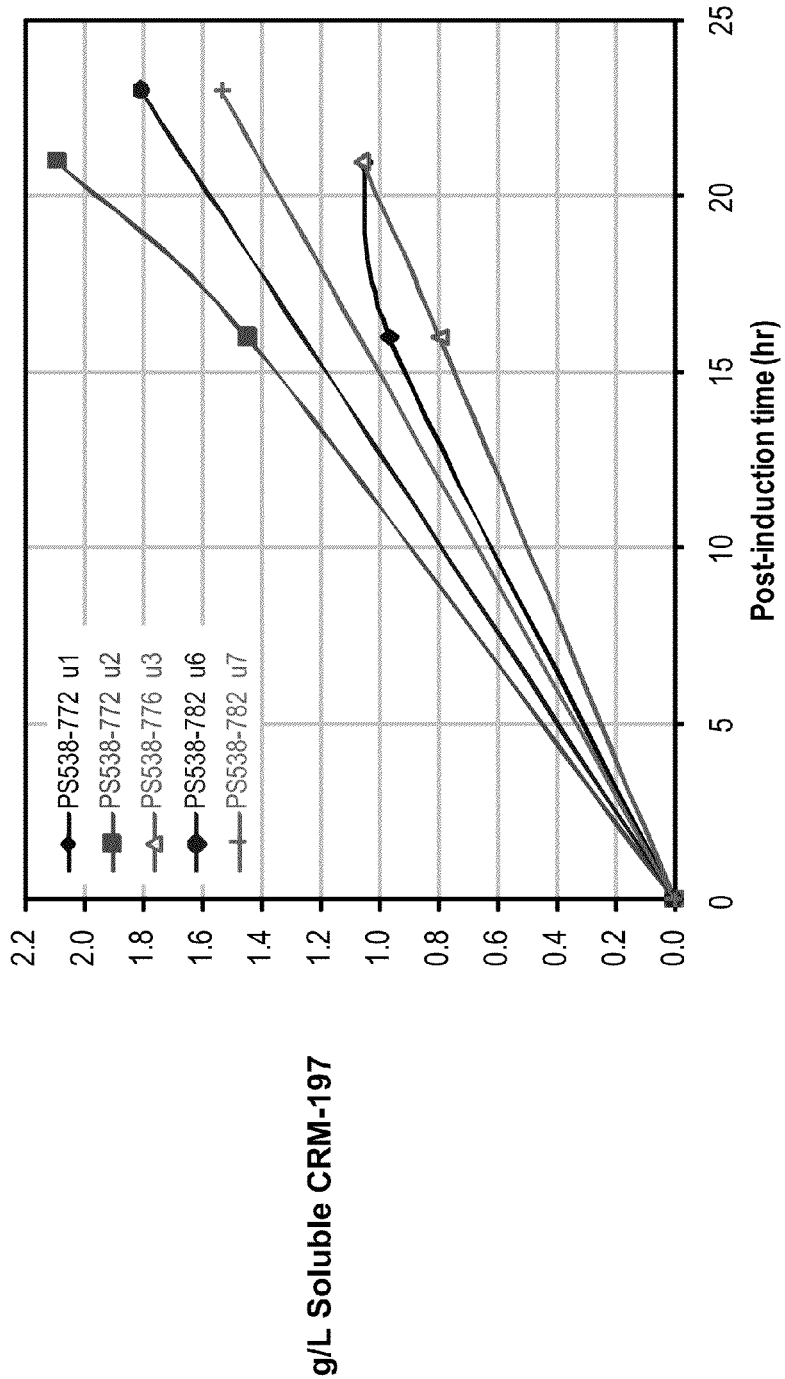

FIG. 24. Soluble CRM197 Production Trends in *P. fluorescens* Fermentation Cultures. Soluble CRM197 expression levels as determined by SDS-CGE from the different strains (PS538-772, PS538-776 and PS538-782) in their respective fermentations (u1, u2, u3, u6 and u7) are plotted against post-induction times.

Figure 25:
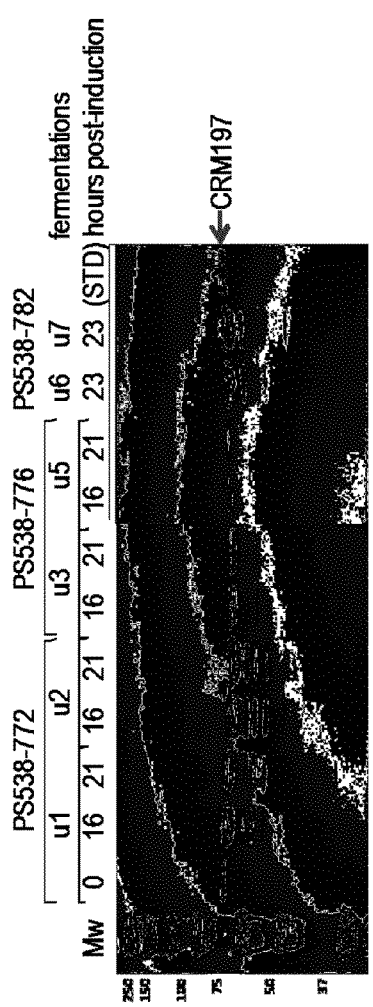

FIG. 25. Western Blot of Soluble CRM197 Production in *P. fluorescens* Fermentation Cultures. CRM197 expressed in fermentation cultures of *P. fluorescens* were analyzed using Western blot analysis. Soluble fractions from various fermentations of expression strains PS538-772 (u1 and u2), PS538-776 (u3 and u5) and PS538-782 (u6 and u7) at various times post-induction (0, 16, 21 and 23 hours) tested are shown in a Western blot analysis using a diphtheria toxin specific antibody. Mw=molecular weight standards (37, 50, 75, 100, 150, and 250 kilodaltons). STD=CRM197standard.

DETAILED DESCRIPTION OF THE INVENTION

Toxins
ADP-Ribosylating Toxins

ADP-ribosylating toxins (ADPRTs) facilitate scission of the N-glycosyl bond between nicotinamide and the N-ribose of NAD and transfer the ADP-ribose moiety to target proteins. ADPRTs are classified into four families based on their respective targets. Type I ADPRTs target heteromeric GTP-binding proteins. They include Cholera Toxin (CTX), Pertussis toxin (PTX), and *Escherichia coli* heat-labile enterotoxin (LT). Type II ADPRTs (Diphtheria toxin and *Pseudomonas* Exotoxin A) modify elongation factor 2 (EF2). Type III ADPRTs (*Clostridium botulinum* C3 exoenzyme) ADP-ribosylate small GTP-binding proteins. Type IV ADPRTs ADP-ribosylate actin. These actin-specific ADPRTs include a family of binary toxins comprising *C. botulinum* C2 toxin, *C. perfringens* ι-toxin, *C. difficile* toxin (a toxin distinct from TcdA and TcdB, described by Popoff, et al., 1988, "Actin-specific ADP-ribosyltransferase produced by a *Clostridium difficile* strain," Infection and Immunity 56(9):2299-2306, incorporated herein by reference), *C. spiroforme* toxin, and *Bacillus cereus* vegetative insecticidal protein (VIP).

The structures of several enzymatic components from each type of ADPRT have been determined with or without NAD, and are discussed by, e.g., Tsuge, et al., 2008, "Structural basis of actin recognition and arginine ADP-ribosylation by *Clostridium perfringens*-toxin," PNAS 105(21):7399-7404, incorporated herein by reference. Typical actin-specific ADPRTs possess two similar domains: the C domain, which is essential for catalytic activity; and the N domain, which is important for the interaction with the binding and translocation subunit. By contrast, SpvB from *Salmonella* and the type III ADPRT C3 have only one ADP-ribosyltransferase domain and lack the N-terminal adaptor domain. In all type IV ADPRTs, the EXE motif, including two key glutamate residues, is present at the catalytic center. The former glutamate of the EXE motif is thought to be a key residue for ADP-ribosyltransferase, which is deprotonated from Arg-177 in actin. The latter glutamate forms a hydrogen bond with the O'2 on N-ribose, which is thought to stabilize the oxocarbenium cation.

ADPRTs are further described by Barth, et al., 2004, "Binary Bacterial Toxins: Biochemistry, Biology, and Application of Common *Clostridium* and *Bacillus* Proteins," Microbiology and Molecular Biology Reviews 68(3):373-402; Mueller-Dieckmann, et al., "Structure of mouse ADP-ribosylhydrolase 3 (mARH3)," Acta Cryst F64:156-162; Kulich, et al., 1995, "Expression of Recombinant Exoenzyme S of *Pseudomonas aeruginosa*," Infection and Immunity 63(1):1-8; Sakurai, et al., 2009, "*Clostridium perfringens* Iota-Toxin: Structure and Function," Toxins 1:208-228; and Schirmer, et al., 2002, "The ADP-ribosylating Mosquitocidal Toxin from *Bacillus sphaericus*," The Journal of Biological Chemistry 277(14): 11941-11948, all incorporated herein by reference.

In embodiments of the present invention, a recombinant toxin protein selected from a group including ADPRTs is produced. In embodiments, the group of ADPRTs consists of CTX (CTA and/or CTB), PTX, DT (CRM197 and/or WT), and *Pseudomonas* Exotoxin A. In embodiments, the group of ADPRTs consists of CTX(CTA and/or CTB), PTX, and *Pseudomonas* Exotoxin A. In other embodiments, a recombinant toxin protein selected from a group including Type I ADPRTs is produced. In embodiments, the group of Type I ADPRTs consists of CTX (CTA and/or CTB), and PTX. In other embodiments, a recombinant toxin protein selected from a group including Type II ADPRTs is produced. In embodiments, the group of Type II ADPRTs consists of DT (CRM197 and/or WT), and *Pseudomonas* Exotoxin A. In other embodiments, a recombinant toxin protein selected from a group including Type IV ADPRTs is produced. In embodiments, the Type IV ADPRT is TcdB.

CRM197 and DT

Cross-reacting material 197 (CRM197) is a Diphtheria toxin (DT) variant produced from a DT gene having a missense mutation. DT is an ADP-ribosylating toxin; CRM197 lacks the ADP-ribosyltransferase (ADPRT) activity of DT, and is thus nontoxic. The gene for CRM197 has a single base substitution, resulting in the incorporation of glutamic acid instead of glycine at residue 52. (See, e.g., Bishai, et al., 1987, "High-Level Expression of a Proteolytically Sensitive Diphtheria toxin Fragment in *Escherichia coli*," J. Bact. 169(11): 5140-51, Giannini, et al., 1984, "The Amino-Acid Sequence of Two Non-Toxic Mutants of Diphtheria toxin: CRM45 and CRM197," Nucleic Acids Research 12(10): 4063-9, and GenBank Acc. No. 1007216A, all incorporated herein by reference.)

CRM197 protein may be prepared at low levels by methods known in the art or by expression in *C. diphtheriae* or other microorganisms. The naturally occurring, or wild-type, Diphtheria toxin may be obtained from toxin producing strains available from a variety of public sources including the American Type Culture Collection. A plasmid system for producing CRM197 protein in *C. diphtheriae* is described by, e.g., U.S. Pat. No. 5,614,382, "Plasmid for Production of CRM Protein and Diphtheria toxin," incorporated herein by reference in its entirety.

The nucleotide sequence may be prepared using the techniques of recombinant DNA technology (described by, e.g., Sambrook et al, Molecular Cloning, a Laboratory Manual, Cold Spring Harbor Laboratory Press, 1989), and also by site-directed mutagenesis, based on the known DT nucleotide sequence of the wild type structural gene for Diphtheria toxin carried by corynebacteriophage β. (See, e.g., Greenfield, et al., 1993, "Nucleotide Sequence of the Structural Gene for Diphtheria toxin Carried by Corynebacteriophage 18," Proc Nat Acad Sci 80:6953-7, incorporated herein by reference.) The nucleotide sequence can be optimized as described elsewhere herein.

In embodiments of the present invention, CRM197 or DT are produced using any of the host strains described herein in Example 1, in combination with any of the expression vectors (plasmids) described in Example 1. In embodiments, the nucleic acid sequence is optimized for expression in the Pseudomonad host cell. In embodiments, the expression vectors used contain constructs expressing any of the secretion leaders described in Table 8 and Table 3 fused to the recombinant CRM197 or DT protein. In embodiments, the native secretion leader is used. In certain embodiments, the CRM197 or DT protein is expressed with a tag, e.g., a purification tag. In embodiments, the methods of the invention are used to produce CRM197 or DT at a yield of about 0.5 g/L to at least about 12 g/L.

Cholera Toxin

Cholera toxin (CTX), produced by *Vibrio cholera*, is also an ADP-ribosylating toxin. The Cholera toxin (CTX) is an oligomeric complex made up of six protein subunits: a single copy of the Cholera toxin A subunit (CTA), and five copies of the Cholera toxin B subunit (CTB). The five B subunits, each weighing 12 kDa, form a five-membered ring. The A subunit has an A1 portion, CTA1, a globular enzyme that ADP-ribosylates G proteins, and an A2 chain, CTA2, that forms an extended alpha helix which sits snugly in the central pore of the B subunit ring. This ring binds to GM1 ganglioside receptors on the host cell surface, resulting in internalization of the entire complex. Once internalized, the CTA1 chain is released by reduction of a disulfide bridge. CTA1 is then activated and catalyzes ADP ribosylation of adenylate cyclase. The resulting increase in adenylate cyclase activity increases cyclic AMP synthesis, which causes massive fluid and electrolyte efflux and results in diarrhea.

The B subunit of CTX, though relatively harmless, retains its ability to bind to the GM1 ganglioside receptor. CTB therefore finds use in facilitating mucosal uptake of chemically or genetically conjugated foreign antigens. It has been demonstrated to induce both mucosal and systemic immunity, and is a candidate for use in edible vaccine production. Because of its binding preference, CTB also finds use as a neuronal tracer.

The use of CTB, as well as its structural features, have been described, e.g., by: Nozoye, et al., 2009, "Production of *Ascaris suum* As14 Protein and Its Fusion Protein with Cholera Toxin B Subunit in Rice Seeds," Parasitology 995-1000; Harakuni, et al., 2005, "Heteropentameric Cholera Toxin B Subunit Chimeric Molecules Genetically Fused to a Vaccine Antigen Induce Systemic and Mucosal Immune Responses: a Potential New Strategy to Target Recombinant Vaccine Antigens to Mucosal Immune Systems," Infection and Immunity 73(9):5654-5665; Price, et al., 2005, "Intranasal Administration of Recombinant *Neisseria gonorrhoeae* Transferrin Binding Proteins A and B Conjugated to the Cholera Toxin B Subunit Induces Systemic and Vaginal Antibodies in Mice," Infection and Immunity 73(7):3945-3953; and Sun, et al., 1999, "Intranasal Administration of a *Schistosoma mansoni*

Glutathione S-Transferase-Cholera Toxoid Conjugate Vaccine Evokes Antiparasitic and Antipathological Immunity in Mice," J. Immunol. 163:1045-1052, all incorporated herein by reference.

In embodiments of the present invention, CTB or CTX is produced using any of the host strains described herein in Example 1, in combination with any of the expression vectors described in Example 3. In embodiments, the nucleic acid sequence is optimized for expression in the Pseudomonad host cell. In embodiments, the expression vectors used contain constructs expressing any of the secretion leaders described in Table 8 and Table 3 fused to the recombinant CTB or CTX protein. In embodiments, the native secretion leader is used. In certain embodiments, the CTB or CTX protein is expressed with a tag, e.g., a purification tag. In embodiments, the methods of the invention are used to produce CTB or CTX at a yield of about 0.2 g/L to at least about 5 g/L.

Pertussis Toxin

Pertussis toxin is an exotoxin and virulence factor produced by *Bordetella pertussis*, a bacterial pathogen of the human respiratory tract that causes the disease whooping cough. The pertussis holotoxin is a multi-subunit complex with an AB 5 structure. The enzymatically active A subunit (S1) is an ADP-ribosyltransferase that modifies the alpha subunit of several heterotrimeric G proteins (primarily G i proteins) in mammalian cells, and the B oligomer (S2, S3, 2 copies of S4, and S5) binds glycoconjugate receptors on cells. S1 is proteolytically processed after cell entry. Carbonetti, et al., 2005, "Proteolytic Cleavage of Pertussis Toxin S1 Subunit is Not Essential for Its Activity in Mammalian Cells," BMC Microbiology 5:7, incorporated herein by reference, reported that processing of S1 is not essential for its cytotoxic activity in mammalian cells.

Nontoxic variants of Pertussis toxin have been explored for use in vaccines. Pertussis toxin protein produced using the methods of the present invention is contemplated for use in a vaccine to protect against pertussis. Pertussis toxin has also been tested as a vaccine adjuvant, e.g., as described by Roberts, et al., 1995, "A Mutant Pertussis Toxin Molecule That Lacks ADP-Ribosyltransferase Activity, PT-9K/129G, Is an Effective Mucosal Adjuvant for Intranasally Delivered Proteins," Infection and Immunity 63(6):2100-2108, incorporated herein by reference. Further, Pertussis toxin is also useful for research purposes, e.g., for studies of G protein signaling pathways (e.g., McCoy, et al., 2010, "PAR1 and PAR2 couple to overlapping and distinct sets of G proteins and linked signaling pathways to differentially regulate cell physiology," Molecular Pharmacology Fast Forward MOL 62018, incorporated herein by reference) and as an adjuvant to enhance induction of autoimmune diseases, e.g., experimental autoimmune encephalomyelitis (EAE), experimental autoimmune orchitis, experimental autoimmune uveitis, etc. (Su, et al., 2001, "Pertussis Toxin Inhibits Induction of Tissue-Specific Autoimmune Disease by Disrupting G Protein-Coupled Signals," J Immunol 167:250-256incorporated herein by reference).

The five subunits of the toxin are expressed from the Pertussis Toxoid operon, shown in FIG. 5. The expression and structure of Pertussis toxin proteins, including certain variants, are described by above-cited reports, as well as by Burnette, et al., 1992, "Properties of Pertussis Toxin B Oligomer Assembled In Vitro from Recombinant Polypeptides Produced by *Escherichia coli*," Infection and Immunity 60(6):2252-2256; U.S. Pat. No. 5,085,862, "Genetic detoxification of pertussis toxin;" and Kaslow, et al., 1987, "Structure-Activity Analysis of the Activation of Pertussis Toxin," Biochemistry 26(1):123-7; all incorporated by reference herein in their entirety.

Pertussis Toxin or PTX as used herein refers to Pertussis Toxin mutant S1 R9K E129A or the wild-type protein. Wild-type Pertussis toxin and Pertussis toxin mutant S1 R9K E129A are described by, e.g.,: Roberts, et al., 1995 (cited above); U.S. Pat. No. 7,427,404 and U.S. Pat. No. 7,666,436, both titled, "Pertussis Toxin Mutants, *Bordetella* Strains Capable of Producing Such Mutants and Their Use in the Development of Antipertussis Vaccines;" U.S. Pat. No. 5,935,580, "Recombinant Mutants for Inducing Specific Immune Responses;" U.S. Pat. No. 7,169,399, "Non-Toxic Double Mutant Forms of Pertussis Toxin as Adjuvants;" U.S. Pat. No. 5,785,971 and U.S. Pat. No. 5,427,788, both titled, "Pertussis Toxin and Use in Vaccines;" and U.S. Pat. No. 5,773,600, "DNA Encoding Pertussis Toxin Muteins," all incorporated herein by reference in their entirety.

In embodiments of the present invention, Pertussis toxin mutant S1 E129A or wild-type Pertussis toxin is produced using any of the host strains described herein in Example 1, 5 and 7. In embodiments, the expression vectors used contain constructs expressing any of the secretion leaders described in Table 8 and Table 3 fused to the recombinant PTX protein. In embodiments, the native secretion leader is used. In embodiments, any or all of the subunit encoding sequences are optimized for expression in the Pseudomonad host selected, as described elsewhere herein. In certain embodiments, the subunits are expressed from two or more constructs, for example, by subcloning the individual sequences according to methods well-known in the art. In certain embodiments, the PTX protein is expressed with a tag, e.g., a purification tag. In embodiments, the methods of the invention are used to produce PTX or each individual subunit of PTX at a yield of about 0.2 g/L to at least about 5 g/L.

Tetanus Toxin Fragment C

Tetanus Toxin, produced by *Clostridium tetani*, is a neurotoxin having a molecular weight of 150 kDa. It is made up of two parts: a 100 kDa heavy or B-chain and a 50 kDa light or A-chain. The chains are connected by a disulfide bond. The B-chain binds to disialogangliosides (GD2 and GD1b) on the neuronal membrane. The A-chain, a zinc endopeptidase, attacks the vesicle-associated membrane protein (VAMP).

The action of the A-chain stops the affected neurons from releasing the inhibitory neurotransmitters GABA (gamma-aminobutyric acid) and glycine by degrading the protein synaptobrevin. The consequence of this is dangerous overactivity in the muscles from the smallest stimulus—the failure of inhibition of motor reflexes by sensory stimulation. This causes generalized contractions of the agonist and antagonist musculature, termed a tetanic spasm.

Tetanus Toxin Fragment C (Tet C or TTC) is a 50 kD polypeptide generated by protease cleavage (e.g., with papain) of Tetanus toxin, or through recombinant expression of the fragment. It corresponds to the 451 amino acids at the C-terminus (amino acid positions 865-1315). Recombinant expression of Fragment C is disclosed in, e.g., U.S. Pat. No. 5,443,966, "Expression of Tetanus Toxin Fragment C," WO/2005/000346, "Carrier Proteins for Vaccines," and 6,010,871, "Modification of Peptide and Protein," all incorporated herein by reference in their entirety.

Fragment C has been shown to be non-toxic and capable of stimulating a protective immune response in mice and guinea pigs. U.S. Pat. No. 5,443,966 describes the sequence of Tetanus Toxin and production of Fragment C in *E. coli*. Expression of recombinant TTC in yeast has been described, e.g., in U.S. Pat. No. 5,571,694, "Expression of Tetanus Toxin Fragment C in Yeast," incorporated herein by reference in its entirety.

Because it binds to neurons with high specificity and affinity, TTC finds use as a targeting molecule for neuronal drug delivery or for research purposes. Such use is described by, e.g., Townsend, et al., 2007, "Tetanus toxin C fragment conjugated nanoparticles for targeted drug delivery to neurons," Biomaterials 28(34):5176-5184, incorporated herein by reference.

TTC protein is also potentially useful as a vaccine carrier protein, as described in, e.g., WO/2005/000346, and has been explored for use in a vaccine to protect against *C. tetani* infection.

In embodiments of the present invention, TTC is produced using any of the host strains described herein in Example 1, in combination with any of the expression vectors described in Example 8. In embodiments, the nucleic acid sequence is optimized for expression in the Pseudomonad host cell. In embodiments, the expression vectors used have constructs expressing any of the secretion leaders described in Table 8 and Table 3 fused to the recombinant TTC protein. In certain embodiments, the TTC protein is expressed with a tag, e.g., a purification tag. In embodiments, the native secretion leader is used. In embodiments, the methods of the invention are used to produce TTC at a yield of about 0.5 g/L to at least about 12 g/L.

*C. difficile* Toxin B

*Clostridium difficile* Toxin B (TcdB) is a virulence factor produced by *Clostridium difficile*, which causes hospital acquired diarrhea and pseudomembranous colitis. TcdB, and a second large clostridial toxin, TcdA, are involved in the development of pseudomembranous colitis.

TcdB, a glucosylating toxin of about 270 kD, can be divided into enzymatic, translocation and receptor binding domains. The first 546 amino acids of TcdB contain the enzymatic region, which is followed by a putative translocation and receptor-binding domain. Enzymatic activity has been reported to require the amino-terminal 546 residues, as amino or carboxy-terminal deletions of this fragment decrease activity. Within the enzymatic region, tryptophan 102 has been shown to be essential for UDP-glucose binding. A conserved DXD motif within LCTs is essential for LCT glucosyltransferase activity. Studies involving analysis of chimeras of the TcdB and TcsL enzymatic domain suggest that residues 364 to 516 confer substrate specificity.

The structure of TcdB and its expression and potential use as a protective vaccine for *C. difficile* infection are discussed in, e.g.: U.S. Pat. No. 7,226,597, "Mutants of *Clostridium Difficile* Toxin B and Methods of Use;" Jank, et al., 2008, "Structure and mode of action of clostridial glucosylating toxins: the ABCD model," Trends in Microbiology 16(5): 222-229; Sullivan, et al., 1982, "Purification and Characterization of Toxins A and B of *Clostridium difficile*," Infection and Immunity 35(3):1032-1040; and Yang, et al., 2008, "Expression of recombinant *Clostridium difficile* toxin A and B in *Bacillus megaterium*," BMC Microbiology 8:192, all incorporated herein by reference in their entirety.

In embodiments of the present invention, TcdB is produced using any of the host strains described herein in Examples 1, 5 and 7. In embodiments, the nucleic acid sequence is optimized for expression in the Pseudomonad host cell. In embodiments, the expression vectors used contain constructs expressing any of the secretion leaders described in Table 8 and Table 3 fused to the recombinant TcdB protein. In embodiments, the native secretion leader is used. In certain embodiments, the TcdB protein is expressed with a tag, e.g., a purification tag. In embodiments, the methods of the invention are used to produce TcdB at a yield of about 0.5 g/L to at least about 10 g/L.

*Pseudomonas Aeruginosa* Exotoxin A

Exotoxin A (ETA or PE) of *Pseudomonas aeruginosa* is a Type II ADPRT. It is one member of a family of secreted bacterial toxins capable of translocating a catalytic domain into mammalian cells and inhibiting protein synthesis by the ADP-ribosylation of cellular elongation factor 2. The protein exists as a monomer, consisting of a single polypeptide chain of 613 amino acids (66 Kd). The x-ray crystallographic structure of exotoxin A, determined to 3.0-A resolution, shows an amino-terminal domain, composed primarily of antiparallel beta-structure and comprising approximately half of the molecule; a middle domain composed of alpha-helices; and a carboxyl-terminal domain comprising approximately one-third of the molecule. The carboxyl-terminal domain is the ADP-ribosyltransferase of the toxin. The other two domains are presumably involved in cell receptor binding and membrane translocation.

The toxin binds to cells through a specific receptor on the cell surface, then the toxin-receptor complex is internalized into the cell. Finally, ETA is transferred to the cytosol where it enzymatically inhibits protein synthesis. The transfer process is believed to occur from an acidic compartment, since cellular intoxication is prevented by weak bases such as NH4+, which raises the pH in acidic vesicles. Upon exposure to acidic conditions, the hydrophobic domain of PE enters into the membrane, resulting in the formation of a channel through which the enzymatic domain, in extended form, passes into the cytosol. The activity of PE and mutants having reduced toxicity are described in, e.g., U.S. Pat. No. 4,892,827, "Recombinant *Pseudomonas* Exotoxins: Construction of an Active Immunotoxin with Low Side Effects," and by Lukac, et al., 1988, "Toxoid of *Pseudomonas aeruginosa* Exotoxin A Generated by Deletion of an Active-Site Residue," Infection and Immunity 56(12): 3095-3098, both incorporated herein by reference in their entirety.

Use of Exotoxin A mutant rEPA as a vaccine conjugate is described by, e.g.: Fattom, et al., 1993, "Laboratory and Clinical Evaluation of Conjugate Vaccines Composed of *Staphylococcus aureus* Type 5 and Type 8 Capsular Polysaccharides Bound to *Pseudomonas aeruginosa* Recombinant Exoprotein A," Infection and Immunity 61(3):1023-1032; Qian, et al., 2007, "Conjugating recombinant proteins to *Pseudomonas aeruginosa* ExoProtein A: a strategy for enhancing immunogenicity of malaria vaccine candidates," Vaccine 25(20):3923-3933; and Lin, et al., 2001. "The Efficacy of a *Salmonella Typhi* Vi Conjugate Vaccine in Two-To-Five-Year-Old Children," N Engl J Med 344(17): 1263-1269, both incorporated herein by reference.

*Pseudomonas aeruginosa* Exotoxin A as used herein refers to *Pseudomonas aeruginosa* Exotoxin A mutant CRM66, deletion rEPA, or the wild-type protein. In embodiments of the present invention, Exotoxin A is produced using any of the host strains described herein in Examples 1, 5 and 7, and using expression vectors having constructs expressing any of the secretion leaders described in Table 8 and Table 3 fused to the recombinant Exotoxin A protein. In embodiments, the nucleic acid sequence is optimized for expression in the Pseudomonad host cell. In embodiments, the native secretion leader is used. In certain embodiments, the ETA protein is expressed with a tag, e.g., a purification tag. In embodiments, the methods of the invention are used to produce Exotoxin A at a yield of about 0.5 g/L to at least about 12 g/L.

Exemplary toxin proteins produced using the methods of the invention are listed in Table 1. It is understood that this list is not limiting. In embodiments of the invention, any of the nucleic acid sequences of the toxins described herein for production using the methods of the invention can be optimized for expression in the Pseudomonad host cell selected. As described elsewhere herein, there are multiple options for optimization of any given sequence. Any of the options as described are contemplated for use in optimizing the sequences of the toxins produced using the methods of the present invention. The optimized sequences provided herein are non-limiting examples of optimized sequences useful in the methods of the present invention.

TABLE 1

Exemplary Toxin Proteins

| Target | Exemplary Sequence Source/Reference | Origin |
|---|---|---|
| CRM197 | GenBank Acc. No. 1007216A | *Corynebacterium diphtheriae* NCTC 13129 |
| Diphtheria toxin (WT) | GenBank NC_002935.2 GenBank CAA00374.1 | *Corynebacterium diphtheriae* |
| Cholera Holotoxin | GenBank NC_002505.1; NP231099.1 and NP23110.1 | *Vibrio cholerae* |
| Cholera Toxin B | GenBank ACH70471 (E1 Tor strain) | *Vibrio cholerae* O1 biovar El tor |
| Pertussis Toxin | GenBank M13223.1 with mutations in S1 | *Bordetella pertussis* |
| Tetanus Toxin C Fragment | GenBank 1A8D_A | *Clostridium tetani* |
| *C. difficile* Tox B VPI (TcdB) | GenBank CAA63562 | *Clostridium difficile* |
| *P. aeruginosa* Exotoxin A | GenBank NP_249839 | *Pseudomonas aeruginosa* PAO1 |

Codon Optimization

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. Methods for optimizing the nucleic acid sequence of to improve expression of a heterologous protein in a bacterial host are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Optimization can thus address any of a number of sequence features of the heterologous gene. As a specific example, a rare codon-induced translational pause can result in reduced heterologous protein expression. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which can result in rare host codons being removed from the synthetic polynucleotide sequence.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

Another feature that can effect heterologous protein expression is the presence of restriction sites. By removing restriction sites that could interfere with subsequent subcloning of transcription units into host expression vectors a polynucleotide sequence can be optimized.

For example, the optimization process can begin by identifying the desired amino acid sequence to be heterologously expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In another embodiment of the invention, the general codon usage in a host organism, such as *P. fluorescens*, can be utilized to optimize the expression of the heterologous polynucleotide sequence. The percentage and distribution of codons that rarely would be considered as preferred for a particular amino acid in the host expression system can be evaluated. Values of 5% and 10% usage can be used as cutoff values for the determination of rare codons. For example, the codons listed in Table 2 have a calculated occurrence of less than 5% in the *P. fluorescens* MB214 genome and would be generally avoided in an optimized gene expressed in a *P. fluorescens* host.

TABLE 2

Codons occurring at less than 5% in *P. fluorescens* MB214

| Amino Acid(s) | Codon(s) Used | % Occurrence |
|---|---|---|
| G Gly | GGA | 3.26 |
| I Ile | ATA | 3.05 |
| L Leu | CTA | 1.78 |
|  | CTT | 4.57 |
|  | TTA | 1.89 |
| R Arg | AGA | 1.39 |
|  | AGG | 2.72 |
|  | CGA | 4.99 |
| S Ser | TCT | 4.28 |

The present invention contemplates the use of any coding sequence for the toxins produced, including any sequence that has been optimized for expression in the *Pseudomonas* host cell being used. Sequences contemplated for use can be optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods of the present invention can be encoded by any appropriate nucleic acid sequence.

Expression Systems

Methods for expressing heterologous proteins, including useful regulatory sequences (e.g., promoters, secretion leaders, and ribosome binding sites), in *Pseudomonas* host cells, as well as host cells useful in the methods of the present invention, are described, e.g., in U.S. Pat. App. Pub. No. 2008/0269070 and U.S. patent application Ser. No. 12/610,207, both titled "Method for Rapidly Screening Microbial Hosts to Identify Certain Strains with Improved Yield and/or Quality in the Expression of Heterologous Proteins," U.S. Pat. App. Pub. No. 2006/0040352, "Expression of Mammalian Proteins in *Pseudomonas Fluorescens*," and U.S. Pat. App. Pub. No. 2006/0110747, "Process for Improved Protein Expression by Strain Engineering," all incorporated herein by reference in their entirety. These publications also describe bacterial host strains useful in practicing the methods of the invention, that have been engineered to overexpress folding modulators or wherein protease mutations, including deletions, have been introduced, in order to increase heterologous protein expression.

Leaders

Sequence leaders are described in detail in U.S. Patent App. Pub. Nos. 2008/0193974 and 2010/0048864, both titled, "Bacterial Leader Sequences for Increased Expression," and U.S. Pat. App. Pub. No. 2006/0008877, "Expression systems with Sec-secretion," all incorporated herein by reference in their entirety, as well as in U.S. Pat. App. Pub. No. 2008/0269070 and U.S. patent application Ser. No. 12/610,207.

In embodiments, a sequence encoding a secretion leader is fused to the sequence encoding the toxin protein. In embodiments, the secretion leader is a periplasmic secretion leader. In embodiments, the secretion leader is the native secretion leader.

TABLE 3

Exemplary Secretion Leader Sequences

| Secretion Leader | Amino Acid Sequence | SEQ ID NO: |
|---|---|---|
| DsbA | MRNLILSAALVTASLFGMTAQA | 3 |
| Azu | MFAKLVAVSLLTLASGQLLA | 4 |
| Ibp-S31A | MIRDNRLKTSLLRGLTLTLLSLTLLSPAAHA | 5 |
| Tpr | MNRSSALLLAFVFLSGCQAMA | 6 |
| CupB2 | MLFRTLLASLTFAVIAGLPSTAHA | 7 |
| CupA2 | MSCTRAFKPLLLIGLATLMCSHAFA | 8 |
| NikA | MRLAALPLLLAPLFIAPMAVA | 9 |
| Pbp A20V | MKLKRLMAAMTFVAAGVATVNAVA | 10 |
| DsbC | MRLTQIIAAAAIALVSTFALA | 11 |
| TolB | MRNLLRGMLVVICCMAGIAAA | 12 |
| Pbp | MKLKRLMAAMTFVAAGVATANAVA | 13 |
| Lao | MQNYKKFLLAAAVSMAFSATAMA | 14 |
| CupC2 | MPPRSIAACLGLLGLLMATQAAA | 15 |
| PorE | MKKSTLAVAVTLGAIAQQAGA | 16 |
| Pbp | MKLKRLMAAMTFVAAGVATANAVA | 17 |
| FlgI | MKFKQLMAMALLLALSAVAQA | 18 |
| ttg2C | MQNRTVEIGVGLFLLAGILALLLLALRVSGLSA | 19 |
| CRM197 native leader | MSRKLFASXLIGALLGIGAPPSAHA | 20 |

It is understood that the secretion leaders useful in the methods of the present invention are not limited to those disclosed in Table 3.

In embodiments, the secretion leader is Azu, IbpS31A, CupA2, or PbpA20V. In other embodiments, the secretion leader is Azu, IbpS31A, CupA2, PbpA20V, or Pbp.

Native CRM197 is transported from *C. diptheriae* to the extracellular space via a secretion leader that is cleaved, leaving an amino terminal sequence of GADD (SEQ ID NO: 21). In order to preserve the natural amino terminus of CRM197 following expression in *P. fluorescens* and ensure disulfide bond formation, the protein is targeted to the periplasmic space.

Promoters

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences can be used to regulate expression of the toxins in accordance with the methods of the invention. In embodiments, inducible promoters useful in the methods of the present invention include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an E. coli organism.

Common examples of non-lac-type promoters useful in expression systems according to the present invention include, e.g., those listed in Table 4.

TABLE 4

Examples of non-lac Promoters

| Promoter | Inducer |
| --- | --- |
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell also may be used to control expression of the transgene encoding the target polypeptide, e.g., a Pseudomonas anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., E. coli catabolite activator protein, MalT protein; AraC family transcriptional activators; repressor proteins, e.g., E. coli LacI proteins; and dual-function regulatory proteins, e.g., E. coli NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lacI gene can also be present in the system. The lacI gene, which is normally a constitutively expressed gene, encodes the Lac repressor protein LacI protein, which binds to the lac operator of lac family promoters. Thus, where a lac family promoter is utilized, the lacI gene can also be included and expressed in the expression system.

Promoter systems useful in Pseudomonas are described in the literature, e.g., in U.S. Pat. App. Pub. No. 2008/0269070, also referenced above.

Other Regulatory Elements

In embodiments, soluble proteins are present in either the cytoplasm or periplasm of the cell during production. Secretion leaders useful for targeting proteins are described elsewhere herein, and in U.S. Pat. App. Pub. No. 2008/0193974, U.S. Pat. App. Pub. No. 2006/0008877, and in U.S. patent application Ser. No. 12/610,207.

Other elements include, but are not limited to, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" polypeptide coding sequences, which facilitates identification, separation, purification, and/or isolation of an expressed polypeptide.

In embodiments, the expression vector further comprises a tag sequence adjacent to the coding sequence for the secretion signal or to the coding sequence for the protein or polypeptide of interest. In one embodiment, this tag sequence allows for purification of the protein. The tag sequence can be an affinity tag, such as a hexa-histidine affinity tag (SEQ ID NO: 46). In another embodiment, the affinity tag can be a glutathione-S-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

An expression construct useful in practicing the methods of the present invention can include, in addition to the protein coding sequence, the following regulatory elements operably linked thereto: a promoter, a ribosome binding site (RBS), a transcription terminator, and translational start and stop signals. Useful RBSs can be obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence of AAGGAAG). Further examples of methods, vectors, and translation and transcription elements, and other elements useful in the present invention are well known in the art and described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox, all incorporated herein by reference, as well as in many of the other publications incorporated herein by reference.

Host Strains

Bacterial hosts, including Pseudomonads, and closely related bacterial organisms are contemplated for use in practicing the methods of the invention. In certain embodiments, the Pseudomonad host cell is *Pseudomonas fluorescens*. The host cell can also be an *E. coli* cell.

Host cells and constructs useful in practicing the methods of the invention can be identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lad gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U.S. Pat. App. Pub. No. 2009/0325230, "Protein Expression Systems," and in Schneider, et al., 2005, "Auxotrophic markers pyrF and proC can replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that can complement the pyrF deletion to restore prototropy. In particular embodiments, a dual pyrF-proC dual auxotrophic selection marker system in a *P. fluorescens* host cell is used. A PyrF production host strain as described can be used as the background for introducing other desired genomic changes, including those described herein as useful in practicing the methods of the invention.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 5 presents these families and genera of organisms.

TABLE 5

Families and Genera Listed in the Part, "Gram-Negative Aerobic Rods and Cocci" (Bergey, 1974)

| | |
|---|---|
| Family I. Pseudomonaceae | Gluconobacter |
| | Pseudomonas |
| | Xanthomonas |
| | Zoogloea |

TABLE 5-continued

Families and Genera Listed in the Part, "Gram-Negative Aerobic Rods and Cocci" (Bergey, 1974)

| | |
|---|---|
| Family II. Azotobacteraceae | Azomonas |
| | Azotobacter |
| | Beijerinckia |
| | Derxia |
| Family III. Rhizobiaceae | Agrobacterium |
| | Rhizobium |
| Family IV. Methylomonadaceae | Methylococcus |
| | Methylomonas |
| Family V. Halobacteriaceae | Halobacterium |
| | Halococcus |
| Other Genera | Acetobacter |
| | Alcaligenes |
| | Bordetella |
| | Brucella |
| | Francisella |
| | Thermus |

*Pseudomonas* and closely related bacteria are generally part of the group defined as "Gram(−) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. App. Pub. No. 2006/0040352, cited above.

"Gram-Negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens,* and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio, Oligella,* and *Teredinibacter;* 3) Rhizobiaceae family bacteria of the genera *Chelatobacter, Ensifer,*

*Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina,* and *Methylosphaera.*

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonasflectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginate* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis.* In one embodiment, the host cell is *Pseudomonas fluorescens.*

The host cell can also be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii;* and *Pseudomonas veronii.*

In embodiments, the *Pseudomonas* host cell is defective in the expression of HslU, HslV, Prc1, DegP1, DegP2, AprA, or a combination thereof. In embodiments, the host cell is defective in proteases HslU, HslV, Prc1, DegP1, DegP2, and AprA, and overexpresses DegP2 S219A. An example of such a strain is disclosed herein as Host Strain 2. These proteases are known in the art and described in, e.g., U.S. Pat. App. Pub. No. 2006/0110747. AprA, an extracellular serralysin-type metalloprotease metalloproteinase, is described by, e.g., Maunsell, et al., 2006, "Complex regulation of AprA metalloprotease in *Pseudomonas fluorescens* M114: evidence for the involvement of iron, the ECF sigma factor, PbrA and pseudobactin M114 siderophore, Microbiology 152(Pt 1):29-42, incorporated herein by reference, and in U.S. Patent App. Pub. Nos. 2008/0193974 and 2010/0048864.

In other embodiments, the *Pseudomonas* host cell overexpresses DsbA, DsbB, DsbC, and DsbD. DsbA, B, C, and D are disulfide bond isomerases, described, e.g., in U.S. Pat. App. Pub. No. 2008/0269070 and U.S. patent application Ser. No. 12/610,207.

In other embodiments, the *Pseudomonas* host cell is wild-type, i.e., having no protease expression defects and not over-expressing any folding modulator.

A host cell that is defective in the expression of a protease can have any modification that results in a decrease in the normal activity or expression level of that protease relative to a wild-type host. For example, a missense or nonsense mutation can lead to expression of protein that not active, and a gene deletion can result in no protein expression at all. A change in the upstream regulatory region of the gene can result in reduced or no protein expression. Other gene defects can affect translation of the protein. The expression of a protease can also be defective if the activity of a protein needed for processing the protease is defective.

Examples of proteases and folding modulators useful in the methods of the present invention are shown in Tables 6 and 7, respectively. RXF numbers refer to the open reading frame. (See, e.g., U.S. Pat. App. Pub. No. 2008/0269070 and U.S. patent application Ser. No. 12/610,207.)

TABLE 6

*P. fluorescens* strain MB214 proteases

| Class | Family | RXF | Gene | Curated Function | Location |
|---|---|---|---|---|---|
| Aspartic Peptidases | A8 (signal peptidase II family) | RXF05383.2 | | Lipoprotein signal peptidase (ec 3.4.23.36) | Cytoplasmic Membrane |
| | A24 (type IV prepilin peptidase family) | RXF05379.1 | | type 4 prepilin peptidase pild (ec 3.4.99.—) | Cytoplasmic Membrane |
| Cysteine Peptidases | C15 (pyroglutamyl peptidase I family) | RXF02161.1 | | Pyrrolidone-carboxylate peptidase (ec 3.4.19.3) | Cytoplasmic |
| | C40 | RXF01968.1 | | invasion-associated protein, P60 | Signal peptide |
| | | RXF04920.1 | | invasion-associated protein, P60 | Cytoplasmic |
| | | RXF04923.1 | | phosphatase-associated protein papq | Signal peptide |
| | C56 (PfpI endopeptidase family) | RXF01816.1 | | protease I (ec 3.4.—.—) | Non-secretory |
| Metallopeptidases | M1 | RXF08773.1 | | Membrane alanine aminopeptidase (ec 3.4.11.2) | Non-secretory |
| | M3 | RXF00561.2 | prlC | Oligopeptidase A (ec 3.4.24.70) | Cytoplasmic |
| | | RXF04631.2 | | Zn-dependent oligopeptidases | Cytoplasmic |
| | M4 (thermolysin family) | RXF05113.2 | | Extracellular metalloprotease precursor (ec 3.4.24.—) | Extracellular |
| | M41 (FtsH endopeptidase family) | RXF05400.2 | | Cell division protein ftsH (ec 3.4.24.—) | Cytoplasmic Membrane |
| | M10 | RXF04304.1 | | Serralysin (ec 3.4.24.40) | Extracellular |
| | | RXF04500.1 | | Serralysin (ec 3.4.24.40) | Extracellular |
| | | RXF01590.2 | | Serralysin (ec 3.4.24.40) | Extracellular |
| | | RXF04497.2 | | Serralysin (ec 3.4.24.40) | Extracellular |
| | | RXF04495.2 | | Serralysin (ec 3.4.24.40) | Extracellular |
| | | RXF02796.1 | | Serralysin (ec 3.4.24.40) | Extracellular |
| | M14 (carboxypeptidase A family) | RXF09091.1 | | Zinc-carboxypeptidase precursor (ec 3.4.17.—) | Cytoplasmic |
| | M16 (pitrilysin family) | RXF03441.1 | | Coenzyme pqq synthesis protein F (ec 3.4.99.—) | Non-secretory |
| | | RXF01918.1 | | zinc protease (ec 3.4.99.—) | Signal peptide |
| | | RXF01919.1 | | zinc protease (ec 3.4.99.—) | Periplasmic |
| | | RXF03699.2 | | processing peptidase (ec 3.4.24.64) | Signal peptide |
| | M17 (leucyl aminopeptidase family) | RXF00285.2 | | Cytosol aminopeptidase (ec 3.4.11.1) | Non-secretory |
| | M18 | RXF07879.1 | | Aspartyl aminopeptidase (ec 3.4.11.21) | Cytoplasmic |
| | M20 | RXF00811.1 | dapE | Succinyl-diaminopimelate desuccinylase (ec 3.5.1.18) | Cytoplasmic |
| | | RXF04052.2 | | Xaa-His dipeptidase (ec 3.4.13.3) | Signal peptide |
| | | RXF01822.2 | | Carboxypeptidase G2 precursor (ec 3.4.17.11) | Signal peptide |
| | | RXF09831.2::RXF04892.1 | | N-acyl-L-amino acid amidohydrolase (ec 3.5.1.14) | Signal peptide |
| | M28 (aminopeptidase Y family) | RXF03488.2 | | Alkaline phosphatase isozyme conversion protein precursor (ec 3.4.11.—) | OuterMembrane |
| | M42 (glutamyl aminopeptidase family) | RXF05615.1 | | Deblocking aminopeptidase (ec 3.4.11.—) | Non-secretory |
| | M22 | RXF05817.1 | | O-sialoglycoprotein endopeptidase (ec 3.4.24.57) | Extracellular |
| | | RXF03065.2 | | Glycoprotease protein family | Non-secretory |
| | M23 | RXF01291.2 | | Cell wall endopeptidase, family M23/M37 | Signal peptide |
| | | RXF03916.1 | | Membrane proteins related to metalloendopeptidases | Signal peptide |
| | | RXF09147.2 | | Cell wall endopeptidase, family M23/M37 | Signal peptide |
| | M24 | RXF04693.1 | | Methionine aminopeptidase (ec 3.4.11.18) | Cytoplasmic |
| | | RXF03364.1 | | Methionine aminopeptidase (ec 3.4.11.18) | Non-secretory |
| | | RXF02980.1 | | Xaa-Pro aminopeptidase (ec 3.4.11.9) | Cytoplasmic |
| | | RXF06564.1 | | Xaa-Pro aminopeptidase (ec 3.4.11.9) | Cytoplasmic |
| | M48 (Ste24 endopeptidase family) | RXF05137.1 | | Heat shock protein HtpX | Cytoplasmic Membrane |
| | | RXF05081.1 | | Zinc metalloprotease (ec 3.4.24.—) | Signal peptide |
| | M50 (S2P protease family) | RXF04692.1 | | Membrane metalloprotease | Cytoplasmic Membrane |

TABLE 6-continued

*P. fluorescens* strain MB214 proteases

| Class | Family | RXF | Gene | Curated Function | Location |
|---|---|---|---|---|---|
| Serine Peptidases | S1 (chymotrypsin family) | RXF01250.2 | | protease do (ec 3.4.21.—) | Periplasmic |
| | | RXF07210.1 | | protease do (ec 3.4.21.—) | Periplasmic |
| | S8 (subtilisin family) | RXF06755.2 | | serine protease (ec 3.4.21.—) | Non-secretory |
| | | RXF08517.1 | | serine protease (ec 3.4.21.—) | Extracellular |
| | | RXF08627.2 | | extracellular serine protease (ec 3.4.21.—) | Signal peptide |
| | | RXF06281.1 | | Extracellular serine protease precursor (ec 3.4.21.—) | Non-secretory |
| | | RXF08978.1 | | extracellular serine protease (ec 3.4.21.—) | OuterMembrane |
| | | RXF06451.1 | | serine protease (ec 3.4.21.—) | Signal peptide |
| | S9 (prolyl oligopeptidase family) | RXF02003.2 | | Protease ii (ec 3.4.21.83) | Periplasmic |
| | | RXF00458.2 | | Hydrolase | Non-secretory |
| | S11 (D-Ala-D-Ala carboxypeptidase A family) | RXF04657.2 | | D-alanyl-D-alanine-endopeptidase (ec 3.4.99.—) | Periplasmic |
| | | RXF00670.1 | | D-alanyl-D-alanine carboxypeptidase (ec 3.4.16.4) | Cytoplasmic Membrane |
| | S13 (D-Ala-D-Ala peptidase C family) | RXF00133.1 | | D-alanyl-meso-diaminopimelate endopeptidase (ec 3.4.—.—) | OuterMembrane |
| | | RXF04960.2 | | D-alanyl-meso-diaminopimelate endopeptidase (ec 3.4.—.—) | Signal peptide |
| | S14 (ClpP endopeptidase family) | RXF04567.1 | clpP | atp-dependent Clp protease proteolytic subunit (ec 3.4.21.92) | Non-secretory |
| | | RXF04663.1 | clpP | atp-dependent Clp protease proteolytic subunit (ec 3.4.21.92) | Cytoplasmic |
| | S16 (lon protease family) | RXF04653.2 | | atp-dependent protease La (ec 3.4.21.53) | Cytoplasmic |
| | | RXF08653.1 | | atp-dependent protease La (ec 3.4.21.53) | Cytoplasmic |
| | | RXF05943.1 | | atp-dependent protease La (ec 3.4.21.53) | Cytoplasmic |
| | S24 (LexA family) | RXF00449.1 | | LexA repressor (ec 3.4.21.88) | Non-secretory |
| | | RXF03397.1 | | LexA repressor (ec 3.4.21.88) | Cytoplasmic |
| | S26 (signal peptidase I family) | RXF01181.1 | | Signal peptidase I (ec 3.4.21.89) | Cytoplasmic Membrane |
| | S33 | RXF05236.1 | pip3 | Proline iminopeptidase (ec 3.4.11.5) | Non-secretory |
| | | RXF04802.1 | pip1 | Proline iminopeptidase (ec 3.4.11.5) | Non-secretory |
| | | RXF04808.2 | pip2 | Proline iminopeptidase (ec 3.4.11.5) | Cytoplasmic |
| | S41 (C-terminal processing peptidase family) | RXF06586.1 | | Tail-specific protease (ec 3.4.21.—) | Signal peptide |
| | | RXF01037.1 | | Tail-specific protease (ec 3.4.21.—) | Signal peptide |
| | S45 | RXF07170.1 | pacB2 | Penicillin acylase (ec 3.5.1.11) | Signal peptide |
| | | RXF06399.2 | pacB1 | Penicillin acylase ii (ec 3.5.1.11) | Signal peptide |
| | S49 (protease IV family) | RXF06993.2 | | possible protease sohb (ec 3.4.—.—) | Non-secretory |
| | | RXF01418.1 | | protease iv (ec 3.4.—.—) | Non-secretory |
| | S58 (DmpA aminopeptidase family) | RXF06308.2 | | D-aminopeptidase (ec 3.4.11.19) | Cytoplasmic Membrane |
| Threonine Peptidases | T1 (proteasome family) | RXF01961.2 | hslV | atp-dependent protease hslV (ec 3.4.25.—) | Cytoplasmic |
| | T3 (gamma-glutamyltransferase family) | RXF02342.1 | ggt1 | Gamma-glutamyltranspeptidase (ec 2.3.2.2) | Periplasmic |
| | | RXF04424.2 | ggt2 | Gamma-glutamyltranspeptidase (ec 2.3.2.2) | Periplasmic |
| Unclassified Peptidases | U32 | RXF00428.1 | | protease (ec 3.4.—.—) | Cytoplasmic |
| | | RXF02151.2 | | protease (ec 3.4.—.—) | Cytoplasmic |
| | U61 | RXF04715.1 | | Muramoyltetrapeptide carboxypeptidase (ec 3.4.17.13) | Non-secretory |
| | U62 | RXF04971.2 | pmbA | PmbA protein | Cytoplasmic |
| | | RXF04968.2 | | TldD protein | Cytoplasmic |
| Non MEROPS Proteases | | RXF00325.1 | | Repressor protein C2 | Non-secretory |
| | | RXF02689.2 | | Microsomal dipeptidase (ec 3.4.13.19) | Cytoplasmic |
| | | RXF02739.1 | | membrane dipeptidase (3.4.13.19) | Signal peptide |
| | | RXF03329.2 | | Hypothetical Cytosolic Protein | Cytoplasmic |
| | | RXF02492.1 | | Xaa-Pro dipeptidase (ec 3.4.13.9) | Cytoplasmic |

TABLE 6-continued

| Class | Family | RXF | Gene | Curated Function | Location |
|---|---|---|---|---|---|
| | | RXF04047.2 | | caax amino terminal protease family | Cytoplasmic Membrane |
| | | RXF08136.2 | | protease (transglutaminase-like protein) | Cytoplasmic |
| | | RXF09487.1 | | Zinc metalloprotease (ec 3.4.24.—) | Non-secretory |

Certain proteases can have both protease and chaperone-like activity. When these proteases are negatively affecting protein yield and/or quality it can be useful to delete them, and they can be overexpressed when their chaperone activity may positively affect protein yield and/or quality. These proteases include, but are not limited to: Hsp100 (Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

TABLE 7

*P. fluorescens* strain MB214 protein folding modulators

| ORF ID | GENE | FUNCTION | FAMILY | LOCATION |
|---|---|---|---|---|
| *GroES/EL* | | | | |
| RXF02095.1 | groES | Chaperone | Hsp10 | Cytoplasmic |
| RXF06767.1::Rxf02090 | groEL | Chaperone | Hsp60 | Cytoplasmic |
| RXF01748.1 | ibpA | Small heat-shock protein (sHSP) IbpA PA3126; Acts as a holder for GroESL folding | Hsp20 | Cytoplasmic |
| RXF03385.1 | hscB | Chaperone protein hscB | Hsp20 | Cytoplasmic |
| *Hsp70 (DnaK/J)* | | | | |
| RXF05399.1 | dnaK | Chaperone | Hsp70 | Periplasmic |
| RXF06954.1 | dnaK | Chaperone | Hsp70 | Cytoplasmic |
| RXF03376.1 | hscA | Chaperone | Hsp70 | Cytoplasmic |
| RXF03987.2 | cbpA | Curved dna-binding protein, dnaJ like activity | Hsp40 | Cytoplasmic |
| RXF05406.2 | dnaJ | Chaperone protein dnaJ | Hsp40 | Cytoplasmic |
| RXF03346.2 | dnaJ | Molecular chaperones (DnaJ family) | Hsp40 | Non-secretory |
| RXF05413.1 | grpE | heat shock protein GrpE PA4762 | GrpE | Cytoplasmic |
| *Hsp100 (Clp/Hsl)* | | | | |
| RXF04587.1 | clpA | atp-dependent clp protease atp-binding subunit clpA | Hsp100 | Cytoplasmic |
| RXF08347.1 | clpB | ClpB protein | Hsp100 | Cytoplasmic |
| RXF04654.2 | clpX | atp-dependent clp protease atp-binding subunit clpX | Hsp100 | Cytoplasmic |
| RXF04663.1 | clpP | atp-dependent Clp protease proteolytic subunit (ec 3.4.21.92) | MEROPS peptidase family S14 | Cytoplasmic |
| RXF01957.2 | hslU | atp-dependent hsl protease atp-binding subunit hslU | Hsp100 | Cytoplasmic |
| RXF01961.2 | hslV | atp-dependent hsl protease proteolytic subunit | MEROPS peptidase subfamily T1B | Cytoplasmic |
| *Hsp33* | | | | |
| RXF04254.2 | yrfI | 33 kDa chaperonin (Heat shock protein 33 homolog) (HSP33). | Hsp33 | Cytoplasmic |
| *Hsp90* | | | | |
| RXF05455.2 | htpG | Chaperone protein htpG | Hsp90 | Cytoplasmic |
| *SecB* | | | | |
| RXF02231.1 | secB | secretion specific chaperone SecB | SecB | Non-secretory |
| *Disulfide Bond Isomerases* | | | | |
| RXF07017.2 | dsbA | disulfide isomerase | DSBA oxido-reductase | Cytoplasmic |

TABLE 7-continued

*P. fluorescens* strain MB214 protein folding modulators

| ORF ID | GENE | FUNCTION | FAMILY | LOCATION |
|---|---|---|---|---|
| RXF08657.2 | dsbA/dsbC/dsbG/fernA | disulfide isomerase | DSBA oxido-reductase | Cytoplasmic |
| RXF01002.1 | dsbA/dsbC | disulfide isomerase | DSBA oxido-reductase/Thioredoxin | Periplasmic |
| RXF03307.1 | dsbC | disulfide isomerase | Glutaredoxin/Thioredoxin | Periplasmic |
| RXF04890.2 | dsbG | disulfide isomerase | Glutaredoxin/Thioredoxin | Periplasmic |
| RXF03204.1 | dsbB | Disulfide bond formation protein B (Disulfide oxidoreductase). | DSBA oxido-reductase | Periplasmic |
| RXF04886.2 | dsbD | Thiol:disulfide interchange protein dsbD | DSBA oxido-reductase | Periplasmic |
| Peptidyl-prolyl cis-trans isomerases | | | | |
| RXF03768.1 | ppiA | Peptidyl-prolyl cis-trans isomerase A (ec 5.2.1.8) | PPIase: cyclophilin type | Periplasmic |
| RXF05345.2 | ppiB | Peptidyl-prolyl cis-trans isomerase B. | PPIase: cyclophilin type | Cytoplasmic |
| RXF06034.2 | fklB | Peptidyl-prolyl cis-trans isomerase FklB. | PPIase: FKBP type | OuterMembrane |
| RXF06591.1 | fklB/fkbP | fk506 binding protein Peptidyl-prolyl cis-trans isomerase (EC 5.2.1.8) | PPIase: FKBP type | Periplasmic |
| RXF05753.2 | fklB; fkbP | Peptidyl-prolyl cis-trans isomerase (ec 5.2.1.8) | PPIase: FKBP type | Outer Membrane |
| RXF01833.2 | slyD | Peptidyl-prolyl cis-trans isomerase SlyD. | PPIase: FKBP type | Non-secretory |
| RXF04655.2 | tig | Trigger factor, ppiase (ec 5.2.1.8) | PPIase: FKBP type | Cytoplasmic |
| RXF05385.1 | yaad | Probable FKBP-type 16 kDa peptidyl-prolyl cis-trans isomerase (EC 5.2.1.8) (PPiase) (Rotamase). | PPIase: FKBP type | Non-secretory |
| RXF00271.1 | | Peptidyl-prolyl cis-trans isomerase (ec 5.2.1.8) | PPIase: FKBP type | Non-secretory |
| pili assembly chaperones (papD like) | | | | |
| RXF06068.1 | cup | Chaperone protein cup | pili assembly papD | Periplasmic |
| RXF05719.1 | ecpD | Chaperone protein ecpD | pili assembly papD | Signal peptide |
| RXF05319.1 | ecpD | Hnr protein | pili assembly chaperone | Periplasmic |
| RXF03406.2 | ecpD; csuC | Chaperone protein ecpD | pili assembly papD | Signal peptide |
| RXF04296.1 | ecpD; cup | Chaperone protein ecpD | pili assembly papD | Periplasmic |
| RXF04553.1 | ecpD; cup | Chaperone protein ecpD | pili assembly papD | Periplasmic |
| RXF04554.2 | ecpD; cup | Chaperone protein ecpD | pili assembly papD | Periplasmic |
| RXF05310.2 | ecpD; cup | Chaperone protein ecpD | pili assembly papD | Periplasmic |
| RXF05304.1 | ecpD; cup | Chaperone protein ecpD | pili assembly papD | Periplasmic |
| RXF05073.1 | gltF | Gram-negative pili assembly chaperone periplasmic function | pili assembly papD | Signal peptide |
| Type II Secretion Complex | | | | |
| RXF05445.1 | YacJ | Histidinol-phosphate aminotransferase (ec 2.6.1.9) | Class-II pyridoxal-phosphate-dependent aminotransferase family. Histidinol-phosphate aminotransferase subfamily. | Membrane |

TABLE 7-continued

P. fluorescens strain MB214 protein folding modulators

| ORF ID | GENE | FUNCTION | FAMILY | LOCATION |
|---|---|---|---|---|
| RXF05426.1 | SecD | Protein translocase subunit secd | Type II secretion complex | Membrane |
| RXF05432.1 | SecF | protein translocase subunit secf | Type II secretion complex | Membrane |
| Disulfide Bond Reductases | | | | |
| RXF08122.2 | trxC | Thioredoxin 2 | Disulfide Bond Reductase | Cytoplasmic |
| RXF06751.1 | Gor | Glutathione reductase (EC 1.8.1.7) (GR) (GRase) PA2025 | Disulfide Bond Reductase | Cytoplasmic |
| RXF00922.1 | gshA | Glutamate--cysteine ligase (ec 6.3.2.2) PA5203 | Disulfide Bond Reductase | Cytoplasmic |

High Throughput Screens

In some embodiments, a high throughput screen can be conducted to determine optimal conditions for expressing a soluble recombinant toxin protein. The conditions that be varied in the screen include, for example, the host cell, genetic background of the host cell (e.g., deletions of different proteases), type of promoter in an expression construct, type of secretion leader fused to the sequence encoding the recombinant protein, growth temperature, OD at induction when an inducible promoter is used, concentration of IPTG used for induction when a lacZ promoter is used, duration of protein induction, growth temperature following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" can be identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, e.g., whether the protein is sequestered or secreted, and in what quantities, whether the protein is properly or desirably processed and/or folded, and the like. In embodiments, improved or desirable quality can be production of toxin protein with high fidelity cleavage of the secretion leader and low levels of degradation. In embodiments, the optimal host strain or optimal expression system produces a yield, characterized by the amount or quantity of soluble heterologous protein, the amount or quantity of recoverable heterologous protein, the amount or quantity of properly processed heterologous protein, the amount or quantity of properly folded heterologous protein, the amount or quantity of active heterologous protein, and/or the total amount or quantity of heterologous protein, of a certain absolute level or a certain level relative to that produced by an indicator strain, i.e., a strain used for comparison.

Methods of screening microbial hosts to identify strains with improved yield and/or quality in the expression of heterologous proteins are described, for example, in U.S. Patent Application Publication No. 20080269070.

Fermentation Format

The expression system according to the present invention can be cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, Pseudomonas medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, referenced and incorporated by reference above. Details of cultivation procedures and mineral salts media useful in the methods of the present invention are described by Riesenberg, D et al., 1991, "High cell density cultivation of Escherichia coli at controlled specific growth rate," J. Biotechnol. 20 (1):17-27.

In embodiments, production can be achieved in bioreactor cultures. Cultures can be grown in, e.g., up to 2 liter bioreactors containing a mineral salts medium, and maintained at 32° C. and pH 6.5 through the addition of ammonia. Dissolved oxygen can be maintained in excess through increases in agitation and flow of sparged air and oxygen into the fermentor. Glycerol can be delivered to the culture throughout the fermentation to maintain excess levels. In embodiments, these conditions are maintained until a target culture cell density, e.g., optical density at 575 nm (A575), for induction is reached, at which time IPTG is added to initiate the target protein production. It is understood that the cell density at induction, the concentration of IPTG, pH and temperature each can be varied to determine optimal conditions for expression. In embodiments, cell density at induction can be varied from A575 of 40 to 200 absorbance units (AU). IPTG concentrations can be varied in the range from 0.02 to 1.0 mM, pH from 6 to 7.5, and temperature from 20 to 35° C. After 16-24 hours, the culture from each bioreactor can be harvested by centrifugation and the cell pellet frozen at −80° C. Samples can then be analyzed, e.g., by SDS-CGE, for product formation.

Fermentation may be performed at any scale. The expression systems according to the present invention are useful for recombinant protein expression at any scale. Thus, e.g., microliter-scale, milliliter scale, centiliter scale, and deciliter scale fermentation volumes may be used, and 1 Liter scale and larger fermentation volumes can be used.

In embodiments, the fermentation volume is at or above about 1 Liter. In embodiments, the fermentation volume is about 1 liter to about 100 liters. In embodiments, the fermentation volume is about 1 liter, about 2 liters, about 3 liters, about 4 liters, about 5 liters, about 6 liters, about 7 liters, about 8 liters, about 9 liters, or about 10 liters. In embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters. In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

Bacterial Growth Conditions

Growth conditions useful in the methods of the provided invention can comprise a temperature of about 4° C. to about 42° C. and a pH of about 5.7 to about 8.8. When an expression construct with a lacZ promoter is used, expression can be induced by adding IPTG to a culture at a final concentration of about 0.01 mM to about 1.0 mM.

The pH of the culture can be maintained using pH buffers and methods known to those of skill in the art. Control of pH during culturing also can be achieved using aqueous ammonia. In embodiments, the pH of the culture is about 5.7 to about 8.8. In certain embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8 In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8. In yet other embodiments, the pH is about 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25.

In embodiments, the growth temperature is maintained at about 4° C. to about 42° C. In certain embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 30° C. to about 33° C., or about 32° C. to about 33° C. In other embodiments, the temperature is changed during culturing. In one embodiment, the temperature is maintained at about 30° C. before an agent to induce expression from the construct, e.g., IPTG, is added to the culture. After adding the induction agent, the temperature is reduced to about 25° C.

Induction

As described elsewhere herein, inducible promoters can be used in the expression construct to control expression of the recombinant toxin protein, e.g., a lac promoter. In the case of the lac promoter derivatives or family members, e.g., the tac promoter, the effector compound is an inducer, such as a gratuitous inducer like IPTG (isopropyl-β-D-1-thiogalactopyranoside, also called "isopropylthiogalactoside"). In embodiments, a lac promoter derivative is used, and recombinant protein expression is induced by the addition of IPTG to a final concentration of about 0.01 mM to about 1.0 mM, when the cell density has reached a level identified by an OD575 of about 80 to about 160. In embodiments, the OD575 at the time of culture induction for the recombinant protein can be about 80, about 90, about 100, about 110, about 120, about 130, about 140, about 150, about 160, about 170 about 180. In other embodiments, the OD575 is about 80 to about 100, about 100 to about 120, about 120 to about 140, about 140 to about 160. In other embodiments, the OD575 is about 80 to about 120, about 100 to about 140, or about 120 to about 160. In other embodiments, the OD575 is about 80 to about 140, or about 100 to 160. The cell density can be measured by other methods and expressed in other units, e.g., in cells per unit volume. For example, an OD575 of about 80 to about 160 of a *Pseudomonas fluorescens* culture is equivalent to approximately 8×10$^{10}$ to about 1.6×10$^{11}$ colony forming units per mL or 35 to 70 g/L dry cell weight. In embodiments, the cell density at the time of culture induction is equivalent to the cell density as specified herein by the absorbance at OD575, regardless of the method used for determining cell density or the units of measurement. One of skill in the art will know how to make the appropriate conversion for any cell culture.

In embodiments, the final IPTG concentration of the culture is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, or about 1 mM. In other embodiments, the final IPTG concentration of the culture is about 0.08 mM to about 0.1 mM, about 0.1 mM to about 0.2 mM, about 0.2 mM to about 0.3 mM, about 0.3 mM to about 0.4 mM, about 0.2 mM to about 0.4 mM, about 0.08 to about 0.2 mM, or about 0.1 to 1 mM.

In embodiments wherein a non-lac type promoter is used, as described herein and in the literature, other inducers or effectors can be used. In one embodiment, the promoter is a constitutive promoter.

After adding and inducing agent, cultures can be grown for a period of time, for example about 24 hours, during which time the recombinant protein is expressed. After adding an inducing agent, a culture can be grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture can be grown for about 1 to 48 hrs, about 1 to 24 hrs, about 10 to 24 hrs, about 15 to 24 hrs, or about 20 to 24 hrs. Cell cultures can be concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Microfluidizer, Constant Cell Disruptor, Niro-Soavi homogenizer or APV-Gaulin homogenizer). Cells expressing the recombinant protein can be disrupted, for example, using sonication. Any appropriate method known in the art for lysing cells can be used to release the soluble fraction. For example, in embodiments, chemical and/or enzymatic cell lysis reagents, such as cell-wall lytic enzyme and EDTA, can be used. Use of frozen or previously stored cultures is also contemplated in the methods of the invention. Cultures can be OD-normalized prior to lysis. For example, cells can be normalized to an OD600 of about 10, about 11, about 12, about 13, about 14, about 15, about 16, about 17, about 18, about 19, or about 20.

Centrifugation can be performed using any appropriate equipment and method. Centrifugation of cell culture or lysate for the purposes of separating a soluble fraction from an insoluble fraction is well-known in the art. For example, lysed cells can be centrifuged at 20,800×g for 20 minutes (at 4° C.), and the supernatants removed using manual or automated liquid handling. The pellet (insoluble) fraction is resuspended in a buffered solution, e.g., phosphate buffered saline (PBS), pH 7.4. Resuspension can be carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures. These two fractions also can be referred to as a "first soluble fraction" and a "first insoluble fraction," respectively.

Evaluation of Product

Numerous assay methods are known in the art for characterizing proteins. Use of any appropriate method for characterizing the yield or quality of the recombinant toxin protein is contemplated herein.

Protein Yield

Protein yield in any purification fraction as described herein can be determined by methods known to those of skill in the art, for example, by capillary gel electrophoresis (CGE), and Western blot analysis. Activity assays, as described herein and known in the art, also can provide information regarding protein yield. In embodiments, these or any other methods known in the art are used to evaluate proper processing of a protein, e.g., proper secretion leader cleavage.

Useful measures of protein yield include, e.g., the amount of recombinant protein per culture volume (e.g., grams or milligrams of protein/liter of culture), percent or fraction of recombinant protein measured in the insoluble pellet obtained after cell lysis (e.g., amount of recombinant protein in extract supernatant/amount of protein in insoluble fraction), percent or fraction of active protein (e.g., amount of active protein/amount protein used in the assay), percent or fraction of total cell protein (tcp), amount of protein/cell, and percent or proportion of dry biomass. In embodiments, the measure of protein yield as described herein is based on the amount of soluble protein or the amount of active protein, or both, obtained.

In embodiments wherein yield is expressed in terms of culture volume the culture cell density may be taken into account, particularly when yields between different cultures are being compared.

In embodiments, the methods of the present invention can be used to obtain a soluble and/or active and/or properly processed (e.g., having the secretion leader cleaved properly) recombinant toxin protein or subunit protein yield of about 0.2 grams per liter to about 12 grams per liter. In embodiments, the yield is about 0.5 grams per liter to about 12 grams per liter. In certain embodiments, the recombinant protein or subunit protein yield is about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

In embodiments, the amount of recombinant toxin protein or subunit protein produced is about 1% to 75% of the total cell protein. In certain embodiments, the amount of toxin protein or subunit protein produced is about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 1% to about 5%, about 1% to about 10%, about 1% to about 20%, about 1% to about 30%, about 1% to about 40%, about 1% to about 50%, about 1% to about 60%, about 1% to about 75%, about 2% to about 5%, about 2% to about 10%, about 2% to about 20%, about 2% to about 30%, about 2% to about 40%, about 2% to about 50%, about 2% to about 60%, about 2% to about 75%, about 3% to about 5%, about 3% to about 10%, about 3% to about 20%, about 3% to about 30%, about 3% to about 40%, about 3% to about 50%, about 3% to about 60%, about 3% to about 75%, about 4% to about 10%, about 4% to about 20%, about 4% to about 30%, about 4% to about 40%, about 4% to about 50%, about 4% to about 60%, about 4% to about 75%, about 5% to about 10%, about 5% to about 20%, about 5% to about 30%, about 5% to about 40%, about 5% to about 50%, about 5% to about 60%, about 5% to about 75%, about 10% to about 20%, about 10% to about 30%, about 10% to about 40%, about 10% to about 50%, about 10% to about 60%, about 10% to about 75%, about 20% to about 30%, about 20% to about 40%, about 20% to about 50%, about 20% to about 60%, about 20% to about 75%, about 30% to about 40%, about 30% to about 50%, about 30% to about 60%, about 30% to about 75%, about 40% to about 50%, about 40% to about 60%, about 40% to about 75%, about 50% to about 60%, about 50% to about 75%, about 60% to about 75%, or about 70% to about 75%, of the total cell protein.

In certain embodiments, multiple proteins are produced from the same host cell. For example, in embodiments, all five subunits of Pertussis toxin are made from the same host cell grown in a single culture. In such embodiments the concentration, % total cell protein, or activity observed is that for each individual toxin subunit or for all the subunits taken together. That is, in embodiments, the methods of the invention are used to obtain a yield of the S1, S2, S3, S4, or S5 subunit of Pertussis toxin protein of about 1 gram per liter to about 12 grams per liter. In embodiments, the amount of S1, S2, S3, S4, or S5 subunit protein produced is 1% to 75% of the total cell protein. Alternatively, the methods of the invention are used to obtain a yield of S1, S2, S3, S4, and S5 subunit protein of about 1 gram per liter to about 12 grams per liter. In embodiments, the amount of S1, S2, S3, S4, and S5 subunit protein produced is 1% to 75% of the total cell protein. In certain embodiments, the amount of each subunit obtained, in grams per liter or % total cell protein, is approximately the same.

The "solubility" and "activity" of a protein, though related qualities, are generally determined by different means. The solubility of a protein, particularly a hydrophobic protein, typically relates to the folding of a protein; insolubility indicates that hydrophobic amino acid residues are improperly located on the outside of the folded protein. Protein activity, which can be evaluated using methods, e.g., those described below, is another indicator of proper protein conformation. "Soluble, active, or both," or "soluble and/or active," as used herein, refers to protein that is determined to be soluble, active, or both soluble and active, by methods known to those of skill in the art and described herein. The "activity" of a given protein can include binding activity, e.g., that represented by binding to a receptor, a specific antibody, or to another known substrate, or by enzymatic activity if relevant. Activity levels can be described, e.g., in absolute terms or in relative terms, as when compared with the activity of a standard or control sample, or any sample used as a reference.

Activity assays for evaluating toxins are known in the art and described in the literature. Activity assays include immunological or antibody binding assays, e.g., Western Blot analysis and ELISA, as well as receptor binding assays, e.g., CRM197 can be evaluated by Diptheria toxin receptor (proHB-EGF) binding assay. Antibodies useful in these assays are commercially available. Activity assays also include enzyme activity assays. Wild-type DT can be assayed immunologically and also by ADP-ribosylation activity, using methods known in the art and described elsewhere herein for *P. aeruginosa* Exotoxin A.

For example, Western blot analysis of CTB can be performed as described, e.g., in U.S. Pat. No. 6,140,082, "Expression of Gene Products from Genetically Manipulated Strains of *Bordetella*," incorporated herein by reference. This patent describes expression of CTB in *Bordetella*. The proteins from culture supernatants were resolved by SDS-PAGE or boiled before being resolved to convert the CTB pentamer to the monomeric form. The proteins were transferred onto nylon membranes and probed with goat anti-choleragenoid IgG antibody (anti-CTB, List Biologicals #GAC-01C). Detection was performed with alkaline phosphatase-conjugated donkey anti-goat IgG, using dig chemiluminescence (Boehringer Mannheim). A Cholera toxin standard (Sigma) containing both CTA and CTB was used for comparison.

Western blot analysis of PTX can be performed, e.g., as described herein in the Examples, using commercially available antibodies. Monoclonal antibodies are available from, e.g., Abcam, Cambridge, Mass.

Tetanus Toxin C Fragment can be evaluated by Western Blot analysis, or by ELISA as described in, e.g., U.S. Pat. No. 5,443,966, "Expression of tetanus toxin fragment C," incorporated herein by reference. Antibodies are available from multiple commercial sources, e.g., Abcam, Cambridge, Mass.

TcdB activity can be evaluated by Western Blot or other detection analysis, as described in the art. Enzymatic activity can be assayed, e.g., using glucosylhydrolase/glucosylation assay methods described in the art, for example in U.S. Pat. No. 7,226,597, incorporated herein by reference in its entirety. Specifically, glucosylation reactions can be carried out in a reaction mix containing 50 mM n-2hydroxyethylpiperazine-n'-2-ethane sulfonic acid, 100 mM KCl, 1 mM MnCl2, 1 mM MgCl2, 100 μgram/ml BSA, 0.2 mM GDP, 40 μMUDP-glucose (303 Ci/mol; ICN Pharmaceuticals), 100 μM UDP-glucose and 3 pmol of TcdB or 10 pmol of each fusion protein. The assay is allowed to incubate overnight at 37° C. and the cleaved glucose is separated using AG1-X2 anion exchange resin and counted in a liquid scintillation counter.

*P. aeruginosa* Exotoxin A activity can be evaluated using immunological methods, e.g., Western Blot analysis. Since ETA is an ADP-ribosylating toxin, it can be assayed for ADP-ribosylation activity, e.g., as described in U.S. Pat. No. 4,892,827, incorporated herein by reference. Specifically, rabbit reticulocyte preparations or wheat germ extracts enriched with elongation factor 2 (EF-2) are used as a source of EF-2. Assays (500 μl total volume) contain about 10 pmole of EF-2, 37 pmole of 14C-NAD (0.06 μCi), 0.25 to 1.25 μg of ETA and buffer (40 mM DTT, 1 mM EDTA, and 50 mM Tris, pH 8.1). Activity is measured as pmoles of NAD transferred to EF-2 in 30 minutes. A standard curve of known concentrations of PE is established and used to determine the activity of PE in extracts from *E. coli*. After incubation for 30 minutes at 37° C., 0.5 ml 12% TCA is added to each assay mixture. The assay mixtures are then set in an ice bath for 15 minutes, followed by centrifugation at 4° C., 3,000×g for 10 minutes. The pellet is washed with 1 ml 6% TCA and centrifuged as above. The pellet is then measured for 14C radioactivity in a liquid scintillation counter as the index of the ADP-ribosylation activity.

Therefore, a measure of activity can represent, e.g., antibody or receptor binding capacity, substrate binding capacity (as to a column material), or enzyme activity.

In embodiments, activity is represented by the % active recombinant toxin protein in the extract supernatant as compared with the total amount assayed. This is based on the amount of recombinant toxin protein determined to be active by the assay relative to the total amount of recombinant toxin protein used in the assay. In other embodiments, activity is represented by the % activity level of the protein compared to a standard, e.g., native protein. This is based on the amount of active recombinant toxin protein in supernatant extract sample relative to the amount of active protein in a standard sample (where the same amount of protein from each sample is used in assay).

In embodiments, about 40% to about 100% of the toxin protein or subunit is determined to be active. In embodiments, about 40%, about 50%, about 60%, about 70%, about 80%, about 90%, or about 100% of the recombinant toxin protein or protein subunit is determined to be active. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the recombinant toxin protein or subunit is determined to be active.

In other embodiments, about 75% to about 100% of the recombinant toxin protein or protein subunit is determined to be active. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the recombinant toxin protein or subunit is determined to be active.

Means of confirming the identity of the induced protein are also known in the art. For example, a protein can analyzed by peptide mass fingerprint using MALDI-TOF mass spectrometry, N-terminal sequencing analysis, or peptide mapping.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

High Throughput Expression of a Recombinant CRM197 Protein

CRM197 expression strains were constructed and the amount of soluble CRM197 protein produced in the strains was analyzed using capillary gel electrophoresis (SDS-CGE). Based on the resulting data, certain strains were selected for use in large-scale expression.

Construction and Growth of CRM197 Expression Strains

Figure 1C:
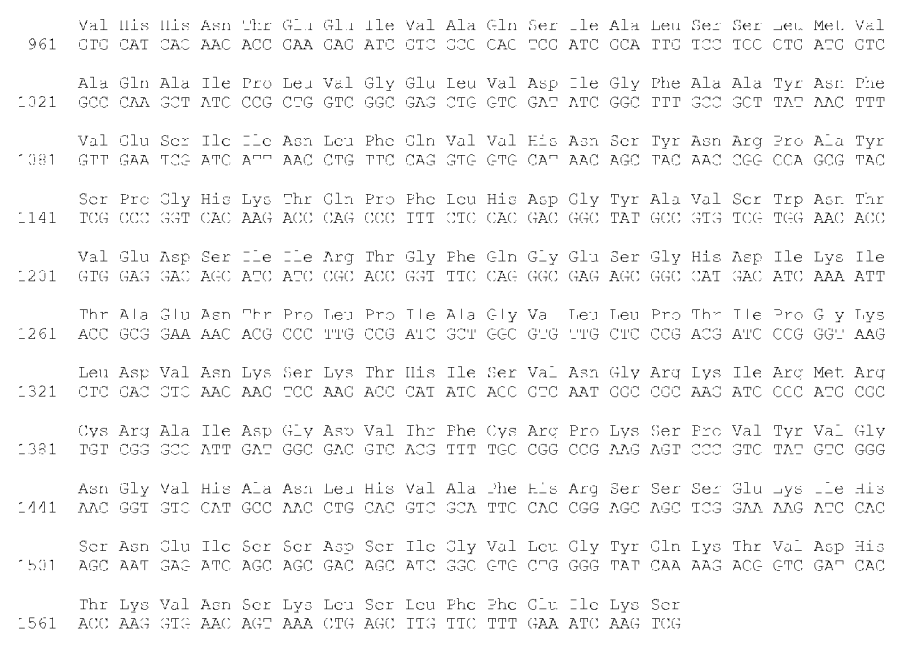

The CRM197 coding sequence was constructed using *P. fluorescens* preferred codons to encode the CRM197 amino acid sequence. FIG. 1 shows the amino acid and DNA sequences of the expressed synthetic CRM197 gene.

Plasmids carrying the optimized CRM197 sequence, fused to ten *P. fluorescens* secretion leaders as shown in Table 8, were constructed. The CRM197 coding sequence was fused in frame with that of *P. fluorescens* secretion leaders to target the protein to the periplasm for recovery in the properly folded and active form.

TABLE 8

Secretion leaders used for CRM197 expression screen

| | Secretion Leader |
|---|---|
| 1 | DsbA |
| 2 | Azu |
| 3 | Ibp-S31A |
| 4 | Tpr |
| 5 | CupB2 |
| 6 | CupA2 |
| 7 | NikA |
| 8 | Pbp A20V |
| 9 | DsbC |
| 10 | TolB |

Constructs containing the ten secretion leaders fused to the recombinant CRM197 coding sequence were tested in *P. fluorescens* hosts. Four hosts, listed in Table 9, were tested with each expression plasmid. Host cells were electroporated with the indicated plasmids, resuspended in HTP growth medium with trace minerals and 5% glycerol and then transferred to 96-well deep well plate with 400 μl M9 salts 1% glucose medium and trace elements. The 96-well plates were incubated at 30° C. with shaking for 48 hours. Ten microliters of each of the forty seed cultures were transferred into triplicate 96-well deep-well plates, each well containing 500 μl of HTP medium supplemented with trace elements and 5% glycerol, and incubated as before for 24 hours.

TABLE 9

Host strains used for CRM197 expression screen

| Host Strain | Genotype | Type |
|---|---|---|
| 1 | lon, la, aprA | PD |
| 2 | hslUV prc1 degP1 degP2 aprA deletions; overexpresses DegP2 S219A | PD + FMO |
| 3 | dsbABCD | FMO |
| 4 | grpE, dnaKJ | FMO |

PD = Protease Deletion (listed proteases are deleted);

FMO = Folding Modulator Overexpressor (listed folding modulators are overexpressed.

Isopropyl-β-D-1-thiogalactopyranoside (IPTG) was added to each well to a final concentration of 0.3 mM to induce the expression of target proteins. Mannitol (Sigma, M1902) was added to each well to a final concentration of 1% to induce the expression of folding modulators in folding modulator over-expressing strains, and the temperature was reduced to 25° C. Twenty four hours after induction, cells were normalized to OD600=15 using PBS in a volume of 400 Samples were frozen for later processing by sonication and centrifugation to generate soluble and insoluble fractions.

Sample Preparation and SDS-CGE Analysis

Soluble and insoluble cellular fractions were prepared by sonication of the normalized cultures followed by centrifugation. Frozen, normalized culture broth (400 µL) was thawed and sonicated for 3.5 minutes. The lysates were centrifuged at 20,800×g for 20 minutes (4° C.) and the supernatants removed using manual or automated liquid handling (soluble fraction). The pellets (insoluble fraction) were frozen and then thawed for re-centrifugation at 20,080×g for 20 minutes at 4 C, to remove residual supernatant. The pellets were then resuspended in 400 µL of 1× phosphate buffered saline (PBS), pH 7.4. Further dilutions of soluble and insoluble samples for SDS-CGE analysis were performed in 1× phosphate buffered saline (PBS), pH 7.4. Soluble and insoluble samples were prepared for SDS capillary gel electrophoresis (CGE) (Caliper Life Sciences, Protein Express LabChip Kit, Part 760301), in the presence of dithiothreitol (DTT).

Representative gel-like images showing the results of the reducing SDS-CGE analysis of the soluble fraction from each strain are shown in FIG. 2. Table 10 shows the mean soluble CRM197 yield and standard deviation of 3 replicates for each of the CRM197-expression strains constructed. The host strain and secretion leader screened for each strain are also indicated.

Both secretion leader and host strain showed a significant impact on CRM197 expression. Expression ranged from no detectable yield to more than 1.2 g/L at the 0.5 mL scale, with the highest expression levels observed in the Host Strain 2 background. The yield observed in PS538-776 was 1263 mg/L, and that in PS538-772 was 1241 mg/L, both well over the average yield of 340 mg/L. Both high and low yields were observed in the same host strain depending on the leader used, and both high and low yields were observed using the same leader in different host strains.

PS538-772, PS538-773, PS538-776, PS538-778, PS538-782 were selected for evaluation in large-scale fermentation.

TABLE 10

Mean CRM197 yield for CRM197-expression strains

| Strain Number | Corresponding Strain Number in U.S. patent application Ser. No. 61/325,235 | Host | Leader | Mean Yield (mg/L) | Std Dev (3 replicates) |
|---|---|---|---|---|---|
| PS538-761 | PS538-731 | 1 | DsbA | 205 | 162 |
| PS538-762 | PS538-732 | 1 | Azu | 427 | 186 |
| PS538-763 | PS538-733 | 1 | Ibp-S31A | 361 | 183 |
| PS538-764 | PS538-734 | 1 | Tpr | 298 | 106 |
| PS538-765 | PS538-735 | 1 | CupB2 | 105 | 109 |
| PS538-766 | PS538-736 | 1 | CupA2 | 175 | 99 |
| PS538-767 | PS538-737 | 1 | NikA | 314 | 85 |
| PS538-768 | PS538-738 | 1 | Pbp A20V | 291 | 204 |
| PS538-769 | PS538-739 | 1 | DsbC | 148 | 91 |
| PS538-770 | PS538-740 | 1 | TolB | 213 | 36 |
| PS538-771 | PS538-741 | 2 | DsbA | 407 | 218 |
| PS538-772 | PS538-742 | 2 | Azu | 1241 | 372 |
| PS538-773 | PS538-743 | 2 | Ibp-S31A | 1107 | 219 |
| PS538-774 | PS538-744 | 2 | Tpr | 280 | 285 |
| PS538-775 | PS538-745 | 2 | CupB2 | 192 | 219 |
| PS538-776 | PS538-746 | 2 | CupA2 | 1263 | 474 |
| PS538-777 | PS538-747 | 2 | NikA | 699 | 259 |
| PS538-778 | PS538-748 | 2 | Pbp A20V | 914 | 416 |
| PS538-779 | PS538-749 | 2 | DsbC | 567 | 141 |
| PS538-780 | PS538-750 | 2 | TolB | 382 | 217 |
| PS538-781 | PS538-751 | 3 | DsbA | 591 | 230 |
| PS538-782 | PS538-752 | 3 | Azu | 1094 | 543 |
| PS538-783 | PS538-753 | 3 | Ibp-S31A | 323 | 143 |
| PS538-784 | PS538-754 | 3 | Tpr | 419 | 70 |
| PS538-785 | PS538-755 | 3 | CupB2 | 75 | 74 |
| PS538-786 | PS538-756 | 3 | CupA2 | 309 | 214 |
| PS538-787 | PS538-757 | 3 | NikA | 52 | 73 |
| PS538-788 | PS538-758 | 3 | Pbp A20V | 356 | 295 |
| PS538-789 | PS538-759 | 3 | DsbC | 319 | 117 |
| PS538-790 | PS538-760 | 3 | TolB | 69 | 88 |
| PS538-791 | PS538-761 | 4 | DsbA | 270 | 106 |
| PS538-792 | PS538-762 | 4 | Azu | 0 | 14 |
| PS538-793 | PS538-763 | 4 | Ibp-S31A | 0 | 6 |
| PS538-794 | PS538-764 | 4 | Tpr | 0 | 0 |
| PS538-795 | PS538-765 | 4 | CupB2 | 18 | 39 |
| PS538-796 | PS538-766 | 4 | CupA2 | 118 | 134 |
| PS538-797 | PS538-767 | 4 | NikA | 0 | 9 |
| PS538-798 | PS538-768 | 4 | Pbp A20V | 0 | 0 |
| PS538-799 | PS538-769 | 4 | DsbC | 0 | 0 |
| PS538-800 | PS538-770 | 4 | TolB | 0 | 0 |

Example 2

Large-Scale Expression of a Recombinant CRM197 Protein

Recombinant CRM197 protein was produced in *Pseudomonas fluorescens* strains PS538-772, PS538-776, and PS538-782 in 2 liter fermentors. Cultures were grown in 2 liter fermentors containing a mineral salts medium as described herein and also by, e.g., Riesenberg, D., et al., 1991, and maintained at 32° C. and pH 6.5 through the addition of ammonia. Dissolved oxygen was maintained in excess through increases in agitation and flow of sparged air and oxygen into the fermentor. Glycerol was delivered to the culture throughout the fermentation to maintain excess levels. These conditions were maintained until a target culture cell density (optical density at 575 nm (A575)) for induction is reached, at which time IPTG is added to initiate CRM197 production. Cell density at induction could be varied from A575 of 40 to 200 absorbance units (AU). IPTG concentrations could be varied in the range from 0.02 to 0.4 mM. pH from 6 to 7.5 and temperature 20 to 35° C. After 16-24 hours, the culture from each bioreactor was harvested by centrifugation and the cell pellet frozen at −80° C. Samples were analyzed by SDS-CGE for product formation.

Multiple fermentation conditions were evaluated resulting in top CRM197 expression as determined by SDS-CGE of 1 to 2 g/L (see FIGS. 23 and 24). The identities of the induced proteins were confirmed by Western blot analysis using a diphtheria toxin specific antibody (FIG. 25).

Example 3

High Throughput Expression of a Recombinant Cholera Toxin B Protein

Construction and Growth of Cholera Toxin B Expression Strains

The Cholera Toxin B coding sequence was constructed using *P. fluorescens* preferred codons to encode the Cholera Toxin B amino acid sequence. FIG. 3 shows the amino acid and DNA sequences of the expressed synthetic Cholera Toxin B gene.

Plasmids carrying the optimized Cholera Toxin B sequence, fused to the same ten *P. fluorescens* secretion leader coding sequences used with CRM197 (shown in Table 8) were constructed. The secretion leaders were included to target the protein to the periplasm for recovery in the properly folded and active form.

Constructs expressing the ten secretion leaders fused to the recombinant Cholera Toxin B protein were tested in *P. fluorescens* hosts. The four hosts listed in Table 9 were tested with each expression plasmid. Host cells were electroporated with the indicated plasmids, and grown and induced in 96-well format as described above for the CRM197 high throughput expression. Samples were prepared and analyzed by SDS-CGE as described above for the CRM197 high throughput expression samples.

Representative gel-like images showing the results of the reducing SDS-CGE analysis of the soluble fraction from each strain are shown in FIG. 4. Table 11 shows the mean soluble Cholera Toxin B yield and standard deviation of 3 replicates for each of the Cholera Toxin B-expression strains constructed.

Both secretion leader and host strain showed a significant impact on Cholera Toxin B expression. Expression ranged from no detectable yield to more than 0.2 g/L at the 0.5 mL scale, with the highest expression levels observed in the hslUV prc1 degP1 degP2 aprA deletion/DegP2 S219A over-expression host background. Expression of Cholera Toxin B fused to leaders 6 (CupA2) and 8 (PbpA20V) appeared to be consistently high in all four strains.

TABLE 11

Cholera Toxin B Expression Summary

| Strain Number | Host Strain | Plasmid | Leader | Mean Yield (mg/L) | Std Dev (3 replicates) |
|---|---|---|---|---|---|
| PS538-081 | 1 | p538-021 | DsbA | 25 | 8 |
| PS538-082 | 1 | p538-022 | Azu | 1 | 8 |
| PS538-083 | 1 | p538-023 | Ibp-S31A | 0 | 5 |
| PS538-084 | 1 | p538-024 | Tpr | 35 | 14 |
| PS538-085 | 1 | p538-025 | CupB2 | 10 | 9 |
| PS538-086 | 1 | p538-026 | CupA2 | 138 | 18 |
| PS538-087 | 1 | p538-027 | NikA | 0 | 5 |
| PS538-088 | 1 | p538-028 | Pbp A20V | 213 | 23 |
| PS538-089 | 1 | p538-029 | DsbC | 0 | 6 |
| PS538-090 | 1 | p538-030 | TolB | 0 | 4 |
| PS538-091 | 2 | p538-021 | DsbA | 133 | 62 |
| PS538-092 | 2 | p538-022 | Azu | 83 | 56 |
| PS538-093 | 2 | p538-023 | Ibp-S31A | 50 | 44 |
| PS538-094 | 2 | p538-024 | Tpr | 61 | 55 |
| PS538-095 | 2 | p538-025 | CupB2 | 62 | 19 |
| PS538-096 | 2 | p538-026 | CupA2 | 147 | 57 |
| PS538-097 | 2 | p538-027 | NikA | 31 | 28 |
| PS538-098 | 2 | p538-028 | Pbp A20V | 223 | 78 |
| PS538-099 | 2 | p538-029 | DsbC | 41 | 24 |
| PS538-100 | 2 | p538-030 | TolB | 6 | 5 |
| PS538-101 | 3 | p538-021 | DsbA | 1 | 7 |
| PS538-102 | 3 | p538-022 | Azu | 1 | 2 |
| PS538-103 | 3 | p538-023 | Ibp-S31A | 19 | 17 |
| PS538-104 | 3 | p538-024 | Tpr | 28 | 36 |
| PS538-105 | 3 | p538-025 | CupB2 | 5 | 9 |
| PS538-106 | 3 | p538-026 | CupA2 | 40 | 12 |
| PS538-107 | 3 | p538-027 | NikA | 5 | 10 |
| PS538-108 | 3 | p538-028 | Pbp A20V | 45 | 19 |
| PS538-109 | 3 | p538-029 | DsbC | 0 | 6 |
| PS538-110 | 3 | p538-030 | TolB | 0 | 3 |
| PS538-111 | 4 | p538-021 | DsbA | 0 | 5 |
| PS538-112 | 4 | p538-022 | Azu | 0 | 3 |
| PS538-113 | 4 | p538-023 | Ibp-S31A | 0 | 2 |
| PS538-114 | 4 | p538-024 | Tpr | 13 | 3 |
| PS538-115 | 4 | p538-025 | CupB2 | 2 | 4 |
| PS538-116 | 4 | p538-026 | CupA2 | 15 | 16 |
| PS538-117 | 4 | p538-027 | NikA | 0 | 2 |
| PS538-118 | 4 | p538-028 | Pbp A20V | 35 | 15 |
| PS538-119 | 4 | p538-029 | DsbC | 0 | 2 |
| PS538-120 | 4 | p538-030 | TolB | 0 | 2 |

Example 4

Large-Scale Expression of a Recombinant Cholera Toxin B Protein

Recombinant Cholera Toxin B protein was produced in *Pseudomonas fluorescens* Pfēnex Expression Technology™ strains PS538-088 and PS538-091. The selected strain was grown in 2 liter fermentors containing a mineral salts medium as described herein and also by, e.g., Riesenberg, D., et al., 1991, and maintained at 32° C. and pH 6.5 through the addition of ammonia. Dissolved oxygen was maintained in excess through increases in agitation and flow of sparged air and oxygen into the fermentor. Glycerol was delivered to the culture throughout the fermentation to maintain excess levels. These conditions were maintained until a target culture cell density (optical density at 575 nm (A575)) for induction was reached, at which time IPTG was added to initiate the target protein production. IPTG was added to initiate CTB production. After 16-24 hours, the culture from each bioreactor was harvested by centrifugation and the cell pellet was frozen at −80° C.

Multiple fermentation conditions were evaluated resulting in top CTB expression as determined by SDS-CGE of 0.6 to 1.0 g/L. The top performing fermentation cultures were induced at approximately 80-160 OD with 0.2 mM IPTG at pH 6.5-7.2 and 32° C. Soluble CTB concentrations were determined by SDS-CGE (see FIG. 14 and Table 12). The identities of the induced proteins were confirmed by peptide mass fingerprint using MALDI-TOF mass spectrometry.

TABLE 12

Soluble Cholera Toxin B Titers

| Strain | Fermentation | Product | Product concentration (g/L) |
|---|---|---|---|
| PS538-088 | U5 | CTB | 0.94 ± 0.03 |
| PS538-088 | U6 | CTB | 0.59 ± 0.01 |
| PS538-091 | U3 | CTB | 0.81 ± 0.09 |

Example 5

High Throughput Expression of a Recombinant Pertussis Toxin Protein

Construction and Growth of Pertussis Toxoid S1 E129A R9K Expression Strains

The sequence of the Pertussis toxoid operon encoding sub-units S1, S2, S3, S4 and S5, with S1 mutations E129A and R9K was used for expression of recombinant Pertussis toxin. FIG. 5 shows a map of the operon. FIG. 6 shows the DNA sequence of the operon, with translation (SEQ ID NO:24). FIG. 7 shows the individual amino acid sequences of S1, S2, S3, S4 and S5.

The construct was expressed in eight *P. fluorescens* hosts, shown in Table 13. Host cells were electroporated with p538-081, and grown and induced in 96-well format as described above for CRM197 high throughput expression. Samples were prepared and analyzed by SDS-CGE as described above for the CRM197 high throughput expression samples.

TABLE 13

Pertussis Toxin S1 E129A R9K Expression Strains

| Strain Number | Host | Genotype | Plasmid | Type |
|---|---|---|---|---|
| PS538-321 | 1 | lon, la, aprA | p538-081 | PD |
| PS538-322 | 2 | hslUV, prc1, degP1, degP2 and aprA | p538-081 | PD |
| PS538-323 | 3 | dsbABCD | p538-081 | FMO |
| PS538-324 | 4 | grpE, dnaKJ | p538-081 | FMO |
| PS538-325 | 5 | htpX | p538-081 | PD |
| PS538-326 | 6 | RXF01590 | p538-081 | PD |
| PS538-327 | 7 | lon, la, aprA deletions; overexpresses grpE and dnaKJ | p538-081 | PD + FMO |
| PS538-328 | 8 | ppiB (RXF05345) | p538-081 | FMO |

PD = Protease Deletion (listed proteases are deleted);
FMO = Folding Modulator Overexpressor (listed folding modulators are overexpressed.

Western Blot Analysis of Expressed Pertussis Toxin

Soluble fractions from the eight cultures described above were analyzed by Western blot to evaluate Pertussis Toxoid expression. Twenty microliters of the soluble fractions (2× diluted, reduced and non-reduced) were run on Bio-Rad 12% Bis-Tris Gel in 1× Bio_Rad MES running buffer. For reduced Western analysis, 1×XT reducing agent was added. Proteins were transferred from SDS-PAGE at 100V for 60 minutes onto a 0.2 µm nitrocellulose membrane (Bio Rad, 162 0232) using 1× NuPAGE Transfer Buffer (Invitrogen, NP0006-1) with 20% methanol. Membranes were blocked for 1 hour at room temperature in Blocker™ 1% Casein in PBS (Pierce, 37528). For detection, the diluents were poured off and more was added containing the combination of 1:1000 dilution each of monoclonal antibodies directed against *Bordetella pertussis* toxin S4 and S1 (Abcam, cat#ab37686 and #37547). The blots were incubated with rocking overnight at 4° C. The blots were washed three times with PBS-Tween for 5 minutes each, and were then incubated in more diluent containing a 1:5,000 dilution of anti-Mouse IgG-Peroxidase derived in goat (Sigma, Cat#A4416) at room temperature for 1 hour. The blots were washed three times with PBS-Tween (Sigma, P3563) for 5 minutes each, before color development using Immunopure Metal Enhanced DAB substrate (Pierce, 34065). Multiple subunits were detected by the anti-S1 and anti-S4 antibodies under both reducing and non reducing conditions (FIG. 8). The banding pattern of reduced and nonreduced samples of the expressed toxoid observed was consistent with that observed for purified Pertussis toxin from strain 165 as reported by Sekura, et al. (J. Biological Chemistry 258: 14647, 1983).

Example 6

Large-Scale Expression of Recombinant Pertussis Toxin Protein

Recombinant Pertussis toxin protein is produced in *Pseudomonas fluorescens* Pfēnex Expression Technology™ strains PS538-321, PS538-324, PS538-325, PS538-326, and PS538-328. The selected strain is grown in 2 liter fermentors, induced with IPTG, and samples prepared for analysis, as described above for CTB large-scale expression. The samples are analyzed by SDS-CGE, for product formation and their activity analyzed by Western Blot.

Example 7

High Throughput Expression of Recombinant Wild-Type Pertussis Toxoid

Construction and Growth of Pertussis Toxoid Expression Strains

The sequence of the wild-type Pertussis toxin operon encoding subunits S1, S2, S3, S4 and S5, with S1 is used for expression of recombinant Pertussis Toxoid. FIG. 17 shows the DNA sequence of the operon, with translation (SEQ ID NO:35).

The construct is expressed in the *P. fluorescens* hosts shown in Table 14. Each strain listed that does not have an overexpression plasmid is tested a) as described (having no overexpression plasmid); b) including a GrpE DnaKJ overexpression plasmid, and c) including a DsbABCD overexpression plasmid. Host cells are electroporated with the PTX WT expression plasmid, and grown and induced in 96-well format as described above for PTX S1 R9K E129A high-throughput expression. Samples are prepared and analyzed by SDS-CGE also as described above.

TABLE 14

Pertussis Toxoid Wild-Type Expression Strains

| Host* | Genotype | Type |
|---|---|---|
| 9 | hslUV prc2 | PD |
| 10 | hslUV degP1 | PD |
| 11 | la | PD |
| 12 | hslUV prc1 prc2 | PD |
| 13 | lon la prc1 prc2 | PD |
| 14 | RXF01590 | PD |
| 1 | lon la aprA | PD |
| 7 | lon la prc1 degP2 aprA; overexpresses GrpE DnaKJ | PD + FMO |
| 15 | RXF02151 RXF00428 | PD |
| 16 | lon la degP2 | PD |
| 17 | overexpresses DsbAB | FMO |
| 18 | overexpresses DsbCD | FMO |
| 19 | prc1 degP2; overexpresses degP2 S219A | PD + FMO |
| 20 | prc1 degP2 clp1 aprA; overexpresses degP2 S219A | PD + FMO |
| 21 | prc1 degP2 lon aprA; overexpresses degP2 S219A | PD + FMO |
| 22 | prc1 degP2 degP1 aprA; overexpresses degP2 S219A | PD + FMO |
| 23 | lon prc1 degP2 degP1 aprA; overexpresses degP2 S219A | PD + FMO |
| 2 | hslUV prc1 degP2 degP1 aprA; overexpresses degP2 S219A | PD + FMO |
| 25 | lon la degP2 prc1 aprA; overexpresses degP2 S219A | PD + FMO |
| 26 | degP2; overexpresses SecB | PD + FMO |
| 27 | degP2; overexpresses FkbP | PD + FMO |
| 28 | degP2; overexpresses GroELES | PD + FMO |
| 29 | lon la aprA; overexpresses SecB | PD + FMO |
| 30 | lon la aprA; overexpresses FkbP | PD + FMO |
| 31 | lon la aprA; overexpresses GroELES | PD + FMO |
| 32 | dsbC | PD |
| 33 | dsbC; ovrexpresses DsbAB | PD + FMO |
| 3 | overexpresses DsbABCD | FMO |
| 35 | lexA aprA | PD |
| 36 | overexpresses SlyD | FMO |
| 37 | lon hslUV | PD |

TABLE 14-continued

Pertussis Toxoid Wild-Type Expression Strains

| Host* | Genotype | Type |
|---|---|---|
| 38 | Wt | — |
| 39 | aprA | PD |
| 4 | overexpresses GrpE DnaKJ | FMO |
| 5 | htpX | PD |
| 40 | lon | PD |
| 41 | prc1 | PD |
| 42 | hslUV | PD |
| 43 | degP2 | PD |
| 44 | degP1 | PD |
| 45 | prc2 | PD |
| 46 | RXF6451 | PD |
| 6 | RXF1590 | PD |
| 48 | RXF4692 | PD |
| 49 | hslUV mic | PD |
| 50 | RXF2161 | PD |
| 51 | RXF00133 | PD |
| 52 | RXF2796 | PD |
| 53 | RXF4968 | PD |
| 54 | overexpresses DsbC | FMO |
| 55 | overexpresses DsbAC | FMO |
| 56 | overexpresses LepB | FMO |
| 57 | overexpresses SecB | FMO |
| 58 | overexpresses ClpA | FMO |
| 59 | overexpresses FklB2 | FMO |
| 60 | overexpresses DnaK-like | FMO |
| 61 | overexpresses FkbP | FMO |
| 62 | overexpresses PpiA | FMO |
| 8 | overexpresses PpiB | FMO |
| 63 | overexpresses HscA | FMO |
| 64 | overexpresses GshA | FMO |
| 65 | overexpresses Gor | FMO |
| 66 | overexpresses TrxC | FMO |
| 67 | overexpresses DsbG | FMO |
| 68 | overexpresses Ppi | FMO |
| 69 | overexpresses GroELES | FMO |
| 70 | prc1 aprA; overexpresses GrpE DnaKJ | PD + FMO |
| 71 | hypersecretion | |
| 72 | overexpresses DsbD | FMO |
| 73 | hypersecretion | |
| 74 | hypersecretion | |
| 75 | prc1 prc2 | PD |
| 76 | hslUV clpA | PD |

*Each strain listed that does not have an overexpression plasmid is tested a) as described (having no overexpression plasmid); b) including a GrpE DnaKJ overexpression plasmid, and c) including a DsbABCD overexpression plasmid.
PD = Protease Deletion (listed proteases are deleted);
FMO = Folding Modulator Overexpressor (listed folding modulators are overexpressed.

Hypersecretion strains, also known as hyper-vesiculating strains, are described, e.g., in WO2010/008764, *"Pseudomonas Fluorescens* Strains for Production of Extracellular Recombinant Protein," incorporated herein by reference in its entirety.

Example 8

High Throughput Expression of a Recombinant Tetanus Toxin Fragment C Protein Construction and Growth of Tetanus Toxin C Expression Strains The Tetanus Toxin C coding sequence was constructed using *P. fluorescens* preferred codons to encode the Tetanus Toxin C amino acid sequence. FIG. 9 shows the amino acid and DNA sequences of the expressed synthetic Tetanus Toxin C gene.

Plasmids carrying the optimized Tetanus Toxin C sequence, fused to the same ten *P. fluorescens* secretion leader coding sequences used with CRM197 (shown in Table 8) were constructed. The secretion leaders were included to target the protein to the periplasm for recovery in the properly folded and active form.

Constructs expressing the ten secretion leaders fused to the recombinant Tetanus Toxin C protein were tested in *P. fluorescens* hosts. The four hosts listed in Table 9 were tested with each leader. Host cells were electroporated with the indicated plasmids, and grown and induced in 96-well format as described above for the CRM197 high throughput expression. Samples were prepared and analyzed by SDS-CGE as described above for the CRM197 high throughput expression samples.

Representative gel-like images showing the results of the reducing SDS-CGE analysis of the soluble fraction from each strain are shown in FIG. 10. Table 15 shows the mean soluble Tetanus Toxin C yield and standard deviation of 3 replicates for each of the Tetanus Toxin C-expression strains constructed. Tetanus Toxin C fragment appeared to be expressed well in most strains tested, with highest yields ranging up to 600 mg/L in the hslUV prc1 degP1 degP2 aprA deletion/ DegP2 S219A overexpression expression host. Strains PS538-529, PS538-538, PS538-544, PS538-546, PS538-547, PS538-548, PS538-558, PS538-565 and PS538-568 were selected for further evaluation.

TABLE 15

Tetanus Toxin C Expression Summary.

| Strain Number | Host | Plasmid | Leader | Mean Yield (mg/L) | Std Dev (3 replicates) |
|---|---|---|---|---|---|
| PS538-529 | 1 | p538-132 | DsbA | 261 | 75 |
| PS538-530 | 1 | p538-133 | Azu | 200 | 82 |
| PS538-531 | 1 | p538-134 | Ibp-S31A | 165 | 64 |
| PS538-532 | 1 | p538-135 | Tpr | 207 | 107 |
| PS538-533 | 1 | p538-136 | CupB2 | 205 | 128 |
| PS538-534 | 1 | p538-137 | CupA2 | 200 | 117 |
| PS538-535 | 1 | p538-138 | NikA | 174 | 96 |
| PS538-536 | 1 | p538-139 | Pbp A20V | 311 | 156 |
| PS538-537 | 1 | p538-140 | DsbC | 188 | 97 |
| PS538-538 | 1 | p538-141 | TolB | 129 | 63 |
| PS538-539 | 2 | p538-132 | DsbA | 486 | 89 |
| PS538-540 | 2 | p538-133 | Azu | 495 | 93 |
| PS538-541 | 2 | p538-134 | Ibp-S31A | 568 | 68 |
| PS538-542 | 2 | p538-135 | Tpr | 589 | 364 |
| PS538-543 | 2 | p538-136 | CupB2 | 534 | 318 |
| PS538-544 | 2 | p538-137 | CupA2 | 504 | 134 |
| PS538-545 | 2 | p538-138 | NikA | 444 | 145 |
| PS538-546 | 2 | p538-139 | Pbp A20V | 637 | 280 |
| PS538-547 | 2 | p538-140 | DsbC | 574 | 68 |
| PS538-548 | 2 | p538-141 | TolB | 438 | 61 |
| PS538-549 | 3 | p538-132 | DsbA | 174 | 37 |
| PS538-550 | 3 | p538-133 | Azu | 180 | 58 |
| PS538-551 | 3 | p538-134 | Ibp-S31A | 88 | 58 |
| PS538-552 | 3 | p538-135 | Tpr | 247 | 134 |
| PS538-553 | 3 | p538-136 | CupB2 | 199 | 39 |
| PS538-554 | 3 | p538-137 | CupA2 | 165 | 69 |
| PS538-555 | 3 | p538-138 | NikA | 97 | 90 |
| PS538-556 | 3 | p538-139 | Pbp A20V | 297 | 112 |
| PS538-557 | 3 | p538-140 | DsbC | 151 | 52 |
| PS538-558 | 3 | p538-141 | TolB | 35 | 13 |
| PS538-559 | 4 | p538-132 | DsbA | 39 | 39 |
| PS538-560 | 4 | p538-133 | Azu | 40 | 43 |
| PS538-561 | 4 | p538-134 | Ibp-S31A | 36 | 40 |
| PS538-562 | 4 | p538-135 | Tpr | 35 | 39 |
| PS538-563 | 4 | p538-136 | CupB2 | 54 | 26 |
| PS538-564 | 4 | p538-137 | CupA2 | 42 | 36 |
| PS538-565 | 4 | p538-138 | NikA | 44 | 37 |
| PS538-566 | 4 | p538-139 | Pbp A20V | 37 | 40 |
| PS538-567 | 4 | p538-140 | DsbC | 39 | 43 |
| PS538-568 | 4 | p538-141 | TolB | 45 | 38 |

Example 9

Large-Scale Expression of a Recombinant Tetanus Toxin Fragment C Protein

Recombinant Tetanus Toxin C protein was produced in *Pseudomonas fluorescens* Pfēnex Expression Technology™ strains PS538-529, PS538-538, PS538-544, PS538-546, PS538-547, PS538-548, PS538-558, PS538-565 and PS538-568. The selected strains were grown in 2 liter fermentors containing a mineral salts medium as described above for CRM197.

Figure 15A:
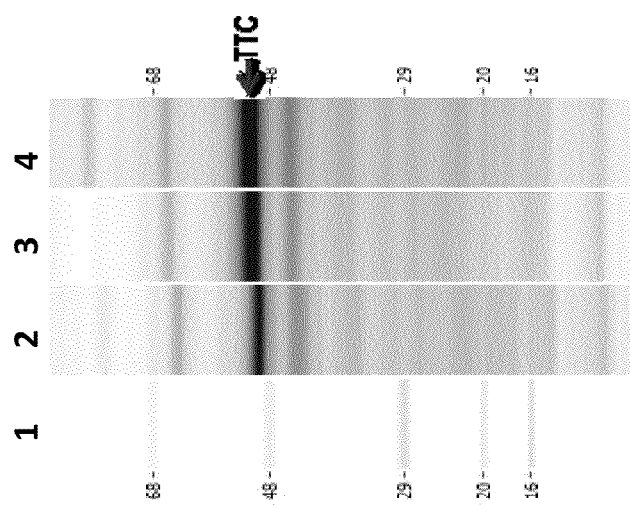
Figure 15B:
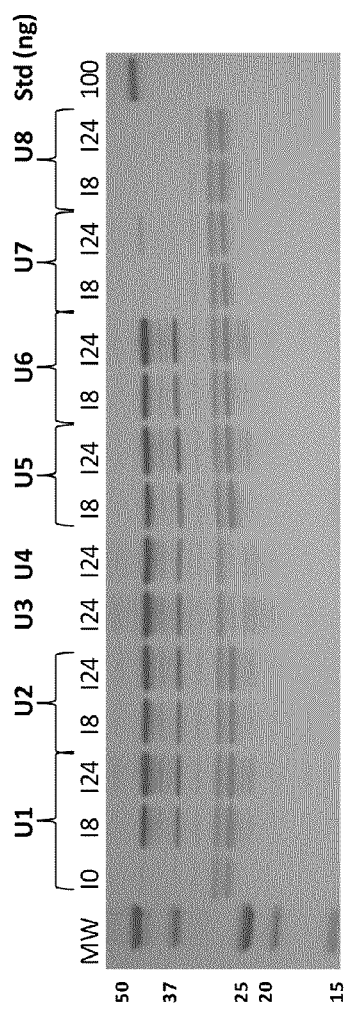

Multiple fermentation conditions were evaluated resulting in top soluble TTC expression from strains PS538-529, PS538-546, and PS538-547 of 6 to 10 g/L as determined by SDS-CGE (see FIG. 15 and Table 16). The top performing fermentation culture was induced at approximately 160 OD with 0.2 mM IPTG at pH 7.2 and 32° C. The identities of the induced proteins were confirmed by peptide mass fingerprint using MALDI-TOF mass spectrometry and Western Blot. Mass spectrometry and Western blot analyses indicated that the secretion leaders of PS538-529, PS538-546 and PS538-547 (DsbA, Pbp A20V and DsbC, respectively) were not processed from 100% of the expressed protein under these expression conditions. However, the TolB leader was identified as being precisely cleaved from the secreted protein (data not shown). TolB-TTC expression strains PS538-538, PS538-548, PS538-558 and PS538-568 were screened at the 2 L fermentation scale, using the conditions outlined above, to identify a strain that enabled production of TTC with high fidelity cleavage of the secretion leader and low levels of degradation. Strains PS538-538, PS538-548 and PS538-558 were observed to produce similar quality and yield of material by Western blot analysis (FIG. 15B).

TABLE 16

Soluble Tetanus Toxin C (TTC) Titers

| Strain | Fermentation | Product | Product concentration (g/L) |
|---|---|---|---|
| PS538-529 | U1 - FIG. 15A | TTC | 5.7 ± 1.3 |
| PS538-546 | U7 - FIG. 15A | TTC | 9.5 ± 1.1 |
| PS538-547 | U5 - FIG. 15A | TTC | 6.2 ± 1.9 |
| PS538-538 | U1 - FIG. 15B | TTC | 2.5 ± 0.09 |
| PS538-538 | U2 - FIG. 15B | TTC | 1.8 ± 0.2 |
| PS538-548 | U3 - FIG. 15B | TTC | 5.3 ± 0.6 |
| PS538-548 | U4 - FIG. 15B | TTC | 4.5 ± 0.2 |
| PS538-558 | U5 - FIG. 15B | TTC | 1.1 ± 0.8 |
| PS538-558 | U6 - FIG. 15B | TTC | 1.9 ± 0.1 |
| PS538-568 | U7 - FIG. 15B | TTC | 0.2 ± 0.01 |
| PS538-568 | U8 - FIG. 15B | TTC | 0.2 ± 0.01 |

Example 10

High Throughput Expression of a Recombinant *C. difficile* B Protein

Construction and Growth of TcdB Expression Strains

The TcdB coding sequence was constructed using *P. fluorescens* preferred codons to encode the TcdB amino acid sequence. FIG. 11 shows the amino acid and DNA sequences of the expressed synthetic TcdB gene.

Plasmids carrying the optimized TcdB sequence were tested in the *P. fluorescens* hosts having genotypes listed in Table 17. Host cells were electroporated with the cytoplasmic expression plasmid p538-211, and grown and induced in 96-well format as described above for the CRM197 high throughput expression. Samples were prepared and analyzed by SDS-CGE as described above for the CRM197 high throughput expression samples.

TABLE 17

TcdB Host Strains

| Host Strain | Genotype | Type |
|---|---|---|
| 37 | hslUV lon | PD |
| 38 | | WT |
| 4 | dnaKJ grpE | FMO |
| 5 | htpX | PD |
| 40 | lon | PD |
| 41 | prc1 | PD |
| 42 | hslUV | PD |
| 43 | degP2 | PD |
| 44 | degP1 | PD |
| 45 | prc2 | PD |
| 47 | RXF01590 | PD |
| 49 | hslUV mic | PD |
| 53 | RXF04968 | PD |
| 55 | dsbAC | FMO |
| 61 | fkbP | FMO |
| 66 | trxC | FMO |
| 72 | dsbD | FMO |
| 76 | hslUV clpA | PD |
| 12 | hslUV prc1 prc2 | PD |
| 1 | lon la aprA | PD |
| 16 | lon la degP2 | PD |
| 2 | hslUV prc1 degP1 degP2 aprA deletions; overexpresses degP2 S219A | PD + FMO |
| 3 | dsbABCD | FMO |
| 21 | lon prc1 degP2 aprA deletions with degP2 S219A overexpression | PD + FMO |

Representative gel-like images showing the results of the reducing SDS-CGE analysis of the soluble fraction from each of the 24 strains tested are shown in FIG. 12. Table 18 shows the mean soluble TcdB yield and standard deviation of 3 replicates for each of the TcdB-expression strains constructed. Strains PS538-654, PS538-659, PS538-669, PS538-671, and PS538-674 were selected for further evaluation.

TABLE 18

TcdB Expression Summary

| Strain Number | Host | Plasmid | Mean Yield (mg/L) | Std Dev (3 replicates) |
|---|---|---|---|---|
| PS538-651 | 37 | p538-211 | 103 | 7 |
| PS538-652 | 38 | p538-211 | 55 | 4 |
| PS538-653 | 4 | p538-211 | 57 | 1 |
| PS538-654 | 5 | p538-211 | 166 | 13 |
| PS538-655 | 40 | p538-211 | 88 | 3 |
| PS538-656 | 41 | p538-211 | 68 | 5 |
| PS538-657 | 42 | p538-211 | 90 | 14 |
| PS538-658 | 43 | p538-211 | 68 | 2 |
| PS538-659 | 44 | p538-211 | 109 | 8 |
| PS538-660 | 45 | p538-211 | 78 | 4 |
| PS538-661 | 6 | p538-211 | 98 | 15 |
| PS538-662 | 49 | p538-211 | 106 | 10 |
| PS538-663 | 53 | p538-211 | 91 | 6 |
| PS538-664 | 55 | p538-211 | 45 | 4 |
| PS538-665 | 61 | p538-211 | 63 | 6 |
| PS538-666 | 66 | p538-211 | 56 | 8 |
| PS538-667 | 72 | p538-211 | 70 | 8 |
| PS538-668 | 76 | p538-211 | 80 | 6 |
| PS538-669 | 12 | p538-211 | 117 | 39 |
| PS538-670 | 1 | p538-211 | 108 | 18 |
| PS538-671 | 16 | p538-211 | 247 | 65 |
| PS538-672 | 2 | p538-211 | 32 | 6 |
| PS538-673 | 3 | p538-211 | 52 | 2 |
| PS538-674 | 21 | p538-211 | 145 | 12 |

Example 11

Large-Scale Expression of Recombinant *C. difficile* Toxin B Protein

Recombinant *C. difficile* toxin B protein was produced in *Pseudomonas fluorescens* Pfēnex Expression Technology™ strain PS538-654, PS538-659, PS538-669, PS538-671, and PS538-674. The selected strains were grown in 2 liter fermentors, induced with IPTG, and samples prepared for analysis, as described above for CTB large-scale expression.

Multiple fermentation conditions were evaluated resulting in top *C. difficile* B Toxin expression as determined by SDS-CGE of approximately 2 g/L. The top performing fermentation culture was induced at approximately 160 OD with 0.08 mM IPTG at pH 6.5 and 32° C. Soluble *C. difficile* B Toxin concentrations were determined by SDS-CGE (see FIG. 16 and Table 19). The identities of the induced proteins were confirmed by Western blot.

TABLE 19

Soluble *C. difficile* B Toxin (TcdB) Titers

| Strain | Fermentation | Product | Product concentration (g/L) |
|---|---|---|---|
| PS538-671 | U5 | TcdB | 1.6 ± 0.4 |
| PS538-671 | U6 | TcdB | 2.1 ± 0.2 |
| PS538-674 | U7 | TcdB | 1.8 ± 0.2 |

Example 12

High Throughput Expression of a Recombinant Exotoxin A Protein

Construction and Growth of *P. aeruginosa* Exotoxin A Expression Strains

The *P. aeruginosa* Exotoxin A mutant rEPA coding sequence was constructed using *P. fluorescens* preferred codons to encode the rEPA amino acid sequence. FIG. 13 shows the amino acid and DNA sequences of the expressed synthetic rEPA gene.

Plasmids carrying the optimized sequences encoding either the deletion mutant rEPA, as indicated in FIG. 13, fused to the same ten *P. fluorescens* secretion leader coding sequences used with CRM197 (shown in Table 8) were constructed. The secretion leader coding sequences were included to target the protein to the periplasm for recovery in the properly folded and active form.

Constructs expressing the ten secretion leaders fused to the rEPA proteins were tested in eight *P. fluorescens* hosts, listed in Table 20. Host cells were electroporated with the indicated plasmids, and grown and induced in 96-well format as described above for the CRM197 high throughput expression. Samples were prepared and analyzed by SDS-CGE as described above for the CRM197 high throughput expression samples. The highest yields ranged from 4.7-6.7 g/L of soluble rEPA.

TABLE 20

Exotoxin A Host Strains

| Host Strain | Genotype | Type |
|---|---|---|
| 5 | htpX | PD |
| 6 | serralysin | PD |
| 7 | Lon La1 aprA; with grpE dnaKJ overexpression | PD/FMO |
| 8 | ppiB | PD |
| 1 | Lon-, La-, aprA- | PD |
| 2 | hslUV-, prc1-, degP1-, degP2-, aprA- with degP2 S219A overexpression | PD + FMO |
| 3 | dsbABCD overexpression | FMO |
| 4 | grpE, dnaKJ overexpression | FMO |

Host cells were electroporated with the indicated plasmids, and grown and induced in 96-well format as described above for the CRM197 high throughput expression. Samples were prepared and analyzed by SDS-CGE as described above for the CRM197 high throughput expression samples. The highest yields ranged from 1.6 to 2.2 g/L of soluble Exotoxin A protein. Table 21 shows the soluble rEPA yield for each of the expression strains selected for further testing.

TABLE 21 rEPA HTP Expression Summary

| Strain Number | Host | Plasmid | Secretion Leader | Volumetric Yield (g/L) |
|---|---|---|---|---|
| PS538-1670 | 3 | p538-250 | DsbC | 6.7 |
| PS538-1663 | 3 | p538-243 | Ibp-s31a | 5.7 |
| PS538-1633 | 1 | p538-243 | Ibp-s31a | 5.7 |
| PS538-1640 | 1 | p538-249 | Pbp-A20V | 4.7 |
| PS538-1662 | 3 | p538-242 | Azu | 4.2 |
| PS538-1632 | 1 | p538-242 | Azu | 3.2 |
| PS538-1671 | 4 | p538-241 | DsbA | 2.9 |
| PS538-1665 | 3 | p538-245 | Tpr | 2.7 |
| PS538-1667 | 3 | p538-247 | CupA2 | 2.6 |
| PS538-1674 | 4 | p538-244 | TolB | 2.3 |
| PS538-1672 | 4 | p538-242 | Azu | 2.2 |
| PS538-1676 | 4 | p538-246 | CupB2 | 2.2 |
| PS538-1677 | 4 | p538-247 | CupA2 | 2.1 |
| PS538-1635 | 1 | p538-245 | Tpr | 2.0 |
| PS538-1675 | 4 | p538-245 | Tpr | 2.0 |
| PS538-1673 | 4 | p538-243 | Ibp-s31a | 2.0 |
| PS538-1680 | 4 | p538-250 | DsbC | 1.9 |
| PS538-1679 | 4 | p538-249 | Pbp-A20V | 1.7 |
| PS538-1669 | 3 | p538-249 | Pbp-A20V | 1.6 |
| PS538-1678 | 4 | p538-248 | NikA | 1.5 |
| PS538-1652 | 2 | p538-242 | Azu | 1.5 |
| PS538-1653 | 2 | p538-243 | Ibp-s31a | 1.4 |
| PS538-1660 | 2 | p538-250 | DsbC | 1.4 |
| PS538-1637 | 1 | p538-247 | CupA2 | 1.3 |
| PS538-1666 | 3 | p538-246 | CupB2 | 1.1 |
| PS538-1636 | 1 | p538-246 | CupB2 | 1.0 |
| PS538-1634 | 1 | p538-244 | TolB | 1.0 |
| PS538-1627 | 8 | p538-247 | CupA2 | 0.8 |
| PS538-1631 | 1 | p538-241 | DsbA | 0.8 |
| PS538-1622 | 8 | p538-242 | Azu | 0.8 |
| PS538-1661 | 3 | p538-241 | DsbA | 0.7 |
| PS538-1603 | 5 | p538-243 | Ibp-s31a | 0.6 |
| PS538-1630 | 8 | p538-250 | DsbC | 0.6 |
| PS538-1602 | 5 | p538-242 | Azu | 0.6 |
| PS538-1605 | 5 | p538-245 | Tpr | 0.6 |
| PS538-1623 | 8 | p538-243 | Ibp-s31a | 0.6 |
| PS538-1664 | 3 | p538-244 | TolB | 0.5 |
| PS538-1668 | 3 | p538-248 | NikA | 0.5 |
| PS538-1610 | 5 | p538-250 | DsbC | 0.5 |
| PS538-1606 | 5 | p538-246 | CupB2 | 0.4 |
| PS538-1659 | 2 | p538-249 | Pbp-A20V | 0.4 |
| PS538-1607 | 5 | p538-247 | CupA2 | 0.4 |
| PS538-1626 | 8 | p538-246 | CupB2 | 0.4 |
| PS538-1625 | 8 | p538-245 | Tpr | 0.4 |
| PS538-1638 | 1 | p538-248 | NikA | 0.3 |
| PS538-1609 | 5 | p538-249 | Pbp-A20V | 0.3 |
| PS538-1604 | 5 | p538-244 | TolB | 0.3 |
| PS538-1629 | 8 | p538-249 | Pbp-A20V | 0.3 |

TABLE 21-continued rEPA HTP Expression Summary

| Strain Number | Host | Plasmid | Secretion Leader | Volumetric Yield (g/L) |
|---|---|---|---|---|
| PS538-1657 | 2 | p538-247 | CupA2 | 0.2 |
| PS538-1651 | 2 | p538-241 | DsbA | 0.2 |
| PS538-1601 | 5 | p538-241 | DsbA | 0.2 |
| PS538-1624 | 8 | p538-244 | TolB | 0.2 |
| PS538-1621 | 5 | p538-241 | DsbA | 0.2 |
| PS538-1608 | 5 | p538-248 | NikA | 0.2 |
| PS538-1654 | 2 | p538-244 | TolB | 0.2 |
| PS538-1628 | 8 | p538-248 | NikA | 0.1 |
| PS538-1658 | 2 | p538-248 | NikA | 0.1 |
| PS538-1655 | 2 | p538-245 | Tpr | 0.1 |
| PS538-1641 | 7 | p538-241 | DsbA | 0.1 |
| PS538-1611 | 6 | p538-241 | DsbA | NQ |
| PS538-1612 | 6 | p538-242 | Azu | NQ |
| PS538-1613 | 6 | p538-243 | Ibp-s31a | NQ |
| PS538-1614 | 6 | p538-244 | TolB | NQ |
| PS538-1615 | 6 | p538-245 | Tpr | NQ |
| PS538-1616 | 6 | p538-246 | CupB2 | NQ |
| PS538-1617 | 6 | p538-247 | CupA2 | NQ |
| PS538-1618 | 6 | p538-248 | NikA | NQ |
| PS538-1619 | 6 | p538-249 | Pbp-A20V | NQ |
| PS538-1620 | 6 | p538-250 | DsbC | NQ |
| PS538-1642 | 7 | p538-242 | Azu | NQ |
| PS538-1643 | 7 | p538-243 | Ibp-s31a | NQ |
| PS538-1644 | 7 | p538-244 | TolB | NQ |
| PS538-1645 | 7 | p538-245 | Tpr | NQ |
| PS538-1646 | 7 | p538-246 | CupB2 | NQ |
| PS538-1647 | 7 | p538-247 | CupA2 | NQ |
| PS538-1648 | 7 | p538-248 | NikA | NQ |
| PS538-1649 | 7 | p538-249 | Pbp-A20V | NQ |
| PS538-1650 | 7 | p538-250 | DsbC | NQ |
| PS538-1656 | 2 | p538-246 | CupB2 | NQ |

NQ = not quantifiable

Example 13

Large-Scale Expression of a Recombinant Pseudomonas aeruginosa Exotoxin A Protein Recombinant P. aeruginosa exotoxin A protein (rEPA) was produced in Pseudomonas fluorescens strains PS538-1633, PS538-1640 and PS538-1670 in 2 liter fermentors. Cultures were grown in 2 liter fermentors containing a mineral salts medium as described herein and also by, e.g., Riesenberg, D., et al., 1991, and maintained at 32° C. and pH 6.5 through the addition of ammonia. Dissolved oxygen was maintained in excess through increases in agitation and flow of sparged air and oxygen into the fermentor. Glycerol is delivered to the culture throughout the fermentation to maintain excess levels. These conditions were maintained until a target culture cell density (optical density at 575 nm (A575)) for induction is reached, at which time IPTG was added to initiate rEPA production. Cell density at induction can be varied from A575 of 40 to 200 absorbance units (AU). IPTG concentrations can be varied in the range from 0.02 to 0.4 mM. pH from 6 to 7.5 and temperature 20 to 35° C. After 16-24 hours, the culture from each bioreactor was harvested by centrifugation and the cell pellet frozen at −80° C. Samples were analyzed by SDS-CGE for product formation.

Multiple fermentation conditions were evaluated resulting in top rEPA expression as determined by SDS-CGE of up to 32 g/L (FIGS. 20 and 21). The identity of the induced protein was confirmed by Western blot analysis using an antibody specific for P. aeruginosa exotoxin A (FIG. 22). The yields obtained are shown in Table 22.

TABLE 22 rEPA Fermentation Analysis

| Strain Number | Fermentation | Yield (g/L) |
|---|---|---|
| PS538-1633 | U1 | 15.5 +/− 0.7 |
| PS538-1633 | U2 | 11.1 +/− 0.6 |
| PS538-1640 | U3 | 20.1 +/− 1.7 |
| PS538-1640 | U5 | 31.9 +/− 1.6 |
| PS538-1670 | U6 | 20.0 +/− 0.7 |
| PS538-1670 | U7 | 14.6 +/− 1.1 |
| PS538-1670 | U8 | 31.0 +/− 1.7 |

Example 14

High Throughput Expression of a Recombinant Wild-Type Diphtheria Toxin Protein Construction and Growth of Wild-Type Diphtheria Toxin Expression Strains A Diphtheria Toxin coding sequence is constructed using P. fluorescens preferred codons to encode the wild-type Diphtheria Toxin amino acid sequence. FIG. 18 shows the amino acid and DNA sequences of the expressed synthetic Diphtheria Toxin gene.

Plasmids carrying the optimized sequences encoding Diphtheria Toxin, fused to the ten P. fluorescens secretion leader coding sequences used with CRM197 (shown in Table 8) are constructed. The secretion leader coding sequences are included to target the protein to the periplasm for recovery in the properly folded and active form.

Constructs expressing the ten secretion leaders fused to the recombinant Diphtheria Toxin proteins are tested in P. fluorescens hosts. The four hosts listed in Table 9 are tested with each leader. Host cells are electroporated with the indicated plasmids, and grown and induced in 96-well format as described above for the CRM197 high throughput expression. Samples are prepared and analyzed by SDS-CGE as described above for the CRM197 high throughput expression samples.

Example 15

Large-Scale Expression of a Recombinant Wild-Type Diphtheria Toxin Protein

Recombinant Wild-Type Diphtheria Toxin protein is produced in selected Pseudomonas fluorescens Pfēnex Expression Technology™ strains. The selected strains are grown in 2 liter fermentors, induced with IPTG, and samples prepared for analysis, as described above for CRM197 large-scale expression. The samples are analyzed by SDS-CGE.

Example 16

High Throughput Expression of a Recombinant Cholera Holotoxin Protein

Construction and Growth of CTX Expression Strains

The CTX coding sequence is constructed using P. fluorescens preferred codons to encode the CTX amino acid sequence. The coding sequence is based on the amino acid and DNA sequences of the CTX gene shown in FIG. 19.

Plasmids carrying the optimized CTX sequence, fused to the ten P. fluorescens secretion leader coding sequences used with CRM197 (shown in Table 8) are constructed. The secretion leaders are included to target the protein to the periplasm for recovery in the properly folded and active form.

Constructs expressing the ten secretion leaders fused to the recombinant CTX protein are tested in *P. fluorescens* hosts. The four hosts listed in Table 9 are tested with each expression plasmid. Host cells are electroporated with the indicated plasmids, and grown and induced in 96-well format as described above for the CRM197 high throughput expression. Samples are prepared and analyzed by SDS-CGE as described above for the CRM197 high throughput expression samples.

Example 17

Large-Scale Expression of a Recombinant Cholera Holotoxin Protein

Recombinant Cholera Holotoxin protein is produced in selected *Pseudomonas fluorescens* Pfēnex Expression Technology™ strains. The selected strains are grown in 2 liter fermentors, induced with IPTG, and samples prepared for analysis, as described above for CRM197 large-scale expression. The samples are analyzed by SDS-CGE.

TABLE 23

Sequence Listings

| SEQ ID NO | DESCRIPTION |
|---|---|
| 1 | CRM197 Amino Acid Sequence |
| 2 | CRM197 DNA Sequence, optimized |
| 3 | DsbA Secretion Leader |
| 4 | Azu |
| 5 | Ibp-S31A |
| 6 | Tpr |
| 7 | CupB2 |
| 8 | CupA2 |
| 9 | NikA |
| 10 | Pbp A20V |

TABLE 23-continued

Sequence Listings

| SEQ ID NO | DESCRIPTION |
|---|---|
| 11 | DsbC |
| 12 | TolB |
| 13 | Pbp |
| 14 | Lao |
| 15 | CupC2 |
| 16 | PorE |
| 17 | Pbp |
| 18 | FlgI |
| 19 | ttg2C |
| 20 | CRM197 native leader |
| 21 | Cleavage product GADD |
| 22 | Cholera Toxin B Amino Acid Sequence |
| 23 | Cholera Toxin B DNA Sequence, optimized |
| 24 | Pertussis toxin S1 R9K E129A DNA sequence |
| 25 | Pertussis toxin S1 R9K E129A Amino Acid Sequence |
| 26 | Pertussis toxin S2 Amino Acid Sequence |
| 27 | Pertussis toxin S3 Amino Acid Sequence |
| 28 | Pertussis toxin S4 Amino Acid Sequence |
| 29 | Pertussis toxin S5 Amino Acid Sequence |
| 30 | Tetanus Toxin C Amino Acid Sequence |
| 31 | Tetanus Toxin C DNA Sequence, optimized |
| 32 | TcdB Amino Acid Sequence |
| 33 | TcdB DNA Sequence, optimized |
| 34 | Exotoxin A Amino Acid Sequence |
| 35 | DNA Sequence of Wild-Type Pertussis Toxoid |
| 36 | Wild-Type Diphtheria Toxin Amino Acid Sequence |
| 37 | Wild-Type Diphtheria Toxin DNA Sequence, optimized |
| 38 | Cholera Toxin A Amino Acid Sequence |
| 39 | Cholera Toxin B Amino Acid Sequence |
| 40 | Cholera Holotoxin (CTX) DNA Sequence |
| 41 | Wild Type Pertussis toxin S1 Amino Acid Sequence |
| 42 | Pertussis toxin S2 Amino Acid Sequence |
| 43 | Pertussis toxin S4 Amino Acid Sequence |
| 44 | Pertussis toxin S5 Amino Acid Sequence |
| 45 | Pertussis toxin S3 Amino Acid Sequence |
| 46 | Hexa-histidine affinity tag |

What is claimed is:

1. A method for producing a recombinant toxin protein in a Pseudomonad host cell, said method comprising:
transforming the Pseudomonad host cell with an expression vector comprising a nucleotide sequence encoding the toxin protein; and
culturing the transformed Pseudomonad host cell in a culture media suitable for the expression of the recombinant toxin protein; wherein the recombinant toxin protein is *Clostridium difficile* Toxin B, and wherein the recombinant *Clostridium difficile* Toxin B protein is produced at a yield of soluble or active toxin protein of about 0.2 grams per liter to about 12 grams per liter.

2. The method of claim 1, wherein the yield of soluble or active toxin protein is 0.2 grams per liter to about 12 grams per liter, about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L, about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

3. The method of claim 1, wherein the nucleotide sequence encoding the toxin protein is fused to a secretion signal coding sequence that when expressed directs transfer of the toxin protein to the periplasm.

4. The method of claim 3, wherein the expression vector further comprises a tag sequence adjacent to the coding sequence for the secretion signal.

5. The method of claim 1, wherein the host cell: is defective in the expression of at least one protease; overexpresses at least one folding modulator selected from the group consisting of: RXF02095.1; RXF06767.1/RXF02090; RXF01748.1; RXF03385.1; RXF05399.1; RXF06954.1; RXF03376.1; RXF03987.2; RXF05406.2; RXF03346.2; RXF05413.1; RXF04587.1; RXF08347.1; RXF04654.2; RXF04663.1; RXF01957.2; RXF01961.2; RXF04254.2; RXF05455.2; RXF02231.1; RXF07017.2; RXF08657.2; RXF01002.1; RXF03307.1; RXF04890.2; RXF03204.1; RXF04886.2; RXF03768.1; RXF05345.2; RXF06034.2; RXF06591.1; RXF05753.2; RXF01833.2; RXF04655.2; RXF05385.1; RXF00271.1; RXF06068.1; RXF05719.1; RXF05319.1; RXF03406.2; RXF04296.1; RXF04553.1; RXF04554.2; RXF05310.2; RXF05304.1; RXF05073.1; RXF05445.1; RXF05426.1; RXF05432.1; RXF08122.2; RXF06751.1; and RXF00922.1; or wherein the host cell is defective in the expression of at least one protease and overexpresses at least one folding modulator selected from the group consisting of: RXF02095.1; RXF06767.1/RXF02090; RXF01748.1; RXF03385.1; RXF05399.1; RXF06954.1; RXF03376.1; RXF03987.2; RXF05406.2; RXF03346.2; RXF05413.1; RXF04587.1; RXF08347.1; RXF04654.2; RXF04663.1; RXF01957.2; RXF01961.2; RXF04254.2; RXF05455.2; RXF02231.1; RXF07017.2; RXF08657.2; RXF01002.1; RXF03307.1; RXF04890.2; RXF03204.1; RXF04886.2; RXF03768.1; RXF05345.2; RXF06034.2; RXF06591.1; RXF05753.2; RXF01833.2; RXF04655.2; RXF05385.1; RXF00271.1; RXF06068.1; RXF05719.1; RXF05319.1; RXF03406.2; RXF04296.1; RXF04553.1; RXF04554.2; RXF05310.2; RXF05304.1; RXF05073.1; RXF05445.1; RXF05426.1; RXF05432.1; RXF08122.2; RXF06751.1; and RXF00922.1, or a combination thereof.

6. The method of claim 1, wherein the host cell: is defective in the expression of the protease HtpX; is defective in the expression of the protease DegP1; is defective in the expression of the proteases HslU, HslV, Prc1 and Prc2; is defective in the expression of the proteases Lon, La and DegP2, or; the host cell is defective in the expression of the proteases Lon, Prc 1, DegP2 and AprA, and overexpresses the protease DegP2 S219A.

7. The method of claim 1, further comprising measuring the activity of the recombinant toxin protein in an activity assay, wherein about 40% to about 100% of the soluble toxin protein produced is determined to be active.

8. The method of claim 7, wherein the activity assay is an immunological assay, a receptor-binding assay, or an enzyme assay.

9. The method of claim 1, wherein the expression vector comprises a lac promoter operatively linked to the protein coding sequence, and wherein the culturing comprises induction of the promoter using IPTG at a concentration of about 0.02 to about 1.0 mM, the cell density at induction is an optical density of about 40 to about 200 absorbance units (AU), the pH of the culture is from about 6 to about 7.5, and the growth temperature is about 20 to about 35° C.

10. The method of claim 9, wherein the lac promoter is selected from the following promoters: tac, trc, Ptac16, P6ac17, PtacII, P1acUV5, and T7lac.

11. The method of claim 1, wherein the host cell is a *Pseudomonas* cell.

12. The method of claim 11, wherein the nucleotide sequence has been optimized for expression in the *Pseudomonas* host cell.

13. The method of claim 1, wherein the host cell is *Pseudomonas fluorescens*.

14. The method of claim 13, wherein the nucleotide sequence has been optimized for expression in the *Pseudomonas fluorescens* host cell.

15. The method of claim 1, wherein the nucleotide sequence has been optimized for expression in the Pseudomonad host cell.

16. The method of claim 1, wherein the expression vector further comprises a tag sequence adjacent to the coding sequence for the toxin protein.

17. The method of claim 1, wherein the recombinant protein is produced at a yield of soluble and active toxin protein of about 0.2 grams per liter to about 12 grams per liter.

18. The method of claim 17, wherein the yield of soluble and active toxin protein is 0.2 grams per liter to about 12 grams per liter, about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L, about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, or about 11 g/L to about 12 g/L.

* * * * *